(12) United States Patent
Plummer et al.

(10) Patent No.: US 8,759,058 B2
(45) Date of Patent: *Jun. 24, 2014

(54) PHOTOSYNTHETIC HYDROGEN PRODUCTION FROM THE GREEN ALGA CHLAMYDOMONAS REINHARDII

(76) Inventors: Scott Plummer, Greenwood Village, CO (US); Mark Plummer, Greenwood Village, CO (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/404,709

(22) Filed: Feb. 24, 2012

(65) Prior Publication Data

US 2012/0220010 A1    Aug. 30, 2012

Related U.S. Application Data

(63) Continuation-in-part of application No. 12/428,471, filed on Apr. 23, 2009, now Pat. No. 8,124,347.

(60) Provisional application No. 61/046,989, filed on Apr. 22, 2008.

(51) Int. Cl.
| | | |
|---|---|---|
| *C12N 9/02* | (2006.01) | |
| *C12P 3/00* | (2006.01) | |
| *C12N 1/12* | (2006.01) | |
| *C12Q 1/26* | (2006.01) | |
| *C12P 21/06* | (2006.01) | |
| *C12P 21/04* | (2006.01) | |
| *C07H 21/04* | (2006.01) | |
| *C40B 10/00* | (2006.01) | |
| *C40B 30/08* | (2006.01) | |

(52) U.S. Cl.
USPC .......... 435/189; 435/257.2; 435/168; 435/25; 435/69.1; 435/69.7; 536/23.1; 536/23.2; 506/1; 506/11

(58) Field of Classification Search
USPC .............. 435/189, 257.2, 168, 25, 69.1, 69.7; 536/23.1, 23.2; 506/1, 11
See application file for complete search history.

(56) References Cited

U.S. PATENT DOCUMENTS 8,124,347 B2 *    2/2012    Plummer et al. ............. 435/6.18

FOREIGN PATENT DOCUMENTS

WO    0218629 A1    3/2002

OTHER PUBLICATIONS

Armstrong FA., Hydrogenases: active site puzzles and progress. Curr. Opin. Chem. Biol., 2004, vol. 8: 133-140.*
Friesner et al., Quantum mechanical calculations on biological systems. Curr. Opin. Struct. Biol., 1998, vol. 8: 257-262.*
Altschul, S.F. And Gish, W., Local Alignment Statistics, Methods in Enzymology, 1996, vol. 266, pp. 460 to 480.
Altschul, S.F. et al, Basic Local Alignment Search Tool, J. Mol. Biol., 1990, vol. 215, pp. 403-410.
Altschul, S.F. et al, Gapped BLAST and PSI-BLAST: a new generation of protein database search programs, Nucleic Acids Research, 1997, vol. 25, pp. 3389-3402.
Gibbs, M.D. et al, Degenerate oligonucleotide gene shuffling (DOGS): a method for enhancing the frequency of recombination with family shuffling, Gene, 2001, vol. 271, pp. 13-20.
Jorgensen, W.L. et al, Development and Testing of the OPLS All-Atom Force Field on Conformational Energetics and Properties of Organic Liquids, J. Am. Chem, Soc., 1996, vol. 118, pp. 11225-11236.
King, P.W. et al, Functional Studies of [FeFe] Hydrogenase Maturation in an *Escherichia coli* Biosynthetic System, J. of Bacteriology, 2006, vol. 188, No. 6, pp. 2163-2172.
Posewitz, M.C. et al, Identification of genes required for hydrogenase activity in Chlamydomonas reinhardtii, Biochemical Society Transactions, 2005, vol. 33, Part 1, pp. 102-104.

* cited by examiner

*Primary Examiner* — Ganapathirama Raghu
(74) *Attorney, Agent, or Firm* — Polsinelli PC

(57) ABSTRACT

The present invention relates generally to hydrogen production for use in fuel cells, foodstuffs and chemical production, and more particularly, to biologically and photosynthetically produced hydrogen. Specifically, disclosed is a method for producing bacteria and green alga that can produce hydrogen in quantities that exceed four hundred percent of the hydrogen produced by green alga in nature; thus, producing organisms which can serve as hydrogen generators for fuel cells, chemical production and numerous other applications.

14 Claims, 37 Drawing Sheets

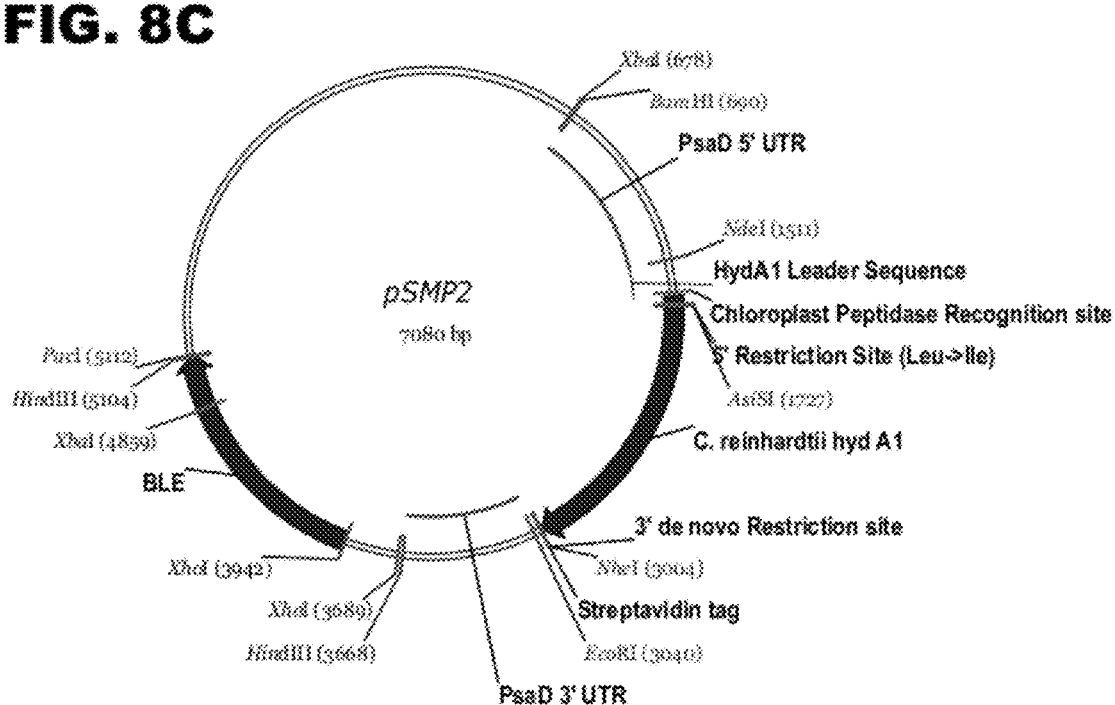

FIG. 12

1.  Strep Tag Insertion

Mutational primer:
5'  GGA CGA GAA GAA GGC TAG CGC CTG GAG CCA CCC GCA GTT CGA GAA GTG AGA ATT CTG GC  3'
Complement primer:
5'  GCC AGA ATT CTC ACT TCT CGA ACT GCG GGT GGC TCC AGG CGC TAG CCT TCT TCT CGT CC  3'

(a)    pSMP1

Mutational primer:
5'  GCT TGC GCG GCT GGG CCC GCC GCA CCC G  3'
Complement primer:
5'  CGG GTG CGG CGG GCC CAG CCG CGC AAG C  3'

(b)    pSMP1c

Mutational primer:
5'  CCC GCT GCG GAG GGG CCC TTG AGT CAT GTC C  3'
Complement primer:
5'  GGA CAT GAC TCA AGG GCC CCT CCG CAG CGG G  3'

(c)    pSMP2

Mutational primer:
5'  CCA GCA GGC GAT CGC CGA GCT TGC  3'
Complement primer:
5'  GCA AGC TCG GCG ATC GCC TGC TGG  3'

(d)    PspOMI site removal

Mutational primer:
5'  CGA GGG GGG GCC CGG TAC CCA GC  3'
Complement primer:
5'  GCT GGG TAC CGG GCC CCC CCT CG  3'

FIG. 17

| Chimera # | Hydrogenase Segment[1] | | | | | | | |
|---|---|---|---|---|---|---|---|---|
| | #1 | #2 | #3 | #4 | #5 | #6 | #7 | #8 |
| 1 | Aceto | Aceto | Aceto | Aceto | Saccharo | Saccharo | Saccharo | Saccharo |
| 2 | Saccharo | Saccharo | Saccharo | Saccharo | Aceto | Aceto | Aceto | Aceto |
| 18A | Aceto | Aceto | Aceto | Aceto | Saccharo | Saccharo | Aceto | Saccharo |
| 18S | Saccharo | Saccharo | Saccharo | Saccharo | Saccharo | Saccharo | Aceto | Saccharo |
| 21A | Aceto | Aceto | Aceto | Aceto | Saccharo | Saccharo | Aceto | Aceto |
| 21S | Saccharo | Saccharo | Saccharo | Saccharo | Saccharo | Saccharo | Aceto | Aceto |
| 24A | Aceto | Aceto | Aceto | Aceto | Saccharo | Aceto | Aceto | Saccharo |
| 24S | Saccharo | Saccharo | Saccharo | Saccharo | Saccharo | Aceto | Aceto | Saccharo |
| 26A | Aceto | Aceto | Aceto | Aceto | Aceto | Saccharo | Aceto | Saccharo |
| 26S | Saccharo | Saccharo | Saccharo | Saccharo | Aceto | Saccharo | Aceto | Saccharo |
| 27S | Saccharo | Saccharo | Saccharo | Saccharo | Saccharo | Aceto | Aceto | Aceto |
| 28A | Aceto | Aceto | Aceto | Aceto | Aceto | Saccharo | Aceto | Aceto |
| 28S | Saccharo | Saccharo | Saccharo | Saccharo | Aceto | Saccharo | Aceto | Aceto |
| 30A | Aceto | Aceto | Aceto | Aceto | Aceto | Aceto | Aceto | Saccharo |
| 30S | Saccharo | Saccharo | Saccharo | Saccharo | Aceto | Aceto | Aceto | Saccharo |
| 44 | Saccharo | Saccharo | Aceto | Saccharo | Aceto | Saccharo | Saccharo | Saccharo |

[1] The 1.8kb hydrogenase gene was divided into eight roughly equal segments. The segments designated as "Aceto" and "Saccharo" are from C. acetobutylicum and C. saccharobutylicum, respectively.

FIG. 19

*C. perfringens*

Upstream primer:
5' GCT ATC CAT GGC GAA TAA AAT AAT AAT CAA TGA TAA GAC 3'
Downstream primer:
5' ATA GGC GCG CCT TTT TTA TAT TTC ATG 3'

*(A) C. thermocellum*

Upstream primer:
5' GCT ATC CAT GGT AAA TGT TAC TAT AGA TAA TTG 3'
Downstream primer:
5' ATT GGC GCG CCT CAT TTA ACA GGG TAG TTT TCC 3'

Mutational primer:
5' GGC TGC TGT TGC GCA TGG TCT TGG C 3'
Complement primer:
5' GCC AAG ACC ATG CGC AAC AGC AGC C 3'

FIG. 22

HydE:
Upstream primer:
5' GCA TCG CAT ATG ACA AAC ATG ACA AAT ATG ATA AAT 3'
Downstream primer:
5' GCA TCG AGA TCT TAA TTT GGC TTT TTG CAG TCG CCT CTT G 3'

HydF:
Upstream primer:
5' GCA TCG CCA TGG GAT TGA ATG AAA CAC CAT CTG CAA ACC G 3'
Downstream primer:
5' GCA TCG GGA TCC CTA AAG AAT TTC TGC AAG TAT GTC CGG GAA G 3'

HydG:
Upstream primer:
5' GCA TCG CAT ATG GTT GAA AAA GTT GAT TTT ATA AAA G 3'
Downstream primer:
5' GCA TCG AGA TCT TTA AAA ATA AAT ATC TCT CTT TCC TTT TTC 3'

To mutate HydE in pET DLS:
Mutational primer:
5' GCG AAT TGC AAA GAC TGG CAA AGG ATC TGA ATG TAA AAG ATA TCA G 3'
Complement primer:
5' CGC TTA ACG TTT CTG ACC GTT TCC TAG ACT TAC ATT TTC TAT AGT C 3'
Additional primer:
5' CAA TAC GGG ATA ATA CCG CGC CAC ATA GCA GAA C 3'
Complement of additional primer:
5' GTT ATG CCC TAT TAT GGC GCG GTG TAT CGT CTT G 3'

To mutate HydF in pCDF:
Mutational primer:
5' GGG CAT TAA AGC CTT TTC CAT ACG CTG ATA GAA TAT TTA ATC AAT CG 3'
Complement primer:
5' CCC GTA ATT TCG GAA AAG GTA TGC GAC TAT CTT ATA AAT TAG TTA GC 3'

Additional primer:
5' CCG ACA GGA CTT AAA GAT CCC CAC CGT TTC C 3'
Complement of additional primer:
5' GGC TGT CCT GAA TTT CTA GGG GTG GCA AAG G 3'

FIG. 26
A)
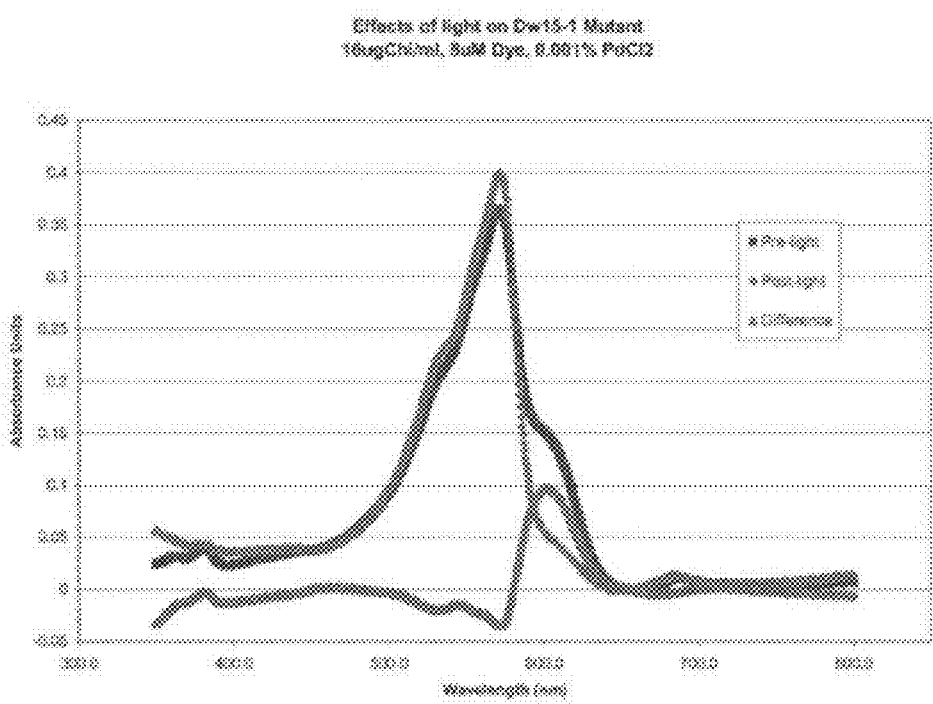
B)
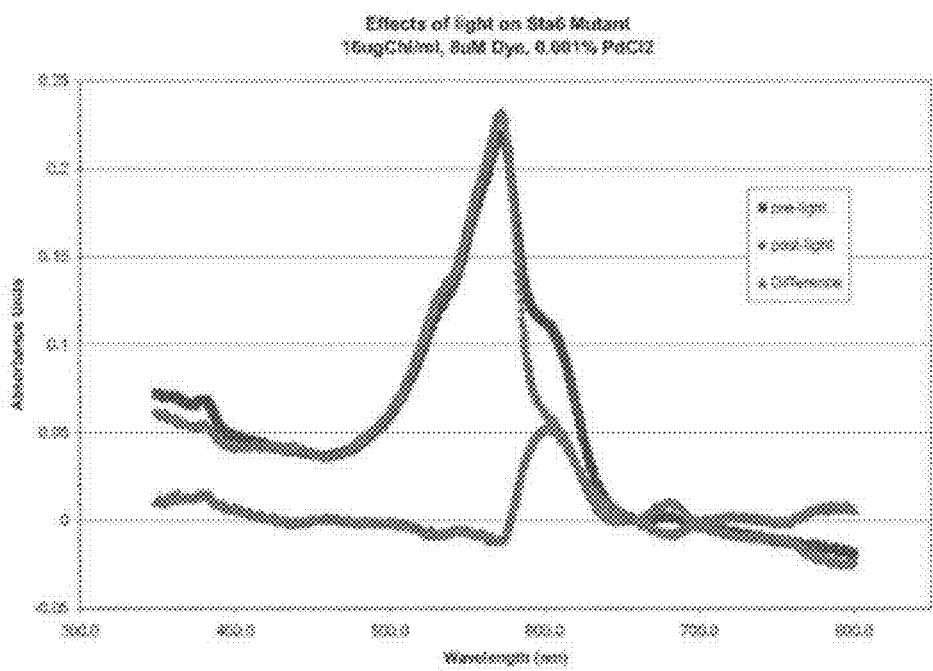

FIG. 30

Basic Fuel Cell Operation
(PEM FC example)

Anode: $2H_2 \rightarrow 4H^+ + 4e^-$

Cathode: $4e^- + 4H^+ + O_2 \rightarrow 2H_2O$

Overall: $2H_2 + O_2 \rightarrow 2H_2O$

Rated Output: 1.75 kWh per Liter of Hydrogen (note: this would cost about 20 - 22 cents at current kWh prices)

e.g.: Fuel Cell Stack weighs 180 pounds and gives continuous output of 100 kW to scale things, your home requires about 2kW of power or therefore 4.5 pounds of Hydrogen fuel cell stack.

```
                            SEQUENCE LISTING

<160> NUMBER OF SEQ ID NOS: 235

<210> SEQ ID NO 1
<211> LENGTH: 584
<212> TYPE: PRT
<213> ORGANISM: Chlamydomonas reinhardtii

<400> SEQUENCE: 1

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320
```

```
Ser Ala Lys Ser Pro Gln Gln Ile Phe Gly Thr Ala Ser Lys Thr Tyr
            325                 330                 335

Tyr Pro Ser Ile Ser Gly Ile Ala Pro Glu Asp Val Tyr Thr Val Thr
        340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
        370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 2
<211> LENGTH: 1752
<212> TYPE: DNA
<213> ORGANISM: Chlamydomonas reinhardtii

<400> SEQUENCE: 2
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata gcatgaatt taaatgtgga     300 ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
```

-continued

```
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggcccat tccctatgtt tacatcttgc      900
tgtcctgcat gggtaagatt agctcaaaat tatcatcctg aattattaga taatctttca      960
tcagcaaaat caccacaaca atatttggt actgcatcaa aaacttacta tccttcaatt     1020
tcaggaatag ctccagaaga tgtttataca gttactatca tgccttgtaa tgataaaaaa     1080
tatgaagcag atattccttt catggaaact aacagcttaa gagatattga tgcatcctta     1140
actacaagag agcttgcaaa aatgattaaa gatgcaaaaa ttaaatttgc agatcttgaa     1200
gatggtgaag ttgatcctgc tatgggtact tacagtggtg ctggagctat ctttggtgca     1260
accggtggcg ttatggaagc tgcaataaga tcagctaaag actttgctga aaataaagaa     1320
cttgaaaatg ttgattacac tgaagtaaga ggctttaaag gcataaaaga agcggaagtt     1380
gaaattgctg aaataaaact aaacgttgct gttataaatg gtgcttctaa cttcttcgag     1440
tttatgaaat ctggaaaaat gaacgaaaaa caatatcact ttatagaagt aatggcttgc     1500
cctggtggat gtataaatgg tggaggtcaa cctcacgtaa atgctcttga tagagaaaat     1560
gttgattaca gaaaactaag agcatcagta ttatacaacc aagataaaaa tgttctttca     1620
aagagaaagt cacatgataa tccagctatt attaaaatgt atgatagcta ctttggaaaa     1680
ccaggtgaag gacttgctca caaattacta cacgtaaaat acacaaaaga taaaaatgtt     1740
tcaaaacatg aa                                                        1752

<210> SEQ ID NO 3
<211> LENGTH: 59
<212> TYPE: DNA
<213> ORGANISM: Chlamydomonas reinhardtii

<400> SEQUENCE: 3
ggacgagaag aaggctagcg cctggagcca cccgcagttc gagaagtgag aattctggc       59

<210> SEQ ID NO 4
<211> LENGTH: 59
<212> TYPE: DNA
<213> ORGANISM: Chlamydomonas reinhardtii

<400> SEQUENCE: 4
gccagaattc tcacttctcg aactgcgggt ggctccaggc gctagccttc ttctcgtcc       59

<210> SEQ ID NO 5
<211> LENGTH: 28
<212> TYPE: DNA
<213> ORGANISM: Chlamydomonas reinhardtii

<400> SEQUENCE: 5
gcttgcgcgg ctgggcccgc cgcacccg                                         28

<210> SEQ ID NO 6
<211> LENGTH: 28
<212> TYPE: DNA
<213> ORGANISM: Chlamydomonas reinhardtii

<400> SEQUENCE: 6
cgggtgcggc gggcccagcc gcgcaagc                                         28
```

<210> SEQ ID NO 7
<211> LENGTH: 31
<212> TYPE: DNA
<213> ORGANISM: Chlamydomonas reinhardtii

<400> SEQUENCE: 7
cccgctgcgg aggggccctt gagtcatgtc c             31

<210> SEQ ID NO 8
<211> LENGTH: 31
<212> TYPE: DNA
<213> ORGANISM: Chlamydomonas reinhardtii

<400> SEQUENCE: 8
ggacatgact caagggcccc tccgcagcgg g             31

<210> SEQ ID NO 9
<211> LENGTH: 24
<212> TYPE: DNA
<213> ORGANISM: Chlamydomonas reinhardtii

<400> SEQUENCE: 9
ccagcaggcg atcgccgagc ttgc                     24

<210> SEQ ID NO 10
<211> LENGTH: 23
<212> TYPE: DNA
<213> ORGANISM: Chlamydomonas reinhardtii

<400> SEQUENCE: 10
gctgggtacc cggcccccccc tcg                     23

<210> SEQ ID NO 11
<211> LENGTH: 23
<212> TYPE: DNA
<213> ORGANISM: Chlamydomonas reinhardtii

<400> SEQUENCE: 11 cgagggggggg ccgggtaccc agc                     23

<210> SEQ ID NO 12
<211> LENGTH: 23
<212> TYPE: DNA
<213> ORGANISM: Chlamydomonas reinhardtii

<400> SEQUENCE: 12
gctgggtacc cggcccccccc tcg                     23

<210> SEQ ID NO 13
<211> LENGTH: 19
<212> TYPE: DNA
<213> ORGANISM: Chlamydomonas reinhardtii

<400> SEQUENCE: 13
ccagctgctg ccagaattc                           19

<210> SEQ ID NO 14
<211> LENGTH: 19
<212> TYPE: DNA
<213> ORGANISM: Chlamydomonas reinhardtii

<400> SEQUENCE: 14

```
ccagctgctg ccagaattc                                                19
```

```
<210> SEQ ID NO 15
<211> LENGTH: 20
<212> TYPE: DNA
<213> ORGANISM: Chlamydomonas reinhardtii

<400> SEQUENCE: 15
gacgagaaga aggctagcgc                                               20
```

```
<210> SEQ ID NO 16
<211> LENGTH: 19
<212> TYPE: DNA
<213> ORGANISM: Chlamydomonas reinhardtii

<400> SEQUENCE: 16
ccagctgctg ccagaattc                                                19
```

```
<210> SEQ ID NO 17
<211> LENGTH: 39
<212> TYPE: DNA
<213> ORGANISM: Chlamydomonas reinhardtii

<400> SEQUENCE: 17
gctatccatg gcgaataaaa taataatcaa tgataagac                          39
```

```
<210> SEQ ID NO 18
<211> LENGTH: 27
<212> TYPE: DNA
<213> ORGANISM: Chlamydomonas reinhardtii

<400> SEQUENCE: 18
ataggcgcgc cttttttata tttcatg                                       27
```

```
<210> SEQ ID NO 19
<211> LENGTH: 33
<212> TYPE: DNA
<213> ORGANISM: Chlamydomonas reinhardtii

<400> SEQUENCE: 19
gctatccatg gtaaatgtta ctatagataa ttg                                33
```

```
<210> SEQ ID NO 20
<211> LENGTH: 33
<212> TYPE: DNA
<213> ORGANISM: Chlamydomonas reinhardtii

<400> SEQUENCE: 20
attggcgcgc ctcatttaac agggtagttt tcc                                33
```

```
<210> SEQ ID NO 21
<211> LENGTH: 25
<212> TYPE: DNA
<213> ORGANISM: Chlamydomonas reinhardtii

<400> SEQUENCE: 21
ggctgctgtt gcgcatggtc ttggc                                         25
```

```
<210> SEQ ID NO 22
<211> LENGTH: 25
<212> TYPE: DNA
<213> ORGANISM: Chlamydomonas reinhardtii

<400> SEQUENCE: 22
```
gccaagacca tgcgcaacag cagcc                                              25

<210> SEQ ID NO 23
<211> LENGTH: 16
<212> TYPE: DNA
<213> ORGANISM: Chlamydomonas reinhardtii

<400> SEQUENCE: 23
cccacgccga aacaag                                                        16

<210> SEQ ID NO 24
<211> LENGTH: 22
<212> TYPE: DNA
<213> ORGANISM: Chlamydomonas reinhardtii

<400> SEQUENCE: 24
accatacctt cttcaacttt tg                                                 22

<210> SEQ ID NO 25
<211> LENGTH: 20
<212> TYPE: DNA
<213> ORGANISM: Chlamydomonas reinhardtii

<400> SEQUENCE: 25
ggtagtaaaa acaaactcag                                                    20

<210> SEQ ID NO 26
<211> LENGTH: 24
<212> TYPE: DNA
<213> ORGANISM: Chlamydomonas reinhardtii

<400> SEQUENCE: 26
acacttagtt ctgtctatta caat                                               24

<210> SEQ ID NO 27
<211> LENGTH: 18
<212> TYPE: DNA
<213> ORGANISM: Chlamydomonas reinhardtii

<400> SEQUENCE: 27
tgtgtgctat gcggaaga                                                      18

<210> SEQ ID NO 28
<211> LENGTH: 23
<212> TYPE: DNA
<213> ORGANISM: Chlamydomonas reinhardtii

<400> SEQUENCE: 28
atgcttatta ggatcttcta atg                                                23

<210> SEQ ID NO 29
<211> LENGTH: 20
<212> TYPE: DNA
<213> ORGANISM: Chlamydomonas reinhardtii

<400> SEQUENCE: 29
catgtaatag ttgctatggc                                                    20

<210> SEQ ID NO 30
<211> LENGTH: 23
<212> TYPE: DNA
<213> ORGANISM: Chlamydomonas reinhardtii

```
<400> SEQUENCE: 30
tttaactctt tcaataaact ctg                                              23

<210> SEQ ID NO 31
<211> LENGTH: 21
<212> TYPE: DNA
<213> ORGANISM: Chlamydomonas reinhardtii

<400> SEQUENCE: 31
aaaaataatg gaccattccc a                                                21

<210> SEQ ID NO 32
<211> LENGTH: 23
<212> TYPE: DNA
<213> ORGANISM: Chlamydomonas reinhardtii

<400> SEQUENCE: 32
tctcttgtag taagtactgc atc                                              23

<210> SEQ ID NO 33
<211> LENGTH: 29
<212> TYPE: DNA
<213> ORGANISM: Chlamydomonas reinhardtii

<400> SEQUENCE: 33
agaattagca aaatgatta aagatgcaa                                         29

<210> SEQ ID NO 34
<211> LENGTH: 29
<212> TYPE: DNA
<213> ORGANISM: Chlamydomonas reinhardtii

<400> SEQUENCE: 34
tattccttgt aatcctctta tttgtgtat                                        29

<210> SEQ ID NO 35
<211> LENGTH: 29
<212> TYPE: DNA
<213> ORGANISM: Chlamydomonas reinhardtii

<400> SEQUENCE: 35
ataaaagagg ctacagtaga aattggtgg                                        29

<210> SEQ ID NO 36
<211> LENGTH: 21
<212> TYPE: DNA
<213> ORGANISM: Chlamydomonas reinhardtii

<400> SEQUENCE: 36
tccaccattt acacatccgc c                                                21

<210> SEQ ID NO 37
<211> LENGTH: 18
<212> TYPE: DNA
<213> ORGANISM: Chlamydomonas reinhardtii

<400> SEQUENCE: 37
ggaggacaac cacacgta                                                    18

<210> SEQ ID NO 38
<211> LENGTH: 24
<212> TYPE: DNA
<213> ORGANISM: Chlamydomonas reinhardtii
```

```
<400> SEQUENCE: 38
tacgattact ttctgttcga ctta                                          24

<210> SEQ ID NO 39
<211> LENGTH: 16
<212> TYPE: DNA
<213> ORGANISM: Chlamydomonas reinhardtii

<400> SEQUENCE: 39
cccacgccga aacaag                                                   16

<210> SEQ ID NO 40
<211> LENGTH: 23
<212> TYPE: DNA
<213> ORGANISM: Chlamydomonas reinhardtii

<400> SEQUENCE: 40
accattccat cttcaacttt ggc                                           23

<210> SEQ ID NO 41
<211> LENGTH: 23
<212> TYPE: DNA
<213> ORGANISM: Chlamydomonas reinhardtii

<400> SEQUENCE: 41
ggtaataaac acagaatccg atg                                           23

<210> SEQ ID NO 42
<211> LENGTH: 24
<212> TYPE: DNA
<213> ORGANISM: Chlamydomonas reinhardtii

<400> SEQUENCE: 42
acattttgat ctgtcaatta caat                                          24

<210> SEQ ID NO 43
<211> LENGTH: 20
<212> TYPE: DNA
<213> ORGANISM: Chlamydomonas reinhardtii

<400> SEQUENCE: 43
tgtgtactat gcggtagatg                                               20

<210> SEQ ID NO 44
<211> LENGTH: 23
<212> TYPE: DNA
<213> ORGANISM: Chlamydomonas reinhardtii

<400> SEQUENCE: 44
atgtttttta gggtcattaa gag                                           23

<210> SEQ ID NO 45
<211> LENGTH: 20
<212> TYPE: DNA
<213> ORGANISM: Chlamydomonas reinhardtii

<400> SEQUENCE: 45
catgtcattg ttgcaatggc                                               20

<210> SEQ ID NO 46
<211> LENGTH: 24
<212> TYPE: DNA
```

<213> ORGANISM: Chlamydomonas reinhardtii

<400> SEQUENCE: 46
tttaactctg cctaaaagtt cagt    24

<210> SEQ ID NO 47
<211> LENGTH: 24
<212> TYPE: DNA
<213> ORGANISM: Chlamydomonas reinhardtii

<400> SEQUENCE: 47
aaaaataatg gcccattccc tatg    24

<210> SEQ ID NO 48
<211> LENGTH: 25
<212> TYPE: DNA
<213> ORGANISM: Chlamydomonas reinhardtii

<400> SEQUENCE: 48
tctcttgtag ttaaggatgc atcaa    25

<210> SEQ ID NO 49
<211> LENGTH: 27
<212> TYPE: DNA
<213> ORGANISM: Chlamydomonas reinhardtii

<400> SEQUENCE: 49
agagcttgca aaaatgatta aagatgc    27

<210> SEQ ID NO 50
<211> LENGTH: 26
<212> TYPE: DNA
<213> ORGANISM: Chlamydomonas reinhardtii

<400> SEQUENCE: 50
tatgccttta aagcctctta cttcag    26

<210> SEQ ID NO 51
<211> LENGTH: 26
<212> TYPE: DNA
<213> ORGANISM: Chlamydomonas reinhardtii

<400> SEQUENCE: 51
ataaaagaag cggaagttga aattgc    26

<210> SEQ ID NO 52
<211> LENGTH: 23
<212> TYPE: DNA
<213> ORGANISM: Chlamydomonas reinhardtii

<400> SEQUENCE: 52
tccaccattt atacatccac cag    23

<210> SEQ ID NO 53
<211> LENGTH: 22
<212> TYPE: DNA
<213> ORGANISM: Chlamydomonas reinhardtii

<400> SEQUENCE: 53
ggaggtcaac ctcacgtaaa tg    22

<210> SEQ ID NO 54
<211> LENGTH: 24

<212> TYPE: DNA
<213> ORGANISM: Chlamydomonas reinhardtii

<400> SEQUENCE: 54
tacgattact ttctgttcga ctta                                          24

<210> SEQ ID NO 55
<211> LENGTH: 39
<212> TYPE: DNA
<213> ORGANISM: Chlamydomonas reinhardtii

<400> SEQUENCE: 55
gtaatagaca gaactaagtg tgtgctatgc ggaagatgt                          39

<210> SEQ ID NO 56
<211> LENGTH: 39
<212> TYPE: DNA
<213> ORGANISM: Chlamydomonas reinhardtii

<400> SEQUENCE: 56
gtaattgaca gatcaaaatg tgtgctatgc ggaagatgt                          39

<210> SEQ ID NO 57
<211> LENGTH: 40
<212> TYPE: DNA
<213> ORGANISM: Chlamydomonas reinhardtii

<400> SEQUENCE: 57
gtaatagaca gaactaagtg tgtactatgc ggtagatgcg                         40

<210> SEQ ID NO 58
<211> LENGTH: 40
<212> TYPE: DNA
<213> ORGANISM: Chlamydomonas reinhardtii

<400> SEQUENCE: 58
gtaattgaca gatcaaaatg tgtactatgc ggtagatgcg                         40

<210> SEQ ID NO 59
<211> LENGTH: 44
<212> TYPE: DNA
<213> ORGANISM: Chlamydomonas reinhardtii

<400> SEQUENCE: 59
cagagtttat tgaaagagtt aaaaataatg gaccattccc aatg                    44

<210> SEQ ID NO 60
<211> LENGTH: 44
<212> TYPE: DNA
<213> ORGANISM: Chlamydomonas reinhardtii

<400> SEQUENCE: 60
cagagtttat tgaaagagtt aaaaataatg gcccattccc tatg                    44

<210> SEQ ID NO 61
<211> LENGTH: 44
<212> TYPE: DNA
<213> ORGANISM: Chlamydomonas reinhardtii

<400> SEQUENCE: 61
ctgaactttt aggcagagtt aaaaataatg gcccattccc tatg                    44

<210> SEQ ID NO 62

```
<211> LENGTH: 44
<212> TYPE: DNA
<213> ORGANISM: Chlamydomonas reinhardtii

<400> SEQUENCE: 62
ctgaactttt aggcagagtt aaaaataatg gaccattccc aatg            44

<210> SEQ ID NO 63
<211> LENGTH: 45
<212> TYPE: DNA
<213> ORGANISM: Chlamydomonas reinhardtii

<400> SEQUENCE: 63
aaataagagg attacaagga ataaaagagg ctacagtaga aattg           45

<210> SEQ ID NO 64
<211> LENGTH: 46
<212> TYPE: DNA
<213> ORGANISM: Chlamydomonas reinhardtii

<400> SEQUENCE: 64
aaataagagg attacaagga ataaaagaag cggaagttga aattgc          46

<210> SEQ ID NO 65
<211> LENGTH: 44
<212> TYPE: DNA
<213> ORGANISM: Chlamydomonas reinhardtii

<400> SEQUENCE: 65
gtaagaggct ttaaaggcat aaaagaagcg gaagttgaaa ttgc            44

<210> SEQ ID NO 66
<211> LENGTH: 43
<212> TYPE: DNA
<213> ORGANISM: Chlamydomonas reinhardtii

<400> SEQUENCE: 66
gtaagaggct ttaaaggcat aaaagaggct acagtagaaa ttg             43

<210> SEQ ID NO 67
<211> LENGTH: 212
<212> TYPE: DNA
<213> ORGANISM: Chlamydomonas reinhardtii

<400> SEQUENCE: 67
atggccaaaa caataatctt aaatggcaat gaagtgcata cagataaaga tattactatc    60
cttgagctag caagagaaaa taatgtagat atcccaacac tctgcttttt aaaggattgt   120
ggcaattttg gaaaatgcgg agtctgtatg gtagaggtag aaggcaaggg ctttagagct   180
gcttgtgttg ccaaagttga agatggaatg gt                                 212

<210> SEQ ID NO 68
<211> LENGTH: 229
<212> TYPE: DNA
<213> ORGANISM: Chlamydomonas reinhardtii

<400> SEQUENCE: 68
aataaacaca gaatccgatg aagtaaaaga acgaatcaaa aaagagtttt caatgcttct    60
tgataagcat gaatttaaat gtggacaatg ttctagaaga gaaaattgtg aattccttaa   120
acttgtaata aagacaaaag caaaagcttc aaaaccattt ttaccagaag ataaggatgc   180
tctagttgat aatagaagta aggctattgt aattgacaga tcaaaatgt              229
```

<210> SEQ ID NO 69
<211> LENGTH: 231
<212> TYPE: DNA
<213> ORGANISM: Chlamydomonas reinhardtii

<400> SEQUENCE: 69
gtactatgcg gtagatgcgt agctgcatgt aaacagcaca caagcacttg ctcaattcaa      60
tttattaaaa aagatggaca aagggctgtt ggaactgttg atgatgtttg tcttgatgac     120
tcaacatgct tattatgcgg tcagtgtgta atcgcttgtc ctgttgctgc tttaaaagaa     180
aaatcccata tagaaaaagt tcaagaagct cttaatgacc taaaaaaca t              231

<210> SEQ ID NO 70
<211> LENGTH: 192
<212> TYPE: DNA
<213> ORGANISM: Chlamydomonas reinhardtii

<400> SEQUENCE: 70
gtcattgttg caatggctcc atcagtaaga actgctatgg gcgaattatt caaaatggga      60
tatggaaaag atgtaacagg aaaactatat actgcactta gaatgttagg ctttgataaa     120
gtatttgata taaactttgg tgcagatatg actataatgg aagaagctac tgaactttta     180
ggcagagtta aa                                                         192

<210> SEQ ID NO 71
<211> LENGTH: 284
<212> TYPE: DNA
<213> ORGANISM: Chlamydomonas reinhardtii

<400> SEQUENCE: 71
aataatggcc cattccctat gtttacatct tgctgtcctg catgggtaag attagctcaa      60
aattatcatc ctgaattatt agataatctt tcatcagcaa aatcaccaca acaaatattt     120
ggtactgcat caaaaactta ctatccttca atttcaggaa tagctccaga agatgtttat     180
acagttacta tcatgccttg taatgataaa aaatatgaag cagatattcc tttcatggaa     240
actaacagct aagagatat tgatgcatcc ttaactacaa gaga                       284

<210> SEQ ID NO 72
<211> LENGTH: 214
<212> TYPE: DNA
<213> ORGANISM: Chlamydomonas reinhardtii

<400> SEQUENCE: 72
gcttgcaaaa atgattaaag atgcaaaaat taaatttgca gatcttgaag atggtgaagt      60
tgatcctgct atgggtactt acagtggtgc tggagctatc tttggtgcaa ccggtggcgt     120
tatggaagct gcaataagat cagctaaaga ctttgctgaa aataaagaac ttgaaaatgt     180
tgattacact gaagtaagag gctttaaagg cata                                 214

<210> SEQ ID NO 73
<211> LENGTH: 159
<212> TYPE: DNA
<213> ORGANISM: Chlamydomonas reinhardtii

<400> SEQUENCE: 73
aaagaagcgg aagttgaaat tgctggaaat aaactaaacg ttgctgttat aaatggtgct      60
tctaacttct tcgagtttat gaaatctgga aaaatgaacg aaaaacaata tcactttata     120
gaagtaatgg cttgccctgg tggatgtata aatggtgga                         159

<210> SEQ ID NO 74
<211> LENGTH: 228
<212> TYPE: DNA
<213> ORGANISM: Chlamydomonas reinhardtii

<400> SEQUENCE: 74
ggtcaacctc acgtaaatgc tcttgataga gaaaatgttg attacagaaa actaagagca    60
tcagtattat acaaccaaga taaaaatgtt ctttcaaaga gaaagtcaca tgataatcca   120
gctattatta aaatgtatga tagctacttt ggaaaaccag gtgaaggact tgctcacaaa   180
ttactacacg taaaatacac aaaagataaa aatgtttcaa acatgaa                 228

<210> SEQ ID NO 75
<211> LENGTH: 215
<212> TYPE: DNA
<213> ORGANISM: Chlamydomonas reinhardtii

<400> SEQUENCE: 75
atggcaataa acatagtaat tgatgaaaaa actattcaag tacaggaaaa tactacagtt    60
atacaagctg ccctagcaaa tgggatagat ataccaagtt tatgctatct taatgagtgt   120
ggtaatgttg gaaagtgtgg agtgtgtgca gtagaaatag aaggaaaaaa taacttagca   180
cttgcatgta taacaaaagt tgaagaaggt atggt                              215

<210> SEQ ID NO 76
<211> LENGTH: 229
<212> TYPE: DNA
<213> ORGANISM: Chlamydomonas reinhardtii

<400> SEQUENCE: 76
agtaaaaaca aactcagaaa aagtacaaga aagagttaaa atgagagttg ctactttgct    60
tgataagcat gaatttaaat gtggaccttg tccaagaaga gaaaattgcg aattttttaaa  120 gttagttata aaaacaaaag ctaaggctaa caagccttt gtggttgaag acaaatcaca    180
atacatagat attagaagta aatcaattgt aatagacaga actaagtgt               229

<210> SEQ ID NO 77
<211> LENGTH: 231
<212> TYPE: DNA
<213> ORGANISM: Chlamydomonas reinhardtii

<400> SEQUENCE: 77
gtgctatgcg gaagatgtga agcagcatgt aaaacaaaga caggtacagg agctatttca    60
atttgtaaga gtgaatcagg aagaatagtg caagcaacag gcggaaagtg ctttgatgat   120
acaaattgtt tattatgtgg acaatgcgtt gcagcatgtc cagtaggagc tttaactgaa   180
aaaacacacg ttgatagagt taagaagca ttagaagatc ctaataagca t             231

<210> SEQ ID NO 78
<211> LENGTH: 192
<212> TYPE: DNA
<213> ORGANISM: Chlamydomonas reinhardtii

<400> SEQUENCE: 78
gtaatagttg ctatggcacc atcaatcaga acttctatgg gagagttatt taaattaggc    60
tatggggttg atgtaactgg aaaattatat gcttcaatga gagcattagg atttgataag   120
gtatttgata ttaactttgg ggctgatatg acaataatgg aagaagcaac agagtttatt   180

```
gaaagagtta aa                                                          192

<210> SEQ ID NO 79
<211> LENGTH: 284
<212> TYPE: DNA
<213> ORGANISM: Chlamydomonas reinhardtii

<400> SEQUENCE: 79
aataatggac cattcccaat gtttacttca tgttgtccgg catgggttag acaagtggaa        60
aattattacc cagaattttt agaaaactta tcatcagcta atcaccaca acaaatattt       120 ggtgcagcaa gcaaaacata ctatcctcaa atatcaggta taagtgctaa agatgtattt       180
actgttacaa taatgccttg tacagcaaag aaatttgagg ctgatagaga agaaatgtat       240
aatgagggaa ttaaaaatat agatgcagta cttactacaa gaga                       284

<210> SEQ ID NO 80
<211> LENGTH: 214
<212> TYPE: DNA
<213> ORGANISM: Chlamydomonas reinhardtii

<400> SEQUENCE: 80
attagcaaaa atgattaaag atgcaaagat taattttgct aatttagaag acgaacaagc        60
tgatccagca atgggagaat acactggggc tggagttata ttcggagcta caggtggagt       120
tatggaagca gcacttagaa ctgctaagga tttcgttgaa gataaagatt taactgatat       180
agaatataca caaataagag gattacaagg aata                                   214

<210> SEQ ID NO 81
<211> LENGTH: 159
<212> TYPE: DNA
<213> ORGANISM: Chlamydomonas reinhardtii

<400> SEQUENCE: 81
aaagaggcta cagtagaaat tggtggagaa aattataacg tagctgtaat taatggtgca        60
gcaaacttag ctgaattcat gaatagcggt aaaatccttg aaaagaacta tcattttatt       120
gaagtaatgg cttgcccagg cggatgtgta atggtgga                              159

<210> SEQ ID NO 82
<211> LENGTH: 201
<212> TYPE: DNA
<213> ORGANISM: Chlamydomonas reinhardtii

<400> SEQUENCE: 82
ggacaaccac acgtaagtgc aaaggaaaga gaaaaagtag atgttagaac tgtaagagca        60
tctgttttat ataaccaaga taaaaattta gagaagagaa aatcacataa aaatacagca       120
ttattaaata tgtactatga ttatatggga gctccaggac aaggaaaagc tcatgaatta       180
ttacacttaa aatacaataa a                                                201

<210> SEQ ID NO 83
<211> LENGTH: 1722
<212> TYPE: DNA
<213> ORGANISM: Chlamydomonas reinhardtii

<400> SEQUENCE: 83
atggccaaaa caataatctt aaatggcaat gaagtgcata cagataaaga tattactatc        60
cttgagctag caagagaaaa taatgtagat atcccaacac tctgcttttt aaaggattgt       120
```

```
ggcaattttg gaaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaagagt ttcaatgctt cttgataagc atgaatttaa atgtggacaa      300
tgttctagaa gagaaaattg tgaattcctt aaacttgtaa taaagacaaa agcaaaagct      360
tcaaaaccat ttttaccaga agataaggat gctctagttg ataatagaag taaggctatt      420
gtaattgaca gatcaaaatg tgtactatgc ggtagatgcg tagctgcatg taaacagcac      480
acaagcactt gctcaattca atttattaaa aaagatggac aaagggctgt tggaactgtt      540
gatgatgttt gtcttgatga ctcaacatgc ttattatgcg gtcagtgtgt aatcgcttgt      600
cctgttgctg ctttaaaaga aaaatcccat atagaaaaag ttcaagaagc tcttaatgac      660
cctaaaaaac atgtcattgt tgcaatggct ccatcagtaa aactgctat gggcgaatta      720 ttcaaaatgg gatatggaaa agatgtaaca ggaaaactat atactgcact tagaatgtta      780
ggctttgata agtatttga tataaacttt ggtgcagata tgactataat ggaagaagct      840
actgaacttt taggcagagt taaaaataat ggaccattcc caatgtttac ttcatgttgt      900
ccggcatggg ttagacaagt ggaaaattat tacccagaat tttagaaaa cttatcatca      960 gctaaatcac cacaacaaat atttggtgca gcaagcaaaa catactatcc tcaaatatca     1020
ggtataagtg ctaagatgt atttactgtt acaataatgc cttgtacagc aaagaaattt     1080
gaggctgata gagaagaaat gtataatgag ggaattaaaa atatagatgc agtacttact     1140
acaagagaat tagcaaaaat gattaaagat gcaaagatta attttgctaa tttagaagac     1200
gaacaagctg atccagcaat gggagaatac actggggctg gagttatatt cggagctaca     1260
ggtggagtta tggaagcagc acttagaact gctaaggatt tcgttgaaga taaagattta     1320
actgatatag aatatacaca aataagagga ttacaaggaa taaagaggc tacagtagaa     1380 attggtggag aaaattataa cgtagctgta attaatggtg cagcaaactt agctgaattc     1440
atgaatagcg gtaaaatcct tgaaaagaac tatcatttta ttgaagtaat ggcttgccca     1500
ggcggatgtg taaatggtgg aggacaacca cacgtaagtg caaaggaaag agaaaaagta     1560
gatgttagaa ctgtaagagc atctgtttta tataaccaag ataaaaattt agagaagaga     1620
aaatcacata aaaatacagc attattaaat atgtactatg attatatggg agctccagga     1680
caaggaaaag ctcatgaatt attacactta aaatacaata aa                        1722
```

<210> SEQ ID NO 84
<211> LENGTH: 1752
<212> TYPE: DNA
<213> ORGANISM: Chlamydomonas reinhardtii

<400> SEQUENCE: 84

```
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg gaaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc ttttgtggt tgaagacaaa tcacaataca tagatattag aagtaaatca      420
attgtaatag acagaactaa gtgtgtgcta tgcggaagat gtgaagcagc atgtaaaaca      480
aagacaggta caggagctat ttcaatttgt aagagtgaat caggaagaat agtgcaagca      540
```

```
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatcttttca    960 tcagcaaaat caccacaaca aatatttggt actgcatcaa aaacttacta tccttcaatt   1020
tcaggaatag ctccagaaga tgttttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag cataaaaga agcggaagtt   1380 gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                       1752

<210> SEQ ID NO 85
<211> LENGTH: 1722
<212> TYPE: DNA
<213> ORGANISM: Chlamydomonas reinhardtii

<400> SEQUENCE: 85
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg cttttaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact agaatgttta    780
ggctttgata agtatttga tataaaacttt ggtgcagata tgactataat ggaagaagct    840
```

```
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagaat tagcaaaaat gattaaagat gcaagatta attttgctaa tttagaagac   1200
gaacaagctg atccagcaat gggagaatac actggggctg agttatatt cggagctaca   1260 ggtggagtta tggaagcagc acttagaact gctaaggatt cgttgaaga taaagattta   1320 actgatatag aatatacaca aataagagga ttacaaggaa taaaagaagc ggaagttgaa   1380
attgctggaa ataaactaaa cgttgctgtt ataaatggtg cttctaactt cttcgagttt   1440
atgaaatctg gaaaatgaa cgaaaaacaa tatcacttta tagaagtaat ggcttgccct   1500
ggtggatgta taaatggtgg aggacaacca cacgtaagtg caaggaaag agaaaaagta   1560 gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                     1722
```

<210> SEQ ID NO 86
<211> LENGTH: 1725
<212> TYPE: DNA
<213> ORGANISM: Chlamydomonas reinhardtii

<400> SEQUENCE: 86

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata gcatgaatt taaatgtgga    300 ccttgtccaa gaagagaaaa ttgcgaattt ttaaagttag ttataaaaac aaaagctaag    360
gctaacaagc ttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aatttttaga aaacttatca   960
tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagagaaga aatgtataat gagggaatta aaaatataga tgcagtactt   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
```

```
acaggtggag ttatggaagc agcacttaga actgctaagg atttcgttga agataaagat    1320
ttaactgata tagaatatac acaaataaga ggattacaag gaataaaaga agcggaagtt    1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725

<210> SEQ ID NO 87
<211> LENGTH: 1749
<212> TYPE: DNA
<213> ORGANISM: Chlamydomonas reinhardtii

<400> SEQUENCE: 87
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaagagt ttcaatgctt cttgataagc atgaatttaa atgtggacaa      300
tgttctagaa gagaaaattg tgaattcctt aaacttgtaa taagacaaa agcaaaagct      360 tcaaaaccat ttttaccaga agataaggat gctctagttg ataatagaag taaggctatt     420
gtaattgaca gatcaaaatg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg cttttaaaga aaaatcccat atagaaaaag ttcaagaagc tcttaatgac     660
cctaaaaaac atgtcattgt tgcaatggct ccatcagtaa gaactgctat gggcgaatta     720
ttcaaaatgg gatatggaaa agatgtaaca ggaaaactat atactgcact tagaatgtta     780
ggctttgata agtatttga tataaacttt ggtgcagata tgactataat ggaagaagct     840
actgaacttt taggcagagt taaaaataat ggaccattcc caatgtttac ttcatgttgt     900
ccggcatggg ttagacaagt ggaaaattat tacccagaat ttttagaaaa cttatcatca     960
gctaaatcac cacaacaaat atttggtgca gcaagcaaaa catactatcc tcaaatatca    1020
ggtataagtg ctaaagatgt atttactgtt acaataatgc cttgtacagc aaagaaattt    1080
gaggctgata gaagagaaat gtaatgag ggaattaaaa atatagatgc agtacttact      1140
acaagagaat tagcaaaaat gattaaagat gcaagattaa ttttctaa tttagaagac     1200 gaacaagctg atccagcaat gggagaatac actggggctg gagttatatt cggagctaca    1260
ggtggagtta tggaagcagc acttagaact gctaaggatt tcgttgaaga taagatttta    1320
actgatatag aatatacaca aataagagga ttacaaggaa taaagaagc ggaagttgaa     1380 attgctggaa taaactaaa cgttgctgtt ataaatggtc ttctaacttt cttcgagttt     1440
atgaaatctg gaaaatgaa cgaaaacaa tatcacttta tagaagtaat ggcttgccct      1500
ggtggatgta taaatggtgg aggtcaacct cacgtaaatg ctcttgatag agaaatgtt    1560 gattacagaa aactaagagc atcagtatta tacaaccaag ataaaaatgt tctttcaaag    1620
```

| agaaagtcac atgataatcc agctattatt aaaatgtatg atagctactt tggaaaacca | 1680 |
| ggtgaaggac ttgctcacaa attactacac gtaaaataca caaagataa aaatgtttca | 1740 |
| aaacatgaa | 1749 |

<210> SEQ ID NO 88
<211> LENGTH: 1752
<212> TYPE: DNA
<213> ORGANISM: Chlamydomonas reinhardtii
<400> SEQUENCE: 88

| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg aaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |
| caagaaagag ttaaaatgag agttgctact ttgcttgata agcatgaatt taaatgtgga | 300 |
| ccttgtccaa gaagagaaaa ttgcgaattt ttaaagttag ttataaaaac aaaagctaag | 360 |
| gctaacaagc cttttgtggt tgaagacaaa tcacaataca tagatattag aagtaaatca | 420 |
| attgtaatag acagaactaa gtgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag gagctttaac tgaaaaaaca cacgttgata gagttaaaga agcattagaa | 660 |
| gatcctaata agcatgtaat agttgctatg gcaccatcaa tcagaacttc tatgggagag | 720 |
| ttatttaaat taggctatgg ggttgatgta actggaaaat tatatgcttc aatgagagca | 780 |
| ttaggatttg ataaggtatt tgatattaac tttggggctg atatgacaat aatgaagaa | 840 |
| gcaacagagt ttattgaaag agttaaaaat aatggaccat tcccaatgtt tacttcatgt | 900 |
| tgtccggcat gggttagaca agtggaaaat tattacccag aattttaga aaacttatca | 960 |
| tcagctaaat caccacaaca aatatttggt gcagcaagca aaacatacta tcctcaaata | 1020 |
| tcaggtataa gtgctaaaga tgtatttact gttacaataa tgccttgtac agcaaagaaa | 1080 |
| tttgaggctg atagagaaga aatgtataat gagggaatta aaaatataga tgcagtactt | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag gaataaaaga agcggaagtt | 1380 |
| gaaattgctg gaaataaact aaacgttgct gttataaatg gtgcttctaa cttcttcgag | 1440 |
| tttatgaaat ctggaaaaat gaacgaaaaa caatatcact ttatagaagt aatggcttgc | 1500 |
| cctggtggat gtataaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |
| ccaggtgaag gacttgctca caaattacta cacgtaaaat acacaaaaga taaaaatgtt | 1740 |
| tcaaaacatg aa | 1752 |

<210> SEQ ID NO 89
<211> LENGTH: 1749
<212> TYPE: DNA
<213> ORGANISM: Chlamydomonas reinhardtii

<400> SEQUENCE: 89

```
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaaagagt ttcaatgctt cttgataagc atgaatttaa atgtggacaa     300
tgttctagaa gagaaaattg tgaattcctt aaacttgtaa taaagacaaa agcaaaagct     360
tcaaaaccat ttttaccaga agataaggat gctctagttg ataatagaag taaggctatt     420
gtaattgaca gatcaaaatg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg ctttaaaaga aaaatcccat atagaaaaag ttcaagaagc tcttaatgac     660
cctaaaaaac atgtcattgt tgcaatggct ccatcagtaa gaactgctat gggcgaatta     720
ttcaaaatgg gatatggaaa agatgtaaca ggaaaactat atactgcact agaatgtta      780
ggctttgata aagtatttga tataaacttt ggtgcagata tgactataat ggaagaagct     840
actgaaccttt taggcagagt taaaaataat ggcccattcc ctatgtttac atcttgctgt     900
cctgcatggg taagattagc tcaaaattat catcctgaat tattagataa tctttcatca     960
gcaaaatcac cacaacaaat atttggtact gcatcaaaaa cttactatcc ttcaatttca    1020
ggaatagctc cagaagatgt ttatacagtt actatcatgc cttgtaatga taaaaaatat    1080
gaagcagata ttcctttcat ggaaactaac agcttaagag atattgatgc atccttaact    1140
acaagagaat tagcaaaaat gattaaagat gcaaagatta attttgctaa tttagaagac    1200
gaacaagctg atccagcaat gggagaatac actgggggctg gagttatatt cggagctaca    1260
ggtggagtta tggaagcagc acttagaact gctaaggatt tcgttgaaga taaagattta    1320
actgatatag aatatacaca aataagagga ttacaaggaa taaaagaagc ggaagttgaa    1380
attgctggaa ataaactaaa cgttgctgtt ataaatggtg cttctaactt cttcgagttt    1440
atgaaatctg gaaaaatgaa cgaaaaacaa tatcacttta tagaagtaat ggcttgccct    1500
ggtggatgta taaatggtgg aggtcaacct cacgtaaatg ctcttgatag agaaaatgtt    1560
gattacagaa aactaagagc atcagtatta taacaaccaag ataaaaatgt tctttcaaag    1620
agaaagtcac atgataatcc agctattatt aaatgtatgt atagctactt tggaaaacca    1680
ggtgaaggac ttgctcacaa attactacac gtaaaataca caaaagataa aaatgtttca    1740
aaacatgaa                                                             1749
```

<210> SEQ ID NO 90
<211> LENGTH: 1752
<212> TYPE: DNA
<213> ORGANISM: Chlamydomonas reinhardtii

<400> SEQUENCE: 90

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
```

```
caagaaagag ttaaaatgag agttgctact ttgcttgata agcatgaatt taaatgtgga    300
ccttgtccaa gaagagaaaa ttgcgaattt taaagttag ttataaaaac aaaagctaag     360
gctaacaagc ttttgtggt tgaagacaaa tcacaataca tagatattag aagtaaatca     420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780 ttaggattg ataaggtatt tgatattaac tttggggctg atatgacaat aatgaagaa      840 gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag gaataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                        1752

<210> SEQ ID NO 91
<211> LENGTH: 1725
<212> TYPE: DNA
<213> ORGANISM: Chlamydomonas reinhardtii

<400> SEQUENCE: 91
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt taaagttag ttataaaaac aaaagctaag     360
gctaacaagc ttttgtggt tgaagacaaa tcacaataca tagatattag aagtaaatca     420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
```

```
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggcccat tccctatgtt tacatcttgc      900
tgtcctgcat gggtaagatt agctcaaaat tatcatcctg aattattaga taatctttca      960
tcagcaaaat caccacaaca aatatttggt actgcatcaa aaacttacta tccttcaatt     1020
tcaggaatag ctccagaaga tgtttataca gttactatca tgccttgtaa tgataaaaaa     1080
tatgaagcag atattccttt catggaaact aacagcttaa gagatattga tgcatcctta     1140
actacaagag agcttgcaaa aatgattaaa gatgcaaaaa ttaaatttgc agatcttgaa     1200
gatggtgaag ttgatcctgc tatgggtact tacagtggtg ctggagctat ctttggtgca     1260
accggtggcg ttatggaagc tgcaataaga tcagctaaag actttgctga aaataaagaa     1320
cttgaaaatg ttgattacac tgaagtaaga ggctttaaag gcataaaaga agcggaagtt     1380
gaaattgctg gaaataaact aaacgttgct gttataaatg gtgcttctaa cttcttcgag     1440
tttatgaaat ctggaaaaat gaacgaaaaa caatatcact ttatagaagt aatggcttgc     1500
cctggtggat gtataaatgg tggaggacaa ccacacgtaa gtgcaaagga aagagaaaaa     1560
gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725

<210> SEQ ID NO 92
<211> LENGTH: 1725
<212> TYPE: DNA
<213> ORGANISM: Chlamydomonas reinhardtii

<400> SEQUENCE: 92
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg aaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420 attgtaaatag acagaactaa gtgtgtacta tgcggtagat gcgtagctgc atgtaaacag      480
cacacaagca cttgctcaat tcaatttatt aaaaaagatg gacaaagggc tgttggaact      540
gttgatgatg tttgtcttga tgactcaaca tgcttattat gcggtcagtg tgtaatcgct      600
tgtcctgttg ctgctttaaa agaaaaatcc catatagaaa aagttcaaga agctctttaat      660 gaccctaaaa aacatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggcccat tccctatgtt tacatcttgc      900
tgtcctgcat gggtaagatt agctcaaaat tatcatcctg aattattaga taatctttca      960
```

```
tcagcaaaat caccacaaca atatttggt  actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag aataaaagaa ggctacagta   1380
gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggacaa ccacacgtaa gtgcaaagga agagaaaaa    1560 gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                   1725

<210> SEQ ID NO 93
<211> LENGTH: 1752
<212> TYPE: DNA
<213> ORGANISM: Chlamydomonas reinhardtii

<400> SEQUENCE: 93
atggcaataa acatagtaat tgatgaaaaa actattcaag tacaggaaaa tactacagtt    60
atacaagctg ccctagcaaa tgggatagat ataccaagtt tatgctatct taatgagtgt   120
ggtaatgttg gaaagtgtgg agtgtgtgca gtagaaatag aaggaaaaaa taacttagca   180
cttgcatgta taacaaaagt tgaagaaggt atggtagtaa aaacaaactc agaaaaagta   240
caagaaagag ttaaaatgag agttgctact ttgcttgata gcatgaatt taaatgtgga   300 ccttgtccaa gaagagaaaa ttgcgaattt ttaaagttag ttataaaaac aaaagctaag   360
gctaacaagc cttttgtggt tgaagacaaa tcacaataca tagatattag aagtaaatca   420
attgtaatag acagaactaa gtgtgtgcta tgcggaagat gtgaagcagc atgtaaaaca   480
aagacaggta caggagctat ttcaatttgt aagagtgaat caggaagaat agtgcaagca   540
acaggcggaa agtgctttga tgatacaaat tgtttattat gtggacaatg cgttgcagca   600
tgtccagtag gagctttaac tgaaaaaaca cacgttgata gagttaaaga agcattagaa   660
gatcctaata gcatgtcat tgttgcaatg gctccatcag taagaactgc tatgggcgaa   720
ttattcaaaa tgggatatgg aaaagatgta acaggaaaac tatatactgc acttagaatg   780
ttaggctttg ataaagtatt tgatataaac tttggtgcag atatgactat aatgaagaa    840 gctactgaac tttaggcag agttaaaaat aatggcccat tccctatgtt tacatcttgc   900
tgtcctgcat gggtaagatt agctcaaaat tatcatcctg aattattaga taatcttca    960 tcagcaaaat caccacaaca atatttggt  actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaattttgc agatcttgaa   1200 gatggtgaag ttgatcctgc tatgggtact tacagtggtg ctggagctat ctttggtgca   1260
accggtggcg ttatggaagc tgcaataaga tcagctaagg actttgctga aaataaagaa   1320
cttgaaaatg ttgattacac tgaagtaaga ggctttaaag gcataaaaga agcggaagtt   1380
```

| gaaattgctg gaaataaact aaacgttgct gttataaatg gtgcttctaa cttcttcgag | 1440 |
| tttatgaaat ctggaaaaat gaacgaaaaa caatatcact ttatagaagt aatggcttgc | 1500 |
| cctggtggat gtataaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |
| ccaggtgaag gacttgctca caaattacta cacgtaaaat acacaaaaga taaaaatgtt | 1740 |
| tcaaaacatg aa | 1752 |

<210> SEQ ID NO 94
<211> LENGTH: 1752
<212> TYPE: DNA
<213> ORGANISM: Chlamydomonas reinhardtii

<400> SEQUENCE: 94

| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg gaaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |
| caagaaagag ttaaaatgag agttgctact ttgcttgata agcatgaatt taaatgtgga | 300 |
| ccttgtccaa gaagagaaaa ttgcgaattt ttaaagttag ttataaaaac aaaagctaag | 360 |
| gctaacaagc ttttgtggt tgaagacaaa tcacaataca tagatattag aagtaaatca | 420 |
| attgtaatag acagaactaa gtgtgtacta tgcggtagat gcgtagctgc atgtaaacag | 480 |
| cacacaagca cttgctcaat tcaatttatt aaaaaagatg gacaaagggc tgttggaact | 540 |
| gttgatgatg tttgtcttga tgactcaaca tgcttattat gcggtcagtg tgtaatcgct | 600 |
| tgtcctgttg ctgctttaaa agaaaaatcc catatagaaa aagttcaaga agctcttaat | 660 |
| gaccctaaaa aacatgtaat agttgctatg gcaccatcaa tcagaacttc tatgggagag | 720 |
| ttatttaaat taggctatgg ggttgatgta actggaaaat tatatgcttc aatgagagca | 780 |
| ttaggatttg ataaggtatt tgatattaac tttggggctg atatgacaat aatggaagaa | 840 |
| gcaacagagt ttattgaaag agttaaaaat aatggcccat tccctatgtt tacatcttgc | 900 |
| tgtcctgcat gggtaagatt agctcaaaat tatcatcctg aattattaga taatctttca | 960 |
| tcagcaaaat caccacaaca aatatttggt actgcatcaa aaacttacta tccttcaatt | 1020 |
| tcaggaatag ctccagaaga tgtttataca gttactatca tgccttgtaa tgataaaaaa | 1080 |
| tatgaagcag atattccttt catggaaact aacagcttaa gagatattga tgcatcctta | 1140 |
| actcaaagag agcttgcaaa aatgattaaa gatgcaaaaa ttaaatttgc agatcttgaa | 1200 |
| gatggtgaag ttgatcctgc tatgggtact tacagtggtg ctggagctat ctttggtgca | 1260 |
| accggtggcg ttatggaagc tgcaataaga tcagctaaag actttgctga aaataaagaa | 1320 |
| cttgaaaatg ttgattacac tgaagtaaga ggctttaaag gcataaaaga agcggaagtt | 1380 |
| gaaattgctg gaaataaact aaacgttgct gttataaatg gtgcttctaa cttcttcgag | 1440 |
| tttatgaaat ctggaaaaat gaacgaaaaa caatatcact ttatagaagt aatggcttgc | 1500 |
| cctggtggat gtataaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |

```
ccaggtgaag gacttgctca caattactac acgtaaaat acacaaaga taaaaatgtt    1740 tcaaaacatg aa                                                      1752
```

<210> SEQ ID NO 95
<211> LENGTH: 1752
<212> TYPE: DNA
<213> ORGANISM: Chlamydomonas reinhardtii

<400> SEQUENCE: 95

```
atggcaataa acatagtaat tgatgaaaaa actattcaag tacaggaaaa tactacagtt      60
atacaagctg ccctagcaaa tgggatagat ataccaagtt tatgctatct taatgagtgt    120
ggtaatgttg aaagtgtgg  agtgtgtgca gtagaaatag aaggaaaaaa taacttagca    180
cttgcatgta taacaaaagt tgaagaaggt atggtaataa acacagaatc cgatgaagta    240
aaagaacgaa tcaaaaaaag agtttcaatg cttcttgata agcatgaatt taaatgtgga    300
caatgttcta agagagaaaa ttgtgaattc cttaaacttg taataaagac aaaagcaaaa    360
gcttcaaaac cattttttacc agaagataag gatgctctag ttgataatag aagtaaggct    420
attgtaattg acagatcaaa atgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg caccatcaa  tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacgagt  ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgttatataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag cataaaaga  agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caattactac acgtaaaat  acacaaaga taaaaatgtt   1740
tcaaaacatg aa                                                       1752
```

<210> SEQ ID NO 96
<211> LENGTH: 1749
<212> TYPE: DNA
<213> ORGANISM: Chlamydomonas reinhardtii

<400> SEQUENCE: 96

```
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtagtaaaaa caaactcaga aaagtacaa     240 gaaagagtta aaatgagagt tgctactttg cttgataagc atgaatttaa atgtggacct     300
tgtccaagaa gagaaaattg cgaatttta aagttagtta taaaaacaaa agctaaggct     360
aacaagcctt ttgtggttga agacaaatca caatacatag atattagaag taaatcaatt     420
gtaatagaca gaactaagtg tgtgctatgc ggaagatgtg aagcagcatg taaaacaaag     480
acaggtacag gagctatttc aatttgtaag agtgaatcag gaagaatagt gcaagcaaca     540
ggcggaaagt gctttgatga tacaaattgt ttattatgtg gacaatgcgt tgcagcatgt     600
ccagtaggag ctttaactga aaaaacacac gttgatagag ttaaagaagc attagaagat     660
cctaataagc atgtaatagt tgctatggca ccatcaatca gaacttctat gggagagtta     720
tttaaattag gctatggggt tgatgtaact ggaaaattat atgcttcaat gagagcatta     780
ggatttgata aggtatttga tattaactt ggggctgata tgacaataat ggaagaagca     840
acagagttta ttgaaagagt taaaaataat ggcccattcc ctatgtttac atcttgctgt     900
cctgcatggg taagattagc tcaaaattat catcctgaat tattagataa tctttcatca     960
gcaaaatcac cacaacaaat atttggtact gcatcaaaaa cttactatcc ttcaatttca    1020
ggaatagctc cagaagatgt ttatacagtt actatcatgc cttgtaatga taaaaatat    1080 gaagcagata ttcctttcat ggaaactaac agcttaagag atattgatgc atccttaact    1140
acaagagagc ttgcaaaaat gattaaagat gcaaaaatta aatttgcaga tcttgaagat    1200
ggtgaagttg atcctgctat gggtacttac agtggtgctg gagctatctt tggtgcaacc    1260
ggtggcgtta tggaagctgc aataagatca gctaaagact ttgctgaaaa taagaaactt    1320
gaaaatgttg attacactga agtaagaggc tttaaaggca taaagaagc ggaagttgaa    1380 attgctggaa ataaactaaa cgttgctgtt ataaatggtg cttctaactt cttcgagttt    1440
atgaaatctg gaaaaatgaa cgaaaaacaa tatcacttta tagaagtaat ggcttgccct    1500
ggtggatgta taaatggtgg aggtcaacct cacgtaaatg ctcttgatag agaaaatgtt    1560
gattacagaa aactaagagc atcagtatta taaaccaag ataaaaatgt tctttcaaag    1620
agaaagtcac atgataatcc agctattatt aaaatgtatg atagctactt tggaaaacca    1680
ggtgaaggac ttgctcacaa attactacac gtaaaataca caaagataa aaatgtttca    1740 aaacatgaa                                                             1749
```

<210> SEQ ID NO 97
<211> LENGTH: 1752
<212> TYPE: DNA
<213> ORGANISM: Chlamydomonas reinhardtii

<400> SEQUENCE: 97

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaagt tgaagaaggt atggtagtaa aaacaaactc agaaaaagta     240
caagaaagag ttaaaatgag agttgctact ttgcttgata agcatgaatt taaatgtgga     300
```

```
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420
attgtaatag acagaactaa gtgtgtacta tgcggtagat gcgtagctgc atgtaaacag      480
cacacaagca cttgctcaat tcaatttatt aaaaaagatg acaaagggc tgttggaact       540 gttgatgatg tttgtcttga tgactcaaca tgcttattat gcggtcagtg tgtaatcgct      600
tgtcctgttg ctgctttaaa agaaaaatcc catatagaaa aagttcaaga agctcttaat      660
gaccctaaaa aacatgtcat tgttgcaatg gctccatcag taagaactgc tatgggcgaa      720
ttattcaaaa tgggatatgg aaaagatgta acaggaaaac tatatactgc acttagaatg      780
ttaggctttg ataaagtatt tgatataaac tttggtgcag atatgactat aatggaagaa      840
gctactgaac ttttaggcag agttaaaaat aatggcccat tccctatgtt tacatcttgc      900
tgtcctgcat gggtaagatt agctcaaaat tatcatcctg aattattaga taatctttca      960
tcagcaaaat caccacaaca atatttggt actgcatcaa aaacttacta tccttcaatt      1020
tcaggaatag ctccagaaga tgtttataca gttactatca tgccttgtaa tgataaaaaa      1080
tatgaagcag atattccttt catggaaact aacagcttaa gagatattga tgcatcctta      1140
actacaagag agcttgcaaa aatgattaaa gatgcaaaaa ttaaatttgc agatcttgaa      1200
gatggtgaag ttgatcctgc tatgggtact tacagtggtg ctggagctat ctttggtgca      1260
accggtggcg ttatgaagc tgcaataaga tcagctaaag actttgctga aaataaagaa       1320
cttgaaaatg ttgattacac tgaagtaaga ggctttaaag cataaaaga agcggaagtt      1380 gaaattgctg gaaataaact aaacgttgct gttataaatg gtgcttctaa cttcttcgag      1440
tttatgaaat ctggaaaaat gaacgaaaaa caatatcact ttatagaagt aatggcttgc      1500
cctggtggat gtataaatgg tggaggtcaa cctcacgtaa atgctcttga tagagaaaat      1560
gttgattaca gaaaactaag agcatcagta ttatacaacc aagataaaaa tgttctttca      1620
aagagaaagt cacatgataa tccagctatt attaaaatgt atgatagcta ctttggaaaa      1680
ccaggtgaag gacttgctca caattacta cacgtaaaat acacaaaaga taaaaatgtt       1740
tcaaaacatg aa                                                         1752
```

<210> SEQ ID NO 98
<211> LENGTH: 1752
<212> TYPE: DNA
<213> ORGANISM: Chlamydomonas reinhardtii

<400> SEQUENCE: 98

```
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg aaagtgtgg agtgtgtgca gtagaaatag aaggaaaaaa taacttagca      180
cttgcatgta taacaaaagt tgaagaaggt atggtaataa acacagaatc cgatgaagta      240
aaagaacgaa tcaaaaaaag agtttcaatg cttcttgata agcatgaatt taaatgtgga      300
caatgttcta gaagagaaaa ttgtgaattc cttaaacttg taataaagac aaaagcaaaa      360
gcttcaaaac cattttttacc agaagataag gatgctctag ttgataatag aagtaaggct      420
attgtaattg acagatcaaa atgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgatacaaat tgtttattat gtggacaatg cgttgcagca      600
tgtccagtag gagctttaac tgaaaaaaca cacgttgata gagttaaaga agcattagaa      660
```

```
gatcctaata agcatgtcat tgttgcaatg gctccatcag taagaactgc tatgggcgaa      720
ttattcaaaa tgggatatgg aaaagatgta acaggaaaac tatatactgc acttagaatg      780
ttaggctttg ataaagtatt tgatataaac tttggtgcag atatgactat aatggaagaa      840
gctactgaac ttttaggcag agttaaaaat aatggcccat tccctatgtt tacatcttgc      900
tgtcctgcat gggtaagatt agctcaaaat tatcatcctg aattattaga taatctttca      960
tcagcaaaat caccacaaca atatttggt actgcatcaa aaacttacta tccttcaatt      1020
tcaggaatag ctccagaaga tgtttataca gttactatca tgccttgtaa tgataaaaaa      1080
tatgaagcag atattccttt catggaaact aacagcttaa gagatattga tgcatcctta      1140
actacaagag agcttgcaaa atgattaaa gatgcaaaaa ttaaatttgc agatcttgaa      1200
gatggtgaag ttgatcctgc tatgggtact tacagtggtg ctggagctat ctttggtgca      1260
accggtggcg ttatggaagc tgcaataaga tcagctaaag actttgctga aaataaagaa      1320
cttgaaaatg ttgattacac tgaagtaaga ggctttaaag cataaaaga gcggaagtt      1380 gaaattgctg gaaataaact aaacgttgct gttataaatg gtgcttctaa cttcttcgag      1440
tttatgaaat ctggaaaaat gaacgaaaaa caatatcact ttatagaagt aatggcttgc      1500
cctggtggat gtataaatgg tggaggtcaa cctcacgtaa atgctcttga tagagaaaat      1560
gttgattaca gaaaactaag agcatcagta ttatacaacc aagataaaaa tgttctttca      1620
aagagaaagt cacatgataa tccagctatt attaaaatgt atgatagcta ctttggaaaa      1680
ccaggtgaag gacttgctca caaattacta cacgtaaaat acacaaaaga taaaaatgtt      1740
tcaaaacatg aa      1752
```

<210> SEQ ID NO 99
<211> LENGTH: 1749
<212> TYPE: DNA
<213> ORGANISM: Chlamydomonas reinhardtii

<400> SEQUENCE: 99

```
atggccaaaa caataatctt aaatggcaat gaagtgcata cagataaaga tattactatc       60
cttgagctag caagagaaaa taatgtagat atcccaacac tctgcttttt aaaggattgt      120
ggcaattttg gaaaatgcgg agtctgtatg gtagaggtag aaggcaaggg ctttagagct      180
gcttgtgttg ccaaagttga agatggaatg gtagtaaaaa caaactcaga aaagtacaa      240 gaaagagtta aaatgagagt tgctactttg cttgataagc atgaatttaa atgtggacct      300
tgtccaagaa gagaaaattg cgaatttta aagttagtta taaaaacaaa agctaaggct      360
aacaagcctt ttgtggttga agacaaatca caatacatag atattagaag taaatcaatt      420
gtaatagaca gaactaagtg tgtgctatgc ggaagatgtg aagcagcatg taaaacaaag      480
acaggtacag gagctatttc aatttgtaag agtgaatcag gaagaatagt gcaagcaaca      540
ggcggaaagt gctttgatga tacaaattgt ttattatgtg acaatgcgt tgcagcatgt      600 ccagtaggag ctttaactga aaaacacac gttgatagag ttaaagaagc attagaagat      660
cctaataagc atgtcattgt tgcaatggct ccatcagtaa gaactgctat gggcgaatta      720
ttcaaaatgg gatatggaaa agatgtaaca ggaaaactat atactgcact tagaatgtta      780
ggctttgata agtatttga tataaacttt ggtgcagata tgactataat ggaagaagct      840
actgaacttt taggcagagt taaaaataat ggcccattcc ctatgtttac atcttgctgt      900
cctgcatggg taagattagc tcaaaattat catcctgaat tattagataa tctttcatca      960
```

```
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
acaagagagc ttgcaaaaat gattaaagat gcaaaaatta aatttgcaga tcttgaagat   1200
ggtgaagttg atcctgctat gggtacttac agtggtgctg gagctatctt tggtgcaacc   1260
ggtggcgtta tggaagctgc aataagatca gctaaagact ttgctgaaaa taagaacttt   1320
gaaaatgttg attacactga gtaagaggc tttaaaggca taaagaagc ggaagttgaa   1380 attgctggaa ataaactaaa cgttgctgtt ataaatggtg cttctaactt cttcgagttt   1440
atgaaatctg gaaaaatgaa cgaaaaacaa tatcacttta tagaagtaat ggcttgccct   1500
ggtggatgta taaatggtgg aggtcaacct cacgtaaatg ctcttgatag agaaaatgtt   1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataa aaatgtttca   1740 aaacatgaa                                                            1749
```

<210> SEQ ID NO 100
<211> LENGTH: 1752
<212> TYPE: DNA
<213> ORGANISM: Chlamydomonas reinhardtii

<400> SEQUENCE: 100

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaaatg aaggaaaaaa taacttagca    180
cttgcatgta taacaaaagt tgaagaaggt atggtaataa acacagaatc cgatgaagta    240
aaagaacgaa tcaaaaaag agtttcaatg cttcttgata agcatgaatt taaatgtgga    300
caatgttcta agagagaaaa ttgtgaattc cttaaacttg taataaagac aaaagcaaaa    360
gcttcaaaac cattttttacc agaagataag gatgctctag ttgataatag aagtaaggct    420
attgtaattg acagatcaaa atgtgtacta tgcggtagat gcgtagctgc atgtaaacag    480
cacacaagca cttgctcaat tcaattttatt aaaaaagatg gacaaagggc tgttggaact    540
gttgatgatg tttgtcttga tgactcaaca tgcttattat gcggtcagtg tgtaatcgct    600
tgtcctgttg ctgcttttaaa agaaaaatcc catatagaaa aagttcaaga agctcttaat    660
gaccctaaaa aacatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac ttttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca atatttggt actgcatcaa aaacttacta tccttcaatt    1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataagaa    1320
```

```
cttgaaaatg ttgattacac tgaagtaaga ggctttaaag gcataaaaga agcggaagtt    1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caattactac acgtaaaaat acacaaaaga taaaaatgtt    1740
tcaaaacatg aa                                                       1752

<210> SEQ ID NO 101
<211> LENGTH: 1749
<212> TYPE: DNA
<213> ORGANISM: Chlamydomonas reinhardtii

<400> SEQUENCE: 101
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaagttgga agatggaatg gtagtaaaaa caaactcaga aaagtacaa      240 gaaagagtta aaatgagagt tgctactttg cttgataagc atgaatttaa atgtggacct     300
tgtccaagaa gagaaaattg cgaattttta agttagttta taaaaacaaa agctaaggct     360
aacaagcctt ttgtggttga agacaaatca caatacatag atattagaag taaatcaatt     420
gtaatagaca gaactaagtg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg ctttaaaaga aaaatcccat atagaaaaag ttcaagaagc tcttaatgac     660
cctaaaaaac atgtaatagt tgctatggca ccatcaatca gaacttctat gggagagtta     720
tttaaattag gctatggggt tgatgtaact ggaaaattat atgcttcaat gagagcatta     780
ggatttgata aggtatttga tattaacttt ggggctgata tgacaataat ggaagaagca     840
acagagttta ttgaaagagt taaaaataat ggcccattcc ctatgtttac atcttgctgt     900
cctgcatggg taagattagc tcaaaattat catcctgaat tattagataa tctttcatca     960
gcaaaatcac cacaacaaat atttggtact gcatcaaaaa cttactatcc ttcaatttca    1020
ggaatagctc cagaagatgt ttatacagtt actatcatgc cttgtaatga taaaaaatat    1080
gaagcagata ttccttttcat ggaaactaac agcttaagag atattgatgc atccttaact    1140
acaagagagc ttgcaaaaat gattaaagat gcaaaaatta aatttgcaga tcttgaagat    1200
ggtgaagtta tcctgctat gggtacttac agtggtgctg gagctatctt tggtgcaacc    1260
ggtggcgtta tggaagctgc aataagatca gctaaagact ttgctgaaaa taagaaactt    1320
gaaaatgttg attacactga gtaagaggc tttaaaggca taaagaagc ggaagttgaa     1380 attgctggaa ataaactaaa cgttgctgtt ataaatggtg cttctaactt cttcgagttt    1440
atgaaatctg gaaaaatgaa cgaaaaacaa tatcacttta tagaagtaat ggcttgccct    1500
ggtggatgta taaatggtgg aggtcaacct cacgtaaatg ctcttgatag agaaaatgtt    1560
gattacagaa aactaagagc atcagtatta taccaccaag ataaaaatgt tctttcaaag    1620
```

| agaaagtcac atgataatcc agctattatt aaaatgtatg atagctactt tggaaaacca | 1680 |
| ggtgaaggac ttgctcacaa attactacac gtaaaataca caaagataa aaatgtttca | 1740 |
| aaacatgaa | 1749 |

<210> SEQ ID NO 102
<211> LENGTH: 1749
<212> TYPE: DNA
<213> ORGANISM: Chlamydomonas reinhardtii

<400> SEQUENCE: 102

| atggccaaaa caataatctt aaatggcaat gaagtgcata cagataaaga tattactatc | 60 |
| cttgagctag caagagaaaa taatgtagat atcccaacac tctgcttttt aaaggattgt | 120 |
| ggcaattttg aaaatgcgg agtctgtatg gtagaggtag aaggcaaggg ctttagagct | 180 |
| gcttgtgttg ccaaagttga agatggaatg gtaataaaca cagaatccga tgaagtaaaa | 240 |
| gaacgaatca aaaaagagt ttcaatgctt cttgataagc atgaatttaa atgtggacaa | 300 |
| tgttctagaa gagaaaattg tgaattcctt aaacttgtaa taagacaaa agcaaaagct | 360 |
| tcaaaaccat ttttaccaga agataaggat gctctagttg ataatagaag taaggctatt | 420 |
| gtaattgaca gatcaaaatg tgtgctatgc ggaagatgtg aagcagcatg taaacaaag | 480 |
| acaggtacag gagctatttc aatttgtaag agtgaatcag gaagaatagt gcaagcaaca | 540 |
| ggcggaaagt gctttgatga tacaaattgt ttattatgtg acaatgcgt tgcagcatgt | 600 |
| ccagtaggag ctttaactga aaaaacacac gttgatagag ttaaagaagc attagaagat | 660 |
| cctaataagc atgtaatagt tgctatggca ccatcaatca gaacttctat gggagagtta | 720 |
| tttaaattag ctatggggt tgatgtaact ggaaaattat atgcttcaat gagagcatta | 780 |
| ggatttgata aggtatttga tattaacttt ggggctgata tgacaataat ggaagaagca | 840 |
| acagagttta ttgaaagagt taaaaataat ggcccattcc ctatgtttac atcttgctgt | 900 |
| cctgcatggg taagattagc tcaaaattat catcctgaat tattagataa tctttcatca | 960 |
| gcaaaatcac cacaacaaat atttggtact gcatcaaaaa cttactatcc ttcaatttca | 1020 |
| ggaatagctc cagaagatgt ttatacagtt actatcatgc cttgtaatga taaaaatat | 1080 |
| gaagcagata ttcctttcat ggaaactaac agcttaagag atattgatgc atccttaact | 1140 |
| acaagagagc ttgcaaaaat gattaaagat gcaaaaatta aatttgcaga tcttgaagat | 1200 |
| ggtgaagttg atcctgctat gggtacttac agtggtgctg gagctatctt tggtgcaacc | 1260 |
| ggtggcgtta tggaagctgc aataagatca gctaaagact ttgctgaaaa taagaacttt | 1320 |
| gaaaatgttg attacactga agtaagaggc tttaaaggca taaagaagc ggaagttgaa | 1380 |
| attgctggaa ataactaaa cgttgctgtt ataaatggtg cttctaactt cttcgagttt | 1440 |
| atgaaatctg gaaaaatgaa cgaaaacaa tatcacttta tagaagtaat ggcttgccct | 1500 |
| ggtggatgta taatggtgg aggtcaacct cacgtaaatg ctcttgatag agaaaatgtt | 1560 |
| gattacagaa aactaagagc atcagtatta tacaaccaag ataaaaatgt tctttcaaag | 1620 |
| agaaagtcac atgataatcc agctattatt aaaatgtatg atagctactt tggaaaacca | 1680 |
| ggtgaaggac ttgctcacaa attactacac gtaaaataca caaagataa aaatgtttca | 1740 |
| aaacatgaa | 1749 |

<210> SEQ ID NO 103
<211> LENGTH: 1752
<212> TYPE: DNA
<213> ORGANISM: Chlamydomonas reinhardtii

<400> SEQUENCE: 103

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaaatg aaggaaaaaa taacttagca     180
cttgcatgta taacaaaagt tgaagaaggt atggtaataa acacagaatc cgatgaagta     240
aaagaacgaa tcaaaaaaag agtttcaatg cttcttgata agcatgaatt taatgtggaa     300
caatgttcta agagagaaaa ttgtgaattc cttaaacttg taataaagac aaaagcaaaa     360
gcttcaaaac cattttttacc agaagataag gatgctctag ttgataatag aagtaaggct     420
attgtaattg acagatcaaa atgtgtacta tgcggtagat gcgtagctgc atgtaaacag     480
cacacaagca cttgctcaat tcaatttatt aaaaaagatg acaaagggc tgttggaact      540
gttgatgatg tttgtcttga tgactcaaca tgcttattat gcggtcagtg tgtaatcgct     600
tgtcctgttg ctgctttaaa agaaaaatcc catatagaaa aagttcaaga agctcttaat     660
gaccctaaaa aacatgtcat tgttgcaatg gctccatcag taagaactgc tatgggcgaa     720
ttattcaaaa tgggatatgg aaaagatgta acaggaaaac tatatactgc acttagaatg     780
ttaggctttg ataaagtatt tgatataaac tttggtgcag atatgactat aatggaagaa     840
gctactgaac ttttaggcag agttaaaaat aatggcccat tccctatgtt tacatcttgc     900
tgtcctgcat gggtaagatt agctcaaaat tatcatcctg aattattaga taatctttca     960
tcagcaaaat caccacaaca aatatttggt actgcatcaa aaacttacta tccttcaatt    1020
tcaggaatag ctccagaaga tgtttataca gttactatca tgccttgtaa tgataaaaaa    1080
tatgaagcag atattccttt catggaaact aacagcttaa gagatattga tgcatcctta    1140
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag cataaaaga agcgaagtt      1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caattacta cacgtaaaat acacaaaaga taaaaatgtt     1740
tcaaaacatg aa                                                        1752
```

<210> SEQ ID NO 104
<211> LENGTH: 1749
<212> TYPE: DNA
<213> ORGANISM: Chlamydomonas reinhardtii

<400> SEQUENCE: 104

```
atggccaaaa caataatctt aaatggcaat gaagtgcata cagataaaga tattactatc      60
cttgagctag caagagaaaa taatgtagat atcccaacac tctgctttt aaaggattgt     120
ggcaattttg gaaatgcgg agtctgtatg gtagaggtag aaggcaaggg ctttagagct     180
gcttgtgttg ccaaagttga agatggaatg gtagtaaaaa caaactcaga aaaagtacaa     240
```

| | |
|---|---|
| gaaagagtta aaatgagagt tgctactttg cttgataagc atgaatttaa atgtggacct | 300 |
| tgtccaagaa gagaaaattg cgaatttta aagttagtta taaaaacaaa agctaaggct | 360 |
| aacaagcctt ttgtggttga agacaaatca caatacatag atattagaag taaatcaatt | 420 |
| gtaatagaca gaactaagtg tgtactatgc ggtagatgcg tagctgcatg taaacagcac | 480 |
| acaagcactt gctcaattca atttattaaa aaagatggac aaagggctgt tggaactgtt | 540 |
| gatgatgttt gtcttgatga ctcaacatgc ttattatgcg gtcagtgtgt aatcgcttgt | 600 |
| cctgttgctg ctttaaaaga aaaatcccat atagaaaaag ttcaagaagc tcttaatgac | 660 |
| cctaaaaaac atgtcattgt tgcaatggct ccatcagtaa gaactgctat gggcgaatta | 720 |
| ttcaaaatgg gatatggaaa agatgtaaca ggaaaactat atactgcact tagaatgtta | 780 |
| ggctttgata agtatttga tataaacttt ggtgcagata tgactataat ggaagaagct | 840 |
| actgaacttt taggcagagt taaaaataat ggcccattcc ctatgtttac atcttgctgt | 900 |
| cctgcatggg taagattagc tcaaaattat catcctgaat tattagataa tctttcatca | 960 |
| gcaaaatcac cacaacaaat atttggtact gcatcaaaaa cttactatcc ttcaatttca | 1020 |
| ggaatagctc cagaagatgt ttatacagtt actatcatgc cttgtaatga taaaaaatat | 1080 |
| gaagcagata ttcctttcat ggaaactaac agcttaagag atattgatgc atccttaact | 1140 |
| acaagagagc ttgcaaaaat gattaaagat gcaaaaatta aatttgcaga tcttgaagat | 1200 |
| ggtgaagttg atcctgctat gggtacttac agtggtgctg gagctatctt tggtgcaacc | 1260 |
| ggtggcgtta tggaagctgc aataagatca gctaaagact ttgctgaaaa taaagaactt | 1320 |
| gaaaatgttg attacactga gtaagaggc tttaaaggca taaagaagc ggaagttgaa | 1380 |
| attgctggaa ataaactaaa cgttgctgtt ataaatggtg cttctaactt cttcgagttt | 1440 |
| atgaaatctg gaaaatgaa cgaaaaacaa tatcacttta tagaagtaat ggcttgccct | 1500 |
| ggtggatgta taatggtgg aggtcaacct cacgtaaatg ctcttgatag agaaaatgtt | 1560 |
| gattacagaa aactaagagc atcagtatta taaccaag ataaaaatgt tctttcaaag | 1620 |
| agaaagtcac atgataatcc agctattatt aaaatgtatg atagctactt tggaaaacca | 1680 |
| ggtgaaggac ttgctcacaa attactacac gtaaaataca caaagataa aaatgtttca | 1740 |
| aaacatgaa | 1749 |

<210> SEQ ID NO 105
<211> LENGTH: 1749
<212> TYPE: DNA
<213> ORGANISM: Chlamydomonas reinhardtii

<400> SEQUENCE: 105

| | |
|---|---|
| atggccaaaa caataatctt aaatggcaat gaagtgcata cagataaaga tattactatc | 60 |
| cttgagctag caagagaaaa taatgtagat atcccaacac tctgcttttt aaaggattgt | 120 |
| ggcaattttg gaaatgcgg agtctgtatg gtagaggtag aaggcaaggg ctttagagct | 180 |
| gcttgtgttg ccaaagttga agatggaatg gtaataaaca cagaatccga tgaagtaaaa | 240 |
| gaacgaatca aaaaagagt ttcaatgctt cttgataagc atgaatttaa atgtggacaa | 300 |
| tgttctagaa gagaaaattg tgaattcctt aaacttgtaa taaagacaaa agcaaaagct | 360 |
| tcaaaaccat ttttaccaga agataaggat gctctagttg ataatagaag taaggctatt | 420 |
| gtaattgaca gatcaaaatg tgtgctatgc ggaagatgtg aagcagcatg taaacaaag | 480 |
| acaggtacag gagctatttc aatttgtaag agtgaatcag gaagaatagt gcaagcaaca | 540 |
| ggcggaaagt gctttgatga tacaaattgt ttattatgtg gacaatgcgt tgcagcatgt | 600 |

```
ccagtaggag ctttaactga aaaaacacac gttgatagag ttaaagaagc attagaagat      660
cctaataagc atgtcattgt tgcaatggct ccatcagtaa gaactgctat gggcgaatta      720
ttcaaaatgg gatatggaaa agatgtaaca ggaaaactat atactgcact tagaatgtta      780
ggctttgata aagtatttga tataaacttt ggtgcagata tgactataat ggaagaagct      840
actgaacttt taggcagagt taaaaataat ggcccattcc ctatgtttac atcttgctgt      900
cctgcatggg taagattagc tcaaaattat catcctgaat tattagataa tctttcatca      960
gcaaaatcac cacaacaaat atttggtact gcatcaaaaa cttactatcc ttcaatttca     1020
ggaatagctc cagaagatgt ttatacagtt actatcatgc cttgtaatga taaaaaatat     1080
gaagcagata ttcctttcat ggaaactaac agcttaagag atattgatgc atccttaact     1140
acaagagagc ttgcaaaaat gattaaagat gcaaaaatta aatttgcaga tcttgaagat     1200
ggtgaagttg atcctgctat gggtacttac agtggtgctg gagctatctt tggtgcaacc     1260
ggtggcgtta tggaagctgc aataagatca gctaaagact ttgctgaaaa taagaaactt     1320
gaaaatgttg attacactga gtaagagagc tttaaaggca taaaagaagc ggaagttgaa     1380
attgctggaa ataaactaaa cgttgctgtt ataaatggtg cttctaactt cttcgagttt     1440
atgaaatctg gaaaaatgaa cgaaaaacaa tatcactttta tagaagtaat ggcttgccct     1500
ggtggatgta taaatggtgg aggtcaacct cacgtaaatg ctcttgatag agaaaatgtt     1560
gattacagaa aactaagagc atcagtatta tacaaccaag ataaaaatgt tctttcaaag     1620
agaaagtcac atgataatcc agctattatt aaaatgtatg atagctactt tggaaaacca     1680
ggtgaaggac ttgctcacaa attactacac gtaaaataca caaagataa aaatgtttca      1740 aaacatgaa                                                             1749
```

<210> SEQ ID NO 106
<211> LENGTH: 1749
<212> TYPE: DNA
<213> ORGANISM: Chlamydomonas reinhardtii

<400> SEQUENCE: 106

```
atggccaaaa caataatctt aaatggcaat gaagtgcata cagataaaga tattactatc       60
cttgagctag caagagaaaa taatgtagat atcccaacac tctgcttttt aaaggattgt      120
ggcaattttg gaaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaaagagt ttcaatgctt cttgataagc atgaatttaa atgtggacaa      300
tgttctagaa gagaaaattg tgaattcctt aaacttgtaa taaagacaaa agcaaaagct      360
tcaaaaccat ttttaccaga agataaggat gctctagttg ataatagaag taaggctatt      420
gtaattgaca gatcaaaatg tgtactatgc ggtagatgcg tagctgcatg taaacagcac      480
acaagcactt gctcaattca atttattaaa aaagatggac aaagggctgt tggaactgtt      540
gatgatgttt gtcttgatga ctcaacatgc ttattatgcg gtcagtgtgt aatcgcttgt      600
cctgttgctg ctttaaaaga aaatcccat atagaaaaag ttcaagaagc tcttaatgac      660
cctaaaaaac atgtaatagt tgctatggca ccatcaatca gaacttctat gggagagtta      720
tttaaattag ctatggggt tgatgtaact ggaaaattat atgcttcaat gagagcatta      780
ggatttgata aggtatttga tattaacttt ggggctgata tgacaataat ggaagaagca      840
acagagttta ttgaaagagt taaaaataat ggcccattcc ctatgtttac atcttgctgt      900
```

| | |
|---|---|
| cctgcatggg taagattagc tcaaaattat catcctgaat tattagataa tctttcatca | 960 |
| gcaaaatcac cacaacaaat atttggtact gcatcaaaaa cttactatcc ttcaatttca | 1020 |
| ggaatagctc cagaagatgt ttatacagtt actatcatgc cttgtaatga taaaaaatat | 1080 |
| gaagcagata ttcctttcat ggaaactaac agcttaagag atattgatgc atccttaact | 1140 |
| acaagagagc ttgcaaaaat gattaaagat gcaaaaatta aatttgcaga tcttgaagat | 1200 |
| ggtgaagttg atcctgctat gggtacttac agtggtgctg agctatcttt ggtgcaacc | 1260 |
| ggtggcgtta tggaagctgc aataagatca gctaaagact ttgctgaaaa taagaacttt | 1320 |
| gaaaatgttg attacactga agtaagaggc tttaaaggca taaagaagc ggaagttgaa | 1380 |
| attgctggaa ataaactaaa cgttgctgtt ataaatggtg cttctaactt cttcgagttt | 1440 |
| atgaaatctg gaaaatgaa cgaaaaacaa tatcactttta tagaagtaat ggcttgccct | 1500 |
| ggtggatgta taatggtgg aggtcaacct cacgtaaatg ctcttgatag agaaaatgtt | 1560 |
| gattacagaa aactaagagc atcagtatta tacaaccaag ataaaaatgt tctttcaaag | 1620 |
| agaaagtcac atgataatcc agctattatt aaaatgtatg atagctactt tggaaaacca | 1680 |
| ggtgaaggac ttgctcacaa attactacac gtaaaataca caaagataaa aatgttttca | 1740 |
| aaacatgaa | 1749 |

<210> SEQ ID NO 107
<211> LENGTH: 1749
<212> TYPE: DNA
<213> ORGANISM: Chlamydomonas reinhardtii

<400> SEQUENCE: 107

| | |
|---|---|
| atggccaaaa caataatctt aaatggcaat gaagtgcata cagataaaga tattactatc | 60 |
| cttgagctag caagagaaaa taatgtagat atcccaacac tctgcttttt aaaggattgt | 120 |
| ggcaattttg gaaaatgcgg agtctgtatg gtagaggtag aaggcaaggg ctttagagct | 180 |
| gcttgtgttg ccaaagttga agatggaatg gtaataaaca cagaatccga tgaagtaaaa | 240 |
| gaacgaatca aaaaagagt ttcaatgctt cttgataagc atgaatttaa atgtggacaa | 300 |
| tgttctagaa gagaaaattg tgaattcctt aaacttgtaa taaagacaaa agcaaaagct | 360 |
| tcaaaaccat ttttaccaga agataaggat gctctagttg ataatagaag taaggctatt | 420 |
| gtaattgaca gatcaaaatg tgtactatgc ggtagatgcg tagctgcatg taaacagcac | 480 |
| acaagcactt gctcaattca atttattaaa aaagatggac aaagggctgt tggaactgtt | 540 |
| gatgatgttt gtcttgatga ctcaacatgc ttattatgcg gtcagtgtgt aatcgcttgt | 600 |
| cctgttgctg ctttaaaaga aaaatcccat atagaaaaag ttcaagaagc tcttaatgac | 660 |
| cctaaaaaac atgtcattgt tgcaatggct ccatcagtaa gaactgctat gggcgaatta | 720 |
| ttcaaaatgg gatatggaaa agatgtaaca ggaaaactat atactgcact tagaatgtta | 780 |
| ggctttgata agtatttga tataaacttt ggtgcagata tgactataat ggaagaagct | 840 |
| actgaacttt taggcagagt taaaaataat ggaccattcc caatgtttac ttcatgttgt | 900 |
| ccggcatggg ttagacaagt ggaaaattat tacccagaat ttttagaaaa cttatcatca | 960 |
| gctaaatcac cacaacaaat atttggtgca gcaagcaaaa catactatcc tcaaatatca | 1020 |
| ggtataagtg ctaaagatgt atttactgtt acaataatgc cttgtacagc aaagaaattt | 1080 |
| gaggctgata gagaagaaat gtataatgag ggaattaaaa atatagatgc agtacttact | 1140 |
| acaagagaat tagcaaaaat gattaaagat gcaaagatta ttttgctaa tttgaagac | 1200 |
| gaacaagctg atccagcaat gggagaatac actggggctg gagttatatt cggagctaca | 1260 |

```
ggtggagtta tggaagcagc acttagaact gctaaggatt tcgttgaaga taaagattta   1320
actgatatag aatatacaca aataagagga ttacaaggaa taaagaggc tacagtagaa     1380 attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggtcaacct cacgtaaatg ctcttgatag agaaaatgtt    1560
gattacagaa aactaagagc atcagtatta tacaaccaag ataaaaatgt tctttcaaag    1620
agaaagtcac atgataatcc agctattatt aaaatgtatg atagctactt tggaaaacca    1680
ggtgaaggac ttgctcacaa attactacac gtaaaataca caaagataaa aatgtttca     1740 aaacatgaa                                                           1749

<210> SEQ ID NO 108
<211> LENGTH: 1722
<212> TYPE: DNA
<213> ORGANISM: Chlamydomonas reinhardtii

<400> SEQUENCE: 108
atggccaaaa caataatctt aaatggcaat gaagtgcata cagataaaga tattactatc    60
cttgagctag caagagaaaa taatgtagat atcccaacac tctgcttttt aaaggattgt    120
ggcaattttg gaaatgcgg agtctgtatg gtagaggtag aaggcaaggg ctttagagct     180
gcttgtgttg ccaaagttga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780 ggcttttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat tttttagaaaa cttatcatca    960 gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gaagaaat gtataatgag ggaattaaaa atatagatgc agtacttact     1140
acaagagaat tagcaaaat gattaaagat gcaagattat ttttgctaa tttgaagac       1200 gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataagagga ttacaaggaa taaagaagc ggaagttgaa     1380 attgctggaa ataaactaaa cgttgctgtt ataaatggtg cttctaactt cttcgagttt   1440
atgaaatctg gaaaatgaa cgaaaaacaa tatcactttta tagaagtaat ggcttgccct    1500
ggtggatgta taaatggtgg aggacaacca cacgtaagtg caaggaaag agaaaaagta     1560
```

```
gatgttagaa ctgtaagagc atctgtttta tataaccaag ataaaaattt agagaagaga      1620
aaatcacata aaaatacagc attattaaat atgtactatg attatatggg agctccagga      1680
caaggaaaag ctcatgaatt attacactta aaatacaata aa                         1722

<210> SEQ ID NO 109
<211> LENGTH: 1722
<212> TYPE: DNA
<213> ORGANISM: Chlamydomonas reinhardtii

<400> SEQUENCE: 109
atggccaaaa caataatctt aaatggcaat gaagtgcata cagataaaga tattactatc        60
cttgagctag caagagaaaa taatgtagat atcccaacac tctgcttttt aaaggattgt       120
ggcaattttg aaaatgcgg agtctgtatg gtagaggtag aaggcaaggg ctttagagct        180
gcttgtgttg ccaaagttga agatggaatg gtaataaaca cagaatccga tgaagtaaaa       240
gaacgaatca aaaaagagt ttcaatgctt cttgataagc atgaatttaa atgtggacaa        300
tgttctagaa gagaaaattg tgaattcctt aaacttgtaa taaagacaaa agcaaaagct       360
tcaaaaccat ttttaccaga agataaggat gctctagttg ataatagaag taaggctatt      420
gtaattgaca gatcaaaatg tgtactatgc ggtagatgcg tagctgcatg taaacagcac      480
acaagcactt gctcaattca atttattaaa aaagatggac aaagggctgt tggaactgtt      540
gatgatgttt gtcttgatga ctcaacatgc ttattatgcg gtcagtgtgt aatcgcttgt      600
cctgttgctg cttttaaaga aaaatcccat atagaaaaag ttcaagaagc tcttaatgac      660
cctaaaaaac atgtcattgt tgcaatggct ccatcagtaa gaactgctat gggcgaatta      720
ttcaaaatgg gatatggaaa agatgtaaca ggaaaactat atactgcact tagaatgtta      780
ggctttgata agtatttga tataaacttt ggtgcagata tgactataat ggaagaagct      840
actgaacttt taggcagagt taaaaataat ggaccattcc caatgtttac ttcatgttgt      900
ccggcatggg ttagacaagt ggaaaattat tacccagaat ttttagaaaa cttatcatca      960
gctaaatcac cacaacaaat atttggtgca gcaagcaaaa catactatcc tcaaatatca     1020
ggtataagtg ctaagatgt atttactgtt acaataatgc cttgtacagc aaagaaattt     1080
gaggctgata gagaagaaat gtataatgag ggaattaaaa atatagatgc agtacttact     1140
acaagagagc ttgcaaaaat gattaaagat gcaaaaatta aatttgcaga tcttgaagat     1200
ggtgaagttg atcctgctat gggtacttac agtggtgctg gagctatctt tggtgcaacc     1260
ggtggcgtta tggaagctgc aataagatca gctaaagact ttgctgaaaa taaagaactt     1320
gaaaatgttg attacactga agtaagaggc tttaaaggca taaagaggc tacagtagaa     1380 attggtggag aaaattataa cgtagctgta attaatggtg cagcaaactt agctgaattc     1440
atgaatagcg gtaaaatcct tgaaaagaac tatcatttta ttgaagtaat ggcttgccca     1500
ggcggatgtg taaatggtgg aggacaacca cacgtaagtg caaggaaaag agaaaaagta     1560
gatgttagaa ctgtaagagc atctgtttta tataaccaag ataaaaattt agagaagaga     1620
aaatcacata aaaatacagc attattaaat atgtactatg attatatggg agctccagga     1680
caaggaaaag ctcatgaatt attacactta aaatacaata aa                       1722

<210> SEQ ID NO 110
<211> LENGTH: 1722
<212> TYPE: DNA
<213> ORGANISM: Chlamydomonas reinhardtii

<400> SEQUENCE: 110
```

```
atggccaaaa caataatctt aaatggcaat gaagtgcata cagataaaga tattactatc      60
cttgagctag caagagaaaa taatgtagat atcccaacac tctgctttttt aaaggattgt    120 ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa     300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg cttttaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaagatgt atttactgtt acaataatgc cttgtacagc aaagaaattt    1080
gaggctgata gagaagaaat gtataatgag ggaattaaaa atatagatgc agtacttact   1140
acaagagaat tagcaaaaat gattaaagat gcaagatta atttgctaa tttagaagac    1200 gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataagagga ttacaaggaa taaaagaggc tacagtagaa   1380
attggtggag aaaattataa cgtagctgta attaatggtg cagcaaactt agctgaattc   1440
atgaatagcg gtaaaatcct tgaaaagaac tatcatttta ttgaagtaat ggcttgccca   1500
ggcggatgtg taaatggtgg aggacaacca cacgtaagtg caaaggaaag agaaaaagta   1560
gatgttagaa ctgtaagagc atctgttta tataaccaag ataaaaattt agagaagaga    1620
aaatcacata aaaatacagc attattaaat atgtactatg attatatggg agctccagga   1680
caaggaaaag ctcatgaatt attacactta aaatacaata aa                      1722
```

<210> SEQ ID NO 111
<211> LENGTH: 1749
<212> TYPE: DNA
<213> ORGANISM: Chlamydomonas reinhardtii

<400> SEQUENCE: 111

```
atggccaaaa caataatctt aaatggcaat gaagtgcata cagataaaga tattactatc      60
cttgagctag caagagaaaa taatgtagat atcccaacac tctgctttttt aaaggattgt    120 ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa     300
tgttctagaa gagaaaattg tgaattcctt aaacttgtaa taaagacaaa agcaaaagct    360
```

```
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg cttttaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtaaatgag ggaattaaaa atatagatgc agtacttact   1140
acaagagaat tagcaaaaat gattaaagat gcaaagatta attttgctaa tttagaagac   1200
gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataagagga ttacaaggaa taaagaagc ggaagttgaa   1380 attgctggaa ataaactaaa cgttgctgtt ataaatggtg cttctaactt cttcgagttt   1440
atgaaatctg gaaaaatgaa cgaaaaacaa tatcacttta tagaagtaat ggcttgccct   1500
ggtggatgta taatggtgg aggtcaacct cacgtaaatg ctcttgatag agaaaatgtt   1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataa aaatgtttca   1740 aaacatgaa                                                           1749

<210> SEQ ID NO 112
<211> LENGTH: 1749
<212> TYPE: DNA
<213> ORGANISM: Chlamydomonas reinhardtii

<400> SEQUENCE: 112
atggccaaaa caataatctt aaatggcaat gaagtgcata cagataaaga tattactatc     60
cttgagctag caagagaaaa taatgtagat atcccaacac tctgcttttt aaaggattgt    120 ggcaatttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg cttttaaaga aaaatcccat atagaaaaag ttcaagaagc tcttaatgac    660
cctaaaaaac atgtcattgt tgcaatggct ccatcagtaa gaactgctat gggcgaatta    720
```

```
ttcaaaatgg gatatggaaa agatgtaaca ggaaaactat atactgcact tagaatgtta      780
ggctttgata aagtatttga tataaacttt ggtgcagata tgactataat ggaagaagct      840
actgaacttt taggcagagt taaaaataat ggaccattcc caatgtttac ttcatgttgt      900
ccggcatggg ttagacaagt ggaaaattat tacccagaat ttttagaaaa cttatcatca      960
gctaaatcac cacaacaaat atttggtgca gcaagcaaaa catactatcc tcaaatatca     1020
ggtataagtg ctaagatgt atttactgtt acaataatgc cttgtacagc aaagaaattt      1080
gaggctgata gagaagaaat gtataatgag ggaattaaaa atatagatgc agtacttact     1140
acaagagagc ttgcaaaaat gattaaagat gcaaaaatta aatttgcaga tcttgaagat     1200
ggtgaagttg atcctgctat gggtacttac agtggtgctg agctatctt tggtgcaacc      1260 ggtggcgtta tggaagctgc aataagatca gctaaagact ttgctgaaaa taagaacttt      1320
gaaaatgttg attacactga agtaagaggc tttaaaggca taaagaggc tacagtagaa      1380 attggtggag aaaattataa cgtagctgta attaatggtg cagcaaactt agctgaattc     1440
atgaatagcg gtaaaatcct tgaaaagaac tatcatttta ttgaagtaat ggcttgccca     1500
ggcggatgtg taaatggtgg aggtcaacct cacgtaaatg ctcttgatag agaaaatgtt     1560
gattacagaa aactaagagc atcagtatta tacaaccaag ataaaaatgt tctttcaaag     1620
agaaagtcac atgataatcc agctattatt aaaatgtatg atagcactt tggaaaacca      1680 ggtgaaggac ttgctcacaa attactacac gtaaaataca caaagataa aatgtttca      1740 aaacatgaa                                                             1749

<210> SEQ ID NO 113
<211> LENGTH: 1749
<212> TYPE: DNA
<213> ORGANISM: Chlamydomonas reinhardtii

<400> SEQUENCE: 113
atggccaaaa caataatctt aaatggcaat gaagtgcata cagataaaga tattactatc       60
cttgagctag caagagaaaa taatgtagat atcccaacac tctgcttttt aaaggattgt      120
ggcaattttg gaaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaaagagt ttcaatgctt cttgataagc atgaatttaa atgtggacaa      300
tgttctagaa gagaaaattg tgaattcctt aaacttgtaa taaagacaaa agcaaaagct      360
tcaaaaccat ttttaccaga agataaggat gctctagttg ataatagaag taaggctatt      420
gtaattgaca gatcaaaatg tgtactatgc ggtagatgcg tagctgcatg taaacagcac      480
acaagcactt gctcaattca atttattaaa aaagatggac aaagggctgt tggaactgtt      540
gatgatgttt gtcttgatga ctcaacatgc ttattatgcg gtcagtgtgt aatcgcttgt      600
cctgttgctg ctttaaaaga aaaatcccat atagaaaaag ttcaagaagc tcttaatgac      660
cctaaaaaac atgtcattgt tgcaatggct ccatcagtaa gaactgctat gggcgaatta      720
ttcaaaatgg gatatggaaa agatgtaaca ggaaaactat atactgcact tagaatgtta      780
ggctttgata aagtatttga tataaacttt ggtgcagata tgactataat ggaagaagct      840
actgaacttt taggcagagt taaaaataat ggcccattcc ctatgtttac atcttgctgt      900
cctgcatggg taagattagc tcaaaattat catcctgaat tattagataa tctttcatca     960
gcaaaatcac cacaacaaat atttggtact gcatcaaaaa cttactatcc ttcaatttca      1020
```

```
ggaatagctc cagaagatgt ttatacagtt actatcatgc cttgtaatga taaaaaatat    1080
gaagcagata ttcctttcat ggaaactaac agcttaagag atattgatgc atccttaact    1140
acaagagaat tagcaaaaat gattaaagat gcaaagatta attttgctaa tttagaagac    1200
gaacaagctg atccagcaat gggagaatac actggggctg agttatatt cggagctaca     1260 ggtggagtta tggaagcagc acttagaact gctaaggatt tcgttgaaga taaagattta    1320
actgatatag aatatacaca aataagagga ttacaaggaa taaagaggc tacagtagaa     1380 attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggtcaacct cacgtaaatg ctcttgatag agaaaatgtt    1560
gattacagaa aactaagagc atcagtatta taaccaag ataaaaatgt tctttcaaag      1620
agaaagtcac atgataatcc agctattatt aaaatgtatg atagctactt tggaaaacca    1680
ggtgaaggac ttgctcacaa attactacac gtaaaataca caaagataa aaatgtttca     1740 aaacatgaa                                                            1749

<210> SEQ ID NO 114
<211> LENGTH: 1722
<212> TYPE: DNA
<213> ORGANISM: Chlamydomonas reinhardtii

<400> SEQUENCE: 114
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg aaaatgcgg agtctgtatg gtagaggtag aaggcaaggg ctttagagct     180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa     300
tgttctagaa gagaaaattg tgaattcctt aaacttgtaa taaagacaaa agcaaaagct    360
tcaaaaccat ttttaccaga gataaggat gctctagttg ataatagaag taggctatt      420 gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttgga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt    1080
gaggctgata gaagagaaat gtataatgag ggaattaaaa atatagatgc agtacttact   1140
acaagagagc ttgcaaaaat gattaaagat gcaaaaatta atttgcaga tcttgaagat   1200 ggtgaagtta tcctgctat gggtacttac agtggtgctg agctatctt tggtgcaacc    1260 ggtggcgtta tggaagctgc aataagatca gctaaagact ttgctgaaaa taagaacttg   1320
gaaaatgttg attacactga agtaagaggc tttaaaggca taaaagaagc ggaagttgaa   1380
```

-continued

```
attgctggaa ataaactaaa cgttgctgtt ataaatggtg cttctaactt cttcgagttt    1440
atgaaatctg gaaaatgaa cgaaaaacaa tatcactttta tagaagtaat ggcttgccct    1500
ggtggatgta taaatggtgg aggacaacca cacgtaagtg caaggaaag agaaaaagta     1560 gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attacactta aaatacaata aa                       1722
```

<210> SEQ ID NO 115
<211> LENGTH: 1722
<212> TYPE: DNA
<213> ORGANISM: Chlamydomonas reinhardtii

<400> SEQUENCE: 115

```
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa     300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct    840
actgaacttt taggcagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
acaagagaat tagcaaaaat gattaaagat gcaaagatta ttttgctaa tttagaagac    1200 gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca ataagagga ttacaaggaa taaagaagc ggaagttgaa      1380 attgctggaa ataaactaaa cgttgctgtt ataaatggtg cttctaactt cttcgagttt   1440
atgaaatctg gaaaatgaa cgaaaaacaa tatcactttta tagaagtaat ggcttgccct   1500
ggtggatgta taaatggtgg aggacaacca cacgtaagtg caaggaaag agaaaaagta    1560 gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722
```

<210> SEQ ID NO 116
<211> LENGTH: 1722
<212> TYPE: DNA
<213> ORGANISM: Chlamydomonas reinhardtii

<400> SEQUENCE: 116

| | | | | | |
|---|---|---|---|---|---|
| atggccaaaa | caataatctt | aaatggcaat | gaagtgcata | cagataaaga | tattactatc | 60 |
| cttgagctag | caagagaaaa | taatgtagat | atcccaacac | tctgctttt | aaaggattgt | 120 |
| ggcaattttg | gaaaatgcgg | agtctgtatg | gtagaggtag | aaggcaaggg | ctttagagct | 180 |
| gcttgtgttg | ccaaagttga | agatggaatg | gtaataaaca | cagaatccga | tgaagtaaaa | 240 |
| gaacgaatca | aaaaagagt | ttcaatgctt | cttgataagc | atgaatttaa | atgtggacaa | 300 |
| tgttctagaa | gagaaaattg | tgaattcctt | aaacttgtaa | taaagacaaa | agcaaaagct | 360 |
| tcaaaaccat | ttttaccaga | agataaggat | gctctagttg | ataatagaag | taaggctatt | 420 |
| gtaattgaca | gatcaaaatg | tgtactatgc | ggtagatgcg | tagctgcatg | taaacagcac | 480 |
| acaagcactt | gctcaattca | atttattaaa | aaagatggac | aaagggctgt | tggaactgtt | 540 |
| gatgatgttt | gtcttgatga | ctcaacatgc | ttattatgcg | gtcagtgtgt | aatcgcttgt | 600 |
| cctgttgctg | ctttaaaaga | aaaatcccat | atagaaaaag | ttcaagaagc | tcttaatgac | 660 |
| cctaaaaaac | atgtcattgt | tgcaatggct | ccatcagtaa | gaactgctat | gggcgaatta | 720 |
| ttcaaaatgg | gatatggaaa | agatgtaaca | ggaaaactat | atactgcact | tagaatgtta | 780 |
| ggctttgata | agtatttga | tataaacttt | ggtgcagata | tgactataat | ggaagaagct | 840 |
| actgaacttt | taggcagagt | taaaaataat | ggcccattcc | ctatgtttac | atcttgctgt | 900 |
| cctgcatggg | taagattagc | tcaaaattat | catcctgaat | tattagataa | tctttcatca | 960 |
| gcaaaatcac | cacaacaaat | atttggtact | gcatcaaaaa | cttactatcc | ttcaatttca | 1020 |
| ggaatagctc | cagaagatgt | ttatacagtt | actatcatgc | cttgtaatga | taaaaaatat | 1080 |
| gaagcagata | ttcctttcat | ggaaactaac | agcttaagag | atattgatgc | atccttaact | 1140 |
| acaagagagc | ttgcaaaaat | gattaaagat | gcaaaaatta | aatttgcaga | tcttgaagat | 1200 |
| ggtgaagtta | tcctgctat | gggtacttac | agtggtgctg | gagctatctt | tggtgcaacc | 1260 |
| ggtggcgtta | tggaagctgc | aataagatca | gctaaagact | ttgctgaaaa | taagaacctt | 1320 |
| gaaaatgttg | attacactga | agtaagaggc | tttaaaggca | taaagagggc | tacagtagaa | 1380 |
| attggtggag | aaaattataa | cgtagctgta | attaatggtg | cagcaaactt | agctgaattc | 1440 |
| atgaatagcg | gtaaaatcct | tgaaaagaac | tatcattta | ttgaagtaat | ggcttgccca | 1500 |
| ggcggatgtg | taaatggtgg | aggacaacca | cacgtaagtg | caaggaaag | agaaaaagta | 1560 |
| gatgttagaa | ctgtaagagc | atctgtttta | tataaccaag | ataaaaattt | agagaagaga | 1620 |
| aaatcacata | aaaatacagc | attattaaat | atgtactatg | attatatggg | agctccagga | 1680 |
| caaggaaaag | ctcatgaatt | attacactta | aaatacaata | aa | | 1722 |

<210> SEQ ID NO 117
<211> LENGTH: 1749
<212> TYPE: DNA
<213> ORGANISM: Chlamydomonas reinhardtii

<400> SEQUENCE: 117

| | | | | | |
|---|---|---|---|---|---|
| atggccaaaa | caataatctt | aaatggcaat | gaagtgcata | cagataaaga | tattactatc | 60 |
| cttgagctag | caagagaaaa | taatgtagat | atcccaacac | tctgctttt | aaaggattgt | 120 |
| ggcaattttg | gaaaatgcgg | agtctgtatg | gtagaggtag | aaggcaaggg | ctttagagct | 180 |

-continued

```
gcttgtgttg ccaaagttga agatggaatg gtaataaaca cagaatccga tgaagtaaaa        240
gaacgaatca aaaaaagagt ttcaatgctt cttgataagc atgaatttaa atgtggacaa        300
tgttctagaa gagaaaattg tgaattcctt aaacttgtaa taaagacaaa agcaaaagct        360
tcaaaaccat ttttaccaga agataaggat gctctagttg ataatagaag taaggctatt        420
gtaattgaca gatcaaaatg tgtactatgc ggtagatgcg tagctgcatg taaacagcac        480
acaagcactt gctcaattca atttattaaa aagatggac aaagggctgt tggaactgtt         540
gatgatgttt gtcttgatga ctcaacatgc ttattatgcg gtcagtgtgt aatcgcttgt        600
cctgttgctg ctttaaaaga aaaatcccat atagaaaaag ttcaagaagc tcttaatgac        660
cctaaaaaac atgtcattgt tgcaatggct ccatcagtaa gaactgctat gggcgaatta        720
ttcaaaatgg gatatggaaa agatgtaaca ggaaaactat atactgcact tagaatgtta        780
ggctttgata aagtatttga tataaacttt ggtgcagata tgactataat ggaagaagct        840
actgaacttt taggcagagt taaaaataat ggaccattcc caatgtttac ttcatgttgt        900
ccggcatggg ttagacaagt ggaaaattat tacccagaat ttttagaaaa cttatcatca        960
gctaaatcac cacaacaaat atttggtgca gcaagcaaaa catactatcc tcaaatatca        1020
ggtataagtg ctaaagatgt atttactgtt acaataatgc cttgtacagc aaagaaattt       1080
gaggctgata gagaagaaat gtataatgag ggaattaaaa atatagatgc agtacttact       1140
acaagagagc ttgcaaaaat gattaaagat gcaaaaatta aatttgcaga tcttgaagat       1200
ggtgaagttg atcctgctat gggtacttac agtggtgctg gagctatctt tggtgcaacc       1260
ggtggcgtta tggaagctgc aataagatca gctaaagact ttgctgaaaa taagaacttt       1320
gaaaatgttg attacactga gtaagaggc tttaaaggca taaagaagc ggaagttgaa         1380 attgctggaa ataaactaaa cgttgctgtt ataaatggtg cttctaactt cttcgagttt       1440
atgaaatctg gaaaaatgaa cgaaaaacaa tatcacttta tagaagtaat ggcttgccct       1500
ggtggatgta taaatggtgg aggtcaacct cacgtaaatg ctcttgatag agaaaatgtt       1560
gattacagaa aactaagagc atcagtatta taacaccaag ataaaaatgt tctttcaaag       1620
agaaagtcac atgataatcc agctattatt aaaatgtatg atagctactt tggaaaacca       1680
ggtgaaggac ttgctcacaa attactacac gtaaaataca caaaagataa aaatgtttca       1740
aaacatgaa                                                                1749
```

<210> SEQ ID NO 118
<211> LENGTH: 1749
<212> TYPE: DNA
<213> ORGANISM: Chlamydomonas reinhardtii

<400> SEQUENCE: 118

```
atggccaaaa caataatctt aaatggcaat gaagtgcata cagataaaga tattactatc        60
cttgagctag caagagaaaa taatgtagat atcccaacac tctgcttttt aaaggattgt       120
ggcaattttg gaaaatgcgg agtctgtatg gtagaggtag aaggcaaggg ctttagagct       180
gcttgtgttg ccaaagttga agatggaatg gtaataaaca cagaatccga tgaagtaaaa       240
gaacgaatca aaaaaagagt ttcaatgctt cttgataagc atgaatttaa atgtggacaa       300
tgttctagaa gagaaaattg tgaattcctt aaacttgtaa taaagacaaa agcaaaagct       360
tcaaaaccat ttttaccaga agataaggat gctctagttg ataatagaag taaggctatt       420
gtaattgaca gatcaaaatg tgtactatgc ggtagatgcg tagctgcatg taaacagcac       480
```

| | |
|---|---|
| acaagcactt gctcaattca atttattaaa aaagatggac aaagggctgt tggaactgtt | 540 |
| gatgatgttt gtcttgatga ctcaacatgc ttattatgcg gtcagtgtgt aatcgcttgt | 600 |
| cctgttgctg ctttaaaaga aaaatcccat atagaaaag ttcaagaagc tcttaatgac | 660 |
| cctaaaaaac atgtcattgt tgcaatggct ccatcagtaa gaactgctat gggcgaatta | 720 |
| ttcaaaatgg gatatggaaa agatgtaaca ggaaaactat atactgcact tagaatgtta | 780 |
| ggctttgata agtatttga tataaacttt ggtgcagata tgactataat ggaagaagct | 840 |
| actgaacttt taggcagagt taaaaataat ggcccattcc ctatgtttac atcttgctgt | 900 |
| cctgcatggg taagattagc tcaaaattat catcctgaat tattagataa tctttcatca | 960 |
| gcaaaatcac cacaacaaat atttggtact gcatcaaaaa cttactatcc ttcaatttca | 1020 |
| ggaatagctc cagaagatgt ttatacagtt actatcatgc cttgtaatga taaaaaatat | 1080 |
| gaagcagata ttcctttcat ggaaactaac agcttaagag atattgatgc atccttaact | 1140 |
| acaagagaat tagcaaaaat gattaaagat gcaaagatta ttttgctaa tttagaagac | 1200 |
| gaacaagctg atccagcaat gggagaatac actggggctg gagttatatt cggagctaca | 1260 |
| ggtggagtta tggaagcagc acttagaact gctaaggatt tcgttgaaga taaagattta | 1320 |
| actgatatag aatatacaca aataagagga ttacaaggaa taaagaagc ggaagttgaa | 1380 |
| attgctggaa ataaactaaa cgttgctgtt ataaatggtg cttctaactt cttcgagttt | 1440 |
| atgaaatctg gaaaatgaa cgaaaaacaa tatcactttta tagaagtaat ggcttgccct | 1500 |
| ggtggatgta taatggtgg aggtcaacct cacgtaaatg ctcttgatag agaaaatgtt | 1560 |
| gattacagaa aactaagagc atcagtatta taaccaag ataaaaatgt tctttcaaag | 1620 |
| agaaagtcac atgataatcc agctattatt aaaatgtatg atagctactt tggaaaacca | 1680 |
| ggtgaaggac ttgctcacaa attactacac gtaaaataca caaagataa aaatgtttca | 1740 |
| aaacatgaa | 1749 |

<210> SEQ ID NO 119
<211> LENGTH: 1749
<212> TYPE: DNA
<213> ORGANISM: Chlamydomonas reinhardtii

<400> SEQUENCE: 119

| | |
|---|---|
| atggccaaaa caataatctt aaatggcaat gaagtgcata cagataaaga tattactatc | 60 |
| cttgagctag caagagaaaa taatgtagat atcccaacac tctgcttttt aaaggattgt | 120 |
| ggcaattttg gaaaatgcgg agtctgtatg gtagaggtag aaggcaaggg ctttagagct | 180 |
| gcttgtgttg ccaaagttga agatggaatg gtaataaaca cagaatccga tgaagtaaaa | 240 |
| gaacgaatca aaaaaagagt ttcaatgctt cttgataagc atgaatttaa atgtggacaa | 300 |
| tgttctagaa gagaaaattg tgaattcctt aaacttgtaa taaagacaaa agcaaaagct | 360 |
| tcaaaaccat ttttaccaga agataaggat gctctagttg ataatagaag taaggctatt | 420 |
| gtaattgaca gatcaaaatg tgtactatgc ggtagatgcg tagctgcatg taaacagcac | 480 |
| acaagcactt gctcaattca atttattaaa aaagatggac aaagggctgt tggaactgtt | 540 |
| gatgatgttt gtcttgatga ctcaacatgc ttattatgcg gtcagtgtgt aatcgcttgt | 600 |
| cctgttgctg ctttaaaaga aaaatcccat atagaaaag ttcaagaagc tcttaatgac | 660 |
| cctaaaaaac atgtcattgt tgcaatggct ccatcagtaa gaactgctat gggcgaatta | 720 |
| ttcaaaatgg gatatggaaa agatgtaaca ggaaaactat atactgcact tagaatgtta | 780 |
| ggctttgata agtatttga tataaacttt ggtgcagata tgactataat ggaagaagct | 840 |

```
actgaacttt taggcagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
acaagagagc ttgcaaaaat gattaaagat gcaaaaatta aatttgcaga tcttgaagat   1200
ggtgaagttg atcctgctat gggtacttac agtggtgctg agctatctt tggtgcaacc   1260 ggtggcgtta tggaagctgc aataagatca gctaaagact ttgctgaaaa taagaacttt   1320
gaaaatgttg attacactga agtaagaggc tttaaaggca taaagaggc tacagtagaa   1380 attggtggag aaaattataa cgtagctgta attaatggtg cagcaaactt agctgaattc   1440
atgaatagcg gtaaaatcct tgaaaagaac tatcatttta ttgaagtaat ggcttgccca   1500
ggcggatgtg taaatggtgg aggtcaacct cacgtaaatg ctcttgatag agaaaatgtt   1560
gattacagaa aactaagagc atcagtatta taccaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataa aaatgttca   1740 aaacatgaa                                                          1749

<210> SEQ ID NO 120
<211> LENGTH: 1722
<212> TYPE: DNA
<213> ORGANISM: Chlamydomonas reinhardtii

<400> SEQUENCE: 120
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa    300
tgttctagaa gagaaaattg tgaattcctt aaacttgtaa taagacaaa agcaaaagct    360 tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct    840 actgaactt taggcagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
```

| acaagagagc ttgcaaaaat gattaaagat gcaaaaatta aatttgcaga tcttgaagat | 1200 |
| ggtgaagttg atcctgctat gggtacttac agtggtgctg agctatcttt tggtgcaacc | 1260 |
| ggtggcgtta tggaagctgc aataagatca gctaaagact ttgctgaaaa taagaacttt | 1320 |
| gaaaatgttg attacactga agtaagaggc tttaaaggca taaagaagc ggaagttgaa | 1380 |
| attgctggaa ataaactaaa cgttgctgtt ataaatggtg cttctaactt cttcgagttt | 1440 |
| atgaaatctg gaaaaatgaa cgaaaaacaa tatcactttta tagaagtaat ggcttgccct | 1500 |
| ggtggatgta taaatggtgg aggacaacca cacgtaagtg caaggaaag agaaaaagta | 1560 |
| gatgttagaa ctgtaagagc atctgtttta tataaccaag ataaaaattt agagaagaga | 1620 |
| aaatcacata aaaatacagc attattaaat atgtactatg attatatggg agctccagga | 1680 |
| caaggaaaag ctcatgaatt attacactta aaatacaata aa | 1722 |

<210> SEQ ID NO 121
<211> LENGTH: 1725
<212> TYPE: DNA
<213> ORGANISM: Chlamydomonas reinhardtii

<400> SEQUENCE: 121

| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg gaaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |
| caagaaagag ttaaaatgag agttgctact ttgcttgata agcatgaatt taaatgtgga | 300 |
| ccttgtccaa gaagagaaaa ttgcgaattt ttaaagttag ttataaaaac aaaagctaag | 360 |
| gctaacaagc cttttgtggt tgaagacaaa tcacaataca tagatattag aagtaaatca | 420 |
| attgtaatag acagaactaa gtgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag agctttaac tgaaaaaaca cacgttgata gagttaaaga agcattagaa | 660 |
| gatcctaata agcatgtcat tgttgcaatg gctccatcag taagaactgc tatgggcgaa | 720 |
| ttattccaaa tgggatatgg aaaagatgta acaggaaaac tatatactgc acttagaatg | 780 |
| ttaggctttg ataaagtatt tgatataaac tttggtgcag atatgactat aatggaagaa | 840 |
| gctactgaac ttttaggcag agttaaaaat aatggaccat tcccaatgtt tacttcatgt | 900 |
| tgtccggcat gggttagaca agtggaaaat tattacccag aattttttaga aaacttatca | 960 |
| tcagctaaat caccacaaca aatatttggt gcagcaagca aaacatacta tcctcaaata | 1020 |
| tcaggtataa gtgctaaaga tgtatttact gttacaataa tgccttgtac agcaaagaaa | 1080 |
| tttgaggctg atagaagaa atgtataat gagggaatta aaaatataga tgcagtactt | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatgaagc agcacttaga actgctaagg atttcgttga agataaagat | 1320 |
| ttaactgata tagaatatac acaaataaga ggattacaag aataaaaga ggctacagta | 1380 |
| gaaattggtg gagaaaatta taacgtagct gtaattaatg gtgcagcaaa cttagctgaa | 1440 |
| ttcatgaata gcggtaaaat ccttgaaaag aactatcatt ttattgaagt aatggcttgc | 1500 |
| ccaggcggat gtgtaaatgg tggaggacaa ccacacgtaa gtgcaaagga aagagaaaaa | 1560 |

```
gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                   1725
```

<210> SEQ ID NO 122
<211> LENGTH: 1725
<212> TYPE: DNA
<213> ORGANISM: Chlamydomonas reinhardtii

<400> SEQUENCE: 122

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg aaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaaatca   420 attgtaatag acagaactaa gtgtgtacta tgcggtagat gcgtagctgc atgtaaacag    480
cacacaagca cttgctcaat tcaatttatt aaaaaagatg acaaagggc tgttggaact    540 gttgatgatg tttgtcttga tgactcaaca tgcttattat gcggtcagtg tgtaatcgct    600
tgtcctgttg ctgctttaaa agaaaaatcc catatagaaa aagttcaaga agctcttaat    660
gaccctaaaa aacatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat cccaatgtt tacttcatgt     900 tgtccggcat gggttagaca agtggaaaat tattacccag aattttaga aaacttatca    960 tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagaagaa aatgtataat gagggaatta aaaatataga tgcagtactt   1140 actcaagag aattagcaaa aatgattaaa gatgcaaaga ttaattttgc taatttagaa    1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag aataaaaga ggctacagta   1380 gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggacaa ccacacgtaa gtgcaaagga aagagaaaaa   1560
gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                   1725
```

<210> SEQ ID NO 123
<211> LENGTH: 1725
<212> TYPE: DNA
<213> ORGANISM: Chlamydomonas reinhardtii

<400> SEQUENCE: 123

```
atggcaataa acatagtaat tgatgaaaaa actattcaag tacaggaaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca      180
cttgcatgta taacaaaagt tgaagaaggt atggtaataa acacagaatc cgatgaagta     240
aaagaacgaa tcaaaaaaag agtttcaatg cttcttgata agcatgaatt taaatgtgga     300
caatgttcta gaagagaaaa ttgtgaattc cttaaacttg taataaagac aaaagcaaaa     360
gcttcaaaac cattttttacc agaagataag gatgctctag ttgataatag aagtaaggct     420
attgtaattg acagatcaaa atgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggaccat cccaatgtt tacttcatgt     900
tgtccggcat gggttagaca agtggaaaat tattacccag aattttaga aaacttatca     960
tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagagaaga aatgtataat gagggaatta aaaatataga tgcagtactt    1140
actacaagag aattagcaaa aatgattaaa gatgcaaaga ttaattttgc taatttagaa    1200
gacgaacaag ctgatccagc aatgggagaa tacactgggg ctggagttat attcggagct    1260
acaggtggag ttatggaagc agcacttaga actgctaagg atttcgttga agataaagat    1320
ttaactgata tagaatatac acaaataaga ggattacaag aataaaaga ggctacagta     1380
gaaattggtg gagaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725
```

<210> SEQ ID NO 124
<211> LENGTH: 1722
<212> TYPE: DNA
<213> ORGANISM: Chlamydomonas reinhardtii

<400> SEQUENCE: 124

```
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtagtaaaaa caaactcaga aaaagtacaa     240
gaaagagtta aaatgagagt tgctactttg cttgataagc atgaatttaa atgtggacct     300
tgtccaagaa gagaaaattg cgaatttttaa agttagtta taaaaacaaa agctaaggct     360
```

```
aacaagcctt tgtgggttga agacaaatca caatacatag atattagaag taaatcaatt        420
gtaatagaca gaactaagtg tgtgctatgc ggaagatgtg aagcagcatg taaaacaaag        480
acaggtacag gagctatttc aatttgtaag agtgaatcag gaagaatagt gcaagcaaca        540
ggcggaaagt gctttgatga tacaaattgt ttattatgtg gacaatgcgt tgcagcatgt        600
ccagtaggag cttttaactga aaaaacacac gttgatagag ttaaagaagc attagaagat        660
cctaataagc atgtaatagt tgctatggca ccatcaatca gaacttctat gggagagtta        720
tttaaattag gctatggggt tgatgtaact ggaaaattat atgcttcaat gagagcatta        780
ggatttgata aggtatttga tattaacttt ggggctgata tgacaataat ggaagaagca        840
acagagttta ttgaaagagt taaaaataat ggaccattcc caatgtttac ttcatgttgt        900
ccggcatggg ttagacaagt ggaaaattat tacccagaat ttttagaaaa cttatcatca        960
gctaaatcac cacaacaaat atttggtgca gcaagcaaaa catactatcc tcaaatatca       1020
ggtataagtg ctaagatgt atttactgtt acaataatgc cttgtacagc aaagaaattt       1080
gaggctgata gagaagaaat gtataatgag ggaattaaaa atatagatgc agtacttact       1140
acaagagaat tagcaaaaat gattaaagat gcaaagatta attttgctaa tttagaagac       1200
gaacaagctg atccagcaat gggagaatac actggggctg gagttatatt cggagctaca       1260
ggtggagtta tggaagcagc acttagaact gctaaggatt tcgttgaaga taaagattta       1320
actgatatag aatatacaca aataagagga ttacaaggaa taaaagaggc tacagtagaa       1380
attggtggag aaaattataa cgtagctgta attaatggtg cagcaaactt agctgaattc       1440
atgaatagcg gtaaaatcct tgaaaagaac tatcatttta ttgaagtaat ggcttgccca       1500
ggcggatgtg taaatggtgg aggacaacca cacgtaagtg caaggaaag agaaaaagta       1560 gatgttagaa ctgtaagagc atctgtttta tataaccaag ataaaaattt agagaagaga       1620
aaatcacata aaaatacagc attattaaat atgtactatg attatatggg agctccagga       1680
caaggaaaag ctcatgaatt attacactta aaatacaata aa                          1722
```

<210> SEQ ID NO 125
<211> LENGTH: 1725
<212> TYPE: DNA
<213> ORGANISM: Chlamydomonas reinhardtii

<400> SEQUENCE: 125

```
atggcaataa acatagtaat tgatgaaaaa actattcaag tacaggaaaa tactacagtt         60
atacaagctg ccctagcaaa tgggatagat ataccaagtt tatgctatct taatgagtgt        120
ggtaatgttg gaaagtgtgg agtgtgtgca gtagaaatag aaggaaaaaa taacttagca        180
cttgcatgta taacaaaagt tgaagaaggt atggtagtaa aaacaaactc agaaaaagta        240
caagaaagag ttaaaatgag agttgctact ttgcttgata agcatgaatt taaatgtgga        300
ccttgtccaa gaagagaaaa ttgcgaattt ttaaagttag ttataaaaac aaaagctaag        360
gctaacaagc cttttgtggt tgaagacaaa tcacaataca tagatattag aagtaaatca        420
attgtaatag acagaactaa gtgtgtacta tgcggtagat gcgtagctgc atgtaaacag        480
cacacaagca cttgctcaat tcaattattat aaaaaagatg gacaagggc tgttggaact        540 gttgatgatg tttgtcttga tgactcaaca tgcttattat gcggtcagtg tgtaatcgct        600
tgtcctgttg ctgcttttaaa agaaaaatcc catatagaaa aagttcaaga agctcttaat        660
gaccctaaaa aacatgtcat tgttgcaatg gctccatcag taagaactgc tatgggcgaa        720
```

```
ttattcaaaa tgggatatgg aaaagatgta acaggaaaac tatatactgc acttagaatg      780
ttaggctttg ataaagtatt tgatataaac tttggtgcag atatgactat aatggaagaa      840
gctactgaac ttttaggcag agttaaaaat aatggaccat tcccaatgtt tacttcatgt      900
tgtccggcat gggttagaca agtggaaaat tattacccag aattttaga aaacttatca       960 tcagctaaat caccacaaca aatatttggt gcagcaagca aaacatacta tcctcaaata     1020
tcaggtataa gtgctaaaga tgtatttact gttacaataa tgccttgtac agcaaagaaa     1080
tttgaggctg atagagaaga aatgtataat gagggaatta aaaatataga tgcagtactt     1140
actacaagag aattagcaaa aatgattaaa gatgcaaaga ttaattttgc taatttagaa     1200
gacgaacaag ctgatccagc aatgggagaa tacactgggg ctggagttat attcggagct     1260
acaggtggag ttatggaagc agcacttaga actgctaagg atttcgttga agataaagat     1320
ttaactgata tagaatatac acaaataaga ggattacaag aataaaaga ggctacagta      1380 gaaattggtg gagaaaatta taacgtagct gtaattaatg gtgcagcaaa cttagctgaa     1440
ttcatgaata gcggtaaaat ccttgaaaag aactatcatt ttattgaagt aatggcttgc     1500
ccaggcggat gtgtaaatgg tggaggacaa ccacacgtaa gtgcaaagga aagagaaaaa     1560
gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725

<210> SEQ ID NO 126
<211> LENGTH: 1725
<212> TYPE: DNA
<213> ORGANISM: Chlamydomonas reinhardtii

<400> SEQUENCE: 126
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg gaaagtgtgg agtgtgtgca gtagaaatag aaggaaaaaa taacttagca      180
cttgcatgta taacaaaagt tgaagaaggt atggtaataa acacagaatc cgatgaagta      240
aaagaacgaa tcaaaaaaag agtttcaatg cttcttgata agcatgaatt taaatgtgga      300
caatgttcta agagagaaaa ttgtgaattc cttaaacttg taataaagac aaaagcaaaa      360
gcttcaaaac cattttttacc agaagataag gatgctctag ttgataatag aagtaaggct      420
attgtaattg acagatcaaa atgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgatacaaat tgtttattat gtggacaatg cgttgcagca      600
tgtccagtag gagctttaac tgaaaaaaca cacgttgata gagttaaaga agcattagaa      660
gatcctaata agcatgtcat tgttgcaatg gctccatcag taagaactgc tatgggcgaa      720
ttattcaaaa tgggatatgg aaaagatgta acaggaaaac tatatactgc acttagaatg      780
ttaggctttg ataaagtatt tgatataaac tttggtgcag atatgactat aatggaagaa      840
gctactgaac ttttaggcag agttaaaaat aatggaccat tcccaatgtt tacttcatgt      900
tgtccggcat gggttagaca agtggaaaat tattacccag aattttaga aaacttatca       960 tcagctaaat caccacaaca aatatttggt gcagcaagca aaacatacta tcctcaaata     1020
tcaggtataa gtgctaaaga tgtatttact gttacaataa tgccttgtac agcaaagaaa     1080
tttgaggctg atagagaaga aatgtataat gagggaatta aaaatataga tgcagtactt     1140
```

```
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag gaataaaaga ggctacagta   1380
gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggacaa ccacacgtaa gtgcaaagga agagaaaaa    1560 gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                   1725
```

<210> SEQ ID NO 127
<211> LENGTH: 1722
<212> TYPE: DNA
<213> ORGANISM: Chlamydomonas reinhardtii

<400> SEQUENCE: 127

```
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtagtaaaaa caaactcaga aaaagtacaa    240
gaaagagtta aaatgagagt tgctactttg cttgataagc atgaatttaa atgtggacct    300
tgtccaagaa gagaaaattg cgaattttta agttagttta aaaaacaaa agctaaggct    360 aacaagcctt ttgtggttga agacaaatca caatacatag atattagaag taaatcaatt    420
gtaatagaca gaactaagtg tgtgctatgc ggaagatgtg aagcagcatg taaaacaaag    480
acaggtacag gagctatttc aatttgtaag agtgaatcag gaagaatagt gcaagcaaca    540
ggcggaaagt gctttgatga tacaaattgt ttattatgtg gacaatgcgt tgcagcatgt    600
ccagtaggag ctttaactga aaaaacacac gttgatagag ttaaagaagc attagaagat    660
cctaataagc atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttgat tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagaat tagcaaaaat gattaaagat gcaagatta attttgctaa tttagaagac   1200
gaacaagctg atccagcaat gggagaatac actggggctg gagttatatt cggagctaca   1260
ggtggagtta tggaagcagc acttagaact gctaaggatt tcgttgaaga taagacttta   1320
actgatatag aatatacaca aataagagga ttacaaggaa taaagaggc tacagtagaa    1380 attggtggag aaaattataa cgtagctgta attaatggtg cagcaaactt agctgaattc   1440
atgaatagcg gtaaaatcct tgaaaagaac tatcatttta ttgaagtaat ggcttgccca   1500
```

```
ggcggatgtg taaatggtgg aggacaacca cacgtaagtg caaaggaaag agaaaaagta    1560
gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attacactta aaatacaata aa                      1722

<210> SEQ ID NO 128
<211> LENGTH: 1725
<212> TYPE: DNA
<213> ORGANISM: Chlamydomonas reinhardtii

<400> SEQUENCE: 128
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaagtgtgg agtgtgtgca gtagaaatag aaggaaaaaa taacttagca     180
cttgcatgta taacaaaagt tgaagaaggt atggtaataa acacagaatc cgatgaagta     240
aaagaacgaa tcaaaaaaag agtttcaatg cttcttgata agcatgaatt taaatgtgga     300
caatgttcta aagagaaaaa ttgtgaattc cttaaacttg taataaagac aaaagcaaaa     360
gcttcaaaac cattttttacc agaagataag gatgctctag ttgataatag aagtaaggct     420
attgtaattg acagatcaaa atgtgtacta tgcggtagat gcgtagctgc atgtaaacag     480
cacacaagca cttgctcaat tcaatttatt aaaaaagatg gacaagggc tgttggaact     540 gttgatgatg tttgtcttga tgactcaaca tgcttattat gcggtcagtg tgtaatcgct     600
tgtcctgttg ctgctttaaa agaaaaatcc catatagaaa aagttcaaga agctcttaat     660 gacccctaaaa aacatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggaccat tcccaatgtt tacttcatgt     900
tgtccggcat gggttagaca agtggaaaat tattcccag aatttttaga aaacttatca     960
tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagaagaa atgtataat gagggaatta aaaatataga tgcagtactt    1140
actacaagag aattagcaaa aatgattaaa gatgcaaaga ttaattttgc taatttagaa    1200
gacgaacaag ctgatccagc aatggggaga tacactgggg ctggagttat attcggagct    1260
acaggtggag ttatggaagc agcacttaga actgctaagg atttcgttga agataaagat    1320
ttaactgata tagaatatac acaaataaga ggattacaag gaataaaaga ggctacagta    1380
gaaattggtg gagaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggacaa ccacacgtaa gtgcaaagga agagaaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725

<210> SEQ ID NO 129
<211> LENGTH: 1722
<212> TYPE: DNA
<213> ORGANISM: Chlamydomonas reinhardtii
```

<400> SEQUENCE: 129

```
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtagtaaaaa caaactcaga aaaagtacaa     240
gaaagagtta aatgagagt tgctactttg cttgataagc atgaatttaa atgtggacct      300
tgtccaagaa gagaaaattg cgaattttta agttagtta taaaaacaaa agctaaggct      360
aacaagcctt ttgtggttga agacaaatca caatacatag atattagaag taaatcaatt     420
gtaatagaca gaactaagtg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg ctttaaaaga aaaatcccat atagaaaaag ttcaagaagc tcttaatgac     660
cctaaaaaac atgtaatagt tgctatggca ccatcaatca gaacttctat gggagagtta     720
tttaaattag gctatggggt tgatgtaact ggaaaattat atgcttcaat gagagcatta     780
ggatttgata aggtatttga tattaacttt ggggctgata tgacaataat ggaagaagca     840
acagagttta ttgaaagagt taaaaataat ggaccattcc caatgtttac ttcatgttgt     900
ccggcatggg ttagacaagt ggaaaattat acccagaat ttttagaaaa cttatcatca      960
gctaaatcac cacaacaaat atttggtgca gcaagcaaaa catactatcc tcaaatatca    1020
ggtataagtg ctaaagatgt atttactgtt acaataatgc cttgtacagc aaagaaattt    1080
gaggctgata gagaagaaat gtataatgag ggaattaaaa atatagatgc agtacttact    1140
acaagagaat tagcaaaaat gattaaagat gcaaagatta atttgctaa tttagaagac     1200
gaacaagctg atccagcaat gggagaatac actggggctg gagttatatt cggagctaca    1260
ggtggagtta tggaagcagc acttagaact gctaaggatt tcgttgaaga taaagattta    1320
actgatatag aatatacaca ataagaggaa ttcaaggaa taaaagaggc tacagtagaa     1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggacaacca cacgtaagtg caaggaaag agaaaaagta     1560
gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attcacactta aaatacaata aa                      1722
```

<210> SEQ ID NO 130
<211> LENGTH: 1722
<212> TYPE: DNA
<213> ORGANISM: Chlamydomonas reinhardtii

<400> SEQUENCE: 130

```
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaaagagt ttcaatgctt cttgataagc atgaatttaa atgtggacaa     300
```

```
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtgctatgc ggaagatgtg aagcagcatg taaaacaaag    480
acaggtacag gagctatttc aatttgtaag agtgaatcag gaagaatagt gcaagcaaca    540
ggcggaaagt gctttgatga tacaaattgt ttattatgtg gacaatgcgt tgcagcatgt    600
ccagtaggag cttaactga aaaaacacac gttgatagag ttaaagaagc attagaagat     660
cctaataagc atgtaatagt tgctatggca ccatcaatca gaacttctat gggagagtta    720
tttaaattag gctatggggt tgatgtaact ggaaaattat atgcttcaat gagagcatta    780
ggatttgata aggtatttga tattaacttt ggggctgata tgacaataat ggaagaagca    840
acagagttta ttgaaagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagaat tagcaaaaat gattaaagat gcaaagatta attttgctaa tttagaagac   1200
gaacaagctg atccagcaat gggagaatac actggggctg gagttatatt cggagctaca   1260
ggtggagtta tggaagcagc acttagaact gctaaggatt cgttgaaga taaagattta    1320 actgatatag aatatacaca aataagagga ttacaaggaa taaaagaggc tacagtagaa   1380
attggtggag aaaattataa cgtagctgta attaatggtg cagcaaactt agctgaattc   1440
atgaatagcg gtaaaatcct tgaaaagaac tatcatttta ttgaagtaat ggcttgccca   1500
ggcggatgtg taaatggtgg aggacaacca cacgtaagtg caaggaaag agaaaaagta     1560 gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722
```

<210> SEQ ID NO 131
<211> LENGTH: 1725
<212> TYPE: DNA
<213> ORGANISM: Chlamydomonas reinhardtii

<400> SEQUENCE: 131

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtaataa acacagaatc cgatgaagta    240
aaagaacgaa tcaaaaaaag agtttcaatg cttcttgata agcatgaatt taaatgtgga    300
caatgttcta gaagagaaaa ttgtgaattc cttaaacttg taataaagac aaaagcaaaa    360
gcttcaaaac cattttttacc agaagataag gatgctctag ttgataatag aagtaaggct    420
attgtaattg acagatcaaa atgtgtacta tgcggtagat gcgtagctgc atgtaaacag    480
cacacaagca cttgctcaat tcaattaatt aaaaagatga gacaaagggc tgttggaact    540
gttgatgatg tttgtcttga tgactcaaca tgcttattat gcggtcagtg tgtaatcgct    600
tgtcctgttg ctgctttaaa agaaaatcc catatagaaa aagttcaaga agctcttaat    660
gaccctaaaa aacatgtcat tgttgcaatg gctccatcag taagaactgc tatgggcgaa    720
```

```
ttattcaaaa tgggatatgg aaaagatgta acaggaaaac tatatactgc acttagaatg      780
ttaggctttg ataaagtatt tgatataaac tttggtgcag atatgactat aatggaagaa      840
gctactgaac ttttaggcag agttaaaaat aatggaccat tcccaatgtt tacttcatgt      900
tgtccggcat gggttagaca agtggaaaat tattacccag aattttttaga aaacttatca     960 tcagctaaat caccacaaca aatatttggt gcagcaagca aaacatacta tcctcaaata     1020
tcaggtataa gtgctaaaga tgtatttact gttacaataa tgccttgtac agcaaagaaa     1080
tttgaggctg atagagaaga aatgtataat gagggaatta aaaatataga tgcagtactt    1140
actacaagag aattagcaaa aatgattaaa gatgcaaaga ttaattttgc taatttagaa     1200
gacgaacaag ctgatccagc aatgggagaa tacactgggg ctggagttat attcggagct    1260
acaggtggag ttatggaagc agcacttaga actgctaagg atttcgttga agataaagat    1320
ttaactgata tagaatatac acaaataaga ggattacaag gaataaaaga ggctacagta    1380
gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggacaa ccacacgtaa gtgcaaagga agagaaaaa    1560 gtagatgtta gaactgtaag agcatctgtt ttatataacc aagataaaaa tttagagaag    1620
agaaaatcac ataaaaatac agcattatta aatatgtact atgattatat gggagctcca   1680
ggacaaggaa aagctcatga attattacac ttaaaataca ataaa                   1725

<210> SEQ ID NO 132
<211> LENGTH: 1722
<212> TYPE: DNA
<213> ORGANISM: Chlamydomonas reinhardtii

<400> SEQUENCE: 132
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtagtaaaaa caaactcaga aaagtacaa    240 gaaagagtta aaatgagagt tgctactttg cttgataagc atgaatttaa atgtggacct   300
tgtccaagaa gagaaaattg cgaatttta aagttagtta taaaaacaaa agctaaggct    360
aacaagcctt tgtggttga agacaaatca caatacatag atattagaag taaatcaatt    420
gtaatagaca gaactaagtg tgtactatgc ggtagatgcg tagctgcatg taaacagcac    480
acaagcactt gctcaattca atttattaaa aaagatggac aaaggctgt tggaactgtt   540 gatgatgttt gtcttgatga ctcaacatgc ttattatgcg gtcagtgtgt aatcgcttgt    600
cctgttgctg ctttaaaaga aaaatcccat atagaaaag ttcaagaagc tcttaatgac   660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct   840
actgaacttt taggcagagt taaaaataat ggaccattcc caatgtttac ttcatgttgt   900
ccggcatggg ttagacaagt ggaaaattat tacccagaat tttttagaaaa cttatcatca    960 gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
```

```
gaggctgata gagaagaaat gtataatgag ggaattaaaa atatagatgc agtacttact    1140
acaagagaat tagcaaaaat gattaaagat gcaaagatta attttgctaa tttagaagac    1200
gaacaagctg atccagcaat gggagaatac actggggctg agttatatt cggagctaca    1260 ggtggagtta tggaagcagc acttagaact gctaaggatt tcgttgaaga taaagattta    1320
actgatatag aatatacaca aataagagga ttacaaggaa taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggacaacca cacgtaagtg caaggaaag agaaaaagta    1560 gatgttagaa ctgtaagagc atctgttta taaccaag ataaaaattt agagaagaga    1620
aaatcacata aaaatacagc attattaaat atgtactatg attatatggg agctccagga    1680
caaggaaaag ctcatgaatt attacactta aaatacaata aa                       1722

<210> SEQ ID NO 133
<211> LENGTH: 1722
<212> TYPE: DNA
<213> ORGANISM: Chlamydomonas reinhardtii

<400> SEQUENCE: 133
atggccaaaa caataatctt aaatggcaat gaagtgcata cagataaaga tattactatc    60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtgctatgc ggaagatgtg aagcagcatg taaaacaaag    480
acaggtacag gagctatttc aatttgtaag agtgaatcag gaagaatagt gcaagcaaca    540
ggcggaaagt gctttgatga tacaaattgt ttattatgtg acaatgcgt tgcagcatgt    600 ccagtaggag ctttaactga aaaaacacac gttgatagag ttaaagaagc attagaagat    660
cctaataagc atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaagatgt attactgtt acaataatgc cttgtacagc aaagaaattt    1080
gaggctgata gagaagaaat gtataatgag ggaattaaaa atatagatgc agtacttact    1140
acaagagaat tagcaaaaat gattaaagat gcaaagatta attttgctaa tttagaagac    1200
gaacaagctg atccagcaat gggagaatac actggggctg agttatatt cggagctaca    1260 ggtggagtta tggaagcagc acttagaact gctaaggatt tcgttgaaga taaagattta    1320
actgatatag aatatacaca aataagagga ttacaaggaa taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
```

```
ggcggatgtg taaatggtgg aggacaacca cacgtaagtg caaaggaaag agaaaaagta   1560
gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722

<210> SEQ ID NO 134
<211> LENGTH: 1722
<212> TYPE: DNA
<213> ORGANISM: Chlamydomonas reinhardtii

<400> SEQUENCE: 134
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtaatagt tgctatggca ccatcaatca gaacttctat gggagagtta    720
tttaaattag gctatggggt tgatgtaact ggaaaattat atgcttcaat gagagcatta    780
ggatttgata ggtatttga tattaacttt ggggctgata tgacaataat ggaagaagca    840 acagagtttta ttgaaagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gaagagaaat gtataatgag ggaattaaaa atatagatgc agtacttact   1140
acaagagaat tagcaaaaat gattaaagat gcaaagatta atttttgctaa tttagaagac   1200 gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataaggagga ttacaaggaa taaagaggc tacagtagaa   1380 attggtggag aaaattataa cgtagctgta attaatggtg cagcaaactt agctgaattc   1440
atgaatagcg gtaaaatcct tgaaaagaac tatcattttt ttgaagtaat ggcttgccca   1500
ggcggatgtg taaatggtgg aggacaacca cacgtaagtg caaaggaaag agaaaaagta   1560
gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722

<210> SEQ ID NO 135
<211> LENGTH: 1752
<212> TYPE: DNA
```

<213> ORGANISM: Chlamydomonas reinhardtii

<400> SEQUENCE: 135

| | |
|---|---|
| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg gaaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |
| caagaaagag ttaaaatgag agttgctact ttgcttgata agcatgaatt taaatgtgga | 300 |
| ccttgtccaa gaagagaaaa ttgcgaattt ttaaagttag ttataaaaac aaaagctaag | 360 |
| gctaacaagc ttttgtggt tgaagacaaa tcacaataca tagatattag aagtaaatca | 420 |
| attgtaatag acagaactaa gtgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag gagctttaac tgaaaaaaca cacgttgata gagttaaaga agcattagaa | 660 |
| gatcctaata agcatgtaat agttgctatg gcaccatcaa tcagaacttc tatgggagag | 720 |
| ttatttaaat taggctatgg ggttgatgta actggaaaat tatatgcttc aatgagagca | 780 |
| ttaggatttg ataaggtatt tgatattaac tttggggctg atatgacaat aatggaagaa | 840 |
| gcaacagagt ttattgaaag agttaaaaat aatggaccat tcccaatgtt tacttcatgt | 900 |
| tgtccggcat gggttagaca agtggaaaat tattacccag aattttagaa aaacttatca | 960 |
| tcagctaaat caccacaaca aatatttggt gcagcaagca aaacatacta tcctcaaata | 1020 |
| tcaggtataa gtgctaaaga tgtatttact gttacaataa tgccttgtac agcaaagaaa | 1080 |
| tttgaggctg atagaagaa aatgtataat gagggaatta aaaatataga tgcagtactt | 1140 |
| actacaagag aattagcaaa aatgattaaa gatgcaaaga ttaattttgc taatttagaa | 1200 |
| gacgaacaag ctgatccagc aatggggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag gaataaaaga ggctacagta | 1380 |
| gaaattggtg gagaaaatta taacgtagct gtaattaatg gtgcagcaaa cttagctgaa | 1440 |
| ttcatgaata gcggtaaaat ccttgaaaag aactatcatt ttattgaagt aatggcttgc | 1500 |
| ccaggcggat gtgtaaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |
| ccaggtgaag gacttgctca caaattacta cacgtaaaat acacaaaaga taaaaatgtt | 1740 |
| tcaaaacatg aa | 1752 |

<210> SEQ ID NO 136
<211> LENGTH: 1725
<212> TYPE: DNA
<213> ORGANISM: Chlamydomonas reinhardtii

<400> SEQUENCE: 136

| | |
|---|---|
| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg gaaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |

```
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420
attgtaatag acagaactaa gtgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgatacaaat tgtttattat gtggacaatg cgttgcagca      600
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggaccat tcccaatgtt tacttcatgt      900
tgtccggcat gggttagaca agtggaaaat tattacccag aattttttaga aaacttatca      960 tcagctaaat caccacaaca aatatttggt gcagcaagca aaacatacta tcctcaaata     1020
tcaggtataa gtgctaaaga tgtatttact gttacaataa tgccttgtac agcaaagaaa     1080
tttgaggctg atagagaaga aatgtataat gagggaatta aaaatataga tgcagtactt     1140
actacaagag aattagcaaa aatgattaaa gatgcaaaga ttaattttgc taatttagaa     1200
gacgaacaag ctgatccagc aatgggagaa tacactgggg ctggagttat attcggagct     1260
acaggtggag ttatggaagc agcacttaga actgctaagg atttcgttga agataaagat     1320
ttaactgata tagaatatac acaaataaga ggattacaag gaataaaaga agcggaagtt     1380
gaaattgctg gaaataaact aaacgttgct gttataaatg gtgcttctaa cttcttcgag     1440
tttatgaaat ctggaaaaat gaacgaaaaa caatatcact ttatagaagt aatggcttgc     1500
cctggtggat gtataaatgg tggaggacaa ccacacgtaa gtgcaaagga aagagaaaaa     1560
gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725
```

<210> SEQ ID NO 137  
<211> LENGTH: 1725  
<212> TYPE: DNA  
<213> ORGANISM: Chlamydomonas reinhardtii

<400> SEQUENCE: 137

```
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg aaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420
attgtaatag acagaactaa gtgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgatacaaat tgtttattat gtggacaatg cgttgcagca      600
```

```
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggaccat tcccaatgtt tacttcatgt      900
tgtccggcat gggttagaca agtggaaaat tattacccag aatttttaga aaacttatca      960
tcagctaaat caccacaaca aatatttggt gcagcaagca aaacatacta tcctcaaata     1020
tcaggtataa gtgctaaaga tgtatttact gttacaataa tgccttgtac agcaaagaaa     1080
tttgaggctg atagagaaga aatgtataat gagggaatta aaaatataga tgcagtactt     1140
actacaagag agcttgcaaa aatgattaaa gatgcaaaaa ttaaatttgc agatcttgaa     1200
gatggtgaag ttgatcctgc tatgggtact tacagtggtg ctggagctat ctttggtgca     1260
accggtggcg ttatggaagc tgcaataaga tcagctaaag actttgctga aaataaagaa     1320
cttgaaaatg ttgattacac tgaagtaaga ggctttaaag gcataaaaga ggctacagta     1380
gaaattggtg gagaaaatta taacgtagct gtaattaatg gtgcagcaaa cttagctgaa     1440
ttcatgaata gcggtaaaat ccttgaaaag aactatcatt ttattgaagt aatggcttgc     1500
ccaggcggat gtgtaaatgg tggaggacaa ccacacgtaa gtgcaaagga agagaaaaa      1560 gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725

<210> SEQ ID NO 138
<211> LENGTH: 1725
<212> TYPE: DNA
<213> ORGANISM: Chlamydomonas reinhardtii

<400> SEQUENCE: 138
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg gaaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420
attgtaatag acagaactaa gtgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgtacaaatt tgtttattat gtggacaatg cgttgcagca      600
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggcccat tcctatgtt tacatcttgc       900 tgtcctgcat gggtaagatt agctcaaaat tatcatcctg aattattaga taatctttca      960
tcagcaaaat caccacaaca aatatttggt actgcatcaa aaacttacta tccttcaatt     1020
```

```
tcaggaatag ctccagaaga tgtttataca gttactatca tgccttgtaa tgataaaaaa    1080
tatgaagcag atattccttt catggaaact aacagcttaa gagatattga tgcatcctta    1140
actacaagag aattagcaaa aatgattaaa gatgcaaaga ttaattttgc taatttagaa    1200
gacgaacaag ctgatccagc aatgggagaa tacactgggg ctggagttat attcggagct    1260
acaggtggag ttatggaagc agcacttaga actgctaagg atttcgttga agataaagat    1320
ttaactgata tagaatatac acaaataaga ggattacaag gaataaaaga ggctacagta    1380
gaaattggtg agaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                   1725
```

<210> SEQ ID NO 139
<211> LENGTH: 1752
<212> TYPE: DNA
<213> ORGANISM: Chlamydomonas reinhardtii

<400> SEQUENCE: 139

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg aaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata gcatgaatt taaatgtgga    300 ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagcttttaac tgaaaaaaca cacgttgata gagttaaaga agcattagaa    660
gatcctaata gcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttgggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aatttttaga aaacttatca    960
tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagaagaa aatgtataat gagggaatta aaaatataga tgcagtactt   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag gaataaaaga agcggaagtt   1380
```

```
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat acacaaaaga taaaaatgtt    1740
tcaaaacatg aa                                                        1752
```

<210> SEQ ID NO 140
<211> LENGTH: 1752
<212> TYPE: DNA
<213> ORGANISM: Chlamydomonas reinhardtii

<400> SEQUENCE: 140

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata gcatgaatt taaatgtgga     300 ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420 attgtaaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatgaagaa     840 gcaacagagt ttattgaaag agttaaaaat aatggaccat tcccaatgtt tacttcatgt     900
tgtccggcat gggttagaca agtggaaaat tattacccag aattttttaga aaacttatca     960 tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagagaaga aatgtataat gagggaatta aaaatataga tgcagtactt    1140
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag gcataaaaga ggctacagta    1380
gaaattggtg gagaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat acacaaaaga taaaaatgtt    1740
```

```
tcaaaacatg aa                                                           1752

<210> SEQ ID NO 141
<211> LENGTH: 1752
<212> TYPE: DNA
<213> ORGANISM: Chlamydomonas reinhardtii

<400> SEQUENCE: 141
atggcaataa acatagtaat tgatgaaaaa actattcaag tacaggaaaa tactacagtt         60
atacaagctg ccctagcaaa tgggatagat ataccaagtt tatgctatct taatgagtgt        120
ggtaatgttg gaaagtgtgg agtgtgtgca gtagaaatag aaggaaaaaa taacttagca        180
cttgcatgta taacaaaagt tgaagaaggt atggtagtaa aaacaaactc agaaaaagta        240
caagaaagag ttaaaatgag agttgctact ttgcttgata agcatgaatt taaatgtgga        300
ccttgtccaa gaagagaaaa ttgcgaattt ttaaagttag ttataaaaac aaaagctaag        360
gctaacaagc cttttgtggt tgaagacaaa tcacaataca tagatattag aagtaaatca        420
attgtaatag acagaactaa gtgtgtgcta tgcggaagat gtgaagcagc atgtaaaaca        480
aagacaggta caggagctat ttcaatttgt aagagtgaat caggaagaat agtgcaagca        540
acaggcggaa agtgctttga tgatacaaat tgtttattat gtggacaatg cgttgcagca        600
tgtccagtag gagctttaac tgaaaaaaca cacgttgata gagttaaaga agcattagaa        660
gatcctaata agcatgtaat agttgctatg gcaccatcaa tcagaacttc tatgggagag        720
ttatttaaat taggctatgg ggttgatgta actggaaaat tatatgcttc aatgagagca        780
ttaggatttg ataaggtatt tgatattaac tttggggctg atatgacaat aatggaagaa        840
gcaacagagt ttattgaaag agttaaaaat aatggcccat tccctatgtt tacatcttgc        900
tgtcctgcat gggtaagatt agctcaaaat tatcatcctg aattattaga taatctttca        960
tcagcaaaat caccacaaca aatatttggt actgcatcaa aaacttacta tccttcaatt       1020
tcaggaatag ctccagaaga tgtttataca gttactatca tgccttgtaa tgataaaaaa       1080
tatgaagcag atattccttt catggaaact aacagcttaa gagatattga tgcatcctta       1140
actacaagag aattagcaaa aatgattaaa gatgcaaaga ttaattttgc taatttagaa       1200
gacgaacaag ctgatccagc aatgggagaa tacactgggg ctggagttat attcggagct       1260
acaggtggag ttatggaagc agcacttaga actgctaagg atttcgttga agataaagat       1320
ttaactgata tagaatatac acaaataaga ggattacaag gaataaaaga ggctacagta       1380
gaaattggtg gagaaaatta taacgtagct gtaattaatg gtgcagcaaa cttagctgaa       1440
ttcatgaata gcggtaaaat ccttgaaaag aactatcatt ttattgaagt aatggcttgc       1500
ccaggcggat gtgtaaatgg tggaggtcaa cctcacgtaa atgctcttga tagagaaaat       1560
gttgattaca gaaaactaag agcatcagta ttatacaacc aagataaaaa tgttctttca       1620
aagagaaagt cacatgataa tccagctatt attaaaatgt atgatagcta ctttggaaaa       1680
ccaggtgaag gacttgctca caattactac cacgtaaaat acacaaaaga taaaaatgtt       1740
tcaaaacatg aa                                                          1752

<210> SEQ ID NO 142
<211> LENGTH: 1725
<212> TYPE: DNA
<213> ORGANISM: Chlamydomonas reinhardtii

<400> SEQUENCE: 142
```

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc ttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggaccat tcccaatgtt tacttcatgt     900
tgtccggcat gggttagaca agtggaaaat tattacccag aatttttaga aaacttatca     960
tcagctaaat caccacaaca atatttggt gcagcaagca aaacatacta tcctcaaata    1020
tcaggtataa gtgctaaaga tgtatttact gttacaataa tgccttgtac agcaaagaaa    1080
tttgaggctg atagaagaa aatgtataat gagggaatta aaatataga tgcagtactt    1140 actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag cataaaaga agcggaagtt    1380 gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa               1725
```

<210> SEQ ID NO 143
<211> LENGTH: 1725
<212> TYPE: DNA
<213> ORGANISM: Chlamydomonas reinhardtii

<400> SEQUENCE: 143

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc ttttgtggt tgaagacaaa tcacaataca tagatattag aagtaaatca     420
```

```
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatccta    1140 actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag gaataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggacaa ccacacgtaa gtgcaaagga aagagaaaaa   1560
gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                   1725
```

<210> SEQ ID NO 144
<211> LENGTH: 1725
<212> TYPE: DNA
<213> ORGANISM: Chlamydomonas reinhardtii

<400> SEQUENCE: 144

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240 caagaaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc ttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
```

```
ttaggatttg ataaggtatt tgatattaac tttggggctg atatgacaat aatggaagaa      840
gcaacagagt ttattgaaag agttaaaaat aatggcccat tccctatgtt tacatcttgc      900
tgtcctgcat gggtaagatt agctcaaaat tatcatcctg aattattaga taatctttca      960
tcagcaaaat caccacaaca aatatttggt actgcatcaa aaacttacta tccttcaatt     1020
tcaggaatag ctccagaaga tgtttataca gttactatca tgccttgtaa tgataaaaaa     1080
tatgaagcag atattccttt catggaaact aacagcttaa gagatattga tgcatcctta     1140
actacaagag agcttgcaaa aatgattaaa gatgcaaaaa ttaaatttgc agatcttgaa     1200
gatggtgaag ttgatcctgc tatgggtact tacagtggtg ctggagctat ctttggtgca     1260
accggtggcg ttatggaagc tgcaataaga tcagctaaag actttgctga aaataaagaa     1320
cttgaaaatg ttgattacac tgaagtaaga ggctttaaag cataaaaga ggctacagta      1380 gaaattggtg gagaaaatta taacgtagct gtaattaatg gtgcagcaaa cttagctgaa     1440
ttcatgaata gcggtaaaat ccttgaaaag aactatcatt ttattgaagt aatggcttgc     1500
ccaggcggat gtgtaaatgg tggaggacaa ccacacgtaa gtgcaaagga aagagaaaaa     1560
gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725
```

<210> SEQ ID NO 145
<211> LENGTH: 1752
<212> TYPE: DNA
<213> ORGANISM: Chlamydomonas reinhardtii

<400> SEQUENCE: 145

```
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg gaaagtgtgg agtgtgtgca gtagaaaatg aaggaaaaaa taacttagca      180
cttgcatgta taacaaaagt tgaagaaggt atggtagtaa aaacaaactc agaaaaagta     240
caagaaagag ttaaaatgag agttgctact ttgcttgata gcatgaatt taaatgtgga      300 ccttgtccaa gaagagaaaa ttgcgaattt ttaaagttag ttataaaaac aaaagctaag    360
gctaacaagc ttttgtggt tgaagacaaa tcacaataca tagatattag aagtaaatca     420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag agcttttaac tgaaaaaaca cacgttgata gagttaaaga agcattagaa    660
gatcctaata gcatgtaat agttgctatg gcaccatcaa tcagaacttc tatgggagag     720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aattttaga aaacttatca     960 tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagaagaa aatgtataat gagggaatta aaaatataga tgcagtactt    1140
actacaagag agcttgcaaa aatgattaaa gatgcaaaaa ttaaatttgc agatcttgaa    1200
```

| | |
|---|---:|
| gatggtgaag ttgatcctgc tatgggtact tacagtggtg ctggagctat ctttggtgca | 1260 |
| accggtggcg ttatggaagc tgcaataaga tcagctaaag actttgctga aaataaagaa | 1320 |
| cttgaaaatg ttgattacac tgaagtaaga ggctttaaag cataaaaga agcggaagtt | 1380 |
| gaaattgctg aaataaaact aaacgttgct gttataaatg tgcttctaa cttcttcgag | 1440 |
| tttatgaaat ctggaaaaat gaacgaaaaa caatatcact ttatagaagt aatggcttgc | 1500 |
| cctggtggat gtataaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |
| ccaggtgaag gacttgctca caattacta cacgtaaaat acacaaaaga taaaaatgtt | 1740 |
| tcaaaacatg aa | 1752 |

<210> SEQ ID NO 146
<211> LENGTH: 1752
<212> TYPE: DNA
<213> ORGANISM: Chlamydomonas reinhardtii

<400> SEQUENCE: 146

| | |
|---|---:|
| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg aaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |
| caagaaagag ttaaaatgag agttgctact ttgcttgata gcatgaatt taaatgtgga | 300 |
| ccttgtccaa gaagagaaaa ttgcgaattt ttaaagttag ttataaaaac aaaagctaag | 360 |
| gctaacaagc cttttgtggt tgaagacaaa tcacaataca tagatattag aagtaaatca | 420 |
| attgtaatag acagaactaa gtgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag gagctttaac tgaaaaaaca cacgttgata gagttaaaga agcattagaa | 660 |
| gatcctaata gcatgtaat agttgctatg caccatcaa tcagaacttc tatgggagag | 720 |
| ttatttaaat taggctatgg ggttgatgta actggaaaat tatatgcttc aatgagagca | 780 |
| ttaggatttg ataaggtatt tgatattaac tttggggctg atatgacaat aatggaagaa | 840 |
| gcaacagagt ttattgaaag agttaaaaat aatggcccat tccctatgtt tacatcttgc | 900 |
| tgtcctgcat gggtaagatt agctcaaaat tatcatcctg aattattaga taatctttca | 960 |
| tcagcaaaat caccacaaca aatatttggt actgcatcaa aaacttacta tccttcaatt | 1020 |
| tcaggaatag ctccagaaga tgttatataca gttactatca tgccttgtaa tgataaaaaa | 1080 |
| tatgaagcag atattccttt catggaaact aacagcttaa gagatattga tgcatcctta | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag aataaaaga agcggaagtt | 1380 |
| gaaattgctg aaataaaact aaacgttgct gttataaatg tgcttctaa cttcttcgag | 1440 |
| tttatgaaat ctggaaaaat gaacgaaaaa caatatcact ttatagaagt aatggcttgc | 1500 |

| | |
|---|---|
| cctggtggat gtataaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |
| ccaggtgaag gacttgctca caaattacta cacgtaaaat acacaaaaga taaaaatgtt | 1740 |
| tcaaaacatg aa | 1752 |

<210> SEQ ID NO 147
<211> LENGTH: 1752
<212> TYPE: DNA
<213> ORGANISM: Chlamydomonas reinhardtii

<400> SEQUENCE: 147

| | |
|---|---|
| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg aaagtgtgg agtgtgtgca gtagaaatag aaggaaaaaa taacttagca | 180 |
| cttgcatgta taacaaaagt tgaagaaggt atggtagtaa aaacaaactc agaaaaagta | 240 |
| caagaaagag ttaaaatgag agttgctact ttgcttgata agcatgaatt taaatgtgga | 300 |
| ccttgtccaa gaagagaaaa ttgcgaattt ttaaagttag ttataaaaac aaaagctaag | 360 |
| gctaacaagc cttttgtggt tgaagacaaa tcacaataca tagatattag aagtaaatca | 420 |
| attgtaatag acagaactaa gtgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag gagctttaac tgaaaaaaca cacgttgata gagttaaaga agcattagaa | 660 |
| gatcctaata agcatgtaat agttgctatg gcaccatcaa tcagaacttc tatgggagag | 720 |
| ttatttaaat taggctatgg ggttgatgta actggaaaat tatatgcttc aatgagagca | 780 |
| ttaggatttg ataaggtatt tgatattaac tttggggctg atatgacaat aatgaaagaa | 840 |
| gcaacagagt ttattgaaag agttaaaaat aatggcccat tccctatgtt tacatcttgc | 900 |
| tgtcctgcat gggtaagatt agctcaaaat tatcatcctg aattattaga taatctttca | 960 |
| tcagcaaaat caccacaaca aatatttggt actgcatcaa aaacttacta tccttcaatt | 1020 |
| tcaggaatag ctccagaaga tgtttataca gttactatca tgccttgtaa tgataaaaaa | 1080 |
| tatgaagcag atattccttt catggaaact aacagcttaa gagatattga tgcatcctta | 1140 |
| actacaagag agcttgcaaa aatgattaaa gatgcaaaaa ttaaatttgc agatcttgaa | 1200 |
| gatggtgaag ttgatcctgc tatgggtact tacagtggtg ctggagctat ctttggtgca | 1260 |
| accggtggcg ttatggaagc tgcaataaga tcagctaaag actttgctga aaataaagaa | 1320 |
| cttgaaaatg ttgattacac tgaagtaaga ggctttaaag gcataaaaga ggctacagta | 1380 |
| gaaattggtg gagaaaatta taacgtagct gtaattaatg gtgcagcaaa cttagctgaa | 1440 |
| ttcatgaata gcggtaaaat ccttgaaaag aactatcatt ttattgaagt aatggcttgc | 1500 |
| ccaggcggat gtgtaaatgg tggaggtcaa cctcacgtaa atgctcttga tagagaaaat | 1560 |
| gttgattaca gaaaactaag agcatcagta ttatacaacc aagataaaaa tgttctttca | 1620 |
| aagagaaagt cacatgataa tccagctatt attaaaatgt atgatagcta ctttggaaaa | 1680 |
| ccaggtgaag gacttgctca caaattacta cacgtaaaat acacaaaaga taaaaatgtt | 1740 |
| tcaaaacatg aa | 1752 |

<210> SEQ ID NO 148
<211> LENGTH: 1725
<212> TYPE: DNA
<213> ORGANISM: Chlamydomonas reinhardtii

<400> SEQUENCE: 148

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag agctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggcccat tccctatgtt tacatcttgc     900
tgtcctgcat gggtaagatt agctcaaaat tatcatcctg aattattaga taatctttca     960
tcagcaaaat caccacaaca aatatttggt actgcatcaa aaacttacta tccttcaatt    1020
tcaggaatag ctccagaaga tgtttataca gttactatca tgccttgtaa tgataaaaaa    1080
tatgaagcag atattccttt catggaaact aacagcttaa gagatattga tgcatcctta    1140
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag cataaaaga agcggaagtt    1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggacaa ccacacgtaa gtgcaaagga agagaaaaa     1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725
```

<210> SEQ ID NO 149
<211> LENGTH: 575
<212> TYPE: PRT
<213> ORGANISM: Chlamydomonas reinhardtii

<400> SEQUENCE: 149

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30
```

```
Ser Leu Cys Tyr Leu Asn Glu Cys Gly Asn Val Gly Lys Cys Gly Val
        35                  40                  45
Cys Ala Val Glu Ile Glu Gly Lys Asn Asn Leu Ala Leu Ala Cys Ile
50                  55                  60
Thr Lys Val Glu Glu Gly Met Val Val Lys Thr Asn Ser Glu Lys Val
65                  70                  75                  80
Gln Glu Arg Val Lys Met Arg Val Ala Thr Leu Leu Asp Lys His Glu
                85                  90                  95
Phe Lys Cys Gly Pro Cys Pro Arg Arg Glu Asn Cys Glu Phe Leu Lys
            100                 105                 110
Leu Val Ile Lys Thr Lys Ala Lys Ala Asn Lys Pro Phe Val Val Glu
        115                 120                 125
Asp Lys Ser Gln Tyr Ile Asp Ile Arg Ser Lys Ser Ile Val Ile Asp
    130                 135                 140
Arg Thr Lys Cys Val Leu Cys Gly Arg Cys Glu Ala Ala Cys Lys Thr
145                 150                 155                 160
Lys Thr Gly Thr Gly Ala Ile Ser Ile Cys Lys Ser Glu Ser Gly Arg
                165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
        195                 200                 205
Lys Thr His Val Asp Arg Val Lys Glu Ala Leu Glu Asp Pro Asn Lys
    210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
                245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
        275                 280                 285
Lys Asn Asn Gly Pro Phe Pro Met Phe Thr Ser Cys Cys Pro Ala Trp
    290                 295                 300
Val Arg Gln Val Glu Asn Tyr Tyr Pro Glu Phe Leu Glu Asn Leu Ser
305                 310                 315                 320
Ser Ala Lys Ser Pro Gln Gln Ile Phe Gly Ala Ala Ser Lys Thr Tyr
                325                 330                 335
Tyr Pro Gln Ile Ser Gly Ile Ser Ala Lys Asp Val Phe Thr Val Thr
            340                 345                 350
Ile Met Pro Cys Thr Ala Lys Lys Phe Glu Ala Asp Arg Glu Glu Met
        355                 360                 365
Tyr Asn Glu Gly Ile Lys Asn Ile Asp Ala Val Leu Thr Thr Arg Glu
    370                 375                 380
Leu Ala Lys Met Ile Lys Asp Ala Lys Ile Asn Phe Ala Asn Leu Glu
385                 390                 395                 400
Asp Glu Gln Ala Asp Pro Ala Met Gly Glu Tyr Thr Gly Ala Gly Val
                405                 410                 415
Ile Phe Gly Ala Thr Gly Gly Val Met Glu Ala Ala Leu Arg Thr Ala
            420                 425                 430
Lys Asp Phe Val Glu Asp Lys Asp Leu Thr Asp Ile Glu Tyr Thr Gln
        435                 440                 445
Ile Arg Gly Leu Gln Gly Ile Lys Glu Ala Thr Val Glu Ile Gly Gly
```

```
            450                 455                 460
Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
            530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 150
<211> LENGTH: 583
<212> TYPE: PRT
<213> ORGANISM: Chlamydomonas reinhardtii

<400> SEQUENCE: 150

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
        210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255
```

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 151
<211> LENGTH: 574
<212> TYPE: PRT
<213> ORGANISM: Chlamydomonas reinhardtii

<400> SEQUENCE: 151

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

```
Cys Met Val Glu Val Glu Gly Lys Gly Phe Arg Ala Ala Cys Val Ala
     50                  55                  60

Lys Val Glu Asp Gly Met Val Ile Asn Thr Glu Ser Asp Glu Val Lys
 65                  70                  75                  80

Glu Arg Ile Lys Lys Arg Val Ser Met Leu Leu Asp Lys His Glu Phe
                 85                  90                  95

Lys Cys Gly Gln Cys Ser Arg Arg Glu Asn Cys Glu Phe Leu Lys Leu
                100                 105                 110

Val Ile Lys Thr Lys Ala Lys Ala Ser Lys Pro Phe Leu Pro Glu Asp
             115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
             180                 185                 190

Cys Gly Gln Cys Val Ile Ala Cys Pro Val Ala Ala Leu Lys Glu Lys
             195                 200                 205

Ser His Ile Glu Lys Val Gln Glu Ala Leu Asn Asp Pro Lys Lys His
     210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
             260                 265                 270

Asp Met Thr Ile Met Glu Glu Ala Thr Glu Leu Leu Gly Arg Val Lys
             275                 280                 285

Asn Asn Gly Pro Phe Pro Met Phe Thr Ser Cys Cys Pro Ala Trp Val
     290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
             340                 345                 350

Met Pro Cys Thr Ala Lys Lys Phe Glu Ala Asp Arg Glu Glu Met Tyr
             355                 360                 365

Asn Glu Gly Ile Lys Asn Ile Asp Ala Val Leu Thr Thr Arg Glu Leu
     370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
             420                 425                 430

Asp Phe Val Glu Asp Lys Asp Leu Thr Asp Ile Glu Tyr Thr Gln Ile
         435                 440                 445

Arg Gly Leu Gln Gly Ile Lys Glu Ala Thr Val Glu Ile Gly Gly Glu
     450                 455                 460
```

```
Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
            530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570
```

<210> SEQ ID NO 152
<211> LENGTH: 584
<212> TYPE: PRT
<213> ORGANISM: Chlamydomonas reinhardtii

<400> SEQUENCE: 152

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270
```

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
            325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
        370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
            405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Glu Val Glu Ile Ala Gly
450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
            485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
        530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 153
<211> LENGTH: 574
<212> TYPE: PRT
<213> ORGANISM: Chlamydomonas reinhardtii

<400> SEQUENCE: 153

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala

-continued

```
                50                  55                  60
Lys Val Glu Asp Gly Met Val Ile Asn Thr Glu Ser Asp Glu Val Lys
 65                  70                  75                  80

Glu Arg Ile Lys Lys Arg Val Ser Met Leu Leu Asp Lys His Glu Phe
                 85                  90                  95

Lys Cys Gly Gln Cys Ser Arg Arg Glu Asn Cys Glu Phe Leu Lys Leu
                100                 105                 110

Val Ile Lys Thr Lys Ala Lys Ala Ser Lys Pro Phe Leu Pro Glu Asp
                115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
                180                 185                 190

Cys Gly Gln Cys Val Ile Ala Cys Pro Val Ala Ala Leu Lys Glu Lys
                195                 200                 205

Ser His Ile Glu Lys Val Gln Glu Ala Leu Asn Asp Pro Lys Lys His
210                 215                 220

Val Ile Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
                260                 265                 270

Asp Met Thr Ile Met Glu Glu Ala Thr Glu Leu Leu Gly Arg Val Lys
                275                 280                 285

Asn Asn Gly Pro Phe Pro Met Phe Thr Ser Cys Cys Pro Ala Trp Val
                290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
                340                 345                 350

Met Pro Cys Thr Ala Lys Lys Phe Glu Ala Asp Arg Glu Glu Met Tyr
                355                 360                 365

Asn Glu Gly Ile Lys Asn Ile Asp Ala Val Leu Thr Thr Arg Glu Leu
                370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
                420                 425                 430

Asp Phe Val Glu Asp Lys Asp Leu Thr Asp Ile Glu Tyr Thr Gln Ile
                435                 440                 445

Arg Gly Leu Gln Gly Ile Lys Glu Ala Glu Val Glu Ile Ala Gly Asn
                450                 455                 460

Lys Leu Asn Val Ala Val Ile Asn Gly Ala Ser Asn Phe Phe Glu Phe
465                 470                 475                 480
```

```
Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
        530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 154
<211> LENGTH: 575
<212> TYPE: PRT
<213> ORGANISM: Chlamydomonas reinhardtii

<400> SEQUENCE: 154

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
```

```
            275                 280                 285
Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
                340                 345                 350

Ile Met Pro Cys Thr Ala Lys Lys Phe Glu Ala Asp Arg Glu Glu Met
                355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Glu Val Glu Ile Ala Gly
                450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gln Pro His
                500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
                530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 155
<211> LENGTH: 583
<212> TYPE: PRT
<213> ORGANISM: Chlamydomonas reinhardtii

<400> SEQUENCE: 155

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
                50                  55                  60

Lys Val Glu Asp Gly Met Val Ile Asn Thr Glu Ser Asp Glu Val Lys
65                  70                  75                  80
```

```
Glu Arg Ile Lys Lys Arg Val Ser Met Leu Leu Asp Lys His Glu Phe
                85                  90                  95
Lys Cys Gly Gln Cys Ser Arg Arg Glu Asn Cys Glu Phe Leu Lys Leu
            100                 105                 110
Val Ile Lys Thr Lys Ala Lys Ala Ser Lys Pro Phe Leu Pro Glu Asp
        115                 120                 125
Lys Asp Ala Leu Val Asp Asn Arg Ser Lys Ala Ile Val Ile Asp Arg
    130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
        275                 280                 285
Asn Asn Gly Pro Phe Pro Met Phe Thr Ser Cys Cys Pro Ala Trp Val
    290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
            340                 345                 350
Met Pro Cys Thr Ala Lys Lys Phe Glu Ala Asp Arg Glu Glu Met Tyr
        355                 360                 365
Asn Glu Gly Ile Lys Asn Ile Asp Ala Val Leu Thr Thr Arg Glu Leu
    370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
            420                 425                 430
Asp Phe Val Glu Asp Lys Asp Leu Thr Asp Ile Glu Tyr Thr Gln Ile
        435                 440                 445
Arg Gly Leu Gln Gly Ile Lys Glu Ala Glu Val Glu Ile Ala Gly Asn
    450                 455                 460
Lys Leu Asn Val Ala Val Ile Asn Gly Ala Ser Asn Phe Phe Glu Phe
465                 470                 475                 480
Met Lys Ser Gly Lys Met Asn Glu Lys Gln Tyr His Phe Ile Glu Val
                485                 490                 495
Met Ala Cys Pro Gly Gly Cys Ile Asn Gly Gly Gly Gln Pro His Val
```

```
                    500                 505                 510
Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
        530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 156
<211> LENGTH: 584
<212> TYPE: PRT
<213> ORGANISM: Chlamydomonas reinhardtii

<400> SEQUENCE: 156

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285
```

```
Lys Asn Asn Gly Pro Phe Pro Met Phe Thr Ser Cys Cys Pro Ala Trp
            290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
                340                 345                 350

Ile Met Pro Cys Thr Ala Lys Lys Phe Glu Ala Asp Arg Glu Met
                355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Glu Val Glu Ile Ala Gly
                450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Asn Ala Leu Asp Arg Glu Asn Val Asp Tyr Arg Lys Leu Arg Ala
                515                 520                 525

Ser Val Leu Tyr Asn Gln Asp Lys Asn Val Leu Ser Lys Arg Lys Ser
                530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580

<210> SEQ ID NO 157
<211> LENGTH: 583
<212> TYPE: PRT
<213> ORGANISM: Chlamydomonas reinhardtii

<400> SEQUENCE: 157

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80
```

```
Glu Arg Ile Lys Lys Arg Val Ser Met Leu Leu Asp Lys His Glu Phe
             85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
        210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
                260                 265                 270

Asp Met Thr Ile Met Glu Glu Ala Thr Glu Leu Leu Gly Arg Val Lys
                275                 280                 285

Asn Asn Gly Pro Phe Pro Met Phe Thr Ser Cys Cys Pro Ala Trp Val
        290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
        370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
                420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Glu Val Glu Ile Ala Gly Asn
        450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495
```

```
Met Ala Cys Pro Gly Gly Cys Ile Asn Gly Gly Gly Gln Pro His Val
                500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
        530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 158
<211> LENGTH: 584
<212> TYPE: PRT
<213> ORGANISM: Chlamydomonas reinhardtii

<400> SEQUENCE: 158

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285
```

```
Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
                340                 345                 350

Ile Met Pro Cys Asn Asp Lys Lys Tyr Glu Ala Asp Ile Pro Phe Met
                355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Glu Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Asn Ala Leu Asp Arg Glu Asn Val Asp Tyr Arg Lys Leu Arg Ala
                515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580

<210> SEQ ID NO 159
<211> LENGTH: 575
<212> TYPE: PRT
<213> ORGANISM: Chlamydomonas reinhardtii

<400> SEQUENCE: 159

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
                50                  55                  60

Thr Lys Val Glu Glu Gly Met Val Val Lys Thr Asn Ser Glu Lys Val
```

```
                65                  70                  75                  80
            Gln Glu Arg Val Lys Met Arg Val Ala Thr Leu Leu Asp Lys His Glu
                            85                  90                  95
            Phe Lys Cys Gly Pro Cys Pro Arg Arg Glu Asn Cys Glu Phe Leu Lys
                           100                 105                 110
            Leu Val Ile Lys Thr Lys Ala Lys Ala Asn Lys Pro Phe Val Val Glu
                           115                 120                 125
            Asp Lys Ser Gln Tyr Ile Asp Ile Arg Ser Lys Ser Ile Val Ile Asp
            130                 135                 140
            Arg Thr Lys Cys Val Leu Cys Gly Arg Cys Glu Ala Ala Cys Lys Thr
            145                 150                 155                 160
            Lys Thr Gly Thr Gly Ala Ile Ser Ile Cys Lys Ser Glu Ser Gly Arg
                           165                 170                 175
            Ile Val Gln Ala Thr Gly Gly Lys Cys Phe Asp Asp Thr Asn Cys Leu
                           180                 185                 190
            Leu Cys Gly Gln Cys Val Ala Ala Cys Pro Val Gly Ala Leu Thr Glu
                           195                 200                 205
            Lys Thr His Val Asp Arg Val Lys Glu Ala Leu Glu Asp Pro Asn Lys
            210                 215                 220
            His Val Ile Val Ala Met Ala Pro Ser Ile Arg Thr Ser Met Gly Glu
            225                 230                 235                 240
            Leu Phe Lys Leu Gly Tyr Gly Val Asp Val Thr Gly Lys Leu Tyr Ala
                           245                 250                 255
            Ser Met Arg Ala Leu Gly Phe Asp Lys Val Phe Asp Ile Asn Phe Gly
                           260                 265                 270
            Ala Asp Met Thr Ile Met Glu Glu Ala Thr Glu Phe Ile Glu Arg Val
                           275                 280                 285
            Lys Asn Asn Gly Pro Phe Pro Met Phe Thr Ser Cys Cys Pro Ala Trp
                           290                 295                 300
            Val Arg Leu Ala Gln Asn Tyr His Pro Glu Leu Leu Asp Asn Leu Ser
            305                 310                 315                 320
            Ser Ala Lys Ser Pro Gln Gln Ile Phe Gly Thr Ala Ser Lys Thr Tyr
                           325                 330                 335
            Tyr Pro Ser Ile Ser Gly Ile Ala Pro Glu Asp Val Tyr Thr Val Thr
                           340                 345                 350
            Ile Met Pro Cys Asn Asp Lys Lys Tyr Glu Ala Asp Ile Pro Phe Met
                           355                 360                 365
            Glu Thr Asn Ser Leu Arg Asp Ile Asp Ala Ser Leu Thr Thr Arg Glu
                           370                 375                 380
            Leu Ala Lys Met Ile Lys Asp Ala Lys Ile Lys Phe Ala Asp Leu Glu
            385                 390                 395                 400
            Asp Gly Glu Val Asp Pro Ala Met Gly Thr Tyr Ser Gly Ala Gly Ala
                           405                 410                 415
            Ile Phe Gly Ala Thr Gly Gly Val Met Glu Ala Ala Ile Arg Ser Ala
                           420                 425                 430
            Lys Asp Phe Ala Glu Asn Lys Glu Leu Glu Asn Val Asp Tyr Thr Glu
                           435                 440                 445
            Val Arg Gly Phe Lys Gly Ile Lys Glu Ala Val Glu Ile Ala Gly
                           450                 455                 460
            Asn Lys Leu Asn Val Ala Val Ile Asn Gly Ala Ser Asn Phe Phe Glu
            465                 470                 475                 480
            Phe Met Lys Ser Gly Lys Met Asn Glu Lys Gln Tyr His Phe Ile Glu
                           485                 490                 495
```

Val Met Ala Cys Pro Gly Gly Cys Ile Asn Gly Gly Gln Pro His
            500             505             510

Val Ser Ala Lys Glu Arg Glu Lys Val Asp Val Arg Thr Val Arg Ala
            515             520             525

Ser Val Leu Tyr Asn Gln Asp Lys Asn Leu Glu Lys Arg Lys Ser His
530             535             540

Lys Asn Thr Ala Leu Leu Asn Met Tyr Tyr Asp Tyr Met Gly Ala Pro
545             550             555             560

Gly Gln Gly Lys Ala His Glu Leu Leu His Leu Lys Tyr Asn Lys
            565             570             575

<210> SEQ ID NO 160
<211> LENGTH: 575
<212> TYPE: PRT
<213> ORGANISM: Chlamydomonas reinhardtii

<400> SEQUENCE: 160

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
            50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Ser Thr Cys Leu
            180                 185                 190

Leu Cys Gly Gln Cys Val Ile Ala Cys Pro Val Ala Ala Leu Lys Glu
            195                 200                 205

Lys Ser His Ile Glu Lys Val Gln Glu Ala Leu Asn Asp Pro Lys Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp

```
                290                 295                 300
Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
                340                 345                 350

Ile Met Pro Cys Asn Asp Lys Lys Tyr Glu Ala Asp Ile Pro Phe Met
                355                 360                 365

Glu Thr Asn Ser Leu Arg Asp Ile Asp Ala Ser Leu Thr Thr Arg Glu
                370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Thr Val Glu Ile Gly Gly
                450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
                500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
                530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 161
<211> LENGTH: 584
<212> TYPE: PRT
<213> ORGANISM: Chlamydomonas reinhardtii

<400> SEQUENCE: 161

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
                50                  55                  60

Thr Lys Val Glu Glu Gly Met Val Lys Thr Asn Ser Glu Lys Val
65                  70                  75                  80

Gln Glu Arg Val Lys Met Arg Val Ala Thr Leu Leu Asp Lys His Glu
                85                  90                  95
```

```
Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
```

```
                515                 520                 525
Ser Val Leu Tyr Asn Gln Asp Lys Asn Val Leu Ser Lys Arg Lys Ser
    530                 535                 540
His Asp Asn Pro Ala Ile Ile Lys Met Tyr Asp Ser Tyr Phe Gly Lys
545                 550                 555                 560
Pro Gly Glu Gly Leu Ala His Lys Leu Leu His Val Lys Tyr Thr Lys
                565                 570                 575
Asp Lys Asn Val Ser Lys His Glu
            580

<210> SEQ ID NO 162
<211> LENGTH: 584
<212> TYPE: PRT
<213> ORGANISM: Chlamydomonas reinhardtii

<400> SEQUENCE: 162

Met Ala Ile Asn Ile Val Ile Asp Glu Lys Thr Ile Gln Val Gln Glu
1               5                   10                  15
Asn Thr Thr Val Ile Gln Ala Ala Leu Ala Asn Gly Ile Asp Ile Pro
            20                  25                  30
Ser Leu Cys Tyr Leu Asn Glu Cys Gly Asn Val Gly Lys Cys Gly Val
        35                  40                  45
Cys Ala Val Glu Ile Glu Gly Lys Asn Asn Leu Ala Leu Ala Cys Ile
    50                  55                  60
Thr Lys Val Glu Glu Gly Met Val Val Lys Thr Asn Ser Glu Lys Val
65                  70                  75                  80
Gln Glu Arg Val Lys Met Arg Val Ala Thr Leu Leu Asp Lys His Glu
                85                  90                  95
Phe Lys Cys Gly Pro Cys Pro Arg Arg Glu Asn Cys Glu Phe Leu Lys
            100                 105                 110
Leu Val Ile Lys Thr Lys Ala Lys Ala Asn Lys Pro Phe Val Val Glu
        115                 120                 125
Asp Lys Ser Gln Tyr Ile Asp Ile Arg Ser Lys Ser Ile Val Ile Asp
    130                 135                 140
Arg Thr Lys Cys Val Leu Cys Gly Arg Cys Val Ala Ala Cys Lys Gln
145                 150                 155                 160
His Thr Ser Thr Cys Ser Ile Gln Phe Ile Lys Lys Asp Gly Gln Arg
                165                 170                 175
Ala Val Gly Thr Val Asp Asp Val Cys Leu Asp Asp Ser Thr Cys Leu
            180                 185                 190
Leu Cys Gly Gln Cys Val Ile Ala Cys Pro Val Ala Ala Leu Lys Glu
        195                 200                 205
Lys Ser His Ile Glu Lys Val Gln Glu Ala Leu Asn Asp Pro Lys Lys
    210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
                245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
        275                 280                 285
Lys Asn Asn Gly Pro Phe Pro Met Phe Thr Ser Cys Cys Pro Ala Trp
    290                 295                 300
```

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
            325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
            370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
            405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Glu Val Glu Ile Ala Gly
            450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
            485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 163
<211> LENGTH: 584
<212> TYPE: PRT
<213> ORGANISM: Chlamydomonas reinhardtii

<400> SEQUENCE: 163

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
            50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
            85                  90                  95

-continued

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Glu Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
            500                 505                 510

```
Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
        530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 164
<211> LENGTH: 583
<212> TYPE: PRT
<213> ORGANISM: Chlamydomonas reinhardtii

<400> SEQUENCE: 164

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Gly Lys Gly Phe Arg Ala Ala Cys Val Ala
    50                  55                  60

Lys Val Glu Asp Gly Met Val Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Glu Asn Cys Glu Phe Leu Lys Leu
            100                 105                 110

Val Ile Lys Thr Lys Ala Lys Ala Asn Lys Pro Phe Val Val Glu Asp
        115                 120                 125

Lys Ser Gln Tyr Ile Asp Ile Arg Ser Lys Ser Ile Val Ile Asp Arg
    130                 135                 140

Thr Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
    290                 295                 300
```

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
            325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
            370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
    515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
            565                 570                 575

Lys Asn Val Ser Lys His Glu
            580

<210> SEQ ID NO 165
<211> LENGTH: 584
<212> TYPE: PRT
<213> ORGANISM: Chlamydomonas reinhardtii

<400> SEQUENCE: 165

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu

```
                    85                  90                  95
Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
            130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
                180                 185                 190

Leu Cys Gly Gln Cys Val Ile Ala Cys Pro Val Ala Ala Leu Lys Glu
                195                 200                 205

Lys Ser His Ile Glu Lys Val Gln Glu Ala Leu Asn Asp Pro Lys Lys
                210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
                260                 265                 270

Ala Asp Met Thr Ile Met Glu Glu Ala Thr Glu Leu Leu Gly Arg Val
                275                 280                 285

Lys Asn Asn Gly Pro Phe Pro Met Phe Thr Ser Cys Cys Pro Ala Trp
                290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
                340                 345                 350

Ile Met Pro Cys Asn Asp Lys Lys Tyr Glu Ala Asp Ile Pro Phe Met
                355                 360                 365

Glu Thr Asn Ser Leu Arg Asp Ile Asp Ala Ser Leu Thr Thr Arg Glu
            370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
                420                 425                 430

Lys Asp Phe Ala Glu Asn Lys Glu Leu Glu Asn Val Asp Tyr Thr Glu
                435                 440                 445

Val Arg Gly Phe Lys Gly Ile Lys Glu Ala Glu Val Glu Ile Ala Gly
            450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510
```

```
Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580

<210> SEQ ID NO 166
<211> LENGTH: 584
<212> TYPE: PRT
<213> ORGANISM: Chlamydomonas reinhardtii

<400> SEQUENCE: 166

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
        275                 280                 285

Lys Asn Asn Gly Pro Phe Pro Met Phe Thr Ser Cys Cys Pro Ala Trp
```

```
                290                 295                 300
Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
            325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
            370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
            405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Glu Val Glu Ile Ala Gly
            450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
            485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
            530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 167
<211> LENGTH: 583
<212> TYPE: PRT
<213> ORGANISM: Chlamydomonas reinhardtii

<400> SEQUENCE: 167

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
            50                  55                  60

Lys Val Glu Asp Gly Met Val Val Lys Thr Asn Ser Glu Lys Val Gln
65                  70                  75                  80
```

```
Glu Arg Val Lys Met Arg Val Ala Thr Leu Leu Asp Lys His Glu Phe
                85                  90                  95
Lys Cys Gly Pro Cys Pro Arg Glu Asn Cys Glu Phe Leu Lys Leu
            100                 105                 110
Val Ile Lys Thr Lys Ala Lys Ala Asn Lys Pro Phe Val Val Glu Asp
        115                 120                 125
Lys Ser Gln Tyr Ile Asp Ile Arg Ser Lys Ser Ile Val Ile Asp Arg
    130                 135                 140
Thr Lys Cys Val Leu Cys Gly Arg Cys Glu Ala Cys Lys Thr Lys
145                 150                 155                 160
Thr Gly Thr Gly Ala Ile Ser Ile Cys Lys Ser Glu Ser Gly Arg Ile
                165                 170                 175
Val Gln Ala Thr Gly Gly Lys Cys Phe Asp Asp Thr Asn Cys Leu Leu
            180                 185                 190
Cys Gly Gln Cys Val Ala Ala Cys Pro Val Gly Ala Leu Thr Glu Lys
        195                 200                 205
Thr His Val Asp Arg Val Lys Glu Ala Leu Glu Asp Pro Asn Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
        275                 280                 285
Asn Asn Gly Pro Phe Pro Met Phe Thr Ser Cys Cys Pro Ala Trp Val
    290                 295                 300
Arg Leu Ala Gln Asn Tyr His Pro Glu Leu Leu Asp Asn Leu Ser Ser
305                 310                 315                 320
Ala Lys Ser Pro Gln Gln Ile Phe Gly Thr Ala Ser Lys Thr Tyr Tyr
                325                 330                 335
Pro Ser Ile Ser Gly Ile Ala Pro Glu Asp Val Tyr Thr Val Thr Ile
            340                 345                 350
Met Pro Cys Asn Asp Lys Lys Tyr Glu Ala Asp Ile Pro Phe Met Glu
        355                 360                 365
Thr Asn Ser Leu Arg Asp Ile Asp Ala Ser Leu Thr Thr Arg Glu Leu
    370                 375                 380
Ala Lys Met Ile Lys Asp Ala Lys Ile Lys Phe Ala Asp Leu Glu Asp
385                 390                 395                 400
Gly Glu Val Asp Pro Ala Met Gly Thr Tyr Ser Gly Ala Gly Ala Ile
                405                 410                 415
Phe Gly Ala Thr Gly Gly Val Met Glu Ala Ala Ile Arg Ser Ala Lys
            420                 425                 430
Asp Phe Ala Glu Asn Lys Glu Leu Glu Asn Val Asp Tyr Thr Glu Val
        435                 440                 445
Arg Gly Phe Lys Gly Ile Lys Glu Ala Glu Val Glu Ile Ala Gly Asn
    450                 455                 460
Lys Leu Asn Val Ala Val Ile Asn Gly Ala Ser Asn Phe Phe Glu Phe
465                 470                 475                 480
Met Lys Ser Gly Lys Met Asn Glu Lys Gln Tyr His Phe Ile Glu Val
                485                 490                 495
Met Ala Cys Pro Gly Gly Cys Ile Asn Gly Gly Gly Gln Pro His Val
```

```
                    500                 505                 510
Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
            565                 570                 575

Lys Asn Val Ser Lys His Glu
            580

<210> SEQ ID NO 168
<211> LENGTH: 584
<212> TYPE: PRT
<213> ORGANISM: Chlamydomonas reinhardtii

<400> SEQUENCE: 168

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
            50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
            115                 120                 125

Asp Lys Asp Ala Leu Val Asp Asn Arg Ser Lys Ala Ile Val Ile Asp
            130                 135                 140

Arg Ser Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
            195                 200                 205

Lys Ser His Ile Glu Lys Val Gln Glu Ala Leu Asn Asp Pro Lys Lys
            210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
            245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285
```

-continued

```
Lys Asn Asn Gly Pro Phe Pro Met Phe Thr Ser Cys Cys Pro Ala Trp
    290                 295                 300
Val Arg Leu Ala Gln Asn Tyr His Pro Glu Leu Leu Asp Asn Leu Ser
305                 310                 315                 320
Ser Ala Lys Ser Pro Gln Gln Ile Phe Gly Thr Ala Ser Lys Thr Tyr
            325                 330                 335
Tyr Pro Ser Ile Ser Gly Ile Ala Pro Glu Asp Val Tyr Thr Val Thr
            340                 345                 350
Ile Met Pro Cys Asn Asp Lys Lys Tyr Glu Ala Asp Ile Pro Phe Met
            355                 360                 365
Glu Thr Asn Ser Leu Arg Asp Ile Asp Ala Ser Leu Thr Thr Arg Glu
370                 375                 380
Leu Ala Lys Met Ile Lys Asp Ala Lys Ile Lys Phe Ala Asp Leu Glu
385                 390                 395                 400
Asp Gly Glu Val Asp Pro Ala Met Gly Thr Tyr Ser Gly Ala Gly Ala
                405                 410                 415
Ile Phe Gly Ala Thr Gly Gly Val Met Glu Ala Ala Ile Arg Ser Ala
                420                 425                 430
Lys Asp Phe Ala Glu Asn Lys Glu Leu Glu Asn Val Asp Tyr Thr Glu
            435                 440                 445
Val Arg Gly Phe Lys Gly Ile Lys Glu Ala Glu Val Glu Ile Ala Gly
    450                 455                 460
Asn Lys Leu Asn Val Ala Val Ile Asn Gly Ala Ser Asn Phe Phe Glu
465                 470                 475                 480
Phe Met Lys Ser Gly Lys Met Asn Glu Lys Gln Tyr His Phe Ile Glu
                485                 490                 495
Val Met Ala Cys Pro Gly Gly Cys Ile Asn Gly Gly Gly Gln Pro His
            500                 505                 510
Val Asn Ala Leu Asp Arg Glu Asn Val Asp Tyr Arg Lys Leu Arg Ala
            515                 520                 525
Ser Val Leu Tyr Asn Gln Asp Lys Asn Val Leu Ser Lys Arg Lys Ser
530                 535                 540
His Asp Asn Pro Ala Ile Ile Lys Met Tyr Asp Ser Tyr Phe Gly Lys
545                 550                 555                 560
Pro Gly Glu Gly Leu Ala His Lys Leu Leu His Val Lys Tyr Thr Lys
                565                 570                 575
Asp Lys Asn Val Ser Lys His Glu
            580
```

<210> SEQ ID NO 169
<211> LENGTH: 583
<212> TYPE: PRT
<213> ORGANISM: Chlamydomonas reinhardtii

<400> SEQUENCE: 169

```
Met Ala Lys Thr Ile Ile Leu Asn Gly Asn Glu Val His Thr Asp Lys
1               5                   10                  15
Asp Ile Thr Ile Leu Glu Leu Ala Arg Glu Asn Asn Val Asp Ile Pro
            20                  25                  30
Thr Leu Cys Phe Leu Lys Asp Cys Gly Asn Phe Gly Lys Cys Gly Val
        35                  40                  45
Cys Met Val Glu Val Glu Gly Lys Gly Phe Arg Ala Ala Cys Val Ala
    50                  55                  60
Lys Val Glu Asp Gly Met Val Val Lys Thr Asn Ser Glu Lys Val Gln
65                  70                  75                  80
```

-continued

```
Glu Arg Val Lys Met Arg Val Ala Thr Leu Leu Asp Lys His Glu Phe
                 85                  90                  95
Lys Cys Gly Pro Cys Pro Arg Arg Glu Asn Cys Glu Phe Leu Lys Leu
                100                 105                 110
Val Ile Lys Thr Lys Ala Lys Ala Asn Lys Pro Phe Val Val Glu Asp
                115                 120                 125
Lys Ser Gln Tyr Ile Asp Ile Arg Ser Lys Ser Ile Val Ile Asp Arg
130                 135                 140
Thr Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
                180                 185                 190
Cys Gly Gln Cys Val Ile Ala Cys Pro Val Ala Leu Lys Glu Lys
                195                 200                 205
Ser His Ile Glu Lys Val Gln Glu Ala Leu Asn Asp Pro Lys Lys His
    210                 215                 220
Val Ile Val Ala Met Ala Pro Ser Ile Arg Thr Ser Met Gly Glu Leu
225                 230                 235                 240
Phe Lys Leu Gly Tyr Gly Val Asp Val Thr Gly Lys Leu Tyr Ala Ser
                245                 250                 255
Met Arg Ala Leu Gly Phe Asp Lys Val Phe Asp Ile Asn Phe Gly Ala
                260                 265                 270
Asp Met Thr Ile Met Glu Glu Ala Thr Glu Phe Ile Glu Arg Val Lys
                275                 280                 285
Asn Asn Gly Pro Phe Pro Met Phe Thr Ser Cys Cys Pro Ala Trp Val
            290                 295                 300
Arg Leu Ala Gln Asn Tyr His Pro Glu Leu Leu Asp Asn Leu Ser Ser
305                 310                 315                 320
Ala Lys Ser Pro Gln Gln Ile Phe Gly Thr Ala Ser Lys Thr Tyr Tyr
                325                 330                 335
Pro Ser Ile Ser Gly Ile Ala Pro Glu Asp Val Tyr Thr Val Thr Ile
                340                 345                 350
Met Pro Cys Asn Asp Lys Lys Tyr Glu Ala Asp Ile Pro Phe Met Glu
                355                 360                 365
Thr Asn Ser Leu Arg Asp Ile Asp Ala Ser Leu Thr Thr Arg Glu Leu
    370                 375                 380
Ala Lys Met Ile Lys Asp Ala Lys Ile Lys Phe Ala Asp Leu Glu Asp
385                 390                 395                 400
Gly Glu Val Asp Pro Ala Met Gly Thr Tyr Ser Gly Ala Gly Ala Ile
                405                 410                 415
Phe Gly Ala Thr Gly Gly Val Met Glu Ala Ala Ile Arg Ser Ala Lys
                420                 425                 430
Asp Phe Ala Glu Asn Lys Glu Leu Glu Asn Val Asp Tyr Thr Glu Val
                435                 440                 445
Arg Gly Phe Lys Gly Ile Lys Glu Ala Glu Val Glu Ile Ala Gly Asn
    450                 455                 460
Lys Leu Asn Val Ala Val Ile Asn Gly Ala Ser Asn Phe Phe Glu Phe
465                 470                 475                 480
Met Lys Ser Gly Lys Met Asn Glu Lys Gln Tyr His Phe Ile Glu Val
                485                 490                 495
```

Met Ala Cys Pro Gly Gly Cys Ile Asn Gly Gly Gln Pro His Val
            500                 505                 510

Asn Ala Leu Asp Arg Glu Asn Val Asp Tyr Arg Lys Leu Arg Ala Ser
        515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 170
<211> LENGTH: 583
<212> TYPE: PRT
<213> ORGANISM: Chlamydomonas reinhardtii

<400> SEQUENCE: 170

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Asp Pro Asn Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
            290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
                340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 171
<211> LENGTH: 584
<212> TYPE: PRT
<213> ORGANISM: Chlamydomonas reinhardtii

<400> SEQUENCE: 171

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
            50                  55                  60

Thr Lys Val Glu Glu Gly Met Val Ile Asn Thr Glu Ser Asp Glu Val

```
             65                  70                  75                  80
Lys Glu Arg Ile Lys Lys Arg Val Ser Met Leu Leu Asp Lys His Glu
                 85                  90                  95

Phe Lys Cys Gly Gln Cys Ser Arg Arg Glu Asn Cys Glu Phe Leu Lys
                100                 105                 110

Leu Val Ile Lys Thr Lys Ala Lys Ala Ser Lys Pro Phe Leu Pro Glu
                115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                    165                 170                 175

Ala Val Gly Thr Val Asp Asp Val Cys Leu Asp Asp Ser Thr Cys Leu
                180                 185                 190

Leu Cys Gly Gln Cys Val Ile Ala Cys Pro Val Ala Ala Leu Lys Glu
            195                 200                 205

Lys Ser His Ile Glu Lys Val Gln Glu Ala Leu Asn Asp Pro Lys Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
                260                 265                 270

Ala Asp Met Thr Ile Met Glu Glu Ala Thr Glu Leu Leu Gly Arg Val
            275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
                340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
                420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Glu Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495
```

```
Val Met Ala Cys Pro Gly Gly Cys Ile Asn Gly Gly Gln Pro His
            500                 505                 510
Val Asn Ala Leu Asp Arg Glu Asn Val Asp Tyr Arg Lys Leu Arg Ala
            515                 520                 525
Ser Val Leu Tyr Asn Gln Asp Lys Asn Val Leu Ser Lys Arg Lys Ser
    530                 535                 540
His Asp Asn Pro Ala Ile Ile Lys Met Tyr Asp Ser Tyr Phe Gly Lys
545                 550                 555                 560
Pro Gly Glu Gly Leu Ala His Lys Leu Leu His Val Lys Tyr Thr Lys
                565                 570                 575
Asp Lys Asn Val Ser Lys His Glu
            580

<210> SEQ ID NO 172
<211> LENGTH: 583
<212> TYPE: PRT
<213> ORGANISM: Chlamydomonas reinhardtii

<400> SEQUENCE: 172

Met Ala Lys Thr Ile Ile Leu Asn Gly Asn Glu Val His Thr Asp Lys
1               5                   10                  15
Asp Ile Thr Ile Leu Glu Leu Ala Arg Glu Asn Asn Val Asp Ile Pro
            20                  25                  30
Thr Leu Cys Phe Leu Lys Asp Cys Gly Asn Phe Gly Lys Cys Gly Val
            35                  40                  45
Cys Met Val Glu Val Gly Lys Gly Phe Arg Ala Ala Cys Val Ala
    50                  55                  60
Lys Val Glu Asp Gly Met Val Val Lys Thr Asn Ser Glu Lys Val Gln
65                  70                  75                  80
Glu Arg Val Lys Met Arg Val Ala Thr Leu Leu Asp Lys His Glu Phe
                85                  90                  95
Lys Cys Gly Pro Cys Pro Arg Arg Glu Asn Cys Glu Phe Leu Lys Leu
            100                 105                 110
Val Ile Lys Thr Lys Ala Lys Ala Asn Lys Pro Phe Val Val Glu Asp
            115                 120                 125
Lys Ser Gln Tyr Ile Asp Ile Arg Ser Lys Ser Ile Val Ile Asp Arg
    130                 135                 140
Thr Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
            195                 200                 205
Ser His Ile Glu Lys Val Gln Glu Ala Leu Asn Asp Pro Lys Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
```

```
            275                 280                 285
Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
                340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 173
<211> LENGTH: 583
<212> TYPE: PRT
<213> ORGANISM: Chlamydomonas reinhardtii

<400> SEQUENCE: 173

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
50                  55                  60
```

```
Lys Val Glu Asp Gly Met Val Ile Asn Thr Glu Ser Asp Glu Val Lys
 65                  70                  75                  80

Glu Arg Ile Lys Lys Arg Val Ser Met Leu Leu Asp Lys His Glu Phe
                 85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
        355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
        435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
```

```
                      485                 490                 495
Met Ala Cys Pro Gly Cys Ile Asn Gly Gly Gln Pro His Val
                500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
        530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
                580

<210> SEQ ID NO 174
<211> LENGTH: 583
<212> TYPE: PRT
<213> ORGANISM: Chlamydomonas reinhardtii

<400> SEQUENCE: 174

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270
```

```
Asp Met Thr Ile Met Glu Glu Ala Thr Glu Phe Ile Glu Arg Val Lys
            275                 280                 285

Asn Asn Gly Pro Phe Pro Met Phe Thr Ser Cys Cys Pro Ala Trp Val
    290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
            325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
    355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
            405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
    435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
            565                 570                 575

Lys Asn Val Ser Lys His Glu
            580

<210> SEQ ID NO 175
<211> LENGTH: 583
<212> TYPE: PRT
<213> ORGANISM: Chlamydomonas reinhardtii

<400> SEQUENCE: 175

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60
```

```
Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
450                 455                 460

Asn Tyr Asn Val Ala Val Ile Asn Gly Ala Ala Asn Leu Ala Glu Phe
465                 470                 475                 480
```

```
Met Asn Ser Gly Lys Ile Leu Glu Lys Asn Tyr His Phe Ile Glu Val
                485                 490                 495

Met Ala Cys Pro Gly Gly Cys Val Asn Gly Gly Gln Pro His Val
            500                 505                 510

Asn Ala Leu Asp Arg Glu Asn Val Asp Tyr Arg Lys Leu Arg Ala Ser
                515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
                580

<210> SEQ ID NO 176
<211> LENGTH: 574
<212> TYPE: PRT
<213> ORGANISM: Chlamydomonas reinhardtii

<400> SEQUENCE: 176

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270
```

-continued

```
Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
        290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
        370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
            405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Thr Val Glu Ile Gly Gly Glu
        450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
        530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Tyr Asn Lys
            565                 570
```

<210> SEQ ID NO 177
<211> LENGTH: 574
<212> TYPE: PRT
<213> ORGANISM: Chlamydomonas reinhardtii

<400> SEQUENCE: 177

```
Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
```

```
             65                  70                  75                  80
        Glu Arg Ile Lys Lys Arg Val Ser Met Leu Leu Asp Lys His Glu Phe
                             85                  90                  95
        Lys Cys Gly Gln Cys Ser Arg Arg Glu Asn Cys Glu Phe Leu Lys Leu
                            100                 105                 110
        Val Ile Lys Thr Lys Ala Lys Ala Ser Lys Pro Phe Leu Pro Glu Asp
                    115                 120                 125
        Lys Asp Ala Leu Val Asp Asn Arg Ser Lys Ala Ile Val Ile Asp Arg
        130                 135                 140
        Ser Lys Cys Val Leu Cys Gly Arg Cys Val Ala Ala Cys Lys Gln His
        145                 150                 155                 160
        Thr Ser Thr Cys Ser Ile Gln Phe Ile Lys Lys Asp Gly Gln Arg Ala
                            165                 170                 175
        Val Gly Thr Val Asp Asp Val Cys Leu Asp Asp Ser Thr Cys Leu Leu
                    180                 185                 190
        Cys Gly Gln Cys Val Ile Ala Cys Pro Val Ala Ala Leu Lys Glu Lys
                    195                 200                 205
        Ser His Ile Glu Lys Val Gln Glu Ala Leu Asn Asp Pro Lys Lys His
            210                 215                 220
        Val Ile Val Ala Met Ala Pro Ser Val Arg Thr Ala Met Gly Glu Leu
        225                 230                 235                 240
        Phe Lys Met Gly Tyr Gly Lys Asp Val Thr Gly Lys Leu Tyr Thr Ala
                            245                 250                 255
        Leu Arg Met Leu Gly Phe Asp Lys Val Phe Asp Ile Asn Phe Gly Ala
                    260                 265                 270
        Asp Met Thr Ile Met Glu Glu Ala Thr Glu Leu Leu Gly Arg Val Lys
                    275                 280                 285
        Asn Asn Gly Pro Phe Pro Met Phe Thr Ser Cys Cys Pro Ala Trp Val
        290                 295                 300
        Arg Gln Val Glu Asn Tyr Tyr Pro Glu Phe Leu Glu Asn Leu Ser Ser
        305                 310                 315                 320
        Ala Lys Ser Pro Gln Gln Ile Phe Gly Ala Ala Ser Lys Thr Tyr Tyr
                            325                 330                 335
        Pro Gln Ile Ser Gly Ile Ser Ala Lys Asp Val Phe Thr Val Thr Ile
                    340                 345                 350
        Met Pro Cys Thr Ala Lys Lys Phe Glu Ala Asp Arg Glu Glu Met Tyr
                    355                 360                 365
        Asn Glu Gly Ile Lys Asn Ile Asp Ala Val Leu Thr Thr Arg Glu Leu
            370                 375                 380
        Ala Lys Met Ile Lys Asp Ala Lys Ile Asn Phe Ala Asn Leu Glu Asp
        385                 390                 395                 400
        Glu Gln Ala Asp Pro Ala Met Gly Glu Tyr Thr Gly Ala Gly Val Ile
                            405                 410                 415
        Phe Gly Ala Thr Gly Gly Val Met Glu Ala Ala Leu Arg Thr Ala Lys
                    420                 425                 430
        Asp Phe Val Glu Asp Lys Asp Leu Thr Asp Ile Glu Tyr Thr Gln Ile
                    435                 440                 445
        Arg Gly Leu Gln Gly Ile Lys Glu Ala Thr Val Glu Ile Gly Gly Glu
            450                 455                 460
        Asn Tyr Asn Val Ala Val Ile Asn Gly Ala Ala Asn Leu Ala Glu Phe
        465                 470                 475                 480
        Met Asn Ser Gly Lys Ile Leu Glu Lys Asn Tyr His Phe Ile Glu Val
                            485                 490                 495
```

```
Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 178
<211> LENGTH: 583
<212> TYPE: PRT
<213> ORGANISM: Chlamydomonas reinhardtii

<400> SEQUENCE: 178

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
```

```
            290                 295                 300
Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
                340                 345                 350

Met Pro Cys Thr Ala Lys Lys Phe Glu Ala Asp Arg Glu Glu Met Tyr
                355                 360                 365

Asn Glu Gly Ile Lys Asn Ile Asp Ala Val Leu Thr Thr Arg Glu Leu
                370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
                435                 440                 445

Arg Gly Phe Lys Gly Ile Lys Glu Ala Thr Val Glu Ile Gly Gly Glu
                450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gln Pro His Val
                500                 505                 510

Asn Ala Leu Asp Arg Glu Asn Val Asp Tyr Arg Lys Leu Arg Ala Ser
                515                 520                 525

Val Leu Tyr Asn Gln Asp Lys Asn Val Leu Ser Lys Arg Lys Ser His
                530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
                580

<210> SEQ ID NO 179
<211> LENGTH: 583
<212> TYPE: PRT
<213> ORGANISM: Chlamydomonas reinhardtii

<400> SEQUENCE: 179

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
                50                  55                  60

Lys Val Glu Asp Gly Met Val Ile Asn Thr Glu Ser Asp Glu Val Lys
65                  70                  75                  80
```

```
Glu Arg Ile Lys Lys Arg Val Ser Met Leu Leu Asp Lys His Glu Phe
             85                  90                  95
Lys Cys Gly Gln Cys Ser Arg Arg Glu Asn Cys Glu Phe Leu Lys Leu
            100                 105                 110
Val Ile Lys Thr Lys Ala Lys Ala Ser Lys Pro Phe Leu Pro Glu Asp
            115                 120                 125
Lys Asp Ala Leu Val Asp Asn Arg Ser Lys Ala Ile Val Ile Asp Arg
            130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
            195                 200                 205
Ser His Ile Glu Lys Val Gln Glu Ala Leu Asn Asp Pro Lys Lys His
            210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
            275                 280                 285
Asn Asn Gly Pro Phe Pro Met Phe Thr Ser Cys Cys Pro Ala Trp Val
            290                 295                 300
Arg Leu Ala Gln Asn Tyr His Pro Glu Leu Leu Asp Asn Leu Ser Ser
305                 310                 315                 320
Ala Lys Ser Pro Gln Gln Ile Phe Gly Thr Ala Ser Lys Thr Tyr Tyr
            325                 330                 335
Pro Ser Ile Ser Gly Ile Ala Pro Glu Asp Val Tyr Thr Val Thr Ile
            340                 345                 350
Met Pro Cys Asn Asp Lys Lys Tyr Glu Ala Asp Ile Pro Phe Met Glu
            355                 360                 365
Thr Asn Ser Leu Arg Asp Ile Asp Ala Ser Leu Thr Thr Arg Glu Leu
            370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
            405                 410                 415
Phe Gly Ala Thr Gly Gly Val Met Glu Ala Ala Leu Arg Thr Ala Lys
            420                 425                 430
Asp Phe Val Glu Asp Lys Asp Leu Thr Asp Ile Glu Tyr Thr Gln Ile
            435                 440                 445
Arg Gly Leu Gln Gly Ile Lys Glu Ala Thr Val Glu Ile Gly Gly Glu
            450                 455                 460
Asn Tyr Asn Val Ala Val Ile Asn Gly Ala Ala Asn Leu Ala Glu Phe
465                 470                 475                 480
Met Asn Ser Gly Lys Ile Leu Glu Lys Asn Tyr His Phe Ile Glu Val
                485                 490                 495
Met Ala Cys Pro Gly Gly Cys Val Asn Gly Gly Gly Gln Pro His Val
```

```
                        500                 505                 510
Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
            565                 570                 575

Lys Asn Val Ser Lys His Glu
            580

<210> SEQ ID NO 180
<211> LENGTH: 574
<212> TYPE: PRT
<213> ORGANISM: Chlamydomonas reinhardtii

<400> SEQUENCE: 180

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
            85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
            130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
            210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
            275                 280                 285
```

```
Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
                340                 345                 350

Met Pro Cys Thr Ala Lys Lys Phe Glu Ala Asp Arg Glu Glu Met Tyr
                355                 360                 365

Asn Glu Gly Ile Lys Asn Ile Asp Ala Val Leu Thr Thr Arg Glu Leu
    370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
                435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
                500                 505                 510

Ser Ala Lys Glu Arg Glu Lys Val Asp Val Arg Thr Val Arg Ala Ser
                515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 181
<211> LENGTH: 574
<212> TYPE: PRT
<213> ORGANISM: Chlamydomonas reinhardtii

<400> SEQUENCE: 181

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Gly Lys Gly Phe Arg Ala Ala Cys Val Ala
                50                  55                  60

Lys Val Glu Asp Gly Met Val Ile Asn Thr Glu Ser Asp Val Lys
65                  70                  75                  80

Glu Arg Ile Lys Lys Arg Val Ser Met Leu Leu Asp Lys His Glu Phe
                85                  90                  95
```

```
Lys Cys Gly Gln Cys Ser Arg Arg Glu Asn Cys Glu Phe Leu Lys Leu
                100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
            210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
            290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510
```

```
Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 182
<211> LENGTH: 574
<212> TYPE: PRT
<213> ORGANISM: Chlamydomonas reinhardtii

<400> SEQUENCE: 182

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Leu Ala Gln Asn Tyr His Pro Glu Leu Leu Asp Asn Leu Ser Ser
305                 310                 315                 320
```

```
Ala Lys Ser Pro Gln Gln Ile Phe Gly Thr Ala Ser Lys Thr Tyr Tyr
            325                 330                 335

Pro Ser Ile Ser Gly Ile Ala Pro Glu Asp Val Tyr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
            370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
            405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Thr Val Glu Ile Gly Gly Glu
            450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 183
<211> LENGTH: 583
<212> TYPE: PRT
<213> ORGANISM: Chlamydomonas reinhardtii

<400> SEQUENCE: 183

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Gly Ser Asp Glu Val Lys
65                  70                  75                  80

Glu Arg Ile Lys Lys Arg Val Ser Met Leu Leu Asp Lys His Glu Phe
            85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
```

-continued

```
            115                 120                 125
Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Asp Gly Gln Arg Ala
            165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
            210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
            245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
            370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
            405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
            530                 535                 540
```

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
                580

<210> SEQ ID NO 184
<211> LENGTH: 583
<212> TYPE: PRT
<213> ORGANISM: Chlamydomonas reinhardtii

<400> SEQUENCE: 184

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
                100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
        290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr

```
            325                 330                 335
Pro Ser Ile Ser Gly Ile Ala Pro Glu Asp Val Tyr Thr Val Thr Ile
            340                 345                 350
Met Pro Cys Asn Asp Lys Lys Tyr Glu Ala Asp Ile Pro Phe Met Glu
            355                 360                 365
Thr Asn Ser Leu Arg Asp Ile Asp Ala Ser Leu Thr Thr Arg Glu Leu
            370                 375                 380
Ala Lys Met Ile Lys Asp Ala Lys Ile Lys Phe Ala Asp Leu Glu Asp
385                 390                 395                 400
Gly Glu Val Asp Pro Ala Met Gly Thr Tyr Ser Gly Ala Gly Ala Ile
                405                 410                 415
Phe Gly Ala Thr Gly Gly Val Met Glu Ala Ala Ile Arg Ser Ala Lys
                420                 425                 430
Asp Phe Ala Glu Asn Lys Glu Leu Glu Asn Val Asp Tyr Thr Glu Val
                435                 440                 445
Arg Gly Phe Lys Gly Ile Lys Glu Ala Thr Val Glu Ile Gly Gly Glu
450                 455                 460
Asn Tyr Asn Val Ala Val Ile Asn Gly Ala Ala Asn Leu Ala Glu Phe
465                 470                 475                 480
Met Asn Ser Gly Lys Ile Leu Glu Lys Asn Tyr His Phe Ile Glu Val
                485                 490                 495
Met Ala Cys Pro Gly Gly Cys Val Asn Gly Gly Gln Pro His Val
                500                 505                 510
Asn Ala Leu Asp Arg Glu Asn Val Asp Tyr Arg Lys Leu Arg Ala Ser
                515                 520                 525
Val Leu Tyr Asn Gln Asp Lys Asn Val Leu Ser Lys Arg Lys Ser His
530                 535                 540
Asp Asn Pro Ala Ile Ile Lys Met Tyr Asp Ser Tyr Phe Gly Lys Pro
545                 550                 555                 560
Gly Glu Gly Leu Ala His Lys Leu Leu His Val Lys Tyr Thr Lys Asp
                565                 570                 575
Lys Asn Val Ser Lys His Glu
            580

<210> SEQ ID NO 185
<211> LENGTH: 574
<212> TYPE: PRT
<213> ORGANISM: Chlamydomonas reinhardtii

<400> SEQUENCE: 185

Met Ala Lys Thr Ile Ile Leu Asn Gly Asn Glu Val His Thr Asp Lys
1               5                   10                  15
Asp Ile Thr Ile Leu Glu Leu Ala Arg Glu Asn Asn Val Asp Ile Pro
            20                  25                  30
Thr Leu Cys Phe Leu Lys Asp Cys Gly Asn Phe Gly Lys Cys Gly Val
        35                  40                  45
Cys Met Val Glu Val Glu Gly Lys Gly Phe Arg Ala Ala Cys Val Ala
    50                  55                  60
Lys Val Glu Asp Gly Met Val Ile Asn Thr Glu Ser Asp Glu Val Lys
65                  70                  75                  80
Glu Arg Ile Lys Lys Arg Val Ser Met Leu Leu Asp Lys His Glu Phe
                85                  90                  95
Lys Cys Gly Gln Cys Ser Arg Arg Glu Asn Cys Glu Phe Leu Lys Leu
            100                 105                 110
```

-continued

```
Val Ile Lys Thr Lys Ala Lys Ala Ser Lys Pro Phe Leu Pro Glu Asp
            115                 120                 125
Lys Asp Ala Leu Val Asp Asn Arg Ser Lys Ala Ile Val Ile Asp Arg
        130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
        275                 280                 285
Asn Asn Gly Pro Phe Pro Met Phe Thr Ser Cys Cys Pro Ala Trp Val
        290                 295                 300
Arg Leu Ala Gln Asn Tyr His Pro Glu Leu Leu Asp Asn Leu Ser Ser
305                 310                 315                 320
Ala Lys Ser Pro Gln Gln Ile Phe Gly Thr Ala Ser Lys Thr Tyr Tyr
                325                 330                 335
Pro Ser Ile Ser Gly Ile Ala Pro Glu Asp Val Tyr Thr Val Thr Ile
            340                 345                 350
Met Pro Cys Asn Asp Lys Lys Tyr Glu Ala Asp Ile Pro Phe Met Glu
        355                 360                 365
Thr Asn Ser Leu Arg Asp Ile Asp Ala Ser Leu Thr Thr Arg Glu Leu
    370                 375                 380
Ala Lys Met Ile Lys Asp Ala Lys Ile Lys Phe Ala Asp Leu Glu Asp
385                 390                 395                 400
Gly Glu Val Asp Pro Ala Met Gly Thr Tyr Ser Gly Ala Gly Ala Ile
                405                 410                 415
Phe Gly Ala Thr Gly Gly Val Met Glu Ala Ala Ile Arg Ser Ala Lys
            420                 425                 430
Asp Phe Ala Glu Asn Lys Glu Leu Glu Asn Val Asp Tyr Thr Glu Val
        435                 440                 445
Arg Gly Phe Lys Gly Ile Lys Glu Ala Glu Val Glu Ile Ala Gly Asn
    450                 455                 460
Lys Leu Asn Val Ala Val Ile Asn Gly Ala Ser Asn Phe Phe Glu Phe
465                 470                 475                 480
Met Lys Ser Gly Lys Met Asn Glu Lys Gln Tyr His Phe Ile Glu Val
                485                 490                 495
Met Ala Cys Pro Gly Gly Cys Ile Asn Gly Gly Gly Gln Pro His Val
            500                 505                 510
Ser Ala Lys Glu Arg Glu Lys Val Asp Val Arg Thr Val Arg Ala Ser
        515                 520                 525
Val Leu Tyr Asn Gln Asp Lys Asn Leu Glu Lys Arg Lys Ser His Lys
```

```
                530           535            540
Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570
```

<210> SEQ ID NO 186
<211> LENGTH: 574
<212> TYPE: PRT
<213> ORGANISM: Chlamydomonas reinhardtii

<400> SEQUENCE: 186

```
Ala Ile Asn Ile Val Ile Asp Glu Lys Thr Ile Gln Val Gln Glu Asn
1               5                   10                  15

Thr Thr Val Ile Gln Ala Ala Leu Ala Asn Gly Ile Asp Ile Pro Ser
                20                  25                  30

Leu Cys Tyr Leu Asn Glu Cys Gly Asn Val Gly Lys Cys Gly Val Cys
            35                  40                  45

Ala Val Glu Ile Glu Gly Lys Asn Asn Leu Ala Leu Ala Cys Ile Thr
        50                  55                  60

Lys Val Glu Glu Gly Met Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Arg Glu Asn Cys Glu Phe Leu Lys Leu
            100                 105                 110

Val Ile Lys Thr Lys Ala Lys Ala Asn Lys Pro Phe Val Val Glu Asp
            115                 120                 125

Lys Ser Gln Tyr Ile Asp Ile Arg Ser Lys Ser Ile Val Ile Asp Arg
        130                 135                 140

Thr Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335
```

```
Pro Gln Ile Ser Gly Ile Ser Ala Lys Asp Val Phe Thr Val Thr Ile
                340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
        370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
    450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gly Gln Pro His Val
            500                 505                 510

Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 187
<211> LENGTH: 575
<212> TYPE: PRT
<213> ORGANISM: Chlamydomonas reinhardtii

<400> SEQUENCE: 187

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140
```

```
Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
            165                 170                 175

Ala Val Gly Thr Val Asp Asp Val Cys Leu Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
            435                 440                 445

Ile Arg Gly Leu Gln Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
            515                 520                 525

Ser Val Leu Tyr Asn Gln Asp Lys Asn Leu Glu Lys Arg Lys Ser His
        530                 535                 540

Lys Asn Thr Ala Leu Leu Asn Met Tyr Tyr Asp Tyr Met Gly Ala Pro
545                 550                 555                 560
```

```
Gly Gln Gly Lys Ala His Glu Leu Leu His Leu Lys Tyr Asn Lys
                565                 570                 575
```

<210> SEQ ID NO 188
<211> LENGTH: 575
<212> TYPE: PRT
<213> ORGANISM: Chlamydomonas reinhardtii

<400> SEQUENCE: 188

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
        355                 360                 365
```

Tyr Asn Glu Gly Ile Lys Asn Ile Asp Ala Val Leu Thr Thr Arg Glu
            370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
                500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 189
<211> LENGTH: 574
<212> TYPE: PRT
<213> ORGANISM: Chlamydomonas reinhardtii

<400> SEQUENCE: 189

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
    50                  55                  60

Lys Val Glu Asp Gly Met Val Val Lys Thr Asn Ser Glu Lys Val Gln
65              70                  75                  80

Glu Arg Val Lys Met Arg Val Ala Thr Leu Leu Asp Lys His Glu Phe
                85                  90                  95

Lys Cys Gly Pro Cys Pro Arg Glu Asn Cys Glu Phe Leu Lys Leu
            100                 105                 110

Val Ile Lys Thr Lys Ala Lys Ala Asn Lys Pro Phe Val Val Glu Asp
            115                 120                 125

Lys Ser Gln Tyr Ile Asp Ile Arg Ser Lys Ser Ile Val Ile Asp Arg
130                 135                 140

Thr Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile

```
              165                 170                 175
Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
            195                 200                 205

Thr His Val Asp Arg Val Lys Glu Ala Leu Glu Asp Pro Asn Lys His
            210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
            245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
            275                 280                 285

Asn Asn Gly Pro Phe Pro Met Phe Thr Ser Cys Cys Pro Ala Trp Val
            290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
            405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Thr Val Glu Ile Gly Gly Glu
            450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 190
```

<211> LENGTH: 575
<212> TYPE: PRT
<213> ORGANISM: Chlamydomonas reinhardtii

<400> SEQUENCE: 190

| | | | | | | | | | | | | | | |
|---|---|---|---|---|---|---|---|---|---|---|---|---|---|---|
| Met | Ala | Ile | Asn | Ile | Val | Ile | Asp | Glu | Lys | Thr | Ile | Gln | Val | Gln | Glu |
| 1 | | | | 5 | | | | | 10 | | | | | 15 | |
| Asn | Thr | Thr | Val | Ile | Gln | Ala | Ala | Leu | Ala | Asn | Gly | Ile | Asp | Ile | Pro |
| | | | 20 | | | | | 25 | | | | | 30 | | |
| Ser | Leu | Cys | Tyr | Leu | Asn | Glu | Cys | Gly | Asn | Val | Gly | Lys | Cys | Gly | Val |
| | | | 35 | | | | | 40 | | | | | 45 | | |
| Cys | Ala | Val | Glu | Ile | Glu | Gly | Lys | Asn | Asn | Leu | Ala | Leu | Ala | Cys | Ile |
| 50 | | | | | 55 | | | | | 60 | | | | | |
| Thr | Lys | Val | Glu | Glu | Gly | Met | Val | Val | Lys | Thr | Asn | Ser | Glu | Lys | Val |
| 65 | | | | | 70 | | | | | 75 | | | | | 80 |
| Gln | Glu | Arg | Val | Lys | Met | Arg | Val | Ala | Thr | Leu | Leu | Asp | Lys | His | Glu |
| | | | | 85 | | | | | 90 | | | | | 95 | |
| Phe | Lys | Cys | Gly | Pro | Cys | Pro | Arg | Arg | Glu | Asn | Cys | Glu | Phe | Leu | Lys |
| | | | 100 | | | | | 105 | | | | | 110 | | |
| Leu | Val | Ile | Lys | Thr | Lys | Ala | Lys | Ala | Asn | Lys | Pro | Phe | Val | Val | Glu |
| | | | 115 | | | | | 120 | | | | | 125 | | |
| Asp | Lys | Ser | Gln | Tyr | Ile | Asp | Ile | Arg | Ser | Lys | Ser | Ile | Val | Ile | Asp |
| | 130 | | | | | 135 | | | | | 140 | | | | |
| Arg | Thr | Lys | Cys | Val | Leu | Cys | Gly | Arg | Cys | Val | Ala | Ala | Cys | Lys | Gln |
| 145 | | | | | 150 | | | | | 155 | | | | | 160 |
| His | Thr | Ser | Thr | Cys | Ser | Ile | Gln | Phe | Ile | Lys | Lys | Asp | Gly | Gln | Arg |
| | | | | 165 | | | | | 170 | | | | | 175 | |
| Ala | Val | Gly | Thr | Val | Asp | Asp | Val | Cys | Leu | Asp | Asp | Ser | Thr | Cys | Leu |
| | | | 180 | | | | | 185 | | | | | 190 | | |
| Leu | Cys | Gly | Gln | Cys | Val | Ile | Ala | Cys | Pro | Val | Ala | Ala | Leu | Lys | Glu |
| | | | 195 | | | | | 200 | | | | | 205 | | |
| Lys | Ser | His | Ile | Glu | Lys | Val | Gln | Glu | Ala | Leu | Asn | Asp | Pro | Lys | Lys |
| | 210 | | | | | 215 | | | | | 220 | | | | |
| His | Val | Ile | Val | Ala | Met | Ala | Pro | Ser | Val | Arg | Thr | Ala | Met | Gly | Glu |
| 225 | | | | | 230 | | | | | 235 | | | | | 240 |
| Leu | Phe | Lys | Met | Gly | Tyr | Gly | Lys | Asp | Val | Thr | Gly | Lys | Leu | Tyr | Thr |
| | | | | 245 | | | | | 250 | | | | | 255 | |
| Ala | Leu | Arg | Met | Leu | Gly | Phe | Asp | Lys | Val | Phe | Asp | Ile | Asn | Phe | Gly |
| | | | 260 | | | | | 265 | | | | | 270 | | |
| Ala | Asp | Met | Thr | Ile | Met | Glu | Glu | Ala | Thr | Glu | Leu | Leu | Gly | Arg | Val |
| | | | 275 | | | | | 280 | | | | | 285 | | |
| Lys | Asn | Asn | Gly | Pro | Phe | Pro | Met | Phe | Thr | Ser | Cys | Cys | Pro | Ala | Trp |
| | 290 | | | | | 295 | | | | | 300 | | | | |
| Val | Arg | Gln | Val | Glu | Asn | Tyr | Tyr | Pro | Glu | Phe | Leu | Glu | Asn | Leu | Ser |
| 305 | | | | | 310 | | | | | 315 | | | | | 320 |
| Ser | Ala | Lys | Ser | Pro | Gln | Gln | Ile | Phe | Gly | Ala | Ala | Ser | Lys | Thr | Tyr |
| | | | | 325 | | | | | 330 | | | | | 335 | |
| Tyr | Pro | Gln | Ile | Ser | Gly | Ile | Ser | Ala | Lys | Asp | Val | Phe | Thr | Val | Thr |
| | | | 340 | | | | | 345 | | | | | 350 | | |
| Ile | Met | Pro | Cys | Thr | Ala | Lys | Lys | Phe | Glu | Ala | Asp | Arg | Glu | Glu | Met |
| | | | 355 | | | | | 360 | | | | | 365 | | |
| Tyr | Asn | Glu | Gly | Ile | Lys | Asn | Ile | Asp | Ala | Val | Leu | Thr | Thr | Arg | Glu |
| | 370 | | | | | 375 | | | | | 380 | | | | |
| Leu | Ala | Lys | Met | Ile | Lys | Asp | Ala | Lys | Ile | Asn | Phe | Ala | Asn | Leu | Glu |

```
                385                 390                 395                 400
Asp Glu Gln Ala Asp Pro Ala Met Gly Glu Tyr Thr Gly Ala Gly Val
                    405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
                500                 505                 510

Val Ser Ala Lys Glu Arg Glu Lys Val Asp Val Arg Thr Val Arg Ala
            515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 191
<211> LENGTH: 575
<212> TYPE: PRT
<213> ORGANISM: Chlamydomonas reinhardtii

<400> SEQUENCE: 191

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Leu Ala Leu Ala Cys Ile
50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190
```

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
            245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
            275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
            325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
            370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
            405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
            435                 440                 445

Ile Arg Gly Leu Gln Gly Ile Lys Glu Ala Thr Val Glu Ile Gly Gly
450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
            485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
            515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
            565                 570                 575

<210> SEQ ID NO 192
<211> LENGTH: 574
<212> TYPE: PRT
<213> ORGANISM: Chlamydomonas reinhardtii

<400> SEQUENCE: 192

-continued

```
Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
    50                  55                  60

Lys Val Glu Asp Gly Met Val Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Arg Glu Asn Cys Glu Phe Leu Lys Leu
            100                 105                 110

Val Ile Lys Thr Lys Ala Lys Ala Asn Lys Pro Phe Val Val Glu Asp
    115                 120                 125

Lys Ser Gln Tyr Ile Asp Ile Arg Ser Lys Ser Ile Val Ile Asp Arg
130                 135                 140

Thr Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
    195                 200                 205

Thr His Val Asp Arg Val Lys Glu Ala Leu Glu Asp Pro Asn Lys His
210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
    275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
    355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415
```

```
Phe Gly Ala Thr Gly Gly Val Met Glu Ala Ala Leu Arg Thr Ala Lys
                420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
    450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Cys Val Asn Gly Gly Gln Pro His Val
                500                 505                 510

Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 193
<211> LENGTH: 575
<212> TYPE: PRT
<213> ORGANISM: Chlamydomonas reinhardtii

<400> SEQUENCE: 193

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
                100                 105                 110

Leu Val Ile Lys Thr Lys Ala Lys Ala Ser Lys Pro Phe Leu Pro Glu
            115                 120                 125

Asp Lys Asp Ala Leu Val Asp Asn Arg Ser Lys Ala Ile Val Ile Asp
        130                 135                 140

Arg Ser Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220
```

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
            245                 250                 255

Ser Met Arg Ala Leu Gly Phe Asp Lys Val Phe Asp Ile Asn Phe Gly
        260                 265                 270

Ala Asp Met Thr Ile Met Glu Glu Ala Thr Glu Phe Ile Glu Arg Val
    275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
            325                 330                 335

Tyr Pro Gln Ile Ser Gly Ile Ser Ala Lys Asp Val Phe Thr Val Thr
        340                 345                 350

Ile Met Pro Cys Thr Ala Lys Lys Phe Glu Ala Asp Arg Glu Glu Met
    355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
            405                 410                 415

Ile Phe Gly Ala Thr Gly Gly Val Met Glu Ala Ala Leu Arg Thr Ala
        420                 425                 430

Lys Asp Phe Val Glu Asp Lys Asp Leu Thr Asp Ile Glu Tyr Thr Gln
    435                 440                 445

Ile Arg Gly Leu Gln Gly Ile Lys Glu Ala Thr Val Glu Ile Gly Gly
450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
            485                 490                 495

Val Met Ala Cys Pro Gly Gly Cys Val Asn Gly Gly Gly Gln Pro His
        500                 505                 510

Val Ser Ala Lys Glu Arg Glu Lys Val Asp Val Arg Thr Val Arg Ala
    515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
            565                 570                 575

<210> SEQ ID NO 194
<211> LENGTH: 574
<212> TYPE: PRT
<213> ORGANISM: Chlamydomonas reinhardtii

<400> SEQUENCE: 194

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro

-continued

```
                20                  25                  30
Thr Leu Cys Phe Leu Lys Asp Cys Gly Asn Phe Gly Lys Cys Gly Val
             35                  40                  45
Cys Met Val Glu Val Glu Gly Lys Gly Phe Arg Ala Ala Cys Val Ala
 50                  55                  60
Lys Val Glu Asp Gly Met Val Val Lys Thr Asn Ser Glu Lys Val Gln
 65                  70                  75                  80
Glu Arg Val Lys Met Arg Val Ala Thr Leu Leu Asp Lys His Glu Phe
                 85                  90                  95
Lys Cys Gly Pro Cys Pro Arg Arg Glu Asn Cys Glu Phe Leu Lys Leu
                100                 105                 110
Val Ile Lys Thr Lys Ala Lys Ala Asn Lys Pro Phe Val Val Glu Asp
            115                 120                 125
Lys Ser Gln Tyr Ile Asp Ile Arg Ser Lys Ser Ile Val Ile Asp Arg
        130                 135                 140
Thr Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
    210                 215                 220
Val Ile Val Ala Met Ala Pro Ser Ile Arg Thr Ser Met Gly Glu Leu
225                 230                 235                 240
Phe Lys Leu Gly Tyr Gly Val Asp Val Thr Gly Lys Leu Tyr Ala Ser
                245                 250                 255
Met Arg Ala Leu Gly Phe Asp Lys Val Phe Asp Ile Asn Phe Gly Ala
            260                 265                 270
Asp Met Thr Ile Met Glu Glu Ala Thr Glu Phe Ile Glu Arg Val Lys
        275                 280                 285
Asn Asn Gly Pro Phe Pro Met Phe Thr Ser Cys Cys Pro Ala Trp Val
    290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
            340                 345                 350
Met Pro Cys Thr Ala Lys Lys Phe Glu Ala Asp Arg Glu Glu Met Tyr
        355                 360                 365
Asn Glu Gly Ile Lys Asn Ile Asp Ala Val Leu Thr Thr Arg Glu Leu
    370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
            420                 425                 430
Asp Phe Val Glu Asp Lys Asp Leu Thr Asp Ile Glu Tyr Thr Gln Ile
        435                 440                 445
```

```
Arg Gly Leu Gln Gly Ile Lys Glu Ala Thr Val Glu Ile Gly Gly Glu
            450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
            530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 195
<211> LENGTH: 574
<212> TYPE: PRT
<213> ORGANISM: Chlamydomonas reinhardtii

<400> SEQUENCE: 195

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
50                  55                  60

Lys Val Glu Asp Gly Met Val Ile Asn Thr Ser Asp Glu Val Lys
65                  70                  75                  80

Glu Arg Ile Lys Lys Arg Val Ser Met Leu Leu Asp Lys His Glu Phe
            85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
            165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
            195                 200                 205

Thr His Val Asp Arg Val Lys Glu Ala Leu Glu Asp Pro Asn Lys His
            210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
```

245                 250                 255
Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
    450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gly Gln Pro His Val
            500                 505                 510

Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 196
<211> LENGTH: 575
<212> TYPE: PRT
<213> ORGANISM: Chlamydomonas reinhardtii

<400> SEQUENCE: 196

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

```
Cys Ala Val Glu Ile Glu Gly Lys Asn Asn Leu Ala Leu Ala Cys Ile
 50                  55                  60
Thr Lys Val Glu Glu Gly Met Val Ile Asn Thr Glu Ser Asp Glu Val
 65                  70                  75                  80
Lys Glu Arg Ile Lys Lys Arg Val Ser Met Leu Leu Asp Lys His Glu
                 85                  90                  95
Phe Lys Cys Gly Gln Cys Ser Arg Arg Glu Asn Cys Glu Phe Leu Lys
                100                 105                 110
Leu Val Ile Lys Thr Lys Ala Lys Ala Ser Lys Pro Phe Leu Pro Glu
                115                 120                 125
Asp Lys Asp Ala Leu Val Asp Asn Arg Ser Lys Ala Ile Val Ile Asp
130                 135                 140
Arg Ser Lys Cys Val Leu Cys Gly Arg Cys Val Ala Ala Cys Lys Gln
145                 150                 155                 160
His Thr Ser Thr Cys Ser Ile Gln Phe Ile Lys Lys Asp Gly Gln Arg
                165                 170                 175
Ala Val Gly Thr Val Asp Asp Val Cys Leu Asp Asp Ser Thr Cys Leu
                180                 185                 190
Leu Cys Gly Gln Cys Val Ile Ala Cys Pro Val Ala Ala Leu Lys Glu
                195                 200                 205
Lys Ser His Ile Glu Lys Val Gln Glu Ala Leu Asn Asp Pro Lys Lys
210                 215                 220
His Val Ile Val Ala Met Ala Pro Ser Val Arg Thr Ala Met Gly Glu
225                 230                 235                 240
Leu Phe Lys Met Gly Tyr Gly Lys Asp Val Thr Gly Lys Leu Tyr Thr
                245                 250                 255
Ala Leu Arg Met Leu Gly Phe Asp Lys Val Phe Asp Ile Asn Phe Gly
                260                 265                 270
Ala Asp Met Thr Ile Met Glu Glu Ala Thr Glu Leu Leu Gly Arg Val
                275                 280                 285
Lys Asn Asn Gly Pro Phe Pro Met Phe Thr Ser Cys Cys Pro Ala Trp
                290                 295                 300
Val Arg Gln Val Glu Asn Tyr Tyr Pro Glu Phe Leu Glu Asn Leu Ser
305                 310                 315                 320
Ser Ala Lys Ser Pro Gln Gln Ile Phe Gly Ala Ala Ser Lys Thr Tyr
                325                 330                 335
Tyr Pro Gln Ile Ser Gly Ile Ser Ala Lys Asp Val Phe Thr Val Thr
                340                 345                 350
Ile Met Pro Cys Thr Ala Lys Lys Phe Glu Ala Asp Arg Glu Glu Met
                355                 360                 365
Tyr Asn Glu Gly Ile Lys Asn Ile Asp Ala Val Leu Thr Thr Arg Glu
370                 375                 380
Leu Ala Lys Met Ile Lys Asp Ala Lys Ile Asn Phe Ala Asn Leu Glu
385                 390                 395                 400
Asp Glu Gln Ala Asp Pro Ala Met Gly Glu Tyr Thr Gly Ala Gly Val
                405                 410                 415
Ile Phe Gly Ala Thr Gly Gly Val Met Glu Ala Ala Leu Arg Thr Ala
                420                 425                 430
Lys Asp Phe Val Glu Asp Lys Asp Leu Thr Asp Ile Glu Tyr Thr Gln
                435                 440                 445
Ile Arg Gly Leu Gln Gly Ile Lys Glu Ala Thr Val Glu Ile Gly Gly
450                 455                 460
Glu Asn Tyr Asn Val Ala Val Ile Asn Gly Ala Ala Asn Leu Ala Glu
```

```
                465             470             475             480
Phe Met Asn Ser Gly Lys Ile Leu Glu Lys Asn Tyr His Phe Ile Glu
                485             490             495
Val Met Ala Cys Pro Gly Gly Cys Val Asn Gly Gly Gln Pro His
                500             505             510
Val Ser Ala Lys Glu Arg Lys Val Asp Val Arg Thr Val Arg Ala
                515             520             525
Ser Val Leu Tyr Asn Gln Asp Lys Asn Leu Glu Lys Arg Lys Ser His
                530             535             540
Lys Asn Thr Ala Leu Leu Asn Met Tyr Tyr Asp Tyr Met Gly Ala Pro
545             550             555             560
Gly Gln Gly Lys Ala His Glu Leu Leu His Leu Lys Tyr Asn Lys
                565             570             575

<210> SEQ ID NO 197
<211> LENGTH: 574
<212> TYPE: PRT
<213> ORGANISM: Chlamydomonas reinhardtii

<400> SEQUENCE: 197

Met Ala Lys Thr Ile Ile Leu Asn Gly Asn Glu Val His Thr Asp Lys
1               5               10              15
Asp Ile Thr Ile Leu Glu Leu Ala Arg Glu Asn Asn Val Asp Ile Pro
                20              25              30
Thr Leu Cys Phe Leu Lys Asp Cys Gly Asn Phe Gly Lys Cys Gly Val
                35              40              45
Cys Met Val Glu Val Glu Gly Lys Gly Phe Arg Ala Ala Cys Val Ala
        50              55              60
Lys Val Glu Asp Gly Met Val Val Lys Thr Asn Ser Glu Lys Val Gln
65              70              75              80
Glu Arg Val Lys Met Arg Val Ala Thr Leu Leu Asp Lys His Glu Phe
                85              90              95
Lys Cys Gly Pro Cys Pro Arg Arg Glu Asn Cys Glu Phe Leu Lys Leu
                100             105             110
Val Ile Lys Thr Lys Ala Lys Ala Asn Lys Pro Phe Val Val Glu Asp
                115             120             125
Lys Ser Gln Tyr Ile Asp Ile Arg Ser Lys Ser Ile Val Ile Asp Arg
        130             135             140
Thr Lys Cys Val Leu Cys Gly Arg Cys Val Ala Ala Cys Lys Gln His
145             150             155             160
Thr Ser Thr Cys Ser Ile Gln Phe Ile Lys Asp Gly Gln Arg Ala
                165             170             175
Val Gly Thr Val Asp Asp Val Cys Leu Asp Asp Ser Thr Cys Leu Leu
                180             185             190
Cys Gly Gln Cys Val Ile Ala Cys Pro Val Ala Ala Leu Lys Glu Lys
                195             200             205
Ser His Ile Glu Lys Val Gln Glu Ala Leu Asn Asp Pro Lys Lys His
        210             215             220
Val Ile Val Ala Met Ala Pro Ser Val Arg Thr Ala Met Gly Glu Leu
225             230             235             240
Phe Lys Met Gly Tyr Gly Lys Asp Val Thr Gly Lys Leu Tyr Thr Ala
                245             250             255
Leu Arg Met Leu Gly Phe Asp Lys Val Phe Asp Ile Asn Phe Gly Ala
                260             265             270
```

```
Asp Met Thr Ile Met Glu Ala Thr Glu Leu Leu Gly Arg Val Lys
            275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
    450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 198
<211> LENGTH: 574
<212> TYPE: PRT
<213> ORGANISM: Chlamydomonas reinhardtii

<400> SEQUENCE: 198

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80
```

```
Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
    370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
    450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495
```

```
Met Ala Cys Pro Gly Gly Cys Val Asn Gly Gly Gln Pro His Val
                500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
        530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 199
<211> LENGTH: 574
<212> TYPE: PRT
<213> ORGANISM: Chlamydomonas reinhardtii

<400> SEQUENCE: 199

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
    290                 295                 300
```

```
Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
            405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Thr Val Glu Ile Gly Gly Glu
450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 200
<211> LENGTH: 584
<212> TYPE: PRT
<213> ORGANISM: Chlamydomonas reinhardtii

<400> SEQUENCE: 200

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
```

```
            100                 105                 110
Leu Val Ile Lys Thr Lys Ala Lys Ala Asn Lys Pro Phe Val Val Glu
            115                 120                 125
Asp Lys Ser Gln Tyr Ile Asp Ile Arg Ser Lys Ser Ile Val Ile Asp
130                 135                 140
Arg Thr Lys Cys Val Leu Cys Gly Arg Cys Glu Ala Ala Cys Lys Thr
145                 150                 155                 160
Lys Thr Gly Thr Gly Ala Ile Ser Ile Cys Lys Ser Glu Ser Gly Arg
            165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
            195                 200                 205
Lys Thr His Val Asp Arg Val Lys Glu Ala Leu Glu Asp Pro Asn Lys
            210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
            245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
            275                 280                 285
Lys Asn Asn Gly Pro Phe Pro Met Phe Thr Ser Cys Cys Pro Ala Trp
            290                 295                 300
Val Arg Gln Val Glu Asn Tyr Tyr Pro Glu Phe Leu Glu Asn Leu Ser
305                 310                 315                 320
Ser Ala Lys Ser Pro Gln Gln Ile Phe Gly Ala Ala Ser Lys Thr Tyr
            325                 330                 335
Tyr Pro Gln Ile Ser Gly Ile Ser Ala Lys Asp Val Phe Thr Val Thr
            340                 345                 350
Ile Met Pro Cys Thr Ala Lys Lys Phe Glu Ala Asp Arg Glu Glu Met
            355                 360                 365
Tyr Asn Glu Gly Ile Lys Asn Ile Asp Ala Val Leu Thr Thr Arg Glu
            370                 375                 380
Leu Ala Lys Met Ile Lys Asp Ala Lys Ile Asn Phe Ala Asn Leu Glu
385                 390                 395                 400
Asp Glu Gln Ala Asp Pro Ala Met Gly Glu Tyr Thr Gly Ala Gly Val
            405                 410                 415
Ile Phe Gly Ala Thr Gly Gly Val Met Glu Ala Ala Leu Arg Thr Ala
            420                 425                 430
Lys Asp Phe Val Glu Asp Lys Asp Leu Thr Asp Ile Glu Tyr Thr Gln
            435                 440                 445
Ile Arg Gly Leu Gln Gly Ile Lys Glu Ala Thr Val Glu Ile Gly Gly
            450                 455                 460
Glu Asn Tyr Asn Val Ala Val Ile Asn Gly Ala Ala Asn Leu Ala Glu
465                 470                 475                 480
Phe Met Asn Ser Gly Lys Ile Leu Glu Lys Asn Tyr His Phe Ile Glu
            485                 490                 495
Val Met Ala Cys Pro Gly Gly Cys Val Asn Gly Gly Gly Gln Pro His
            500                 505                 510
Val Asn Ala Leu Asp Arg Glu Asn Val Asp Tyr Arg Lys Leu Arg Ala
            515                 520                 525
```

```
Ser Val Leu Tyr Asn Gln Asp Lys Asn Val Leu Ser Lys Arg Lys Ser
            530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 201
<211> LENGTH: 575
<212> TYPE: PRT
<213> ORGANISM: Chlamydomonas reinhardtii

<400> SEQUENCE: 201

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
```

```
                305                 310                 315                 320
Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
                340                 345                 350

Ile Met Pro Cys Thr Ala Lys Lys Phe Glu Ala Asp Arg Glu Glu Met
                355                 360                 365

Tyr Asn Glu Gly Ile Lys Asn Ile Asp Ala Val Leu Thr Thr Arg Glu
                370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
                420                 425                 430

Lys Asp Phe Ala Glu Asn Lys Glu Leu Glu Asn Val Asp Tyr Thr Glu
                435                 440                 445

Val Arg Gly Phe Lys Gly Ile Lys Glu Ala Thr Val Glu Ile Gly Gly
                450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
                500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
                530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 202
<211> LENGTH: 575
<212> TYPE: PRT
<213> ORGANISM: Chlamydomonas reinhardtii

<400> SEQUENCE: 202

Met Ala Ile Asn Ile Val Ile Asp Glu Lys Thr Ile Gln Val Gln Glu
1               5                   10                  15

Asn Thr Thr Val Ile Gln Ala Ala Leu Ala Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
                50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
                100                 105                 110
```

```
Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
            435                 440                 445

Ile Arg Gly Leu Gln Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
    515                 520                 525

Ser Val Leu Tyr Asn Gln Asp Lys Asn Leu Glu Lys Arg Lys Ser His
```

```
            530                 535                 540
Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 203
<211> LENGTH: 584
<212> TYPE: PRT
<213> ORGANISM: Chlamydomonas reinhardtii

<400> SEQUENCE: 203

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335
```

```
Tyr Pro Gln Ile Ser Gly Ile Ser Ala Lys Asp Val Phe Thr Val Thr
                340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
        370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 204
<211> LENGTH: 584
<212> TYPE: PRT
<213> ORGANISM: Chlamydomonas reinhardtii

<400> SEQUENCE: 204

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125
```

-continued

```
Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
                180                 185                 190

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
                340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
530                 535                 540
```

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 205
<211> LENGTH: 575
<212> TYPE: PRT
<213> ORGANISM: Chlamydomonas reinhardtii

<400> SEQUENCE: 205

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
        340                 345                 350

Ile Met Pro Cys Thr Ala Lys Lys Phe Glu Ala Asp Arg Glu Glu Met
        355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
                420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Glu Val Glu Ile Ala Gly
        450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
        530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 206
<211> LENGTH: 575
<212> TYPE: PRT
<213> ORGANISM: Chlamydomonas reinhardtii

<400> SEQUENCE: 206

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp

```
                130                 135                 140
Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
                180                 185                 190

Leu Cys Gly Gln Cys Val Ala Ala Cys Pro Val Gly Ala Leu Thr Glu
                195                 200                 205

Lys Thr His Val Asp Arg Val Lys Glu Ala Leu Glu Asp Pro Asn Lys
                210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
                260                 265                 270

Ala Asp Met Thr Ile Met Glu Glu Ala Thr Glu Phe Ile Glu Arg Val
                275                 280                 285

Lys Asn Asn Gly Pro Phe Pro Met Phe Thr Ser Cys Cys Pro Ala Trp
                290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
                340                 345                 350

Ile Met Pro Cys Asn Asp Lys Lys Tyr Glu Ala Asp Ile Pro Phe Met
                355                 360                 365

Glu Thr Asn Ser Leu Arg Asp Ile Asp Ala Ser Leu Thr Thr Arg Glu
                370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Glu Val Glu Ile Ala Gly
                450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
                530                 535                 540

Lys Asn Thr Ala Leu Leu Asn Met Tyr Tyr Asp Tyr Met Gly Ala Pro
545                 550                 555                 560
```

Gly Gln Gly Lys Ala His Glu Leu Leu His Leu Lys Tyr Asn Lys
                565                 570                 575

<210> SEQ ID NO 207
<211> LENGTH: 575
<212> TYPE: PRT
<213> ORGANISM: Chlamydomonas reinhardtii

<400> SEQUENCE: 207

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met

```
                355                 360                 365
Glu Thr Asn Ser Leu Arg Asp Ile Asp Ala Ser Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
                420                 425                 430

Lys Asp Phe Ala Glu Asn Lys Glu Leu Glu Asn Val Asp Tyr Thr Glu
                435                 440                 445

Val Arg Gly Phe Lys Gly Ile Lys Glu Ala Thr Val Glu Ile Gly Gly
                450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
                500                 505                 510

Val Ser Ala Lys Glu Arg Glu Lys Val Asp Val Arg Thr Val Arg Ala
                515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 208
<211> LENGTH: 584
<212> TYPE: PRT
<213> ORGANISM: Chlamydomonas reinhardtii

<400> SEQUENCE: 208

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
                50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
                100                 105                 110

Leu Val Ile Lys Thr Lys Ala Lys Ala Asn Lys Pro Phe Val Val Glu
                115                 120                 125

Asp Lys Ser Gln Tyr Ile Asp Ile Arg Ser Lys Ser Ile Val Ile Asp
                130                 135                 140

Arg Thr Lys Cys Val Leu Cys Gly Arg Cys Glu Ala Ala Cys Lys Thr
145                 150                 155                 160
```

```
Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp
            290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Glu Val Glu Ile Ala Gly
            450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
```

<210> SEQ ID NO 209
<211> LENGTH: 584
<212> TYPE: PRT
<213> ORGANISM: Chlamydomonas reinhardtii

<400> SEQUENCE: 209

```
Met Ala Ile Asn Ile Val Ile Asp Glu Lys Thr Ile Gln Val Gln Glu
1               5                   10                  15
Asn Thr Thr Val Ile Gln Ala Ala Leu Ala Asn Gly Ile Asp Ile Pro
            20                  25                  30
Ser Leu Cys Tyr Leu Asn Glu Cys Gly Asn Val Gly Lys Cys Gly Val
        35                  40                  45
Cys Ala Val Glu Ile Glu Gly Lys Asn Asn Leu Ala Leu Ala Cys Ile
    50                  55                  60
Thr Lys Val Glu Glu Gly Met Val Val Lys Thr Asn Ser Glu Lys Val
65                  70                  75                  80
Gln Glu Arg Val Lys Met Arg Val Ala Thr Leu Leu Asp Lys His Glu
                85                  90                  95
Phe Lys Cys Gly Pro Cys Pro Arg Arg Glu Asn Cys Glu Phe Leu Lys
            100                 105                 110
Leu Val Ile Lys Thr Lys Ala Lys Ala Asn Lys Pro Phe Val Val Glu
        115                 120                 125
Asp Lys Ser Gln Tyr Ile Asp Ile Arg Ser Lys Ser Ile Val Ile Asp
    130                 135                 140
Arg Thr Lys Cys Val Leu Cys Gly Arg Cys Glu Ala Ala Cys Lys Thr
145                 150                 155                 160
Lys Thr Gly Thr Gly Ala Ile Ser Ile Cys Lys Ser Glu Ser Gly Arg
                165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
        195                 200                 205
Lys Thr His Val Asp Arg Val Lys Glu Ala Leu Glu Asp Pro Asn Lys
    210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
                245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
        275                 280                 285
Lys Asn Asn Gly Pro Phe Pro Met Phe Thr Ser Cys Cys Pro Ala Trp
    290                 295                 300
Val Arg Leu Ala Gln Asn Tyr His Pro Glu Leu Leu Asp Asn Leu Ser
305                 310                 315                 320
Ser Ala Lys Ser Pro Gln Gln Ile Phe Gly Thr Ala Ser Lys Thr Tyr
                325                 330                 335
Tyr Pro Ser Ile Ser Gly Ile Ala Pro Glu Asp Val Tyr Thr Val Thr
            340                 345                 350
Ile Met Pro Cys Asn Asp Lys Lys Tyr Glu Ala Asp Ile Pro Phe Met
        355                 360                 365
```

```
Glu Thr Asn Ser Leu Arg Asp Ile Asp Ala Ser Leu Thr Thr Arg Glu
    370             375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420             425                 430

Lys Asp Phe Ala Glu Asn Lys Glu Leu Glu Asn Val Asp Tyr Thr Glu
                435                 440                 445

Val Arg Gly Phe Lys Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
                500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580

<210> SEQ ID NO 210
<211> LENGTH: 36
<212> TYPE: DNA
<213> ORGANISM: Chlamydomonas reinhardtii

<400> SEQUENCE: 210
gcatcgcata tgacaaacat gacaaatatg ataaat                              36

<210> SEQ ID NO 211
<211> LENGTH: 40
<212> TYPE: DNA
<213> ORGANISM: Chlamydomonas reinhardtii

<400> SEQUENCE: 211
gcatcgagat cttaatttgg cttttgcag tcgcctcttg                            40

<210> SEQ ID NO 212
<211> LENGTH: 40
<212> TYPE: DNA
<213> ORGANISM: Chlamydomonas reinhardtii

<400> SEQUENCE: 212
gcatcgccat gggattgaat gaaacaccat ctgcaaaccg                           40

<210> SEQ ID NO 213
<211> LENGTH: 43
<212> TYPE: DNA
<213> ORGANISM: Chlamydomonas reinhardtii

<400> SEQUENCE: 213
```
gcatcgggat ccctaaagaa tttctgcaag tatgtccggg aag         43

<210> SEQ ID NO 214
<211> LENGTH: 37
<212> TYPE: DNA
<213> ORGANISM: Chlamydomonas reinhardtii

<400> SEQUENCE: 214
gcatcgcata tggttgaaaa agttgatttt ataaaag               37

<210> SEQ ID NO 215
<211> LENGTH: 42
<212> TYPE: DNA
<213> ORGANISM: Chlamydomonas reinhardtii

<400> SEQUENCE: 215
gcatcgagat ctttaaaaat aaatatctct ctttcctttt tc         42

<210> SEQ ID NO 216
<211> LENGTH: 46
<212> TYPE: DNA
<213> ORGANISM: Chlamydomonas reinhardtii

<400> SEQUENCE: 216
gcgaattgca aagactggca aaggatctga atgtaaaaga tatcag     46

<210> SEQ ID NO 217
<211> LENGTH: 46
<212> TYPE: DNA
<213> ORGANISM: Chlamydomonas reinhardtii

<400> SEQUENCE: 217
cgcttaacgt ttctgaccgt ttcctagact tacattttct atagtc     46

<210> SEQ ID NO 218
<211> LENGTH: 34
<212> TYPE: DNA
<213> ORGANISM: Chlamydomonas reinhardtii

<400> SEQUENCE: 218
caatacggga taataccgcg ccacatagca gaac                  34

<210> SEQ ID NO 219
<211> LENGTH: 34
<212> TYPE: DNA
<213> ORGANISM: Chlamydomonas reinhardtii

<400> SEQUENCE: 219
gttatgccct attatggcgc ggtgtatcgt cttg                  34

<210> SEQ ID NO 220
<211> LENGTH: 47
<212> TYPE: DNA
<213> ORGANISM: Chlamydomonas reinhardtii

<400> SEQUENCE: 220
gggcattaaa gccttttcca tacgctgata gaatatttaa tcaatcg    47

<210> SEQ ID NO 221
<211> LENGTH: 47
<212> TYPE: DNA
<213> ORGANISM: Chlamydomonas reinhardtii

<400> SEQUENCE: 221
cccgtaattt cggaaaaggt atgcgactat cttataaatt agttagc                47

<210> SEQ ID NO 222
<211> LENGTH: 31
<212> TYPE: DNA
<213> ORGANISM: Chlamydomonas reinhardtii

<400> SEQUENCE: 222
ccgacaggac ttaaagatcc ccaccgtttc c                                 31

<210> SEQ ID NO 223
<211> LENGTH: 31
<212> TYPE: DNA
<213> ORGANISM: Chlamydomonas reinhardtii

<400> SEQUENCE: 223
ggctgtcctg aatttctagg ggtggcaaag g                                 31

<210> SEQ ID NO 224
<211> LENGTH: 583
<212> TYPE: PRT
<213> ORGANISM: Artificial Sequence
<220> FEATURE:
<223> OTHER INFORMATION: SYNTHESIZED

<400> SEQUENCE: 224

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Ile Arg Thr Ser Met Gly Glu Leu
225                 230                 235                 240

```
Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
    290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
        355                 360                 365

Thr Asn Ser Leu Arg Asp Ile Asp Ala Ser Leu Thr Thr Arg Glu Leu
    370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
        435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
        515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 225
<211> LENGTH: 1749
<212> TYPE: DNA
<213> ORGANISM: Artificial Sequence
<220> FEATURE:
<223> OTHER INFORMATION: synthesized

<400> SEQUENCE: 225
atggccaaaa caataatctt aaatggcaat gaagtgcata cagataaaga tattactatc    60
cttgagctag caagagaaaa taatgtagat atcccaacac tctgcttttt aaaggattgt   120
```

-continued

```
ggcaattttg gaaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaaagagt ttcaatgctt cttgataagc atgaatttaa atgtggacaa      300
tgttctagaa gagaaaattg tgaattcctt aaacttgtaa taaagacaaa agcaaaagct      360
tcaaaaccat ttttaccaga agataaggat gctctagttg ataatagaag taaggctatt      420
gtaattgaca gatcaaaatg tgtactatgc ggtagatgcg tagctgcatg taaacagcac      480
acaagcactt gctcaattca atttattaaa aaagatggac aaagggctgt tggaactgtt      540
gatgatgttt gtcttgatga ctcaacatgc ttattatgcg gtcagtgtgt aatcgcttgt      600
cctgttgctg ctttaaaaga aaaatcccat atagaaaaag ttcaagaagc tcttaatgac      660
cctaaaaaac atgtaatagt tgctatggca ccatcaatca gaacttctat gggagagtta      720
tttaaattag gctatggggt tgatgtaact ggaaaattat atgcttcaat gagagcatta      780
ggatttgata aggtatttga tattaacttt ggggctgata tgacaataat ggaagaagca      840
acagagttta ttgaaagagt taaaaataat ggcccattcc ctatgtttac atcttgctgt      900
cctgcatggg taagattagc tcaaaattat catcctgaat tattagataa tctttcatca      960
gcaaaatcac cacaacaaat atttggtact gcatcaaaaa cttactatcc ttcaatttca     1020
ggaatagctc cagaagatgt ttatacagtt actatcatgc cttgtaatga taaaaaatat     1080
gaagcagata ttcctttcat ggaaactaac agcttaagag atattgatgc atccttaact     1140
acaagagagc ttgcaaaaat gattaaagat gcaaaaatta aatttgcaga tcttgaagat     1200
ggtgaagttg atcctgctat gggtacttac agtggtgctg gagctatctt tggtgcaacc     1260
ggtggcgtta tggaagctgc aataagatca gctaaagact ttgctgaaaa taagaacctt     1320
gaaaatgttg attacactga agtaagaggc tttaaaggca taaagaagc ggaagttgaa     1380
attgctggaa ataaactaaa cgttgctgtt ataaatggtg cttctaactt cttcgagttt     1440
atgaaatctg gaaaatgaa cgaaaaacaa tatcactttta tagaagtaat ggcttgccct     1500
ggtggatgta taatggtgg aggtcaacct cacgtaaatg ctcttgatag agaaaatgtt     1560
gattacagaa aactaagagc atcagtatta tacaaccaag ataaaaatgt tctttcaaag     1620
agaaagtcac atgataatcc agctattatt aaaatgtatg atagctactt tggaaaacca     1680
ggtgaaggac ttgctcacaa attactacac gtaaaataca caaagataa aaatgtttca     1740
aaacatgaa                                                             1749
```

<210> SEQ ID NO 226  
<211> LENGTH: 574  
<212> TYPE: PRT  
<213> ORGANISM: Artificial Sequence  
<220> FEATURE:  
<223> OTHER INFORMATION: synthesized

<400> SEQUENCE: 226

```
Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60
```

```
Lys Val Glu Asp Gly Met Val Ile Asn Thr Glu Ser Asp Glu Val Lys
 65                  70                  75                  80

Glu Arg Ile Lys Lys Arg Val Ser Met Leu Leu Asp Lys His Glu Phe
                 85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
```

```
                485                 490                 495
Met Ala Cys Pro Gly Gly Cys Val Asn Gly Gly Gln Pro His Val
                500                 505                 510

Ser Ala Lys Glu Arg Glu Lys Val Asp Val Arg Thr Val Arg Ala Ser
                515                 520                 525

Val Leu Tyr Asn Gln Asp Lys Asn Leu Glu Lys Arg Lys Ser His Lys
        530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 227
<211> LENGTH: 1722
<212> TYPE: DNA
<213> ORGANISM: Artificial Sequence
<220> FEATURE:
<223> OTHER INFORMATION: synthesized

<400> SEQUENCE: 227
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaagagt ttcaatgctt cttgataagc atgaatttaa atgtggacaa     300
tgttctagaa gagaaaattg tgaattcctt aaacttgtaa taaagacaaa agcaaaagct     360
tcaaaaccat ttttaccaga agataaggat gctctagttg ataatagaag taaggctatt     420
gtaattgaca gatcaaaatg tgtgctatgc ggaagatgtg aagcagcatg taaaacaaag     480
acaggtacag gagctatttc aatttgtaag agtgaatcag gaagaatagt gcaagcaaca     540
ggcggaaagt gctttgatga tacaaattgt ttattatgtg gacaatgcgt tgcagcatgt     600
ccagtaggag ctttaactga aaaaacacac gttgatagag ttaaagaagc attagaagat     660
cctaataagc atgtcattgt tgcaatggct ccatcagtaa gaactgctat gggcgaatta     720
ttcaaaatgg gatatggaaa agatgtaaca ggaaaactat atactgcact tagaatgtta     780
ggctttgata agtatttga tataaacttt ggtgcagata tgactataat ggaagaagct     840
actgaacttt taggcagagt taaaaataat ggaccattcc caatgtttac ttcatgttgt     900
ccggcatggg ttagacaagt ggaaaattat tacccagaat ttttagaaaa cttatcatca     960
gctaaatcac cacaacaaat atttggtgca gcaagcaaaa catactatcc tcaaatatca    1020
ggtataagtg ctaagatgt atttactgtt acaataatgc cttgtacagc aaagaaattt    1080
gaggctgata gaagaaat gtataatgag ggaattaaaa atatagatgc agtacttact    1140
acaagagaat tagcaaaaat gattaaagat gcaaagatta ttttgctaa tttagaagac    1200 gaacaagctg atccagcaat gggagaatac actggggctg gagttatatt cggagctaca    1260
ggtggagtta tggaagcagc acttagaact gctaaggatt tcgttgaaga taaagattta    1320
actgatatag aatatacaca aataagagga ttacaaggaa taaagaggc tacagtagaa    1380 attggtggag aaaattataa cgtagctgta attaatggtg cagcaaactt agctgaattc    1440
atgaatagcg gtaaaatcct tgaaagaaac tatcattttta ttgaagtaat ggcttgccca    1500
ggcggatgtg taaatggtgg aggacaacca cacgtaagtg caaggaaag agaaaaagta    1560
```

```
gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attacactta aaatacaata aa                       1722
```

<210> SEQ ID NO 228
<211> LENGTH: 56
<212> TYPE: PRT
<213> ORGANISM: Artificial Sequence
<220> FEATURE:
<223> OTHER INFORMATION: synthesized

<400> SEQUENCE: 228

```
Met Ser Ala Leu Val Leu Lys Pro Cys Ala Ala Val Ser Ile Arg Gly
1               5                   10                  15

Ser Ser Cys Arg Ala Arg Gln Val Ala Pro Arg Ala Pro Leu Ala Ala
            20                  25                  30

Ser Thr Val Arg Val Ala Leu Ala Thr Leu Glu Ala Pro Ala Arg Arg
        35                  40                  45

Leu Gly Asn Val Ala Cys Ala Ala
    50                  55
```

<210> SEQ ID NO 229
<211> LENGTH: 168
<212> TYPE: DNA
<213> ORGANISM: Artificial Sequence
<220> FEATURE:
<223> OTHER INFORMATION: synthesized

<400> SEQUENCE: 229

```
atgtcggcgc tcgtgctgaa gccctgcgcg gccgtgtcta ttcgcggcag ctcctgcagg     60
gcgcggcagg tcgcccccg cgctccgctc gcagccagca ccgtgcgtgt agcccttgca    120
acacttgagg cgcccgcacg ccgcctaggc aacgtcgctt gcgcggct               168
```

<210> SEQ ID NO 230
<211> LENGTH: 439
<212> TYPE: PRT
<213> ORGANISM: Artificial Sequence
<220> FEATURE:
<223> OTHER INFORMATION: synthesized

<400> SEQUENCE: 230

```
Met Ala Ala Pro Ala Ala Glu Ala Pro Leu Ser His Val Gln Gln Ala
1               5                   10                  15

Leu Ala Glu Leu Ala Lys Pro Lys Asp Asp Pro Thr Arg Lys His Val
            20                  25                  30

Cys Val Gln Val Ala Pro Ala Val Arg Val Ala Ile Ala Glu Thr Leu
        35                  40                  45

Gly Leu Ala Pro Gly Ala Thr Thr Pro Lys Gln Leu Ala Glu Gly Leu
    50                  55                  60

Arg Arg Leu Gly Phe Asp Glu Val Phe Asp Thr Leu Phe Gly Ala Asp
65                  70                  75                  80

Leu Thr Ile Met Glu Glu Gly Ser Glu Leu Leu His Arg Leu Thr Glu
                85                  90                  95

His Leu Glu Ala His Pro His Ser Asp Glu Pro Leu Pro Met Phe Thr
            100                 105                 110

Ser Cys Cys Pro Gly Trp Ile Ala Met Leu Glu Lys Ser Tyr Pro Asp
        115                 120                 125

Leu Ile Pro Tyr Val Ser Ser Cys Lys Ser Pro Gln Met Met Leu Ala
```

```
                130                 135                 140
Ala Met Val Lys Ser Tyr Leu Ala Glu Lys Lys Gly Ile Ala Pro Lys
145                 150                 155                 160

Asp Met Val Met Val Ser Ile Met Pro Cys Thr Arg Lys Gln Ser Glu
                165                 170                 175

Ala Asp Arg Asp Trp Phe Cys Val Ala Asp Pro Thr Leu Arg Gln
            180                 185                 190

Leu Asp His Val Ile Thr Thr Val Glu Leu Gly Asn Ile Phe Lys Glu
            195                 200                 205

Arg Gly Ile Asn Leu Ala Glu Leu Pro Glu Gly Glu Trp Asp Asn Pro
210                 215                 220

Met Gly Val Gly Ser Gly Ala Gly Val Leu Phe Gly Thr Thr Gly Gly
225                 230                 235                 240

Val Met Glu Ala Ala Leu Arg Thr Ala Tyr Glu Leu Phe Thr Gly Thr
                245                 250                 255

Pro Leu Pro Arg Leu Ser Leu Ser Glu Val Arg Gly Met Asp Gly Ile
            260                 265                 270

Lys Glu Thr Asn Ile Thr Met Val Pro Ala Pro Gly Ser Lys Phe Glu
            275                 280                 285

Glu Leu Leu Lys His Arg Ala Ala Arg Ala Glu Ala Ala Ala His
290                 295                 300

Gly Thr Pro Gly Pro Leu Ala Trp Asp Gly Gly Ala Gly Phe Thr Ser
305                 310                 315                 320

Glu Asp Gly Arg Gly Gly Ile Thr Leu Arg Val Ala Val Ala Asn Gly
                325                 330                 335

Leu Gly Asn Ala Lys Lys Leu Ile Thr Lys Met Gln Ala Gly Glu Ala
            340                 345                 350

Lys Tyr Asp Phe Val Glu Ile Met Ala Cys Pro Ala Gly Cys Val Gly
            355                 360                 365

Gly Gly Gly Gln Pro Arg Ser Thr Asp Lys Ala Ile Thr Gln Lys Arg
370                 375                 380

Gln Ala Ala Leu Tyr Asp Leu Asp Glu Arg Asn Thr Leu Arg Arg Ser
385                 390                 395                 400

His Glu Asn Glu Ala Val Asn Gln Leu Tyr Lys Glu Phe Leu Gly Glu
                405                 410                 415

Pro Leu Ser His Arg Ala His Glu Leu Leu His Thr His Tyr Val Pro
            420                 425                 430

Gly Gly Ala Glu Ala Asp Ala
            435

<210> SEQ ID NO 231
<211> LENGTH: 1320
<212> TYPE: DNA
<213> ORGANISM: Artificial Sequence
<220> FEATURE:
<223> OTHER INFORMATION: synthesized

<400> SEQUENCE: 231
atggccgcac ccgctgcgga ggcgcctttg agtcatgtcc agcaggcgct cgccgagctt      60
gccaagccca aggacgaccc cacgcgcaag cacgtctgcg tgcaggtggc tccggccgtt     120
cgtgtcgcta ttgccgagac cctgggcctg gcgccgggcg ccaccacccc caagcagctg     180
gccgagggcc tccgccgcct cggctttgac gaggtgtttg acacgctgtt tggcgccgac     240
ctgaccatca tggaggaggg cagcgagctg ctgcaccgcc tcaccgagca cctggaggcc     300
```

```
cacccgcact ccgacgagcc gctgcccatg ttcaccagct gctgcccgg ctggatcgct    360 atgctggaga atcttaccc ggacctgatc ccctacgtga gcagctgcaa gagccccag    420 atgatgctgg cggcaatggt caagtcctac ctagcggaaa agaagggcat cgcgccaaag    480
gacatggtca tggtgtccat catgccctgc acgcgcaagc agtcggaggc tgaccgcgac    540
tggttctgtg tggacgccga ccccaccctg cgccagctgg accacgtcat caccaccgtg    600
gagctgggca acatcttcaa ggagcgcggc atcaacctgg ccgagctgcc cgagggcgag    660
tgggacaatc caatgggcgt gggctcgggc gccggcgtgc tgttcggcac accggcggt    720 gtcatggagg cggcgctgcg cacggcctat gagctgttca cgggcacgcc gctgccgcgc    780
ctgagcctga gcgaggtgcg cggcatggac ggcatcaagg agaccaacat cacaatggtg    840
cccgcgcccg gtccaagtt tgaggagctg ctgaagcacc gcgccgccgc gcgcgccgag    900
gccgccgcgc acggcacccc cgggccgctg gcctgggacg gcggcgcggg cttcaccagc    960
gaggacggca ggggcggcat cacactgcgc gtggccgtgg ccaacgggct ggcaacgcc   1020 aagaagctga tcaccaagat gcaggccggc gaggccaagt acgactttgt ggagatcatg   1080
gcctgccccg cgggctgtgt gggcggcggc ggccagcccc gctccaccga caaggccatc   1140
acgcagaagc ggcaggcggc tctgtacgac ctggacgagc gcaacacgct gcgccgcagc   1200
cacgaaaacg aggcggtcaa ccagctgtac aaggagttcc tgggcgagcc cctgtcccac   1260
cgcgcccacg agctgctgca cacccactac gtgccaggcg cgccgaggc cgatgcttag   1320
```

<210> SEQ ID NO 232
<211> LENGTH: 442
<212> TYPE: PRT
<213> ORGANISM: Artificial Sequence
<220> FEATURE:
<223> OTHER INFORMATION: synthesized

<400> SEQUENCE: 232

```
Met Ala Ala Pro Ala Ala Glu Ala Pro Leu Ser His Val Gln Gln Ala
1               5                   10                  15

Leu Ala Glu Leu Ala Lys Pro Lys Asp Asp Pro Thr Arg Lys His Val
            20                  25                  30

Cys Val Gln Val Ala Pro Ala Val Arg Val Ala Ile Ala Glu Thr Leu
        35                  40                  45

Gly Leu Ala Pro Gly Ala Thr Thr Pro Lys Gln Leu Ala Glu Gly Leu
    50                  55                  60

Arg Arg Leu Gly Phe Asp Glu Val Phe Asp Thr Leu Phe Gly Ala Asp
65                  70                  75                  80

Leu Thr Ile Met Glu Glu Gly Ser Glu Leu Leu His Arg Leu Thr Glu
                85                  90                  95

His Leu Glu Ala His Pro His Ser Asp Glu Pro Leu Pro Met Phe Thr
            100                 105                 110

Ser Cys Cys Pro Gly Trp Ile Ala Met Leu Glu Lys Ser Tyr Pro Asp
        115                 120                 125

Leu Ile Pro Tyr Val Ser Ser Cys Lys Ser Pro Gln Met Met Leu Ala
    130                 135                 140

Ala Met Val Lys Ser Tyr Leu Ala Glu Lys Lys Gly Ile Ala Pro Lys
145                 150                 155                 160

Asp Met Val Met Val Ser Ile Met Pro Cys Thr Arg Lys Gln Ser Glu
                165                 170                 175

Ala Asp Arg Asp Trp Phe Cys Val Asp Ala Asp Pro Thr Leu Arg Gln
            180                 185                 190
```

Leu Asp His Val Ile Thr Thr Val Glu Leu Gly Asn Ile Phe Lys Glu
        195                 200                 205

Arg Gly Ile Asn Leu Ala Glu Leu Pro Glu Gly Glu Trp Asp Asn Pro
    210                 215                 220

Met Gly Val Gly Ser Gly Ala Gly Val Leu Phe Gly Thr Thr Gly Gly
225                 230                 235                 240

Val Met Glu Ala Ala Leu Arg Thr Ala Tyr Glu Leu Phe Thr Gly Thr
                245                 250                 255

Pro Leu Pro Arg Leu Ser Leu Ser Glu Val Arg Gly Met Asp Gly Ile
                260                 265                 270

Lys Glu Thr Asn Ile Thr Met Val Pro Ala Pro Gly Ser Lys Phe Glu
            275                 280                 285

Glu Leu Leu Lys His Arg Ala Ala Arg Ala Glu Ala Ala His
        290                 295                 300

Gly Thr Pro Gly Pro Leu Ala Trp Asp Gly Ala Gly Phe Thr Ser
305                 310                 315                 320

Glu Asp Gly Lys Gly Gly Leu Lys Leu Arg Val Ala Val Ala Asn Gly
                325                 330                 335

Leu Gly Asn Ala Lys Lys Leu Ile Gly Lys Met Val Ser Gly Glu Ala
            340                 345                 350

Lys Tyr Asp Phe Val Glu Ile Met Ala Cys Pro Ala Gly Cys Val Gly
        355                 360                 365

Gly Gly Gly Gln Pro Arg Ser Thr Asp Lys Gln Ile Thr Gln Lys Arg
    370                 375                 380

Gln Ala Ala Leu Tyr Asn Leu Asp Glu Lys Ser Thr Leu Arg Arg Ser
385                 390                 395                 400

His Glu Asn Pro Ser Ile Arg Glu Leu Tyr Asp Thr Tyr Leu Gly Glu
                405                 410                 415

Pro Leu Gly His Lys Ala His Glu Leu Leu His Thr His Tyr Val Ala
            420                 425                 430

Gly Gly Val Glu Glu Lys Asp Glu Lys Lys
        435                 440

<210> SEQ ID NO 233
<211> LENGTH: 1329
<212> TYPE: DNA
<213> ORGANISM: Artificial Sequence
<220> FEATURE:
<223> OTHER INFORMATION: synthesized

<400> SEQUENCE: 233
atggccgcac ccgctgcgga ggcgcctttg agtcatgtcc agcaggcgct cgccgagctt      60
gccaagccca aggacgaccc cacgcgcaag cacgtctgcg tgcaggtggc tccggccgtt     120
cgtgtcgcta ttgccgagac cctgggcctg gcgccgggcg ccaccacccc caagcagctg     180
gccgagggcc tccgccgcct cggctttgac gaggtgtttg acacgctgtt tggcgccgac     240
ctgaccatca tggaggaggg cagcgagctg ctgcaccgcc tcaccgagca cctggaggcc     300
cacccgcact ccgacgagcc gctgcccatg ttcaccagct gctgcccggc tggatcgct      360 atgctggaga atcttaccc ggacctgatc ccctacgtga gcagctgcaa gagccccag      420 atgatgctgg cggcaatggt caagtcctac ctagcggaaa agaagggcat cgcgccaaag     480
gacatggtca tggtgtccat catgcccgtgc acgcgcaagc agtcggaggc tgaccgcgac     540
tggttctgtg tggacgccga ccccaccctg cgccagctgg accacgtcat caccaccgtg     600

```
gagctgggca acatcttcaa ggagcgcggc atcaacctgg ccgagctgcc cgagggcgag    660
tgggacaatc caatgggcgt gggctcgggc gccggcgtgc tgttcggcac caccggcggt    720
gtcatggagg cggcgctgcg cacggcctat gagctgttca cgggcacgcc gctgccgcgc    780
ctgagcctga gcgaggtgcg cggcatggac ggcatcaagg agaccaacat cacaatggtg    840
cccgcgcccg ggtccaagtt tgaggagctg ctgaagcacc gcgccgccgc gcgcgccgag    900
gccgccgcgc acggcacccc cgggccgctg gcctgggacg gcggcgcggg cttcaccagc    960
gaggacggca agggcggcct gaagctgcgg gtggcggtgg cgaacggcct gggcaacgcc   1020
aagaagctga tcggcaagat ggtatctggc gaggccaagt acgacttcgt agaaatcatg   1080
gcctgccctg ccggctgcgt gggcggcggc ggccagcccc gctccaccga caagcagatc   1140
acccagaagc ggcaggcggc gctgtacaac ctggacgaga agtccacgct cgccgcagc    1200 cacgagaacc cgtccatccg cgagctgtac gacacgtacc tcggagagcc gctgggccac   1260
aaggcgcacg agctgctgca cacccactac gtggccggcg cgtggaggga aaggacgag    1320 aagaagtga                                                           1329
```

<210> SEQ ID NO 234
<211> LENGTH: 451
<212> TYPE: PRT
<213> ORGANISM: Artificial Sequence
<220> FEATURE:
<223> OTHER INFORMATION: synthesized

<400> SEQUENCE: 234

```
Met Ala Pro Ala Ala Glu Ala Pro Leu Ser His Val Gln Gln Ala
1               5                   10                  15

Leu Ala Glu Leu Ala Lys Pro Lys Asp Asp Pro Thr Arg Lys His Val
            20                  25                  30

Cys Val Gln Val Ala Pro Ala Val Arg Val Ala Ile Ala Glu Thr Leu
        35                  40                  45

Gly Leu Ala Pro Gly Ala Thr Thr Pro Lys Gln Leu Ala Glu Gly Leu
    50                  55                  60

Arg Arg Leu Gly Phe Asp Glu Val Phe Asp Thr Leu Phe Gly Ala Asp
65                  70                  75                  80

Leu Thr Ile Met Glu Glu Gly Ser Glu Leu Leu His Arg Leu Thr Glu
                85                  90                  95

His Leu Glu Ala His Pro His Ser Asp Glu Pro Leu Pro Met Phe Thr
            100                 105                 110

Ser Cys Cys Pro Gly Trp Ile Ala Met Leu Glu Lys Ser Tyr Pro Asp
        115                 120                 125

Leu Ile Pro Tyr Val Ser Ser Cys Lys Ser Pro Gln Met Met Leu Ala
    130                 135                 140

Ala Met Val Lys Ser Tyr Leu Ala Glu Lys Lys Gly Ile Ala Pro Lys
145                 150                 155                 160

Asp Met Val Met Val Ser Ile Met Pro Cys Thr Arg Lys Gln Ser Glu
                165                 170                 175

Ala Asp Arg Asp Trp Phe Cys Val Asp Ala Asp Pro Thr Leu Arg Gln
            180                 185                 190

Leu Asp His Val Ile Thr Thr Val Glu Leu Gly Asn Ile Phe Lys Glu
        195                 200                 205

Arg Gly Ile Asn Leu Ala Glu Leu Pro Glu Gly Glu Trp Asp Asn Pro
    210                 215                 220

Met Gly Val Gly Ser Gly Ala Gly Val Leu Phe Gly Thr Thr Gly Gly
```

```
                225                 230                 235                 240
Val Met Glu Ala Ala Leu Arg Thr Ala Tyr Glu Leu Phe Thr Gly Thr
                    245                 250                 255
Pro Leu Pro Arg Leu Ser Leu Ser Glu Val Arg Gly Leu Asp Gly Ile
                260                 265                 270
Lys Glu Ala Ser Val Thr Leu Val Pro Ala Pro Gly Ser Lys Phe Ala
            275                 280                 285
Glu Leu Val Ala Glu Arg Leu Ala His Lys Val Glu Ala Ala Ala
        290                 295                 300
Ala Glu Ala Ala Ala Val Glu Gly Ala Val Lys Pro Pro Ile Ala
305                 310                 315                 320
Tyr Asp Gly Gly Gln Gly Phe Ser Thr Asp Asp Gly Arg Gly Ile
                325                 330                 335
Thr Leu Arg Val Ala Val Ala Asn Gly Leu Gly Asn Ala Lys Lys Leu
                340                 345                 350
Ile Thr Lys Met Gln Ala Gly Glu Ala Lys Tyr Asp Phe Val Glu Ile
                355                 360                 365
Met Ala Cys Pro Ala Gly Cys Val Gly Gly Gly Gln Pro Arg Ser
        370                 375                 380
Thr Asp Lys Ala Ile Thr Gln Lys Arg Gln Ala Ala Leu Tyr Asn Leu
385                 390                 395                 400
Asp Glu Lys Ser Thr Leu Arg Arg Ser His Glu Asn Pro Ser Ile Arg
                405                 410                 415
Glu Leu Tyr Asp Thr Tyr Leu Gly Gly Pro Leu Gly His Lys Ala His
                420                 425                 430
Glu Leu Leu His Thr His Tyr Val Ala Gly Gly Val Glu Glu Lys Asp
            435                 440                 445
Glu Lys Lys
    450

<210> SEQ ID NO 235
<211> LENGTH: 1356
<212> TYPE: DNA
<213> ORGANISM: Artificial Sequence
<220> FEATURE:
<223> OTHER INFORMATION: synthesized

<400> SEQUENCE: 235
atggccgcac ccgctgcgga ggcgcctttg agtcatgtcc agcaggcgct cgccgagctt       60
gccaagccca aggacgaccc cacgcgcaag cacgtctgcg tgcaggtggc tccggccgtt     120
cgtgtcgcta ttgccgagac cctgggcctg gcgccgggcg ccaccacccc caagcagctg     180
gccgagggcc tccgccgcct cggctttgac gaggtgtttg acacgctgtt tggcgccgac     240
ctgaccatca tggaggaggg cagcgagctg ctgcaccgcc tcaccgagca cctggaggcc     300
cacccgcact ccgacgagcc gctgcccatg ttcaccagct gctgcccggg ctggatcgct     360
atgctggaga atcttaccc ggacctgatc cctacgtga gcagctgcaa gagcccccag      420
atgatgctgg cggcaatggt caagtcctac ctagcggaaa agaagggcat cgcgccaaag     480
gacatggtca tggtgtccat catgcccctg acgcgcaagc agtcggaggc tgaccgcgac     540
tggttctgtg tggacgccga ccccaccctg cgccagctgg accacgtcat caccaccgtg     600
gagctgggca acatcttcaa ggagcgcggc atcaacctgg ccgagctgcc gagggcgag      660 tgggacaatc caatgggcgt gggctcgggc gccggcgtgc tgttcggcac caccggcggt     720
gtcatggagg cggcgctgcg cacggcctat gagctgttca cgggcacgcc gctgccgcgc     780
```

```
ctgagcctga gcgaggtgcg cggcttggac ggcatcaagg aggcgtccgt gacgctggtc      840
cccgctccgg gctccaagtt cgccgagctg gtggcggagc gcctggcgca caaggtcgag      900
gaggcggccg cggctgaggc ggcggcggcg gtggagggcg ccgtgaagcc gcccatcgcg      960
tacgacggcg gccagggttt ctccacggat gacggcaggg gcggcatcac actgcgcgtg     1020
gccgtggcca acgggctggg caacgccaag aagctgatca ccaagatgca ggccggcgag     1080
gccaagtacg actttgtgga gatcatggcc tgccccgcgg gctgtgtggg cggcggcggc     1140
cagccccgct ccaccgacaa ggccatcacg cagaagcggc aggcggcgct gtacaacctg     1200
gacgagaagt ccacgctgcg ccgcagccac gagaacccgt ccatccgcga gctgtacgac     1260
acgtacctcg gagagccgct gggccacaag gcgcacgagc tgctgcacac ccactacgtg     1320
gccggcggcg tggaggagaa ggacgagaag aagtga                                1356
```

PHOTOSYNTHETIC HYDROGEN PRODUCTION FROM THE GREEN ALGA CHLAMYDOMONAS REINHARDII

CROSS REFERENCE TO RELATED APPLICATIONS

This application is a continuation-in-part of U.S. Pat. No. 8,124,347 issued on Feb. 28, 2012 and filed as U.S. patent application Ser. No. 12/428,471 on Apr. 23, 2009, which claims the benefit of U.S. Provisional Patent Application No. 61/046,989 filed on Apr. 22, 2008, entitled "Photosynthetic Hydrogen Production from the Green Alga *Chlamydomonas Reinhardii*", the entire disclosures of which are hereby incorporated by reference for all purposes.

INCORPORATION OF SEQUENCE LISTING

The entire contents of a paper copy of the "Sequence Listing" and a computer readable form of the sequence listing on diskette, containing the file named Seq_Listing_ST25.txt, which is 489 kilobytes in size and was created on Apr. 23, 2009 are herein incorporated by reference.

TECHNICAL FIELD

The present invention relates generally to hydrogen production for use in fuel cells, foodstuffs and chemical production, and more particularly to biologically and photosynthetically produced hydrogen.

BACKGROUND OF THE INVENTION

Evidence has shown that the combustion of fossil fuels is causing a change in the composition of our atmosphere. The resulting increase in average global temperature requires an immediate and global response. A recent British climate change report suggests that we would have to decrease emissions of carbon dioxide and other greenhouse gases by 25% by the year 2050 to avoid as much as a 20% decrease in global Gross Domestic Product (GDP) caused by catastrophic drought, flooding, and disease. Ultimately, an 80% decrease in emissions would be necessary. So, if not fossil fuels, what should we use as a source of energy? If we switched to a hydrogen economy and utilized molecular hydrogen and fuel cells in all of our cars, trucks, trains, etc., a 50% reduction in the emission of carbon monoxide and nitrous oxides is likely. Of course, a decrease in emissions and a concomitant improvement in climate change is dependant on how the hydrogen is produced. Climate change would not occur if we continue to produce hydrogen by the steam reformation of natural gas and coal as this process results in localized emissions, but emissions nonetheless. However, if the hydrogen were produced biologically from water, perhaps by a photosynthetic organism, there would be little or no release of carbon dioxide, nitrous oxides, or methane.

Hydrogen is currently produced by steam reforming the hydrogen atoms from coal or natural gas. The reactions are: $CH_4+H_2O \rightarrow CO+3H_2$ (natural gas) or $C+H_2O \rightarrow CO+H_2$ (coal) and $CO+H_2O \rightarrow CO_2+H_2$. Either fuel could be the basis of a national hydrogen economy; however both fuels generate carbon dioxide, which would add greenhouse gases to our atmosphere. If future coal driven hydrogen power plants utilized carbon sequestration, pumping the carbon dioxide into a deep underground location, this problem could be minimized. Alternatively, a carbon neutral hydrogen economy could be realized if hydrogen could be produced from the electrolysis of water where the electricity, the impetus for the reaction, is generated from a nuclear reactor, wind energy, or solar power or through photosynthetic hydrogen generation.

The study of biological hydrogen production in green algae began as a curiosity and after 75 years of research, its evolutionary origin still remains an enigma. General progress in the field has been ongoing since Hans Gaffron early 1940s discovery that the green alga *Scenedesmus obliquus* produced hydrogen; however, the last decade is marked by dramatic advances. Specifically, the hydrogenase genes for several species of green algae have been sequenced and the crystal structure determined, for two homologous bacterial hydrogenases, *C. pasteurinum* and *D. desulfuricans*. In addition, the mechanism by which a hydrogenase creates molecular hydrogen has been elucidated from extensive research on the structure, assembly, and biological properties of all hydrogenases.

Hydrogenases are iron-sulfur proteins, which have played an important role in the energy metabolism of bacteria since the earliest life on Earth. In fact, homologous non-hydrogen producing iron-sulfur proteins are common in most living cells, including humans and pathogenic bacteria. The hydrogenases, however, are different from their evolutionary cousins in that their iron sulfur clusters contain unique cyanide and carbon monoxide ligands (FIG. 1).

Hydrogen is produced by enzymatically combining protons with electrons from the photosynthetic electron transport chain. The protons and the electrons are generated from the first step in the photosynthetic cycle, the splitting of water into oxygen and protons. The electrons are immediately energized by a photon ($\lambda=680$ nm) in Photosystem II and passed from one compound to another, all of which compose the electron transport chain (FIG. 2). Most of the electron carriers are quinones (Q), plastiquinones (PQ), or cytochromes (Cyt). A second input of light energy ($\lambda=700$ nm) occurs during Photosystem I and the energized electrons are passed to the terminal electron carrier, ferredoxin. At this point, the electrons can participate in $CO_2$ fixation, i.e. cell growth, or be transferred to the hydrogenase to produce hydrogen.

SUMMARY OF THE INVENTION

In one aspect, the present disclosure provides a method for selecting a chimeric hydrogenase which produces hydrogen at an increased rate relative to the hydrogen production rate of a wild type hydrogenase following transformation of a cell with the chimeric hydrogenase and expression of the chimeric hydrogenase in the transformed cell, the method comprising: calculating a positive to negative electrostatic potential surface area (EPSA) ratio for the chimeric hydrogenase, wherein a positive to negative EPSA ratio of about 1 to about 115 is indicative of an increased hydrogen production rate in the cell by the chimeric hydrogenase relative to the hydrogen production rate of the wild type hydrogenase. In the method, the cell may be an algal cell and the chimeric hydrogenase may be a chimeric algal hydrogenase. The cell may be for example a *Chlamydomonas* cell. Alternatively, the cell may be a bacterial cell and the chimeric hydrogenase may be a chimeric bacterial hydrogenase. In another aspect, the present disclosure also provides a chimeric hydrogenase selected according to the preceding method.

In another aspect, the present disclosure provides a method of producing an algae capable of enhanced hydrogen production, the method comprising: making and testing one or more mutated algal hydrogenases for amount of hydrogen production; identifying one or more of the mutated algal hydrogenases as capable of causing enhanced hydrogen production in algae, wherein an amount of hydrogen production higher than that of a wild type hydrogenase is indicative of the ability to cause enhanced hydrogen production in algae; expressing in the algae cells a DNA sequence coding for at least one mutated algal hydrogenase identified as capable of increased hydrogen production; selecting an algae expressing the mutated algal hydrogenase identified as capable of increased hydrogen production, wherein the mutated algal hydrogenase has a positive to negative EPSA ratio in the range of about 1 to about 115, which is indicative that the algae is capable of enhanced hydrogen production. In the method, making one or more mutated algal hydrogenases may comprise: identifying two or more hydrogenase parent proteins; obtaining cDNAs coding for said parent hydrogenases; producing multiple DNA fragments corresponding to segments of each of said cDNA coding for said parent hydrogenases; and reconstructing full-length chimeric hydrogenase cDNAs by putting segments from cDNAs coding for different parent hydrogenases together in the same order as they occur in the parent hydrogenase coding sequences. Full-length chimeric hydrogenase cDNAs encoding mutated algal hydrogenases can be tested for example in a bacterial system or an algal system to identify mutations capable of enhanced hydrogen production. Full-length chimeric hydrogenase cDNAs encoding mutated algal hydrogenases can be analyzed to identify specific mutations that lead to enhanced hydrogen production. The method may further comprise the step of expressing one or more mutated algal hydrogenases by transforming algae using a plasmid comprising the full-length chimeric hydrogenase cDNAs. The plasmid may be for example pSMP. In another aspect, the present disclosure also provides a recombinat algal cell produced according to the preceding method. The recombinant algal cell may be a *Chlamydomonas* cell, such as but not limited to a *C. reinhardtii* cell.

In any of the methods, calculating the positive to negative EPSA ratio may comprise computing the positive EPSA, the negative EPSA, and the ratio of the positive EPSA to the negative EPSA. The positive to negative EPSA ratio can be for example from about 2 to about 50, or from about 5 to about 20.

BRIEF DESCRIPTION OF THE DRAWINGS

FIG. 12 shows the primers (SEQ ID NOS: 3-12) utilized to create restriction sites in the pSMP1, pSMP1c, and pSMP2 plasmids.

FIG. 17 illustrates the chimeric hydrogenases that were tested for hydrogen production.

FIG. 19 shows the primers (SEQ ID NOS: 17-22) utilized to clone the Clostridial hydrogenases into the pET DLS expression vector.

FIG. 22 shows the list of primers (SEQ ID NOS: 210-223) used for isolating the *C. thermocellum* accessory proteins from a genomic DNA preparation and for cloning the proteins into the pET DLS and pCDF plasmids.

FIG. 26 illustrates the effects of light on two algal strains.

FIG. 30 shows the reactions that occur in a PEM fuel cell.

DETAILED DESCRIPTION

Figure 1:
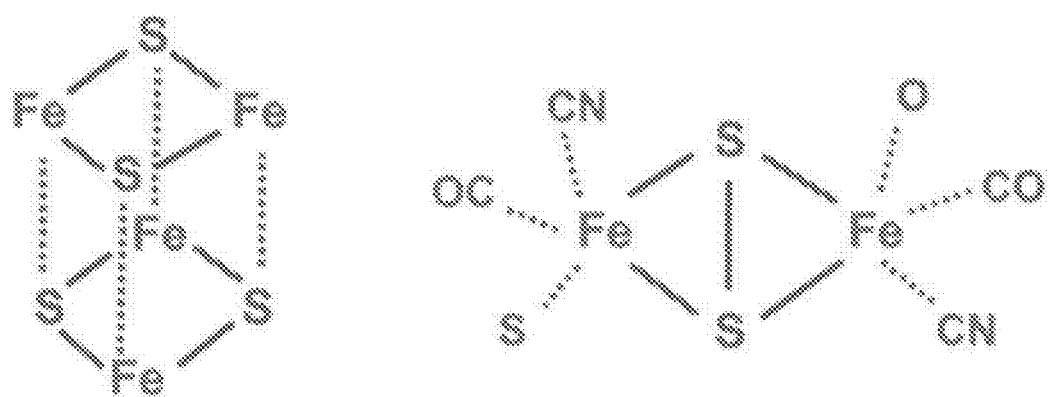
FIG. 1 is a diagram illustrating the four-iron four-sulfur (4Fe-4S) cluster and the two-iron two-sulfur (2Fe-2S) active site cluster that is present in Fe-only hydrogenases.
Figure 2:
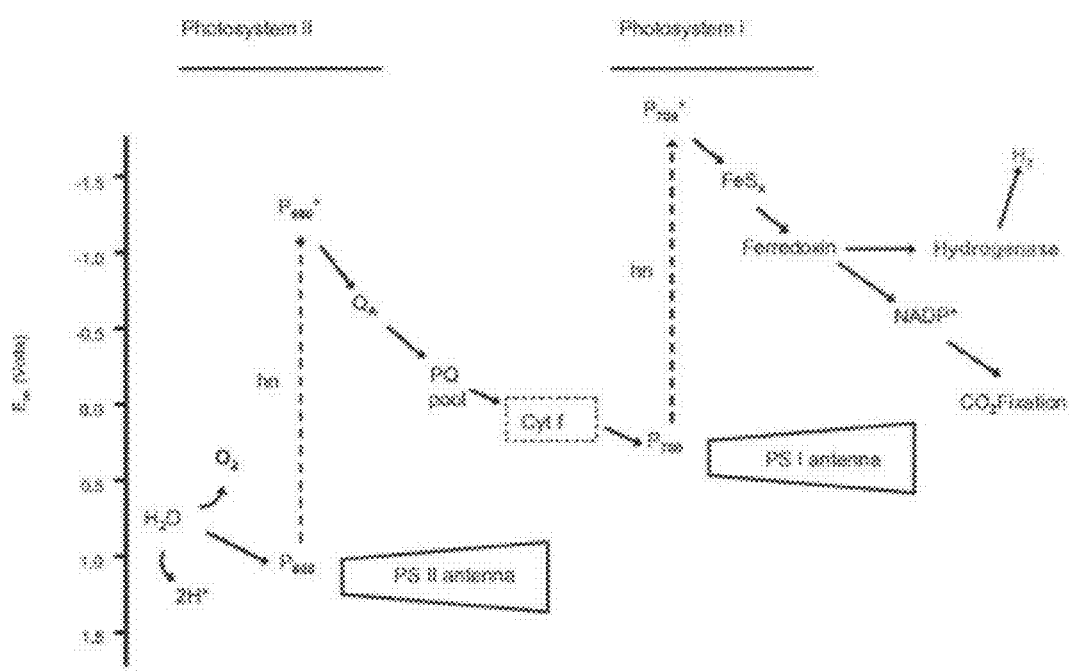
FIG. 2 illustrates the photosynthetic electron transport chain, known as the "Z-scheme."

The present disclosure is based in part on the surprising demonstration of methods for producing photosynthetic alga capable of enhanced hydrogen production relative to wild type algae. The methods also involve production of genetically-modified bacteria which produce hydrogen, and full-length chimeric libraries of mutant hydrogenases. To produce the alga and bacteria, a technique known as directed evolution is used, whereby mutations are introduced into the DNA of hydrogenases native to the organism, and these tested for an increased rate of hydrogen production.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" refers to approximately a +/−10% variation from the stated value. It is to be understood that such a variation is always included in any given value provided herein, whether or not it is specifically referred to.

Unless defined otherwise herein, all technical and scientific terms used herein have the same meaning as commonly understood by one of ordinary skill in the art to which this invention belongs.

The following terms and abbreviations will have the following meanings throughout this disclosure:
aa: amino acid.
bp: base pair.
nt: nucleotide.
kD: kilodalton.
PCR: polymerase chain reaction.
RT-PCR: reverse transcriptase polymerase chain reaction.
ssDNA: single stranded deoxyribonucleic acid.
DNase I: enzyme that degrades DNA.
Restriction enzymes: enzymes that cleave DNA at a specific sequence. XhoI, PacI, NdeI, NheI, EcoRI, PspOMI, AsiSI are the names of restriction enzymes that cleave unique sequences which are listed in the New England Biolabs catalog.
cDNA: copy DNA, the same DNA as the original gene of interest, except all the introns, or non-coding material, have been removed.
LB (or NZY) and TAP: nutrient broths that are used to grow bacteria and algae, respectively Vector or Plasmid: circular DNA that can be transformed (inserted) into cells to express a gene of interest from its promoter.
HydA1 and HydA2: hydrogenase A1 and A2 in *Chlamydomonas reinhardtii*.
UTR: untranslated region (of the DNA).
Intron: an untranslated region of a gene within a translated region.
GOI: gene of interest.
Hydrons: hydrogen atoms with two electrons (H).
pGenD: the name of a plasmid (p) that expresses some cDNA in algae.
pSMP1: the name of a plasmid derived from pGenD that expresses hydrogenase cDNA and has a PspOMI restriction site immediately after the HydA1 leader sequence and before the coding sequence for the HydA1.
pSMP1c: the same as pSMP1, but the PspOMI restriction site was added 20 nts downstream from the one in pSMP1.
pSMP2: the same as pSMP1, but an AsiSI restriction site instead of a PspOMI site was added 45 nts downstream of the HydA1 leader sequence.
IPTG: isopropyl-beta-D-thiogalactopyranoside, a chemical that artificially induces expression SDS-PAGE: sodium docecyl sulfate-polyacrylamide gel electrophoresis, a technique used to separate a mixture of multiple proteins.
Western Blot: in combination with SDS-PAGE, a technique used to identify one protein from a mixture of multiple proteins.
StEP: staggered extension process.
ITCHY: iterative truncation for the creation of hybrid enzymes.
RATCHITT: random chimeragenesis on transient templates.
DOGS: degenerative oligonucleotide gene shuffling.

B. Genetically Modified Alga and Bacteria with Enhanced Hydrogen Production

Hydrogenases are enzymes that generate hydrogen by combining protons with electrons from the photosynthetic electron transport chain. Molecular hydrogen is then released into the environment. It would be very beneficial to have a biological source of molecular hydrogen, in particular a photosynthetic organism capable of an increased rate of hydrogen production, to use as an energy source that reduces emissions of carbon dioxide, nitrous oxides, and/or methane. For example, fuel cells using an organism capable of sufficient hydrogen generation would efficiently generate power for numerous uses. Molecular hydrogen is the ideal fuel for use in fuel cells, if it could be produced at a cost that is competitive with current sources of energy.

Biohydrogen production from photosynthetic algae has the potential to be a viable alternative to hydrogen production from fossil fuels. It would not produce greenhouse gases ($H_2O$+sunlight→$O_2$+$H_2$); in fact, algae, like most plants, utilizes carbon dioxide for cellular growth, so it would serve as a carbon sink. In addition, a bioreactor would not produce toxic waste, but only algae and wastewater, similar to a fish tank. Also, a bioreactor would likely be about the size of an air conditioner and survive on low amounts of sunlight, so it would occupy a small amount of space and it could be located anywhere.

However, present commercial photosynthetic hydrogen production is not viable because of two major problems that prevent the hydrogenase from producing useful amounts of molecular hydrogen. First, the hydrogenase has a short half-life that prevents it from producing hydrogen for longer than a minute. Second, it is necessary that the hydrogenase be tolerant of oxygen. Since all known hydrogenases have a short half-life even in the presence of very low concentrations of oxygen, only a modified hydrogenase with increased hydrogen production and/or decreased oxygen sensitivity will allow for the commercial production of photosynthetically generated hydrogen.

Despite the evident challenges, the green alga *Chlamydomonas reinhardtii* (*C. reinhardtii*) has substantial potential as a candidate hydrogen producer. Each *C. reinhardtii* hydrogenase is capable of generating 6000-9000 molecules of molecular hydrogen per second. Once sustainable, a mole of hydrogenases, producing hydrogen at this rate, would generate enough hydrogen to fill the Graf Zeppelin in 10 minutes, or the main tank of the space shuttle in just 2 hours. In addition, *C. reinhardtii*, is a common lab research organism whose genome has been sequenced.

Figure 3:
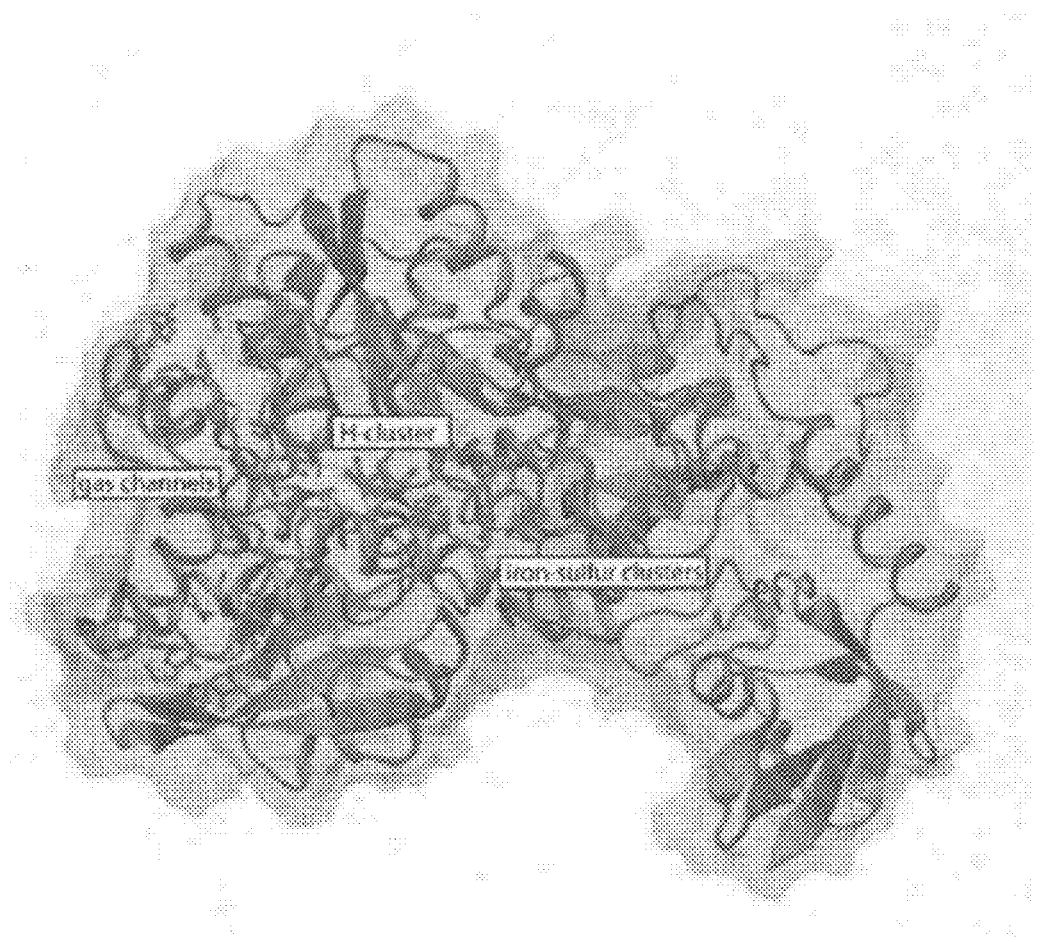
FIG. 3 shows the crystal structure of the *C. pasteurinum* bacterial hydrogenase.

Additionally, the crystal structures of homologous bacterial Fe-only hydrogenases have recently been described, which has provided insight into how oxygen irreversibly inhibits the enzyme. The active site for the production of hydrogen ($2H+2e^- \rightarrow H_2$) is protected by its location deep within the center of the mature hydrogenase (FIG. 3). Each of the reactants and the resulting hydrogen has a channel to the surface. The hydrogenase structures all have different ferredoxin binding motifs, but they all exhibit a chain of four iron, four sulfur clusters (4Fe-4S) that pass the electrons from the surface of the hydrogenase to the active site (FIG. 1 and FIG. 3). The modular 4Fe-4S clusters are separated by 1-1.5 nm intervals that allow for efficient electron transport to the active site. The protons pass through a putative second channel to reach the active site. This channel is lined with amino acids and protein-bound water molecules that are capable of binding the protons as they pass down the channel. Two putative channels exist for the release of molecular hydrogen resulting from the enzymatic reaction of the protons with the electrons at the active site (FIG. 3). Unfortunately, these channels also allow for the passage of the larger oxygen molecule, which irreversibly inhibits the hydrogenase, probably by oxidizing an iron (II) to an iron (III) in the active site cluster. In brief then, photosynthesis generates oxygen as well as protons and energized electrons, and hydrogen production is dependent upon the photosynthetic process. Hence, an evolutionary enigma lies in the extreme sensitivity of hydrogenase to oxygen. Enzymatic hydrogen production is a short-term shunt to rid the cell of excess electrons. Therefore, the enzyme has probably been exposed too little if any selective pressure, which infers that its evolutionary potential is likely untapped.

The present disclosure provides the solution to the two major barriers preventing commercialization of photosynthetic hydrogen production to date: 1) the hydrogenase enzyme that produces the molecular hydrogen is sensitive to oxygen and, 2) the amount of hydrogen production needs to be increased. Since the *C. reinhardtii* hydrogenase genes have been cloned, mutation of the original parental genes is disclosed herein, as well as a method to search among a library of such mutants and select a mutant algal hydrogenase with an improved phenotype with respect to hydrogen production rate. After the mutant genes are created, this disclosure further describes insertion and expression of the mutants in *C. reinhardtii*. A novel method of selecting or screening the mutants for enhanced traits in algae is also disclosed. The present disclosure further provides for a chimeric hydrogenase with a mutation(s) that decreases the diameter of the proton channels described above, thereby restricting the larger oxygen molecules by size exclusion, while still allowing for passage of the smaller bio-hydrogen molecules.

As will be further apparent from the Examples provided herein below, the present disclosure encompasses methods for mutating bacterial hydrogenases to produce increased amounts of hydrogen after just one round of a combinatorial shuffle. Additionally, exogenous DNA of hydrogenases can be successfully re-introduced into the genome of *C. reinhardtii*. Once transformed, the plasmid containing the hydrogenase gene can be successfully expressed at both the RNA and protein levels, thus illustrating that mutated *C. reinhardtii* hydrogenase genes can also be inserted and expressed. Therefore, the present disclosure provides for expression of chimeric hydrogenases in *C. reinhardtii*, and expression of chimeric algal hydrogenases containing mutations with improved function. Further disclosed then is a method for using these chimeric algal hydrogenases, when expressed for example in *C. reinhardtii*, for photosynthetic hydrogen production.

Additionally, disclosed is a model system by which different mutations can readily be created and tested. Further analysis of the hydrogen production of the remainder of the existing mutant library in conjunction with molecular modeling determines what characteristics are shared between the mutants with improved hydrogen production. Considerable improvement frequently results from the comparison and combination of mutations isolated in the first round of shuffling. In addition, future rounds of directed evolution might benefit by the inclusion of the other four Clostridial parent sequences. In order to link the photosynthetic transport chain with an improved hydrogenase, the mutations that result in the most improved bacterial mutant should be re-created in the algal hydrogenase. Since the algal hydrogenase has a disparate codon bias and is merely homologous, not identical, to the bacterial hydrogenase, mutations in the algal enzyme need to be created and tested to determine if the same improvement is realized. Ultimately, an improved chimeric algal hydrogenase, transformed into *C. reinhardtii*, is the basis for an economically viable method of hydrogen production.

Clostridal hydrogenases were selected because they share homology with their eukaryotic algal *C. reinhardtii* cousins, so that mutations resulting in an enhanced clostridial phenotype had an increased likelihood of producing the same enhancement when the analogous mutation was created in *C. reinhardtii*. Therefore, the present disclosure also describes the creation of libraries of mutated clostridial hydrogenase genes, and their subsequent testing for enhanced hydrogen production.

To create the chimeric mutant hydrogenase libraries using homologous bacterial hydrogenases, a process known as directed evolution was applied. The process mimics natural evolution in that multiple mutations are created. Albeit on a shorter timescale, proteins of interest are submitted to repeat cycles of evolutionary pressure to produce a variety of mutations. Resulting mutants are then tested for desirable traits, such as in the present case, increased rate of hydrogen production relative to wild type hydrogenases. Mutants demonstrating desirable traits are then transformed into an algae such as *C. reinhardtii*.

Bacterial hydrogenases with enhanced hydrogen production can be generated using degenerative oligonucleotide gene shuffling (DOGS). (For a description of the DOGS technique, see, for example, M. D. Gibbs et al., Gene 271(1): 13-20 (2001), and WO/2002/018629, the entire disclosures of which are incorporated by reference in their entireties). Briefly, DOGS involves assigning at least one segment of at least one gene, typically at least two homologous genes, based on regions of encoded amino acid sequence; amplifying the one or more assigned segments of the gene(s) using primers specific for each segment; and combining, or causing recombination of the one or more amplified segments to form a mutant or chimeric gene. An oligonucleotide primer suitable for use in gene shuffling can be used, wherein the primer has a non-degenerate core based on a segment or template of a gene to be amplified, and the core is flanked by both 5' and 3' degenerate ends. As described herein, the method may involve forming a mutant or chimeric gene from two or more genes, in which one or more segments of each gene are assigned based on regions of encoded amino acid sequence; amplifying the one or more segments of the genes; and combining at least some of the amplified segments so as to form a mutant or chimeric gene. The two or more genes may belong to the same gene family encoding the same functional protein. According to the present disclosure, the two or more genes are homologous genes that each encode a hydrogenase.

Suitable bacterial parental hydrogenases include but are not limited to those obtained from Clostridial bacteria, such as for example *Clostridium saccharobutylium, Clostridium acetobutylicum, Clostridium pasteurinum, Clostridium perfringens, Clostridium tetani*, and *Clostridium thermocellum*.

The DOGS technique may be applied by dividing each parental hydrogenase gene from the bacteria into the multiple segments of roughly equal length. As described herein, the homologous parental genes are divided into multiple, e.g. eight (8), segments of roughly equal length. The segment boundaries are specifically chosen with positions within regions of high homology amongst the two parental genes. Except for the first and last segments (which in examples described herein are segments #1 and #8) each segment has two unique sticky ends created by a restriction endonuclease such as, in non-limiting example, SapI. The uniqueness of each sticky end allows it to overlap only with its neighboring segments. For example, as described herein, the downstream end of segment #2 could only overlap with the upstream end of segment #3 and the downstream end of segment #3 would overlap with only the upstream end of segment #4, thereby generating a full-length chimeric gene library with, segments from both parental genes.

A variation to the DOGS technique may also be used as in which only three base pairs of homology are required as the overlap is created by a restriction enzyme thus allowing elimination of the overlap PCR steps in favor of a simple annealing of the sticky ends generated by the enzyme.

Either version of the DOGS technique can be used to produce a full-length chimeric gene library wherein the overlap positions occur in regions of high homology. The gene shuffling technique effectively swaps segments of the parental genes by choosing the segment intersections in advance. It has the advantage of capitalizing on the evolutionary differences amongst the parent genes including the regions of high homology while maintaining the overall length of the gene.

As is known in the art, a number of different programs can be used to identify whether a nucleic acid or polypeptide has sequence identity or similarity to a known sequence, after aligning the sequences and introducing gaps, if necessary, to achieve the maximum percent sequence similarity. The sequence alignment for purposes of determining percent amino acid sequence similarity may be achieved in any of a number of established various ways that are known to those of routine skill in the art. Readily available computer software can be used to determine sequence similarity. For example, BLAST, gapped BLAST, BLAST-2, ALIGN or Megalign (DNASTAR) software is generally widely known and used in the art (see, e.g., Altschul et al., J. Mol. Biol. 215, 403-410, (1990); Altschul et al., Methods in Enzymology, 266, 460-480 (1996); Altschul et al., Nucleic Acids Res. 25, 3389-3402 (1997)). A hydrogenase mutant polypeptide will have at least about 80% amino acid sequence similarity, alternatively at least about 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% amino acid sequence similarity, to a full-length wild type hydrogenase (control) sequence as disclosed herein.

Expression of mutant hydrogenases can be achieved in a suitable host organism such as but not limited to a bacterial host such as *E. coli*, and a green algae such as *C. reinhardtii*, according to techniques well known and described in the art. A wide variety of molecular and biochemical methods and tools including suitable vectors are available for generating mutant hydrogenases, transforming host organisms and expressing mutant hydrogenases as described herein. See, e.g., MOLECULAR CLONING, A LABORATORY MANUAL (Sambrook et al., Cold Spring Harbor Laboratory); CURRENT PROTOCOLS IN MOLECULAR BIOLOGY (Eds. Ausubel et al., Greene Publ. Assoc., Wiley-Interscience, NY). Alga used according to the present disclosure may be any alga capable of producing hydrogen. Preferably a green or blue-green alga, such as but not limited to *C. reinhardtii*, is selected.

Hydrogen production by mutant dehydrogenases can be measured using any established method, such as but not limited to the methyl viologen assay, the resazurin assay and the metronidazole assay as described in further detail in the Examples herein below. Alternatively, a batch reactor can be employed, and the headspace above the reaction mixture sampled periodically, for example every hour to obtain a hydrogen content in the headspace using gas chromatography. Efficiency of each mutant can be determined for example by comparing the time required for a mutant to produce the maximum amount of hydrogen obtained from the wild type hydrogenase under standard conditions.

The present disclosure describes calculation of a positive to negative electrostatic potential surface area (EPSA) ratio for each mutant hydrogenase. As described herein, the positive to negative EPSA is indicative of hydrogen production capability, wherein bacterial and algal mutants with a positive to negative EPSA ratio from about 1 to about 115, preferably from about 2 to about 50, more preferably about 5 to about 20, yield hydrogen at a faster rate than that observed with a wild type control organism. A positive to negative EPSA ratio for any hydrogenase mutant may be determined according to the method described in detail in Examples 5-7 herein below. Briefly, amino acid sequences are used to construct alpha-helix structures for each mutant. These structures are then energy minimized using an established energy optimization or geometry optimization algorithm, such as but not limited to the simple gradient algorithm, the nonlinear conjugate gradient algorithm, or preferably the physics-based all atom force field for proteins (OPLS-AA). (See, e.g., W. Jorgensen et al., J. Am. Chem. Soc. 118(45): 11225-36 (1996)). Next, the positive and negative electrostatic potential surface areas (EPSA) for each structure are calculated using a selected probe radius of 0.5 to 1.5 Å. The probe radius must be selected to yield the most accurate correlation between the EPSA ratio and hydrogen production as described below. Actual values in the calculations described herein were either 1.0 and 1.4 Å. Overlapping positive and negative regions may or may not be excluded in the calculations. Computations may be performed with computational chemistry software, such as but not limited to the HyperChem 7.5 computational chemistry program. In the calculations herein, a 32 bit computer was used. Each positive to negative EPSA ratio thus obtained may be plotted versus experimentally measured hydrogen production for any mutant, and compared to that observed with a wild type control. Such a plot may be best fit with a Log Normal Gaussian function, which can be used as the prediction model. The selected prediction model suggests that the ratio of positive to negative electrostatic potential surface areas is a measure of how a given protein mutant will fold into its tertiary state and how the final tertiary state affects hydrogen production. Initial results showed that an EPSA ratio in the range of about 15 to about 115, obtained with a probe radius of 1.4 Å, is required to achieve hydrogen production from bacterial hydrogenases greater than that obtained with a wild type bacterial control, and that maximum hydrogen production is achieved with a positive to negative EPSA ratio of about 42 (see FIG. 32). Later more accurate results, using a probe radius of 1.0 Å, showed that an EPSA ratio in the preferable range of about 2 to about 50, and more preferably from about 5 to about 20, to be indicative of the highest rates of hydrogen production observed from bacterial hydrogenases, relative to a wild type control. (See FIG. 33). For example, the model predicts that an EPSA ratio of about 16 will produce hydrogen from a bacterial hydrogenase at a rate of about 530 times that of a wild type hydrogenase.

C. Adaptations of the Methods of the Present Disclosure

By way of example, not of limitation, examples of the present invention shall now be given.

Example 1

Generation of Mutant and Chimeric Hydrogenase Libraries

Figure 4:
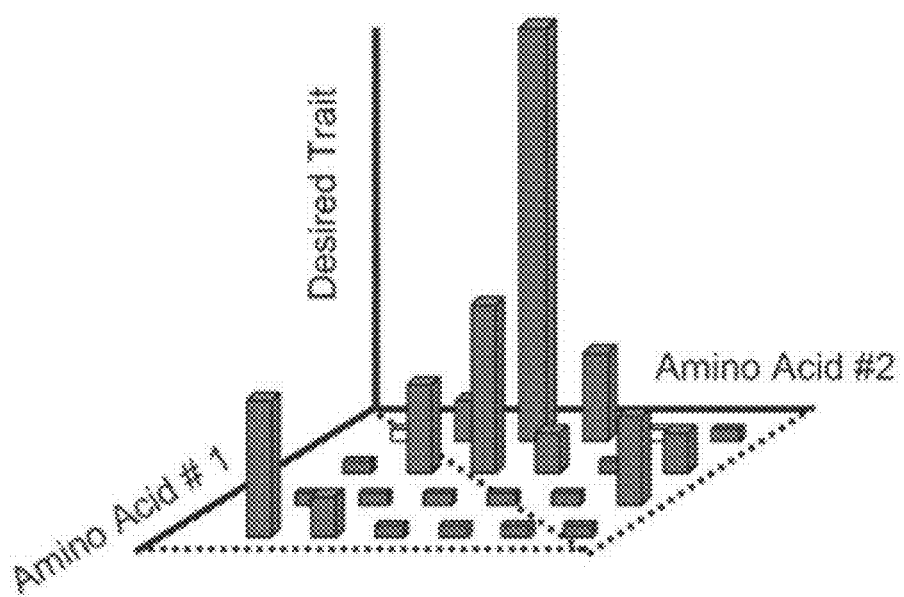
FIG. 4 is an example of sequence space; the set of all possible amino acid sequences. According to the disclosure, the protein of interest is just 2 amino acids in length.

Gene shuffling is the process of creating mutant DNA sequences which codes for a protein with an improved or a novel function. Most frequently, the DNA sequence represents a gene and the goal is to modify it by mutating it into many thousands of new genes, each mutated in a different manner, to create a new phenotype with the desired characteristics. A sizeable percentage of these genes will encode for non-functional proteins or for proteins with no improvement over the original. However, several mutant or chimeric proteins will exhibit a significantly improved functionality. The proteins with improved function can be re-shuffled, thereby amplifying the improved function. Thousands or millions of mutants can be created and all of "sequence space" can, in principle, be successfully surveyed (FIG. 4).

The sequence space (20 n) is the set of all 20 possible (common) amino acids in each position for a protein of a particular length. (n). A plot of the sequence space versus the desired trait shows local maxima and minima in the desired trait. After several rounds of shuffling, it is common to find that the protein cannot be improved any further. Protein function improvements of 500×–32,000× are known to result from this method in other organisms, thereby confirming that this method can produce significant positive changes in a protein. Consequently, we can use gene shuffling to create a library of chimeric proteins. By selecting for an improved trait from that library, we can direct the evolution of the original parental protein. This technique is referred to herein as "Directed Evolution".

Figure 5:
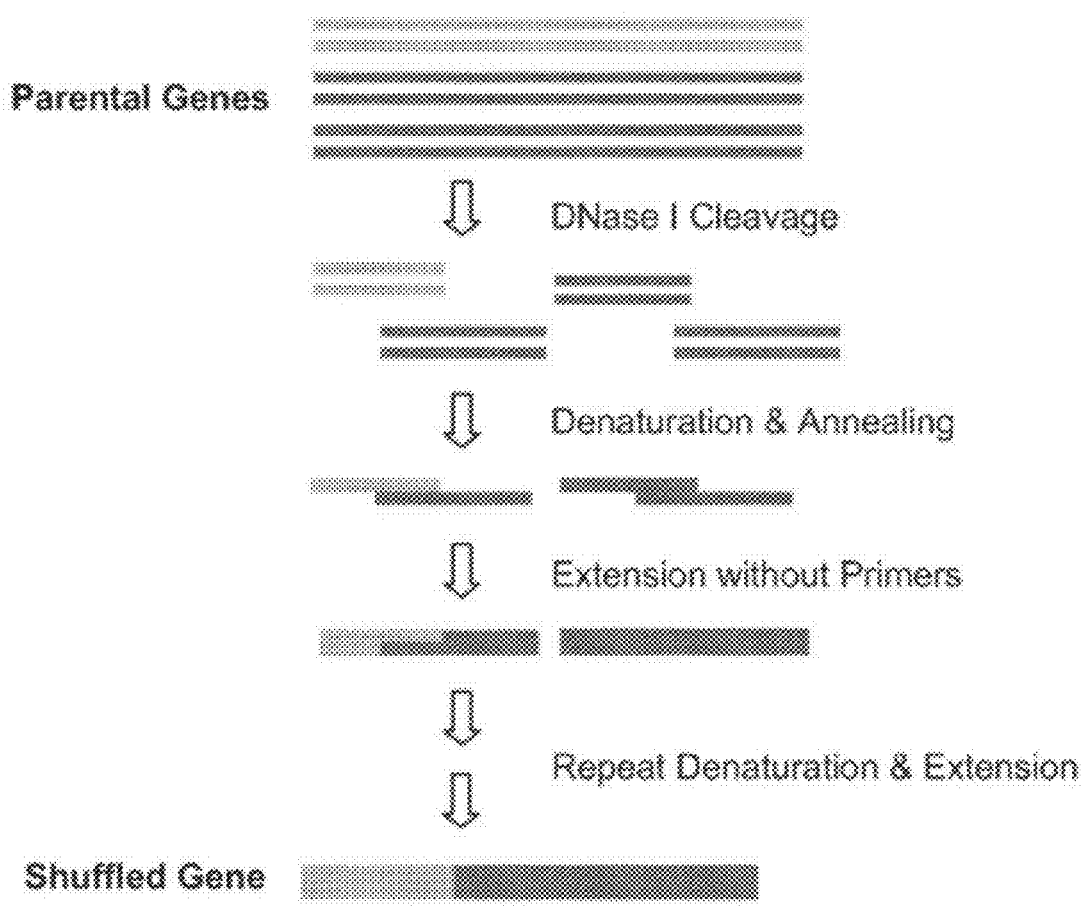
FIG. 5 is a diagram of a "Family Shuffle."

Gene shuffling using Willem Stemmer's family shuffling technique can be used to effect direct evolution. In Stemmer's protocol, multiple parent genes were digested. The fragments were recombined using multiple cycles of PCR to form chimeric progeny (FIG. 5). Other techniques soon followed, including: family shuffling with single stranded DNA (ssDNA), staggered extension process (StEP), iterative truncation for the creation of hybrid enzymes (ITCHY), random chimeragenesis on transient templates (RACHITT), and degenerative oligonucleotide gene shuffling (DOGS). Each technique generates a large number of diverse gene sequences, referred to as a library. A selection is then performed on the chimeric proteins that are generated from the library of genes; a selection for an enhanced trait such as enzyme selectivity, stability, or activity. For algal hydrogenase research, organisms with enhanced tolerance for oxygen and/or an increased capacity for the production of hydrogen are favored in the selection process. As described herein, this directed evolution may also be achieved with gene shuffling via a technique known as error-prone PCR. This method of creating a mutant library merely alters the conditions of standard PCR so that they were no longer optimal, thereby forcing the polymerase to make mistakes. This method in practice proved to be not sufficiently random and resulting mutant offspring were not significantly different from the parent genes.

Figure 6:
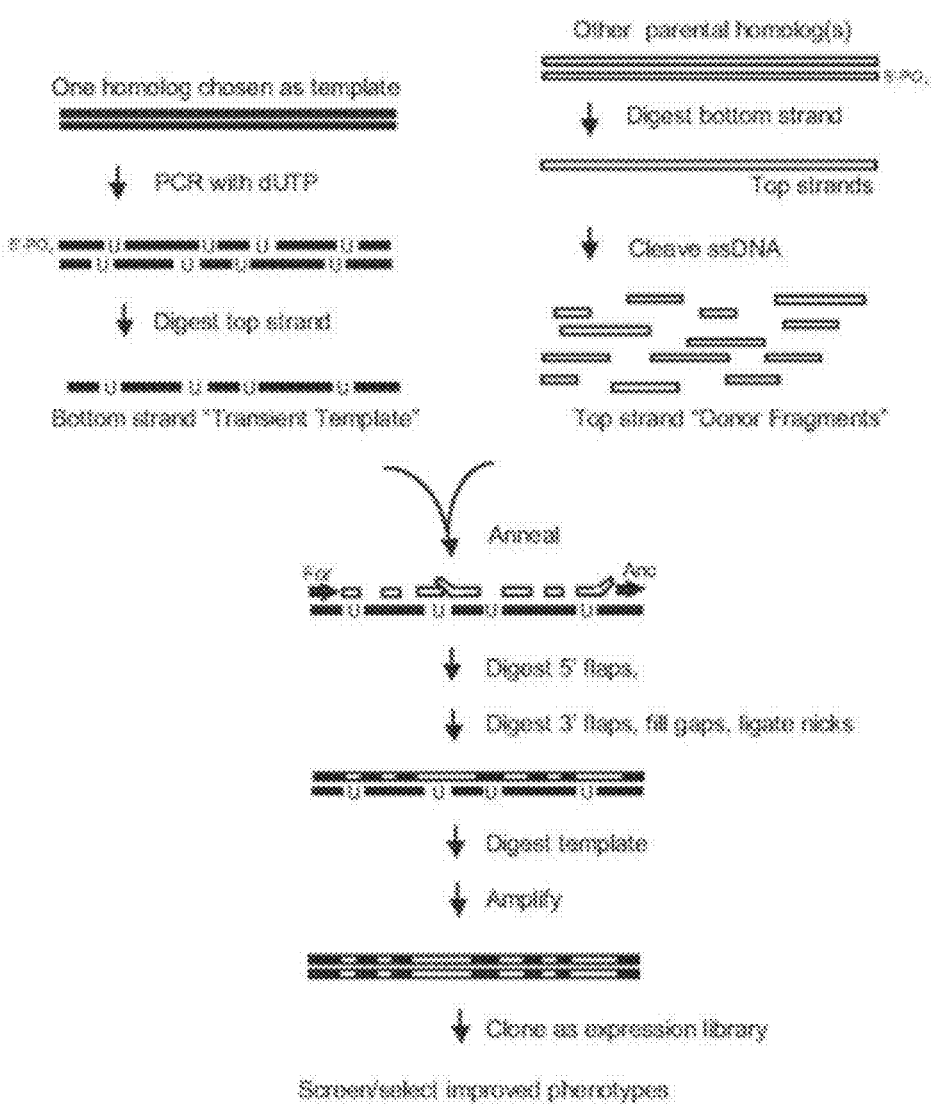
FIG. 6 is the RACHITT technique for generating a combinatorial library.

In order to find the optimal method to generate a library, several of the above shuffling methods can be used, alone or in combination. The RACHITT method generates a library containing a high percentage of diverse chimeras with little or no representation of the original parental genes (FIG. 6). It does so by choosing one of the parental genes to be a template strand, while the others are designated as donor strands. All the parental DNA is made single-stranded (ssDNA). In addition, the donor strands are digested into pieces of about 200-800 nt. The digested donor DNA oligonucleotides bind to the template strand. Once the gaps are filled in, the template strand is removed by completely digesting it down to the level of individual bases. Since all of the parental DNA was digested, a library of full-length chimeras is created. Next, the standard family shuffle (FIG. 5) was used. Error-prone PCR and the DOGS technique, as described below, are particularly useful in creating chimeric libraries.

In order to find the optimal method to generate a library of chimeric hydrogenases, several shuffling methods can be tried, alone or in combination. Here, to create a library of chimeras, several mutational techniques were used. The family shuffle and random chimeragenesis on transient templates (RACHITT) were used initially, but were found to be less effective than other methods. However, two other techniques, random mutagenesis by error-prone PCR and a variation of degenerative oligonucleotide gene shuffling (DOGS) were highly successful and led to the creation of the mutational libraries disclosed herein.

Error-prone PCR is similar to standard PCR in that it uses the same primers to replicate the gene of interest (GOI). However, the polymerase has been altered so that errors in the replication process occur more often. This technique generated a mutant library with an average of 10 point mutations per gene. Although libraries of mutated genes are readily created, error-prone PCR is not the most efficient technique for the creation of a protein with improved function, as it is not known which or where a point mutation would be beneficial.

Figure 13:
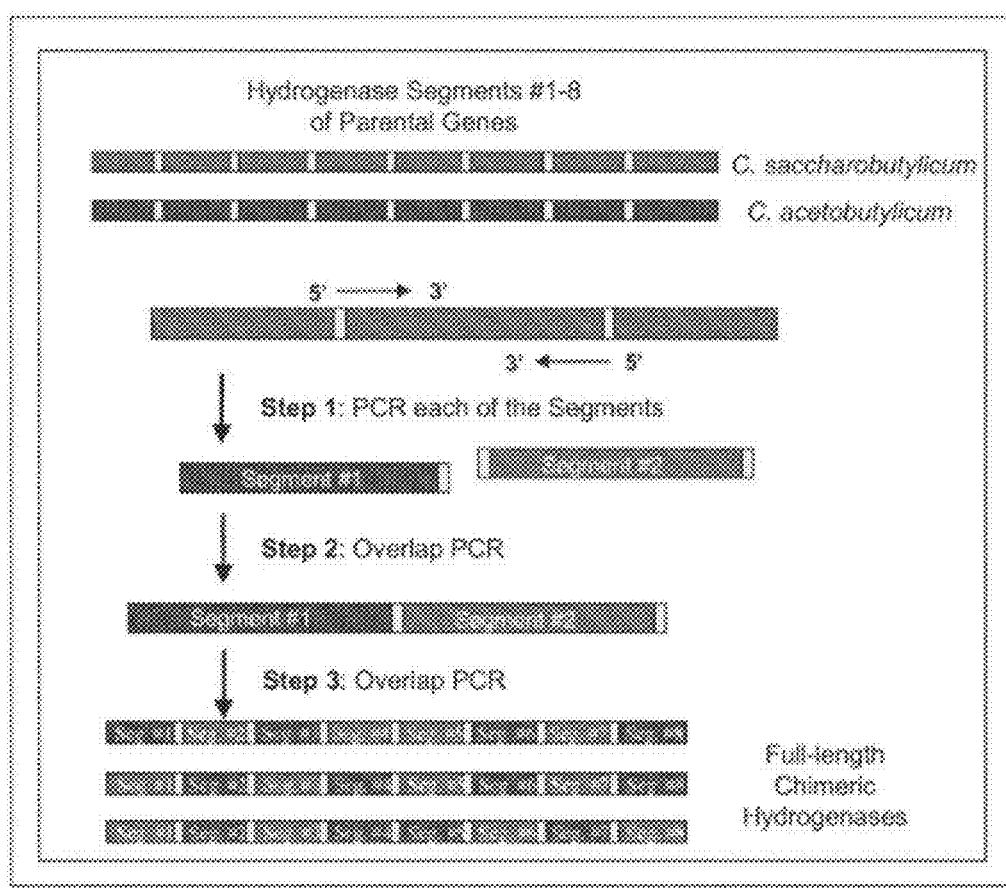
FIG. 13 illustrates the degenerative oligonucleotide gene shuffling (DOGS), the technique used to create the chimeric library.

The DOGS technique divides each parental GOI into roughly equal segments (see FIG. 13). In this study, the segment boundaries were specifically chosen within regions of high homology amongst the parent genes. Each segment of each gene was generated by an initial PCR. Forward and reverse degenerate primers were employed on both sides of the segment boundary in order to facilitate an overlap of the two segments (see FIG. 14). Each segment boundary is a unique sequence. A second PCR combined the segments in the same segment order as the original parent genes, thereby generating a full-length chimeric library.

Figure 15:
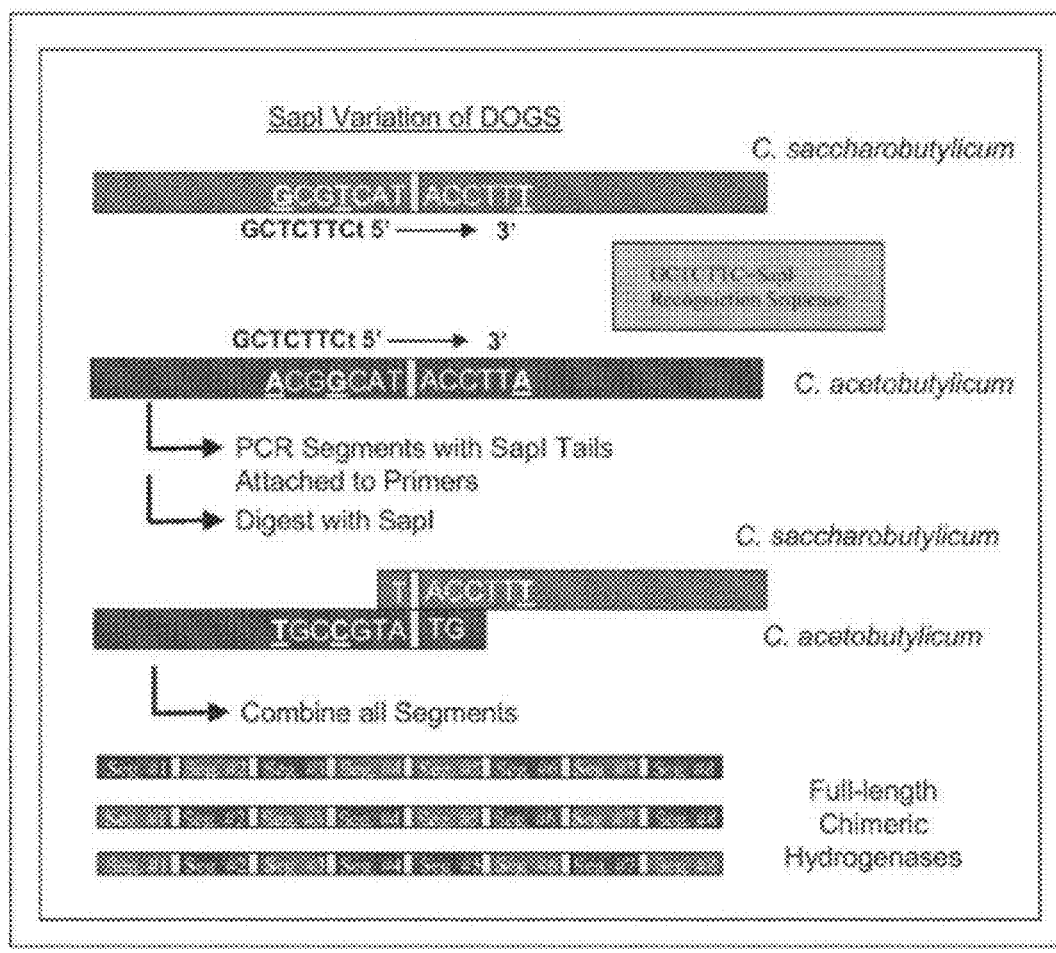
FIG. 15 illustrates the variation of the degenerative oligonucleotide gene shuffling (DOGS) technique that utilizes the exonuclease SapI.

A variation to the DOGS technique was also used; it required only three base pairs of homology as the overlap is created by a restriction enzyme (see FIG. 15). The overlap PCR steps are eliminated in favor of a simple annealing of the sticky ends generated by the enzyme.

Either version of the DOGS technique lead to a full-length chimeric gene library wherein the overlap positions occur in regions of high homology. Therefore, this shuffling technique effectively swaps segments of the parental genes by choosing the segment intersections in advance. It has the advantage of capitalizing on the evolutionary differences amongst the parent genes including the regions of high homology while maintaining the overall length of the gene.

Two mutagenesis libraries were created. The first library was generated using a random mutagenesis kit (Stratagene GeneMorph II: #200550) according to the manufacturer's protocol. The PCR protocol that generated the highest number of mutations was followed: an initial denaturation of 2' at 95° C. followed by 30 cycles of [0.5° at 95° C., 0.5° at 59° C. 2' at 72° C.].

Figure 14:
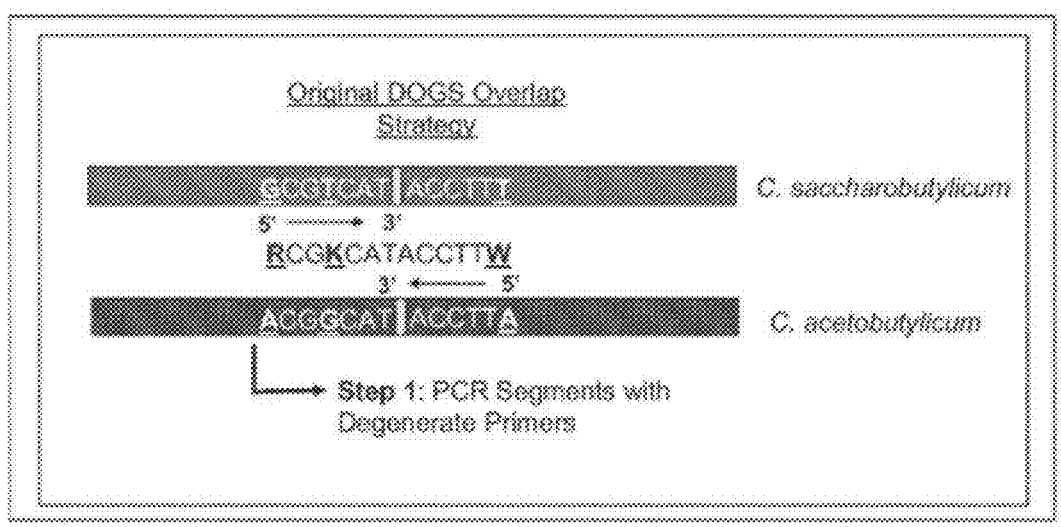
FIG. 14 illustrates the design of the primers for the original (DOGS) technique.

A second mutagenesis library was created using a variation of the original DOGS method (see FIGS. 13 through 15). The total length of the gene was first divided into eight segments of equal length. The segment lengths varied from 160 bp to 290 bp, as it was necessary to choose the segment boundaries within regions of homology (see Table 1, SEQ ID NOs. 23-38 (middle column); SEQ ID NOs: 39-54 (right hand column)). Each segment was individually generated by PCR using 30 ng of the plasmid containing the parent hydrogenase. The PCR protocol utilized Phusion polymerase (New England Biolabs (NEB): #F530L) according to the manufacturer's protocol: an initial denaturation of 30. sec. at 98° C. followed by 35 cycles of [10 sec. at 98° C., 20 sec. at 57° C. Δ7° C., 20 sec. at 72° C.], and a final extension of 10' at 72° C. The segments were gel purified (Qiagen Qiaex II kit: #20021) and digested with SapI (NEB: #R0569L).

The digested segments were column purified (Qiagen QiaQuick PCR kit: #28104) and 50-100 ng of each segment was mixed together and ligated (Lucigen T4 ligase: #30025-2). To generate the full-length hydrogenases, the ligated segments were amplified by PCR using 1-2 µl of the ligation mixture and primers that complemented the homologous regions just upstream and downstream of segment numbers one and eight, respectively.

The SapI variation of the DOGS method could generate ligations of up to four segments, so the library was ultimately created using a combination of the original DOGS method and the SapI variation. The SapI variation on the DOGS method was utilized, as above, to combine the eight individual segments, from both parental genes, into four ¼-length chimeras, each with a combination of two segments, i.e. all the possible combinations of segment 1 and segment 2 were generated as well as segment 3 with segment 4, etc. After ligating the SapI generated segments, the ¼-length chimeras were amplified by PCR using primers appropriate for the particular ligation.

The appropriate primers (see Table 1, SEQ ID NOs. 23-38 (middle column); SEQ ID NOs: 39-54 (right hand column)) had extra bases added (see Table 2, SEQ ID NOs. 55-66) that included 10-15 bp of overlap with the ¼-length chimeras on either side. The quarter genes were purified (Qiagen Qiaex II kit: #20021) and then re-amplified into ½-length or full-length chimeras using a two-step program that first allowed the individual ¼-length chimeras to overlap before the outside primers generated the full-length gene: an initial denaturation of 30 sec. at 98° C. followed by two cycles of [10 sec. at 98° C., 30 sec. at 60° C., 30 sec. at 72° C.], a pause at 93° C., 35 cycles of [10 sec. at 98° C., 20 sec. at 59° C., 40 sec. at 72° C.], and a final extension of 10' at 72° C.

The first two cycles allowed the segments to self-prime and extend from the overlapping regions. The outside primers were added during the pause, which lasted approximately three minutes before the full-length chimeras were generated. The resulting full-length chimeras were gel purified, digested with NcoI & AscI (NEB: #R0193S and #R0558S), column purified, and cloned into the pET DLS vector. The above procedure, of digestion with SapI followed by ligation and PCR amplification, can be repeated several times, as necessary, to obtain a full-length chimeric hydrogenase.

TABLE 1

[SEQ ID NOs. 23-38 (middle column); SEQ ID NOs: 39-54 (right hand column)]

| Segment | Segment Length[1] | SapI Generated Overhang[2] | Overhang Location[3] | Upstream & Downstream Primers for C. saccharobutylicum[4] | Upstream & Downstream Primers for C. acetobutylicum[4] |
|---|---|---|---|---|---|
| 1 | 211 (462) | ggt | 212-214 | 5' cccacgccgaaacaag 3'<br>5' accataccttcttcaactttg 3' | 5' cccacgccgaaacaag 3'<br>5' accattccatcttcaactttggc 3' |
| 2 | 229 | tgt | 441-443 | 5' ggtagtaaaaacaaactcag 3'<br>5' acacttagttctgtctattacaat 3' | 5' ggtaataaacacagaatccgatg 3'<br>5' acattttgatctgtcaattacaat 3' |
| 3 | 231 | cat | 672-674 | 5' tgtgtgctatgcggaaga 3'<br>5' atgcttattaggatcttctaatg 3' | 5' tgtgtactatgcggtagatg 3'<br>5' atgttttttagggtcattaagag 3' |
| 4 | 192 | aaa | 864-866 | 5' catgtaatagttgctatggc 3'<br>5' tttaactctttcaataaactctg 3' | 5' catgtcattgttgcaatggc 3'<br>5' tttaactctgcctaaaagttcagt 3' |
| 5 | 284 | aga | 1148-1150 | 5' aaaaataatggaccattccca 3'<br>5' tctcttgtagtaagtactgcatc 3' | 5' aaaaataatggcccattccctatg 3'<br>5' tctcttgtagttaaggatgcatcaa 3' |
| 6 | 214 | ata | 1362-1364 | 5' agaattagcaaaaatgattaaagatg caa 3'<br>5' tattccttgtaatcctcttatttgtg tat 3' | 5' agagcttgcaaaaatgattaaagatg c 3'<br>5' tatgcctttaaagcctcttacttcag 3' |
| 7 | 159 | gga | 1521-1523 | 5' ataaagaggctacagtagaaattgg tgg 3'<br>5' tccaccatttacacatccgcc 3' | 5' ataaagaagcggaagttgaaattgc 3'<br>5' tccaccatttatacatccaccag 3' |
| 8 | 205 (455) | N/A | N/A | 5' ggaggacaaccacacgta 3'<br>5' tacgattactttctgttcgactta 3' | 5' ggaggtcaacctcacgtaaatg 3'<br>5' tacgattactttctgttcgactta 3' |

[1]The first and last segments were longer to allow for nested primers. The total length of the segment is listed in parenthesis.
[2]The overhang was generated at the end of the listed segment.
[3]The location in C. Saccharobutylicum.
[4]Each of these primers had a SapI "gactgactGCTCTTCt" tail.

TABLE 2

[SEQ ID NOs. 55-66]

| Overlapping Segments[1] | Overlapping Parental Segments[2] | Forward/Reverse Degenerate Overlap Primers[3] |
|---|---|---|
| 1&2 with 3&4 | Saccharo & Saccharo | 5' gtaatagacagaactaagtgtgtgctatgcggaagatgt 3' |
|  | Saccharo & Aceto | 5' gtaattgacagatcaaaatgtgtgctatgcggaagatgt 3' |
|  | Aceto & Aceto | 5' gtaatagacagaactaagtgtgtactatgcggtagatgcg 3' |
|  | Aceto & Saccharo | 5' gtaattgacagatcaaaatgtgtactatgcggtagatgcg 3' |
| 3&4 with 5&6 | Saccharo & Saccharo | 5' cagagtttattgaaagagttaaaaataatggaccattcccaatg 3' |
|  | Saccharo & Aceto | 5' cagagtttattgaaagagttaaaaataatggcccattccctatg 3' |
|  | Aceto & Aceto | 5' ctgaacttttaggcagagttaaaaataatggcccattccctatg 3' |
|  | Aceto & Saccharo | 5' ctgaacttttaggcagagttaaaaataatggaccattcccaatg 3' |
| 5&6 with 7&8 | Saccharo & Saccharo | 5' aaataagaggattacaaggaataaaagaggctacagtagaaattg 3' |
|  | Saccharo & Aceto | 5' aaataagaggattacaaggaataaaagaagcggaagttgaaattgc 3' |
|  | Aceto & Aceto | 5' gtaagaggctttaaaggcataaaagaagcggaagttgaaattgc 3' |
|  | Aceto & Saccharo | 5' gtaagaggctttaaaggcataaaagaggctacagtagaaattg 3' |

[1]The original parental genes were divided into eight segments.
[2]The parents are *C. saccharobutylicum* (Saccharo) and *C. acetobutylicum* (Aceto).
[3]The reverse primers are simply the inverse complement of the listed forward primer.

Example 2

Hydrogenase Library

The error-prone PCR technique created a library of progeny genes that contained an average of 10 point mutations per hydrogenase gene. The DOGS technique created a library of 254 full-length hydrogenase genes, but each of the 254 chimeras was unique and contained sizeable amounts of shuffled genetic material.

*C. reinhardtii* is known to contain two hydrogenases (HydA1 and HydA2), both of which produce molecular hydrogen. However, both the transcription of the RNA and the mature hydrogenase protein are sensitive to oxygen, a by-product of photosynthesis, which results in only a brief evolution of molecular hydrogen. However, mutations engineered into the native algal hydrogenase will generate chimeric hydrogenases with an increased rate of hydrogen production and/or an increased tolerance to the presence of oxygen. Each type of chimeric hydrogenase would result in an increased amount of hydrogen production. More importantly, subsequent rounds of mutation have the potential for further improvement. In order to successfully create a mutant version of *C. reinhardtii*, the goal was to identify, clone, sequence, and express the hydrogenase genes that were responsible for the generation of hydrogen in algae.

*C. reinhardtii* contains an enzyme (hydrogenase) that produces molecular hydrogen from electrons donated by ferredoxin, an enzyme in the photosynthetic electron transport pathway, and in fact, according to the present disclosure, it was determined that *C. reinhardtii* actually contains two hydrogenases, HydA1 and HydA2.

Example 3

Vector Creation

HydA1 and HydA2 were cloned and a vector that could express the hydrogenases in algae designed and tested. The transformation of heterogeneous DNA, via a vector, into *C. reinhardtii* was difficult due to the distinct codon bias of the alga. Subsequent extraction of the transformed DNA was also difficult due to the alga's predilection for digesting the transformed DNA and incorporating it at random locations within the genome.

Figure 7:
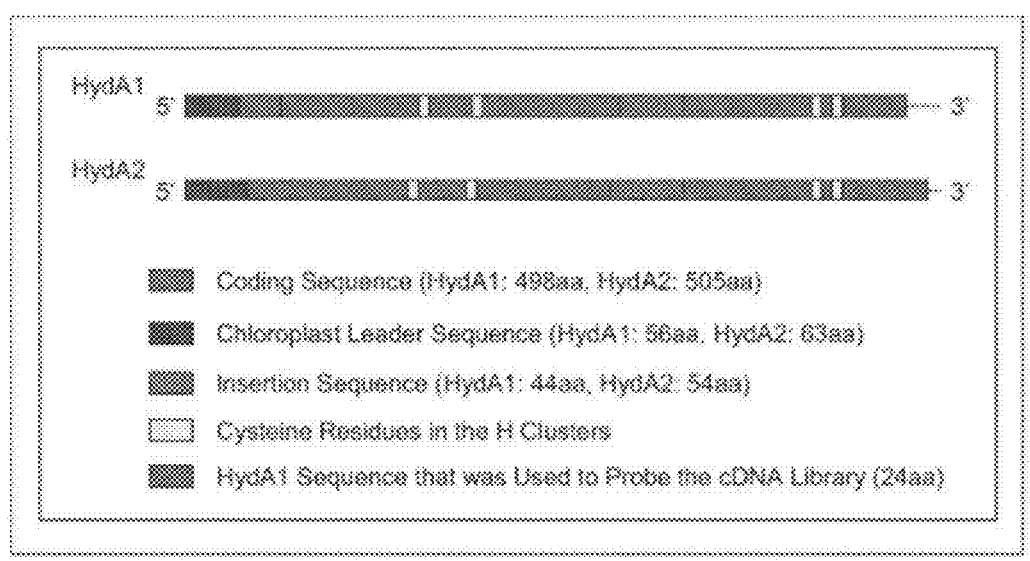
FIG. 7 is the sequence comparison of the two *C. reinhardtii* hydrogenase genes.

Probing the cDNA library successfully identified two hydrogenases, designated as HydA1 and HydA2, which were cloned and sequenced (FIG. 7). HydA1 and HydA2 are similar in that they both have the ability to produce molecular hydrogen and are sensitive to molecular oxygen. HydA2 is 68% identical and 74% similar (i.e. a related amino acid) to HydA1. Although functionally similar and approximately the same length, HydA1 (495 aa) and HydA2 (505 aa) are distinct proteins from separate genes with different promoter regions. In addition, the leader sequences in HydA1 and HydA2 are quite distinct, which indicates that they may function in different locations of the chloroplast. First, the un-translated regions (UTR) immediately upstream (5' UTR) and downstream (3' UTR) of the gene were utilized to create a vector (pGenD) that is capable of driving the expression of cDNA in algae, including cDNA foreign to the alga.

Then apGenD vector was used to create a pGenD+Ble by inserting a Bleomycin antibiotic resistance gene (BLE) into XhoI/PacI downstream of the 3' un-translated region. Antibiotic resistance confers selectivity for the alga containing the plasmid, allowing it to grow in the presence of Bleomycin antibiotic, while repressing the growth of bacteria or algae without the plasmid.

Then, the pGenD+Ble vector was altered to the new vector, named "pSMP", by inserting the cDNA of one of the *C. reinhardtii* hydrogenases (HydA1) between the NdeI and NheI restriction sites thereby replacing the original coding sequence (FIG. 8). A strepII tag was added at the 3' terminus of the HydA1 gene between the NheI and EcoRI restrictions sites (FIG. 8). The tag allows ready detection and differentiation of the HydA1 DNA, RNA, and protein from the indigenous hydrogenases. Lastly, a restriction site was created, so as to separate the HydA1 leader sequence from the DNA that codes for the mature protein.

Figure 8A:
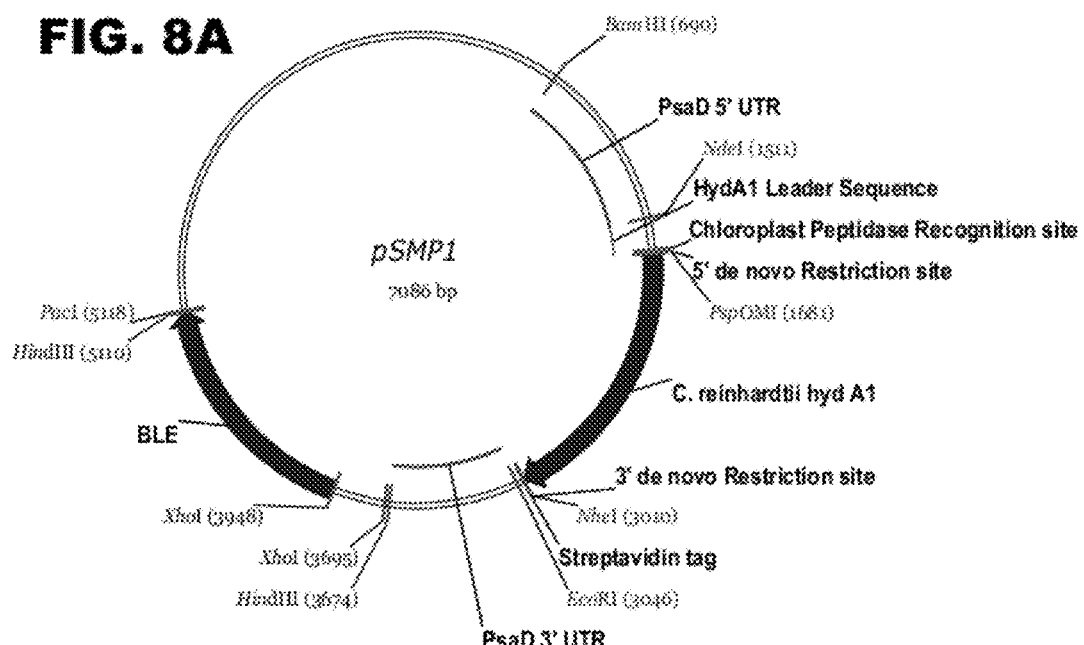
FIG. 8 is a plasmid map of the algal expression vectors: A) pSMP1, B) pSMP1c, and C) pSMP2.

The leader sequence contains cellular instructions for the placement of the mature protein in the correct location within the algal chloroplast. It was important to insert mutated coding sequences without changing the leader sequence. Since it was unknown whether or not an internal restriction site would impede the successful expression of the vector, three pSMP vectors (pSMP1, pSMP1c, and pSMP2) were created, each with a slightly different restriction site. In the case of pSMP1, a PspOMI restriction site was inserted, de novo, immediately downstream of the leader sequence (FIG. 8A).

Figure 8B:
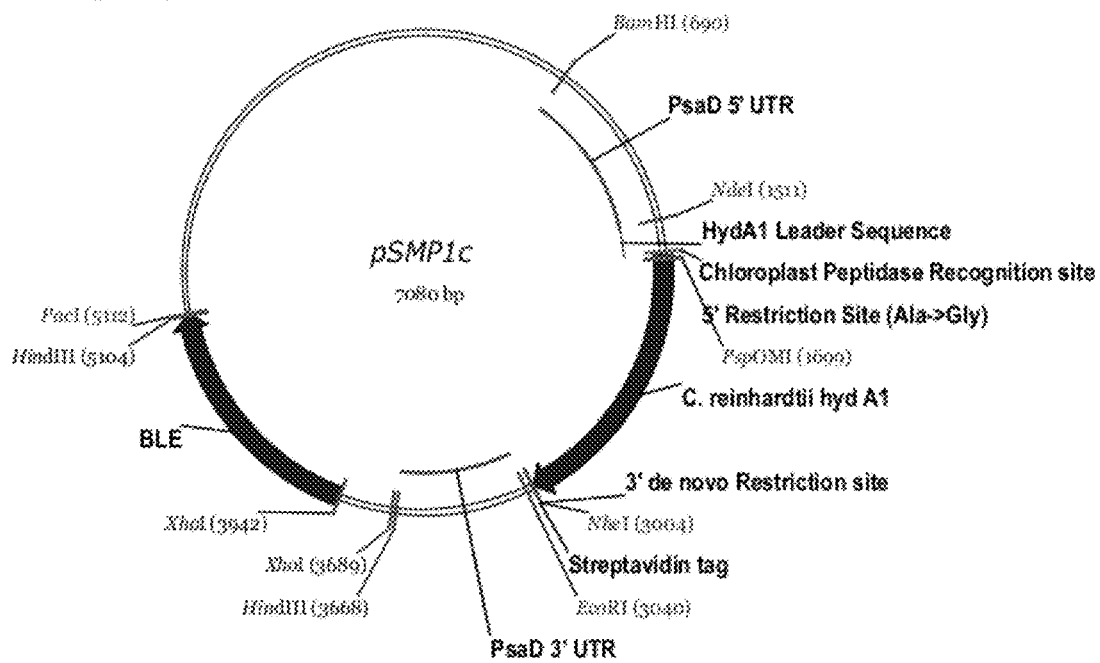

As it was possible that even a small (6 bp) de novo insertion could interfere with expression, two additional pSMP vectors were created. The vector pSMP1c had a PspOMI site created from a conservative mutation about 20 nucleotides (nt) downstream of the end of the leader sequence (FIG. 8B). The vector pSMP2 had an AsiSI site created from a conservative mutation about 45 nt downstream from the end of the leader sequence (FIG. 8C). These vectors were tested for expression of HydA1 cDNA in C. reinhardtii.

Figure 9:
FIG. 9 is a picture of an agarose gel (1%) showing the results of PCR on the genomic DNA extracts of algal transformants.

The vectors each containing the hydrogenase, HydA1, were transformed into C. reinhardtii. Genomic DNA was extracted from 20 different transformations of the pSMP vectors. The hydrogenase DNA was amplified by polymerase chain reaction (PCR) with primers specific to the 3' end of the hydrogenase and the transformed vector. The 800 base pair (bp) band indicated that each of the 20 genomic extracts received the plasmid (FIG. 9). There was no difference in the transformation efficiency of the three vectors.

Figure 10:
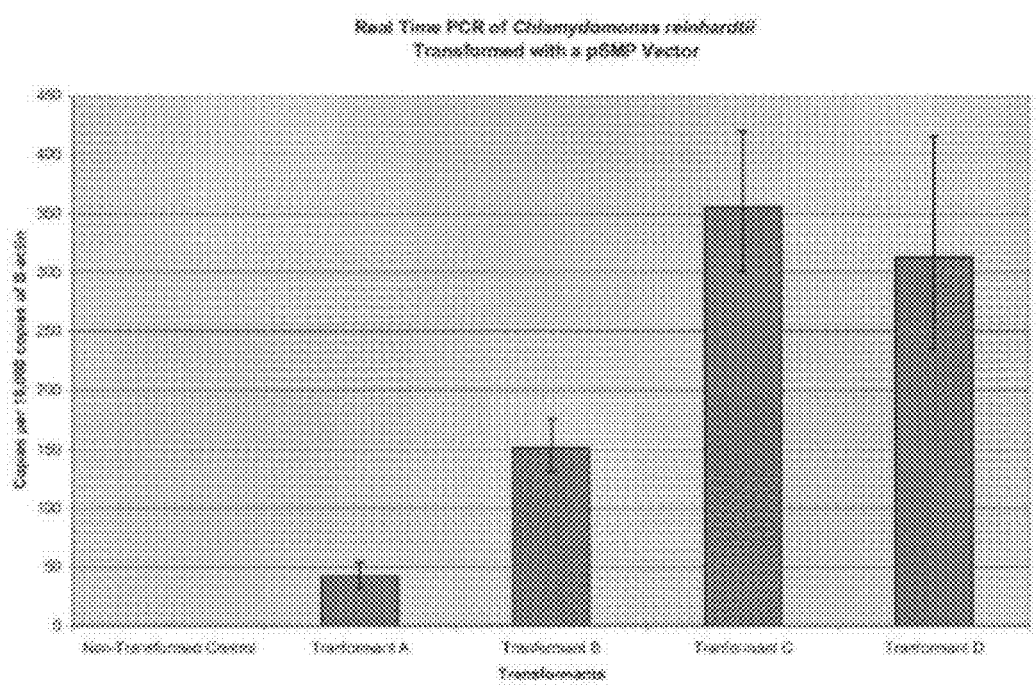
FIG. 10 shows the RNA expression levels by real time PCR of cDNA from algal transformants.

Twelve of the above transformants were tested for RNA expression using real-time reverse transcriptase PCR(RT-PCR) and four were positive for expression (FIG. 10). Five of the twelve had been transformed with pSMP1 and two (A & B in FIG. 10) of the five were positive for expression (40%). In addition, three of the twelve were transformed with pSMP1c and two (C & D in FIG. 10) of the three were positive for expression (67%). The remaining four transformants were transformed with pSMP2 and all were negative. The pSMP1 and pSMP1c vectors are therefore useful for expressing the hydrogenases in C. reinhardtii. Plasmid pSMP1c appears to be the best transformation vector given that two-thirds of the transformants were positive for expression and they had a higher level of expression than the pSMP1 transformants.

Figure 11:
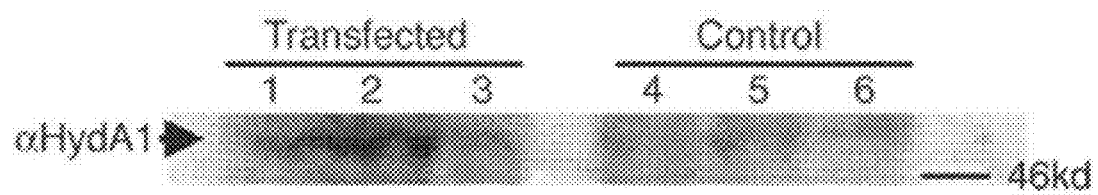
FIG. 11 shows the western blot of one of the transformants and a non-transformed control.

A transformant containing pSMP1 was tested for protein expression by Western blot (FIG. 11). Two proteins, at approximately 49 kiloDaltons (kD) and 97 kD, were present in the transformed sample and not present in the non-transformed control. The 49 kD band is the correct molecular weight of the HydA1 protein and the faint band at 97 kD (data not shown) is likely a dimer.

The results show that pSMP1 and pSMP1c vectors are useful for expressing the hydrogenases in C. reinhardtii. Plasmid pSMP1c appears to be the best transformation vector given that two-thirds of the transformants were positive for expression and they both had a higher level of expression than the pSMP1 transformants. Because the RT-PCR and Western blot were positive for expression insertion and expression of the wild-type hydrogenase (cDNA) in C. reinhardtii was accomplished.

In order to isolate the HydA1 and HydA2, a cDNA library was obtained (John Davies, Exelixis Inc.: San Francisco, Calif.), which had been created under anaerobic conditions and believed to contain the hydrogenases. The library consisted of viral particles, known as phage, which contained the cDNA of C. reinhardtii. In order to detect cDNA that contained a hydrogenase, the phage library was allowed to infect XL-1 Blue bacteria (Stratagene: #211204 and #211203). The infected cells were then mixed with top agarose and plated on LB-agar plates at a density of 5000 plaques per plate. The phage-infected bacteria formed a lawn punctuated with plaques, clear spots where the cDNA containing phage have infected and lysed all the bacteria surrounding the initial infection. The pattern of clear spots on the plates were copied by overlaying the plate with a membrane (ISC BioExpress: #F-3193-82) for three minutes. Afterwards, the plate was sealed with Para film and saved at 4° C. until it could be determined whether any of the plaques contained a hydrogenase. The membrane was treated and washed three times (Promega Technical Bulletin #72) before the DNA was cross-linked to the membrane via exposure to UV light (.lamda.=365 nm).

The membrane, which then contained a copy of the plaques on the LB plate, was pre-hybridized (Sigma Perfect-Hyb: #H-3032) for 30 minutes at 68° C. to block non-specific binding sites, before it was hybridized to a chemiluminescent probe for 3 hours at 68° C. The chemiluminescent probe was created by binding a reporter molecule, digoxigenin, to the oligonucleotide of putative hydrogenase DNA mentioned above. First though, the oligonucleotide was purified and concentrated before it was labeled with digoxigenin-dUTP (Roche: #1-573-152) using a random labeling kit (MBI Fermentas: #K0621). The suspected hydrogenase portion of the probe binds homologous cDNA on the membrane, presumably hydrogenase containing cDNA. After the probe bound to the cDNA on the membrane, it was washed, blocked, and treated with an anti-digoxigenin antibody, which is bound to alkaline phosphatase (Roche: #1-093-274). Detection of the bound antibody was accomplished by providing two substrates to the alkaline phosphatase, which results in a purple color wherever the probe is bound to the membrane. (Roche: #1-175-041).

The purple spots on the treated membrane corresponded to plaques on the LB plate that contained cDNA, which bound the probe. The bound cDNA were possible hydrogenases, so the designated plaques were removed from the agar with a wide bore pipette tip. Phage were purified from the agar by incubating the plaques in 1 ml of phage buffer while shaking for three hours at room temperature. The purified phage were diluted and allowed to re-infect fresh XL-1 Blue bacteria. Afterwards, they were re-plated at an approximate density of 100 plaques per plate. The purification process was repeated, as above, by copying the new plates with membranes, treating the membranes with the chemiluminescent probe, and isolating the positive plaques. The initial positive plaques were considered "plaque purified" after performing three rounds of plating and purifying.

The cDNA were extracted from the purified phage by infecting XPORT bacteria (Stratagene: #211204) and plating with NZY top agarose on NZY plates. The plates were incubated overnight at 37° C. The phage was collected by overlaying the plate with 3 ml of SM buffer (recipe in Appendix D) for 30 minutes, centrifuging, and resuspending in 100 µl of SM Buffer. The concentrated cells were used to infect XLOLR cells (Stratagene: #211204) before plating on LB plates. As a result, cDNA was now contained as a plasmid within the XLOLR bacteria.

The C. reinhardtii hydrogenase HydA1 gene was amplified by PCR from the cDNA described above. Restriction sites (NdeI and NheI) were added to the primers to facilitate cloning into the vector. The pSMP1, pSMP1c, and pSMP2 plasmids were created by replacing the original gene (PsaD) with the HydA1 DNA. Both the pGenD+Ble plasmid and the HydA1 gene were digested with NdeI and NheI (New England Biolabs (NEB): NdeI: #R0111S and NheI: #R0131S), purified (Qiagen Qiaex II kit: #20021), and ligated (Lucigen T4 ligase: #30025-2). The strepII tag (IBA GmbH: Gottingen, Germany) was inserted, by PCR mutagenesis, at the 3' terminus of the HydA1 gene between the NheI and EcoRI (NEB: #R0101S) restriction sites. The mutagenesis (Stratagene QuikChange Site-Directed Mutagenesis kit: #200519) was performed according to the manufacturer's protocol, except the extension time was increased to 2-3 minutes/kb in order to accommodate the large insertion (30 bp) (FIG. 12). The PspOMI (NEB: #V0215S) restriction sites in pSMP1 and pSMP1c and the AsiSI (NEB: #R0630S)

restriction site in pSMP2 were created by site directed mutation (Stratagene Quik-change Multi site directed mutagenesis kit: #200515) after an existing PspOMI site was removed from a different location. The PCR protocol and the mutational primers were designed according to the manufacturer's protocol (FIG. 12).

All of the algal strains, including the pSMP1 transformants, were grown under oxygenic conditions in 50 ml of sterile TAP media utilizing 250 ml Erlenmeyer flasks. The flasks were shaken at 100-1.50 rpm and exposed to 100 µE (1 µE=1 µEinstein=1 µmoles photons/$m^2$sec=500 foot candles) of light from standard fluorescent fixtures.

Each of the three pSMP vectors were transformed into the dw15-1 (courtesy of Barb Sears: Michigan State Univ.), a fast growing variant of the common *C. reinhardtii* cc425 strain, using a BTX ECM 630 electroporator with the following settings: 750 Volts, 25 and 1575 ohms. Immediately after electroporation, the algae were mixed with 3 ml of cornstarch suspended in TAP+60 µM sucrose and plated on Tris-Acetate-Phosphate (TAP) plates containing 10 µg/ml of the antibiotic Zeocin (140). The resulting transformants were grown, as above, for one week before they were transferred to standard TAP plates containing no antibiotics. The transformants were transferred to plates without antibiotics as Zeocin is a presumed mutagen and antibiotics are not necessary to maintain the transformants, since the plasmid DNA is incorporated into the alga's genome.

Algal transformants containing the pSMP1, pSMP1c, or pSMP2 vectors, were inoculated from plates into liquid culture. The cultures were harvested at chlorophyll (Chl) concentrations between 15-18 µg Chl/ml (exponential growth phase) and all 50 ml was centrifuged at 4000 g for 5 minutes. The genomic DNA was isolated (Qiagen DNAeasy Plant kit: #69104) and PCR was performed on the genomic preparations from each of the three different pSMP transformations. The primers were specific to the 3' end of the hydrogenase cDNA. The PCR conditions were: 1' initial denaturation at 95° C., 35 cycles of [30 sec. at 95° C., 30 sec at 60° C., and 2' at 72° C.], and 10' final extension 72° C. The upstream primer (5' CCAGCTGCTGCCAGAATTC 3', SEQ ID NO. 16) and the downstream primer (5' CCAGCTGCTGCCAGAATTC 3', SEQ ID NO. 13) amplify the last 800 bases at the 3' end of the HydA1 hydrogenase.

Cells were harvested at chlorophyll (Chl) concentrations between 18-25 µg Chl/ml by centrifuging 10 ml of algal culture at 2000 g for 1 minute. RNA was obtained (Qiagen RNAeasy kit: #74104) and treated with a DNaseI (Ambion Turbo DNA-free kit: #1907) to remove the residual plasmid DNA. The cDNA was generated from the purified RNA (Qiagen Quantitect Reverse Transcription kit: #205311). Real-Time RT-PCR was performed on all of the samples using an upstream primer (5' GACGAGAAGAAGGCTAGCGC 3', SEQ ID NO. 15) specific to the 3' end of the hydrogenase and a downstream primer (5' CCAGCTGCTGCCAGAATTC 3', SEQ ID NO. 14) that was specific to the strepII tag (IBA GmbH: Germany). DyNAmo SYBR Green (Applied Biosystems: #4367660) on an Applied Biosystems 7300 Real Time PCR system was used. The real time RTPCR program was: an initial dissociation of 10 minutes at 95° C. followed by 40 cycles of 95° C. for 15 seconds and 60° C. for one minute, and lastly, a dissociation stage of 95° C. for 15 seconds, 60° C. for 30 seconds, and 95° C. for 15 seconds.

Cells were harvested at chlorophyll (Chl) concentrations between 16-20 µg Chl/ml by centrifuging 10 ml of algal culture at 2000 g for one minute. The pellet was resuspended in lysis buffer (6% SDS in 1×PBS) plus 10 µl/ml each of Phosphatase Inhibitor Cocktails 1 & 2 (Sigma: #P5726-5 ml and #P2850-5 ml). The samples were vortexed, mixed with loading buffer, and separated by SDS-PAGE under reducing conditions (1% β-mercaptoethanol) using an 8-16% Tris-Glycine gel (Invitrogen: #EC6048BOX).

Since SDS interferes with the Bradford total protein assay, the chlorophyll concentration of each of the samples was determined by the method of Harris (76) and equal amounts of chlorophyll (and thereby of protein) were loaded onto the gel. The gel was subjected to 125 Volts for approximately 2 hours, or until the dye front reached the bottom of the gel. The proteins were transferred to a PVDF Hybond-P membrane (Amersham: #RPN303F) for 1.5 hours at 25 Volts. Proof of equal loading of the gel lanes was obtained by staining the gel (for total protein) overnight in Coomasie (Pierce: #24590) (not shown). The stained gel was dried and sealed in cellophane (Invitrogen: #NC2380).

The membrane was blocked in 1×PBS containing 0.5% Tween-20, 3% BSA, and 1/1000 Biotin Blocking Buffer (IBA GmbH: #2-0501-002) following the IBA protocol for all washes. The membrane was probed with an anti strepII tag mouse antibody (IBA GmbH: #2-1507-001) at 4° C. overnight at a concentration of 1000 ng/ml (1/200 dilution of the stock concentration). The secondary antibody (donkey anti-mouse conjugated to horse radish peroxidase (HRP)) (Jackson Labs: #715-035-151) was allowed to incubate for one hour at room temperature at a concentration of 67 ng/ml (1:3000 dilution of the stock). Protein was detected using ECL-plus developing solutions (Amersham: #RPN2132) and visualized using a Kodak DS Image Station 440CF using 1D Image Analysis Software.

Bacterial hydrogenases were cloned and the best two were used as the parent genes in a combinatorial shuffle that resulted in a library of chimeric hydrogenases. Several chimeric hydrogenases showed hydrogen production, including three chimeras that produced hydrogen at levels three to four times higher than the parent hydrogenases.

Since several chimeras produced hydrogen, despite significant differences in their amino acid sequences, several mutational pathways may result in mutants with improved hydrogen production. The remainder of the mutant library can be tested for hydrogen production. The chimeric proteins with an improved hydrogen production can be sequenced and computationally modeled, both of which are capable of identifying the mutations that result in the improved chimeric proteins. Such modeling has been initiated and is described below. When such a comparison is made of the diversity of successful chimeras, it is possible that a combination of the individual mutations will result in a chimera with a dramatically increased level of hydrogen production. Shuffles with additional parent genes or successive shuffles of the improved chimeric hydrogenases from the first shuffle may also result in a highly evolved hydrogenase.

Example 4

Expression of Bacterial Hydrogenases and Measurement of Hydrogen Production

Figure 16:
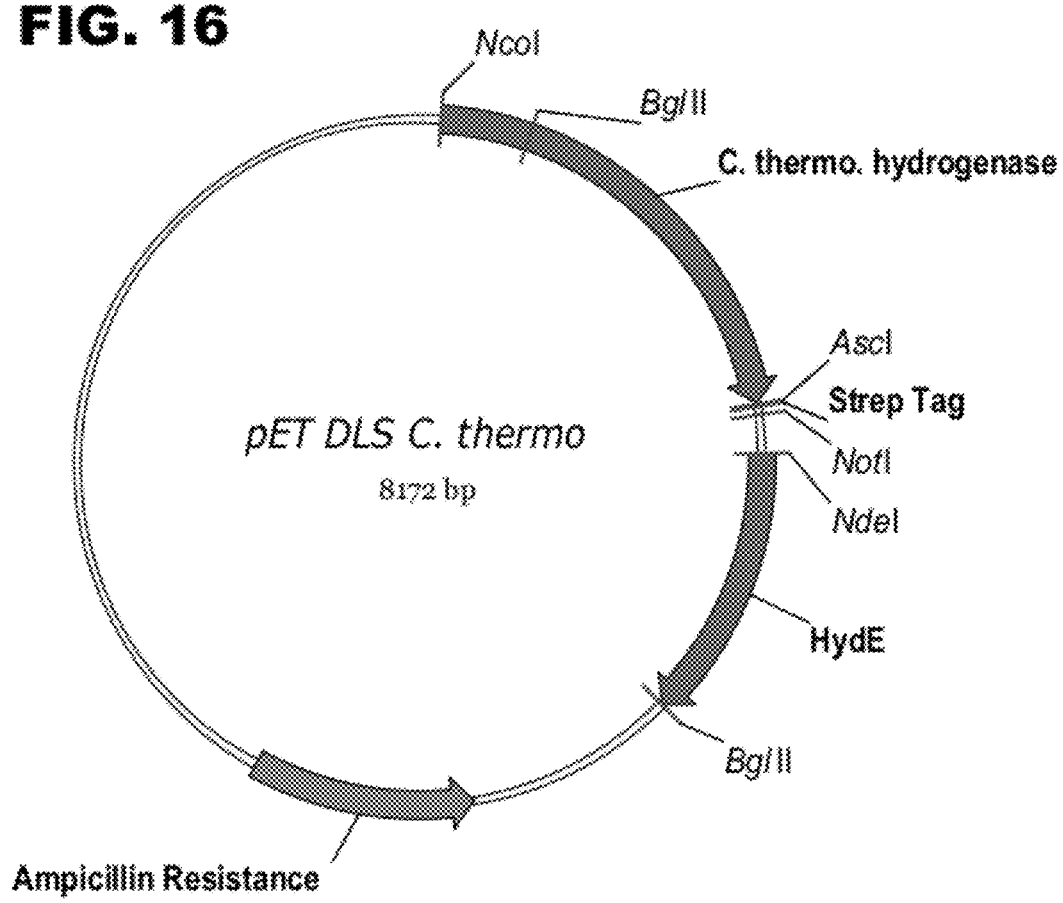
FIG. 16 is shows the pET DLS plasmid (8.2 kb) containing the *C. acetobutylicum* HydE accessory protein and the *C. thermocellum* hydrogenase (pET DLS C. thermo plasmid).

Five clostridial hydrogenases were cloned: *Clostridium saccharobutylicum* (*C. saccharobutylicum*), *Clostridium pasteurinum* (*C. pasteurinum*), *Clostridium perfringens* (*C. perfringens*), *Clostridium tetani* (*C. tetani*), and *Clostridium thermocellum* (*C. thermocellum*). All hydrogenases were cloned via restriction sites (NcoI/AscI) into the pET DLS expression vector as described further below (see also FIG. 16) and subsequently tested for hydrogen production using the Methyl Viologen assay. The Methyl Viologen assay was used because bacteria need an artificial electron donor in place of the photosynthetic machinery that provides electrons to algal hydrogenases.

The original Clostridial hydrogenase, *C. acetobutylicum*, along with its accessory proteins, were cloned by King et al. into two dual expression vectors, pET Duet and pCDF (Novagen: #TB337 and #TB390). These two vectors were used as the positive control. The Strep II tag "SAWSH-PQFEK" (IBA GmbH: Göttingen, Germany) and a stop codon were cloned between the AscI and NotI restriction sites of the pET Duet vector (see FIG. 16). Thus, the Strep II tag is in frame and immediately downstream of the AscI restriction enzyme site which is just downstream of the hydrogenase gene. This plasmid, renamed "pET DLS", was designed in this manner so that both the hydrogenase and the tag were easy to insert and readily removable from the plasmid backbone. The pCDF plasmid was used without alterations.

Figure 20:
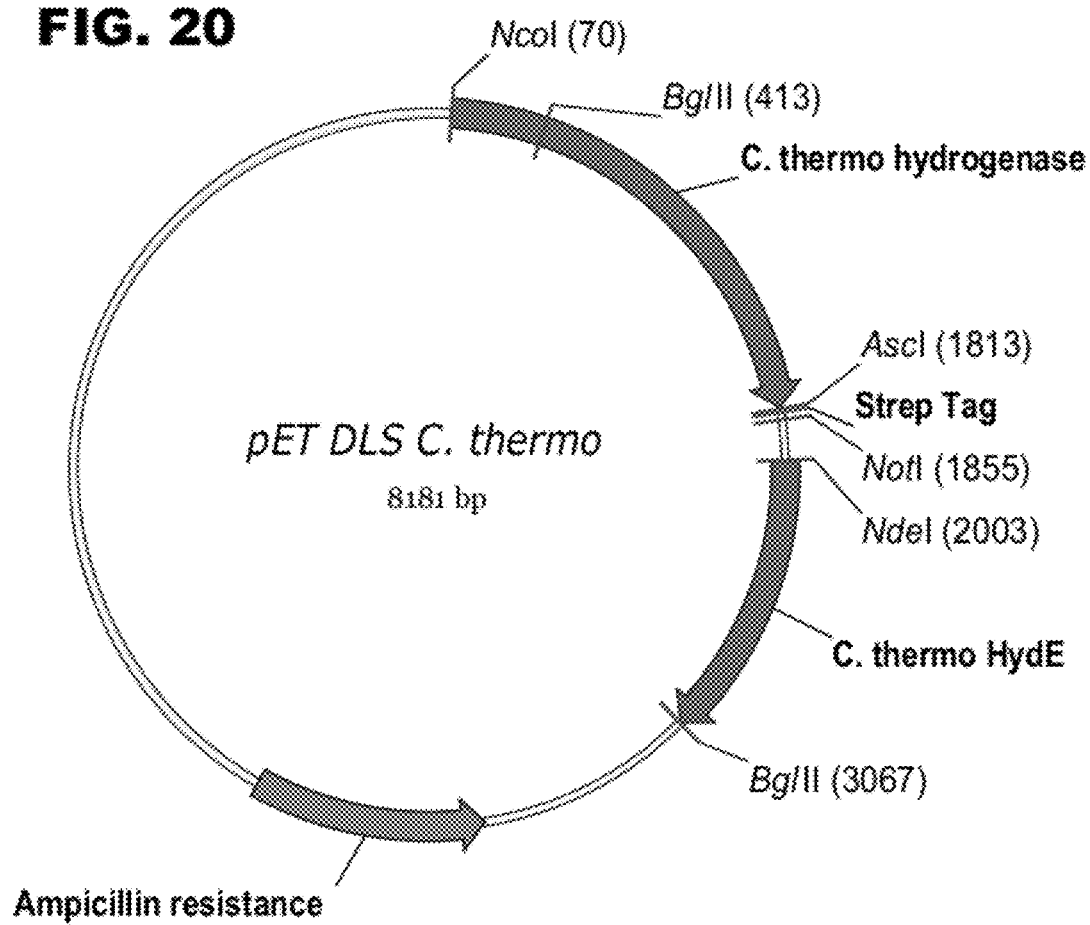
FIG. 20 shows the pET DLS Plasmid (8.2 kb) which contains the *C. thermocellum* hydrogenase and the HydE accessory protein.

Genomic DNA for *C. perfringens* was obtained from the American Type Culture Collection (ATCC: #13124D-5). The hydrogenase in *C. perfringens* (CpeI) was isolated by amplifying the DNA by PCR from aliquots of the genomic DNA.

The *C. thermocellum* (Cthl) hydrogenase, encoded in a plasmid, was obtained from the Lee Lynd Laboratory (Dartmouth College, NH), but was found to be missing a portion of sequence on the 3' end. The missing sequence corresponded to an additional two amino acids (lysine and a stop codon), which were identified by comparison to the genomic information at the Joint Genome Institute (JGI: genome.jgi-psf.org/draft_microbes/cloth/cloth.home.html). The missing DNA sequence was added to the end of the gene using PCR and a new downstream primer with the additional bases included (see FIG. 19, SEQ ID NOS: 17-22).

The upstream and downstream PCR primers (see FIG. 19) were designed to be homologous to the start and stop codons of the published sequences (NCBI: *C. perfringens* #AB035092 and BAA95936; *C. thermocellum*#AAD33071 and AF148212). Both primers had extra bases (tails) that corresponded to either a NcoI restriction site (upstream primer (5' CCAGCTGCTGCCAGAATTC 3', SEQ ID NO. 13)) or an AscI restriction site (downstream primer (5' CCAGCTGCTGCCAGAATTC 3', SEQ ID NO. 14)). The *C. perfringens* PCR product was digested with NcoI and AscI (New England Biolabs (NEB): #R0193S and #R0558S) and cloned into the pET DLS vector (see FIG. 16). Prior to the cloning of the *C. thermocellum* PCR product into pET DLS, it was blunt cloned into a shuttle vector (Lucigen's Clonesmart HC Kan: #40728-1) and mutated (GCC (Ala)→GCG (Ala) at 1410 bp) (Stratagene Quikchange II site directed mutagenesis kit: #200523) in order to remove an internal NcoI site (see FIG. 19). Post mutation, the *C. thermocellum* PCR product was digested, as above, and cloned into the pET DLS vector.

BL21 *E. coli* cells (Lucigen: #60300-1) were co-transformed with 30 ng of pCDF and 30 ng of pET DLS (FIG. 16) using an electroporator (Bio-Rad Micropulser: #165-2100) and 1 mm cuvettes (Bio-Rad: #165-2089). The pET DLS vector contains the hydrogenase to be tested and also codes for the *C. acetobutylicum* HydE accessory protein. The pCDF vector codes for the HydF and HydG accessory proteins, also from *C. acetobutylicum*. The standard settings for electroporating *E. coli* were: 1800 Volts, 600 Ohms, and 10 μF. After electroporation, the cultures were allowed to grow for one hour and plated (200 μL) on standard LB plates containing Ampicillin (50 μg/ml) and Streptomycin (50 μg/ml).

Expression of the hydrogenases was performed using the method of Posewitz et al. (M. C. Posewitz, M. C. et al., Identification of genes required for hydrogenase activity in *chlamydomonas reinhardtii*, Biochem. Soc. Trans. 33: 102□4 (2005)). Overnight cultures (10 ml) were started from a single colony and used to inoculate sterile flasks containing 125 ml of LB media supplemented with Ampicillin and Streptomycin. The flasks were shaken (300 rpm) at 37° C. until they reached an optical density of A600=0.6-0.8 (approx. 5-6 hours). The optical density was measured on a spectrophotometer (Nanodrop Technologies: #ND-1000, Software Version 3.1.0).

In order to induce expression, IPTG was added to a final concentration of 100 mM and the flasks were transferred to a room temperature shaker (150 rpm) for one hour. The solutions were then transferred to 125 ml serum bottles (Wheaton: #223748), rubber septa (Chemglass: #CG-3022-24) were inserted, and the cultures were thoroughly degassed with Argon 5.0 (General Air: #UN 1006)) for 4-6 hours. The cultures were allowed to sit overnight at room temperature before being analyzed further.

The genome of *C. thermocellum* has been sequenced, so its accessory proteins (HydE, HydF, and HydG) were found by electronically searching the published genome (maple.1sd.oml.gov/microbial/cthe/) for comparable sequences to the known accessory protein sequences of *C. acetobutylicum*). *C. thermocellum* HydE, HydF, and HydG were designated as gene 2382 on contig 245, gene 3099 on contig 253, and gene 1213 on contig 221, respectively.

All three *C. thermocellum* accessory proteins were cloned into the same locations within the same vectors as their corresponding genes from *C. acetobutylicum*. The new pET DLS (FIG. 20) and pCDF plasmids (FIG. 21), with the substituted *C. thermocellum* accessory proteins, were tested for hydrogen production using the Methyl Viologen assay described in Chapter Three. A second new pCDF plasmid was also created wherein the *C. thermocellum* HydG replaced the *C. acetobutylicum* version, but the *C. acetobutylicum* HydF was still intact. This hybrid vector, along with the first pCDF plasmid was constructed to determine if all three of the *C. thermocellum* accessory proteins are necessary for expression or if some combination of *C. thermocellum* and *C. acetobutylicum* proteins is needed.

Along with a positive and negative control, the above mentioned plasmids were tested for hydrogen expression. Five different combinations (see Table 3) of plasmids were tested and all were negative. These plasmids were also given to Matthew Posewitz (NREL: Golden, Colo.) and his lab obtained negative results as well. Hence, it seems that the hydrogenase from *C. thermocellum* requires a higher temperature or something yet to be determined, in order to produce molecular hydrogen.

TABLE 3

| pDLS plasmid | pCDF plasmid | Result |
|---|---|---|
| Positive Control | Standard pCDF | Positive H2 production |
| Standard pDLS | Standard pCDF | No $H_2$ production |
| Plasmid #1 | Standard pCDF | No $H_2$ production |
| Plasmid #1 | Plasmid #2 | No $H_2$ production |
| Plasmid #1 | Plasmid #3 | No $H_2$ production |
| Standard pDLS | Plasmid #2 | No $H_2$ production |
| Standard pDLS | Plasmid #3 | No $H_2$ production |

Using primers that were designed for these putative sequences (FIG. 22) and genomic DNA from *C. thermocellum* (American Type Culture Collection: #27405D), the genes for all three accessory proteins were obtained by PCR. KOD polymerase (VWR: #80511-384) was utilized with the following PCR conditions: 2' initial denaturation at 94° C., 35 cycles of [15 sec. at 94° C., 30 sec at 55-60° C. gradient, and 1.5° at 72° C.], and a 10' final extension at 72.degree. C The *C. thermocellum* HydE gene was cloned into the *C. thermocellum* pET DLS vector, replacing the *C. acetobutylicum* HydE gene (FIG. 20). However, the first step was to silently mutate the BglII site found within the *C. thermocellum* hydrogenase, so that the *C. acetobutylicum* HydE protein could be ligated only into the NdeI/BglII site (FIG. 22). The Quikchange Multi site directed mutagenesis kit (Stratagene: #200515-5) was employed with the following PCR conditions: 1' initial denaturation at 95° C., 30 cycles of [1' at 95° C., 1' at 55° C., and 16.5' at 65° C.]. Since a silent mutation was made in the *C. thermocellum* hydrogenase, it needed to be re-inserted in the NcoI/AscI site, once the *C. thermocellum* HydE gene was successfully ligated. The resulting plasmid was sequenced and compared to the expected sequence in the published genome.

Figure 21:
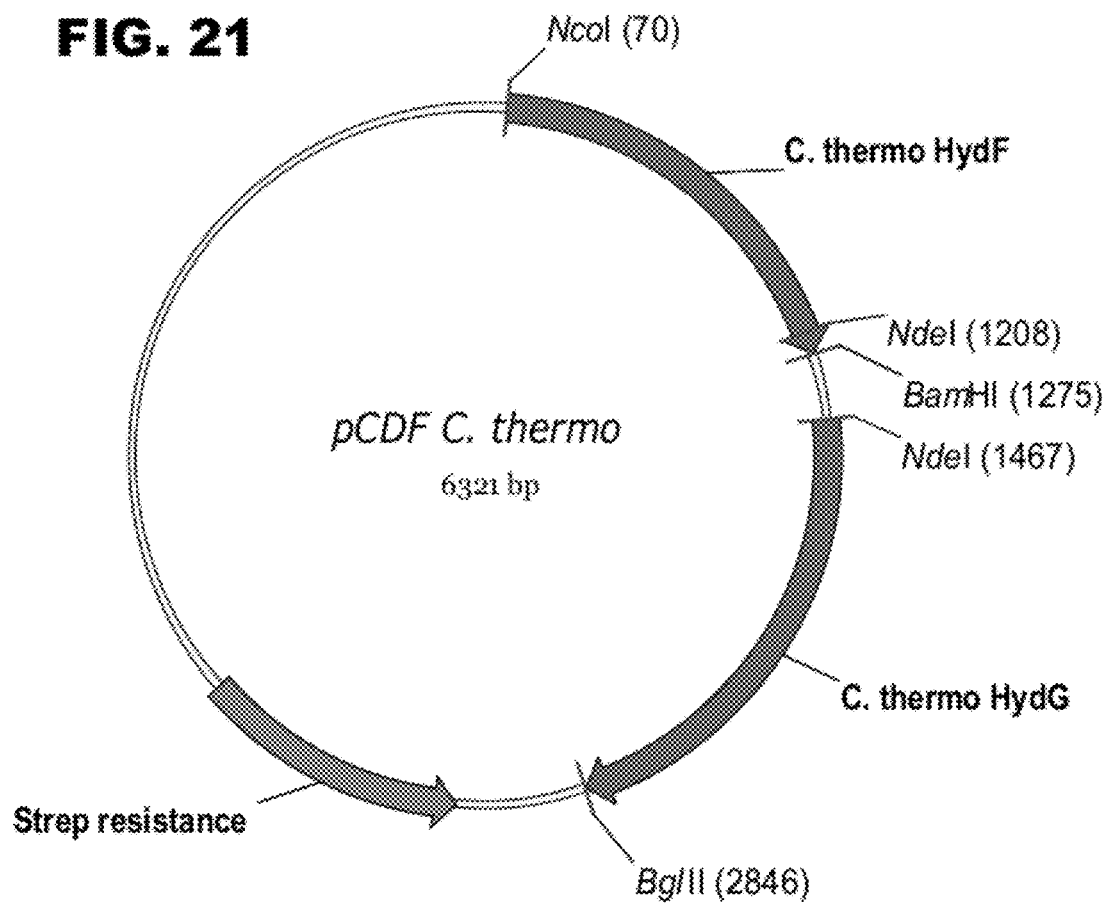
FIG. 21 shows the pCDF Plasmid (6.3 kb) which contains the *C. thermocellum* HydF and HydG accessory proteins.

The *C. thermocellum* HydF and HydG genes were cloned into pCDF, also in place of the corresponding *C. acetobutylicum* genes (FIG. 21). As was done for the pET DLS plasmid, a silent mutation was introduced into the *C. acetobutylicum* HydF to remove an internal NdeI site (FIG. 22). Again, the Quikchange Multi site directed mutagenesis kit (Stratagene: #200515-5) was utilized under similar PCR conditions: 1' initial denaturation at 95° C., 30 cycles of [1' at 95° C., 1' at 55° C., and 13' at 65° C.]. This mutation allowed us to replace the *C. acetobutylicum* HydG gene with the *C. thermocellum* version into the NdeI/BglII site without disrupting the HydF gene. The new *C. thermocellum* HydF was then cloned into the NcoI/BamHI sites, thereby replacing the mutated *C. acetobutylicum* HydF gene. The pCDF plasmid with the *C. acetobutylicum* HydF gene and the *C. thermocellum* HydG gene was kept, so it could be determined if all or just one of the *C. thermocellum* accessory proteins were necessary for successful expression.

Two sets of primers were used to create each of the silent mutations in the *C. thermocellum* pET DLS and pCDF vectors. The second set of complementary primers was non-mutational and hybridized, approximately half way around the plasmid from the engineered point mutation. The second set of primers was designed to eliminate any problems due to the processivity of the polymerase, so that it could successfully copy these large plasmids (FIG. 22).

Methyl Viologen Assay:

Using an argon purged gas-tight syringe (Hamilton: #81430), 1 ml of 2× Methyl Viologen solution and 100 µL of a 100 mM dithionite solution were added through a septum into an anaerobic 10 ml serum bottle (Wheaton: #223739). Subsequently, 1 ml of cells was transferred anaerobically to the serum bottle. The serum bottles were allowed to sit for at least 60 minutes, mixing occasionally by inversion.

The headspace of the serum bottles was tested for molecular hydrogen by gas chromatography. A 400 µL sample of the headspace gas was injected into a GC(SRI Instruments: #310C) containing a molecular sieve column (SRI Instruments: #5A 2 feet long) at a constant temperature of 40° C. The results were recorded using the PeakSimple Software (SRI Instruments version 3.29).

Three hydrogenases, those isolated from *C. saccharobutylicum*, *C. pasteurinum*, and *C. perfringens*, showed hydrogen production that was comparable to the values published for *C. acetobutylicum*. However, the hydrogenase isolated from *C. tetani* showed attenuated hydrogen production and the *C. thermocellum* hydrogenase showed no hydrogen production whatsoever. Since *C. thermocellum* is a thermophilic organism (55° C.) and it has the lowest homology of the five Clostridial hydrogenases that were cloned, it is possible that this hydrogenase needs its own accessory proteins in order to fold correctly.

Example 5

Cloning and Expression of Chimeric Hydrogenases and Measurement of Hydrogen Production Two chimeric libraries, by two separate methods, were created in an attempt to realize an improvement in the hydrogen production and/or oxygen tolerance over the parental Clostridial hydrogenases. First, a random mutagenesis library was created from C. saccharobutylicum. Utilizing the two wild-type hydrogenases that produced the most hydrogen, the hydrogenases from C. saccharobutylicum and *C. acetobutylicum*, a second library was created utilizing the variation on the DOGS technique as described herein above (see also FIGS. 13 through 15).

Cloning and expression of the resulting chimeras was achieved in *E. coli* substantially as described above in Examples 3 and 4, except that the random mutagenesis library was cloned via restriction sites (NcoI/AscI) into the pET DLS vector in place of the parent hydrogenase. The sequenced clones had an average of six mutations per gene (1.8 kb). A predominance of Adenine (A) & Thymine (T) transitions over Guanine (G) & Cytosine (C) transitions was observed, but was in accordance with the relative percentage of As and Ts to Gs and Cs. None of the mutations were identical. This library was not tested for hydrogen production and would benefit from a high through-put screen.

Figure 18:
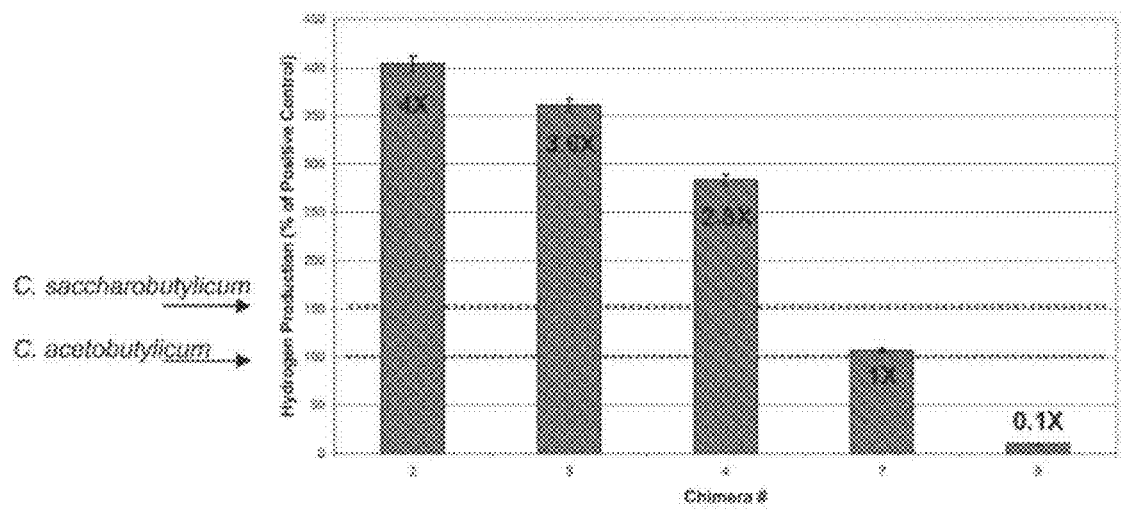
FIG. 18 shows the hydrogen production of the specified chimeric hydrogenases as a percentage of the positive control (*C. acetobutylicum*).

The library created by the DOGS method, using the SapI variation, generated 254 distinct chimeras. Sixteen chimeras, which were representative of the possible mutations in the second half of the protein, were randomly chosen and tested for hydrogen production (see FIG. 17). Several showed normalized hydrogen production at or greater than the positive control (see FIG. 18). The positive control was the non-mutated hydrogenase from *C. acetobutylicum* used in an earlier study (King et al., Functional Studies of [FeFe] Hydrogenase Maturation in an *Escherichia Coli* Biosynthetic System. J. Bacteriol. 188:2163-72 (2006)). Specifically, chimera #2 (protein sequence—SEQ ID NO: 1 and DNA sequence—SEQ ID NO: 2) shows the most hydrogen production (4× the hydrogen production of the positive control). In addition to producing more hydrogen, chimera #2 also produced molecular hydrogen at a faster rate than the other mutants; the rate for chimera #2 dramatically decreased after one hour of incubation. The other chimeras produced 3.0-50% more hydrogen in the second hour of incubation, which likely indicates that they have a slower turnover of the hydrogenase protein. The remaining hydrogenase chimeras, #18A (protein sequence—SEQ ID NO: 85 and DNA sequence—SEQ ID NO: 153), 18S (protein sequence—SEQ ID NO: 86 and DNA sequence—SEQ ID NO: 154), and 28A (protein sequence—SEQ ID NO: 89 and DNA sequence—SEQ ID NO: 157), produced 3×, 2.8×, and 1× the amount of hydrogen of the positive control, respectively. Of the mutants tested, chimera #28S (protein sequence—SEQ ID NO: 158 and DNA sequence—SEQ ID NO: 90) was the only hydrogenase that exhibited attenuated hydrogen production, approximately 10% of the positive control.

Thus the approach described herein produced mutant hydrogenases capable of producing hydrogen at a faster rate than the wild-type control, the hydrogenase from *C. acetobutylicum*. Chimeras such as #2, 18A, and 18S showed more hydrogen production than the positive control. In fact, after one hour of incubation in the Methyl Viologen assay, these chimeras show 1-4× the amount of hydrogen production relative to the positive control. Since nearly all of the chimeras tested produced hydrogen above the level of the positive control (Chimeras #2, 18A, 18S, and 28A), or else produced no hydrogen at all (Chimeras #1, (protein sequence—SEQ ID NO: 83 and DNA sequence—SEQ ID NO: 151), 21A (protein sequence—SEQ ID NO: 87 and DNA sequence—SEQ ID NO: 155), 21S (protein sequence—SEQ ID NO: 88 and DNA sequence—SEQ ID NO: 156), 30S (protein sequence—SEQ ID NO: 91 and DNA sequence—SEQ ID NO: 159), and 44 (protein sequence—SEQ ID NO: 92 and DNA sequence—SEQ ID NO: 160)), which indicates that protein folding is critical and impacts hydrogen production in a rather Boolean fashion.

Several structure/function relationships can be noted of the chimeras tested thus far. For example, chimera #1 and #18A are identical except for segment #7, and chimeras #18A and #18S are identical to chimeras #21A and #21S, except for segment #8 (see FIG. 17). Since chimeras #18A and #18S are positive for hydrogen production, whereas chimeras #1, #21A and #21S show no hydrogen production, it appears that beneficial results occur when segment #7 is derived from *C. acetobutylicum* and segment #8 be derived from C. saccharobutylicum. However, if both segments #5 and #8 are derived from *C. acetobutylicum* (Chimeras #28A and #28S) instead of just segment #8 (Chimeras #21A and #21S), hydrogen production is restored, although not to the levels of chimeras #18A and #18S.

Chimera #2 is a simple amalgam whose first half is derived from C. saccharobutylicum while its second half is derived from *C. acetobutylicum*. Again, the simple change of one segment (segment #8) is enough to decrease hydrogen production to zero (Chimera #30S), but changing segments #5 and #6 results in the hydrogen production being restored (Chimera #18S). Chimera #2 produced the most hydrogen of all the mutants tested, while its mirror image (Chimera #1) showed no discernible hydrogen production.

Example 6

Expression of Hydrogenases in *C. reinhardtii* and Measurement of Hydrogen Production Chimeric and wild-type hydrogenases were cloned into plasmid pSMP1c for expression in *C. reinhardtii*. The pSMP vectors were transformed into dw15-1, a fast growing variant of the common *C. reinhardtii* cc425 strain, using a BTX ECM 630 electroporator with the following settings: 750 Volts, 25 µF, and 1575 ohms. Immediately after electroporation, the algae were mixed with 3 ml of cornstarch suspended in TAP+ 60 µM sucrose and plated on Tris-Acetate-Phosphate (TAP) plates containing 10 µg/ml of the antibiotic Zeocin. The resulting transformants were grown under oxygenic conditions in 50 ml of sterile TAP media utilizing 250 ml Erlenmeyer flasks. The flasks were shaken at 100-150 rpm and exposed to 100 µE (Einstein) of light from standard fluorescent fixtures. After one week, they were transferred to standard TAP plates containing no antibiotics. The transformants were transferred to plates without antibiotics as Zeocin is a presumed mutagen and antibiotics are not necessary to maintain the transformants, since the plasmid DNA is incorporated into the alga's genome.

For hydrogen production, algal transformants were inoculated from plates into liquid 10, culture (TAP, pH=7.2, or TAP plus arginine) and grown as detailed above. Cells were harvested at chlorophyll (Chl) concentrations between 10-18 µg Chl/ml (exponential growth phase), centrifuged at 4000 g for 5 minutes, and resuspended at 16 µg Chl/ml in anaerobic induction buffer (AIB) plus 0.001% (wt) PdC12 and 8 µM Resazurin. AIB consists of 40 mM K2HPO4, 10 mM KH2PO4, and 3 mM MgCl2. A stock suspension of 0.05% (wt) PdCl2 was made by mixing water and powdered PdCl2 (Pressure Chemical: #1735) in a serum bottle, which was capped, flushed with nitrogen gas (General Air: purity 4.8) for 15 min, and then autoclaved. A working solution of 0.01% (wt) Resazurin (Research Chemicals Ltd: #21187) in AIB was created by diluting a 0.1% (wt) stock solution.

Figure 23:
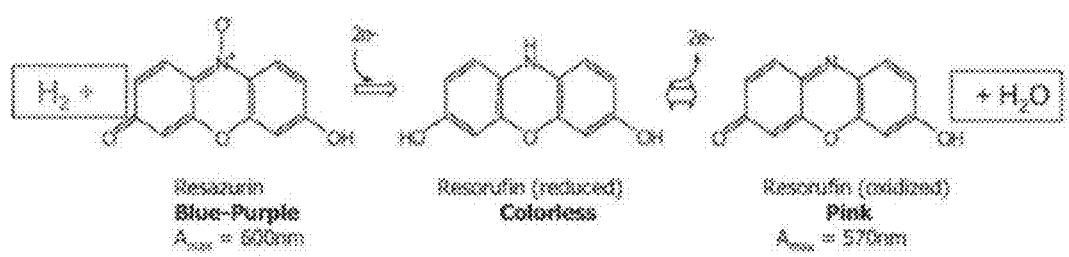
FIG. 23 illustrates the reaction mechanism for the reaction of molecular hydrogen with the redox dye, resazurin.

Resazurin Assay:

The resazurin assay was developed to measure the evolution of molecular hydrogen from *C. reinhardtii* cells. Resazurin is a redox dye that reacts with molecular hydrogen (FIG. 23). Since resazurin has two oxidized forms rather than just one, its reaction kinetics are quite complex. For example, molecular hydrogen reacts irreversibly with resazurin (blue, $A_{max}$ of 600 nm) to form reduced resorufin (colorless). The oxidized form of resorufin (pink, $A_{max}$ of 580 nm) is in a fast equilibrium with the reduced form. In theory, the reaction between molecular hydrogen and resazurin could be measured by the decrease in absorbance of resazurin or the increase in absorption of the oxidized form of resorufin.

Using sterile technique, 2.5 ml of the algal suspensions were added to a sterile anaerobic cuvette, made to order by Allen Scientific Glass (Boulder, Colo.) by fusing the top 2 cm of a serum bottle to about 4 cm of square glass tubing. Each cuvette contained a stir bar (VWR #58949-030) and was capped with a butyl rubber stopper (VWR #80062-438). The cuvettes were wrapped in aluminum foil to inhibit photosynthetic oxygen generation and purged with Argon (General Air: purity 5.0) for 15 minutes to remove the oxygen using 25G 7/8" needles (VWR #BD305124). The purged cuvettes were incubated at room temperature, in the dark, for four hours in order to induce production of oxygen sensitive hydrogenases.

After induction, cuvettes were placed on a stir plate and exposed to blue light (Dolan-Jenner #BG2820) filtered by a solution of 1% CUSO4. The cuvettes were exposed for 6 minutes at 5001 µE. Following illumination, the cuvettes were immediately placed in 50 ml Falcon tubes and centrifuged for 5 min at 5000 g. Spectra (350-800 nm) of the cell-free supernatants were obtained using a Varian CARY 5E UV/Vis/NIR spectrophotometer.

Hydrogen gas in the headspace of each cuvette was quantified using a HP 5890 series II gas chromatograph equipped with a molecular sieve column (Supelco 5A 60/80) and a thermal conductivity (TCD) detector. A simple constant temperature (60° C.) program is sufficient to separate $H_2$ from $O_2$ and $N_2$.

Figure 24:
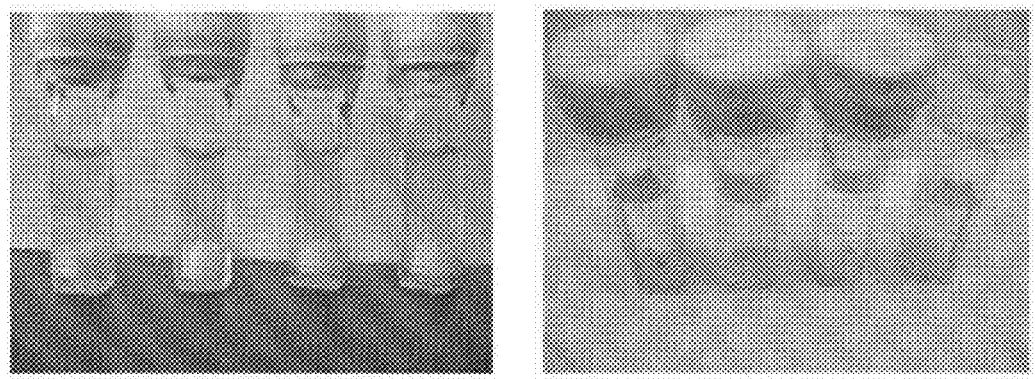
FIG. 24 are before and after pictures of four cuvettes containing resazurin.
Figure 25:
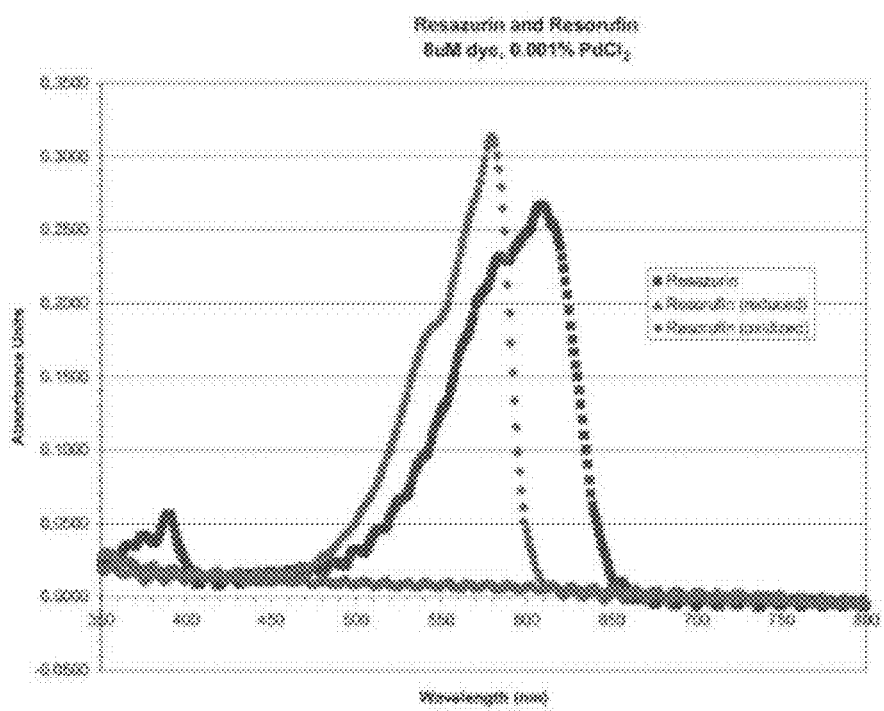
FIG. 25 shows the spectra of the various forms of resazurin and resorufin.

With no algae present, resazurin successfully reacted with 10% molecular hydrogen (Balance Nitrogen, General Air) in anaerobic cuvettes (Allen Scientific Glass: Boulder, Colo.). (FIG. 24). Hydrogen gas (100 µl of 10% H2) was injected into cuvette #2 (the second cuvette from the left), which was enough hydrogen to turn the solution slightly pink. Cuvettes #3 and #4 both had an excess of hydrogen injected, which forced the equilibrium into the reduced and colorless form of resorufin. Afterwards, cuvette #4 was opened to the air and thereby completely converted into the oxidized form of resorufin. The resulting UV/Vis spectra were overlapping but distinguishable from each other (FIG. 25).

Alternatively, if the alga transformants were exposed to oxygen before they were tested for molecular hydrogen production this assay could also be used to select for alga that contained mutant hydrogenases that are less sensitive to oxygen. If the alga were exposed to a concentration of oxygen at or slightly above their tolerance level, the hydrogenase chimeras that survived and produced hydrogen would have a higher oxygen tolerance. Finally, the enhanced hydrogenase chimeras from both of these selection techniques are sequenced and their individual mutations combined to create a mutant that exhibits both enhancements.

As indicated by the reduced size of the 600 nm peak in FIG. 26, a yet to be determined compound(s) in the algae is responsible for reducing the resazurin before it could be reduced by hydrogen generated from the algae. This reduced spectra occurred, regardless of when the resazurin/$PdCl_2$ mixture was added to the cells. Furthermore, this technique is not recommended because the spectrum of hydrogen producing algae (dw15-1, FIG. 26A) was not significantly different from the spectrum of non-hydrogen producing algae (sta6 mutant, FIG. 26B). A difference of approximately 0.07 absorbance units, at $\lambda=610$ nm, between these two strains was common. Duplicate samples produced spectra that were similar but whose absorbencies, at $\lambda=610$ nm, deviated slightly from each other. In addition to sta6, several other mutants with retarded hydrogen production were tested. Thus, the present disclosure provides that while spectra similar to sta6 were evident, there is no evident relationship between hydrogen production and the absorbance differences ($A_{610}$ of dw15-1 minus the $A_{610}$ of a mutant). However, molecular hydrogen definitely reacts with resazurin and the difference is significant. Yet, when algae generated the molecular hydrogen the resulting spectra showed a reaction with molecular hydrogen or a reaction with some unknown compound(s) within the algae.

Figure 27:
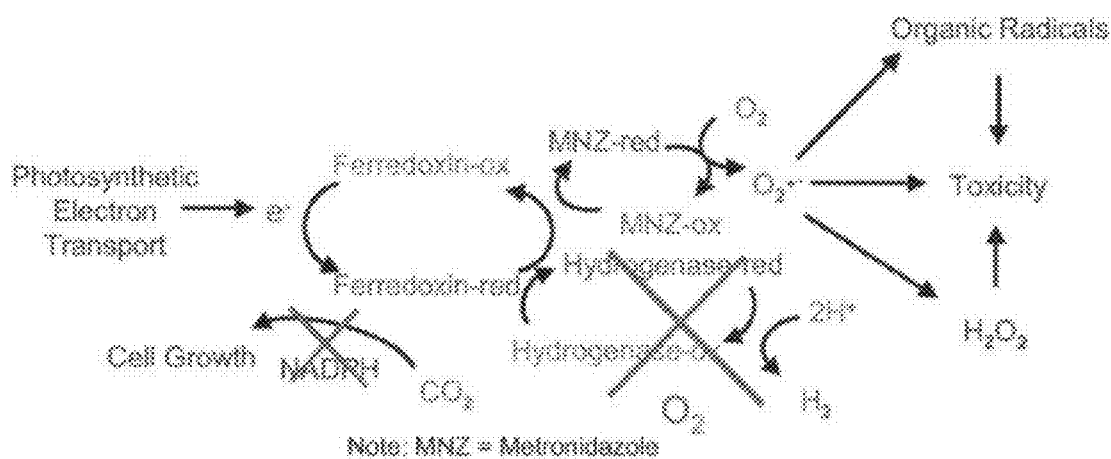
FIG. 27 is a diagram of the metronidazole method of selection for algae with an enhanced hydrogenase.
Figure 28:
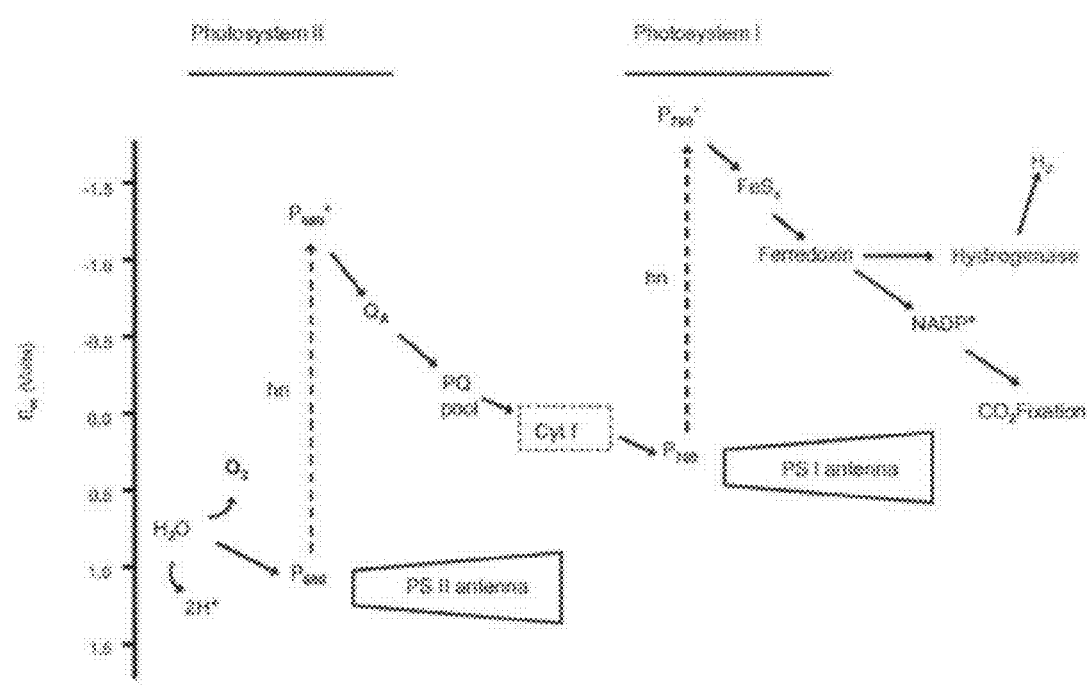
FIG. 28 illustrates the photosynthetic electron transport chain, known as the "Z-scheme".

Alternatively, selection of algal mutants can be accomplished using the metronidazole assay. The electrons created by the hydrolysis of water are ultimately transported to ferredoxin (FIG. 27). Ferredoxin is a common compound that is involved in many electron transport pathways. In *C. reinhardtii*, as in most plants, ferredoxin normally transfers electrons to the Calvin cycle, the pathway that is responsible for cell growth by converting carbon dioxide from the atmosphere into glucose. In *C. reinhardtii*, ferredoxin can also transfer electrons to a hydrogenase when the algae experiences dark and anaerobic conditions.

The photo-hydrogen group at the National Renewable Energy Lab (NREL: Golden, Colo.) developed a chemical method to select for oxygen tolerant mutants. The *C. reinhardtii* cells were induced to produce hydrogenases and then treated with metronidazole (MNZ), a toxic substance that non-specifically kills cells by creating oxygen free radicals known as superoxide radicals (FIG. 27). Superoxide radicals spawn organic radicals and hydrogen peroxide, all of which are quite toxic to *C. reinhardtii* cells. When the algal cells are induced to produce hydrogenases, cell growth ceases and a brief period of hydrogen production ensues when the cells are exposed to light.

If, however, sufficient concentrations of metronidazole and oxygen are added before the cells are exposed to the light, the hydrogenase is irreversibly inhibited by the oxygen, ferredoxin transfers all of its electrons to MNZ, and the algal cells die. It was theorized that, if little or no oxygen were added, a proportion of the electrons would be transferred to the surviving hydrogenases; hydrogenases that likely have a higher tolerance to oxygen. Given a constant number of available electrons, the algal cells containing hydrogenases with a higher tolerance to oxygen would then see more electrons transferred to the hydrogenase and fewer electrons transferred to MNZ; a lower concentration of toxic radicals and enhanced cell viability would result. The *C. reinhardtii* cells containing enhanced hydrogenases could then be isolated and analyzed.

Wild type strains of *Chlamydomonas reinhardtii*, dw15-1 (Barb Sears, MSU) and cc425 were grown in tris-acetate-phosphate (TAP), pH=7.2, or TAP plus 50-200 μg/ml arginine (cc425) in sterile 250 ml Erlenmeyer flasks on a shaker rotating at 150 rpm in a 25° C. constant temperature room and constantly illuminated with 100 μE of white fluorescent light (1 μE=1 μEinstein=1 μmoles photons/$m^2$sec=500 foot candles). Cells were harvested when they reached a concentration of $2.4\times10^6$ cells/ml, centrifuged at 2-3000 g for 5 minutes at 22° C., and resuspended to a final concentration of $1\times10^7$ cells/ml in sterile induction buffer (AIB) plus 20 μl of sterile 0.5M sodium acetate (10 mM final concentration) per ml of cells. AIB consists of 40 mM $K_2HPO_4$, 10 mM $KH_2PO_4$, and 3 mM $MgCl_2$ and was prepared according to Ghirardi et al.

Using sterile technique, 1 ml of the resuspended algae was transferred to a 12 ml serum vial with a flea sized stir bar and sealed with a sterile septum (VWR #80062-438) using sterilized forceps. The serum vials were wrapped in aluminum foil to inhibit photosynthetic oxygen generation and gently purged with Argon (General Air: purity 5.0) for 2 hours using 25G7/8 needles (VWR #BD305124). A manifold was used to flush multiple samples simultaneously. The purged serum vials were incubated at room temperature, in the dark, an additional 2 hours in order to induce production of oxygen sensitive hydrogenases. Metronidazole treatment was started immediately or the samples were refrigerated overnight to minimize the loss of hydrogenase activity. If refrigerated overnight, the vials were allowed to warm to room temperature, approximately 15-30 minutes, and flushed with argon for 15 minutes before the metronidazole selection.

During this procedure, the septa were frequently wiped with ethanol to insure sterility. A maximum of 45 ml of fresh Metronidazole stock solution (50 mM Metronidazole & 1.25 mM $NaN_3$) was added to 70 ml serum vials wrapped in aluminum foil. The metronidazole containing vials were sealed with a septum and gently flushed with argon for 30 minutes, as described above. Add 4 ml of the anaerobic MNZ stock, using a 5 ml syringe and a 20 gauge needle. The MNZ-cell mixture was placed on a stir plate until the solution was well mixed. After mixing, an initial 100 μl sample of cells was removed using a 1 ml syringe and a 23 gauge needle in a dark sterile hood in a very dark lab. The cells were dispensed into an eppendorf tube and stored at room temperature in the dark. An aliquot of 100% oxygen (2.2 ml of 100% oxygen results in an approximate final headspace oxygen concentration of 25% given 9 ml of headspace in a 15 ml serum vial) was added to the headspace of the MNZ-cell mixture. The vial was shaken vigorously, by hand, for 5-10 seconds and then allowed to mix vigorously on a stir plate for 4 minutes. Afterwards, the aluminum foil was removed and the serum vial was exposed to 320 μE (approx. 2200 ft. candles) of light using a source (Dolan-Jenner #BG2820) filtered by a solution of 1% $CuSO_4$. The cells were exposed to the light for 6 minutes and then a second 100 μl sample of cells was removed to a second Eppendorf tube and store, as above. The serum vials were re-wrapped in aluminum foil and also stored in the dark at room temperature.

In a dark laminar flow hood, the time point samples were washed and resuspended in TAP before making the following dilutions: 1/100, 1/1000 and 1/10,000. For each of the dilutions, 100 μl was plated using 1-2 ml of cornstarch solution (25% cornstarch in TAP+60 mM sucrose). In order to obtain all of the surviving algae, the serum vials were washed several times in TAP and inoculated in 50 ml of TAP and grown, as above.

MNZ is quite toxic, so gloves were always used when it was handled. The excess MNZ solutions, as well as the MNZ/cell mixtures, were disposed into a waste bottle and submitted to the Environmental Health and Safety department.

However, the metronidazole failed to kill more than 90% of the wild type C. reinhardtii cells, regardless of the amount of oxygen that was injected into the serum vials. In fact, the cell death rate did not increase even when the cells were bubbled with 100% oxygen. Therefore, the technique was abandoned. Several brands of MNZ were tried with identical outcomes, so possibilities for why this technique didn't work include that the MNZ was unable to enter the algal cell or that the MNZ entered the cytoplasm, only to be destroyed. Since very little remained of the original NREL MNZ technique and the originally published algal selected mutants contained hydrogenases that were only slightly enhanced over the wild-type, it remains unknown as whether this technique was responsible for the published mutants.

More recently, hydrogen has been used in the "hydrotreating" or purification of fuel oil, the hydrogenation of oils to form margarine, in the production of ammonia-based fertilizers, in rocket fuel, and in fuel cells. The chemical reactions forming the basis of the fuel cell were first realized by William Nicholson, Anthony Carlisle, Christian Schoenbein, and William Grove; Swiss and English scientists in the early 1800s who were the first to combine oxygen and hydrogen gases in order to produce water. The term "fuel cell" was coined in 1889 when the very first fuel cell was created by Ludwig Mond and Charles Langer. Francis Bacon invented the first practical fuel cell in 1959. Since his invention, fuel cells have been used to power a diverse range of vehicles from a simple farm tractor to the Apollo mission and the space shuttles. It wasn't until the year 2000 that practical fuel cells for cars were unveiled by Ballard Power Systems. Perhaps someday soon, John Bockris' 1970 prediction of a "hydrogen economy" will become a reality and a national network of hydrogen energy will become the norm. In order to have a national network, reliable method of producing molecular hydrogen is needed. Hydrogen is currently produced by steam reforming the hydrogen atoms from coal or natural gas. However, the present disclosure providing for biohydrogen production from photosynthetic algae has the potential to be a viable alternative to hydrogen production from fossil fuels. It would not produce greenhouse gases ($H_2O$+sunlight→$O_2$+$H_2$); in fact, algae like most plants, utilizes carbon dioxide for cellular growth, so it would serve as a carbon sink. In addition, a bioreactor would not produce toxic waste, just algae and wastewater; similar to a fish tank. Also, a bioreactor would likely be about the size of an air conditioner and survive on low amounts of sunlight, so it would occupy a small amount of space and it could be located anywhere in the country.

Hydrogen could be generated locally by on-site electrolyzers or more likely by a centralized power plant. If molecular hydrogen is generated in a central location, it could eventually be piped to on site compressors and storage tanks or in the near-term, it could be simply delivered in trucks, just as gasoline is today. Often hydrogen is safer than gasoline in that it is non-toxic and non-poisonous. In addition and unlike gasoline, hydrogen will not contribute to groundwater pollution when it leaks from an underground storage tank.

Molecular hydrogen could be used to power cars directly as well as truck and trains, personal residences, and the workplace. In fact, the first area of significant usage of hydrogen power is via stationary fuel cells in industrial applications. Stationary and modular fuel cells already provide the benefit of highly reliable power with a consistent voltage, which is ideal for modern industries, which depend on computers. Fuel cells are also available for portable uses such as remote construction/military sites, laptop computers, and cell phones. To date, fuel cells have also been installed and demonstrated in 50 different types of mobile vehicles from "buses to bicycles." Lastly, home usage of fuel cells is possible as modular fuel cells, about the size of a common refrigerator, can provide enough power for a residence.

Figure 29:
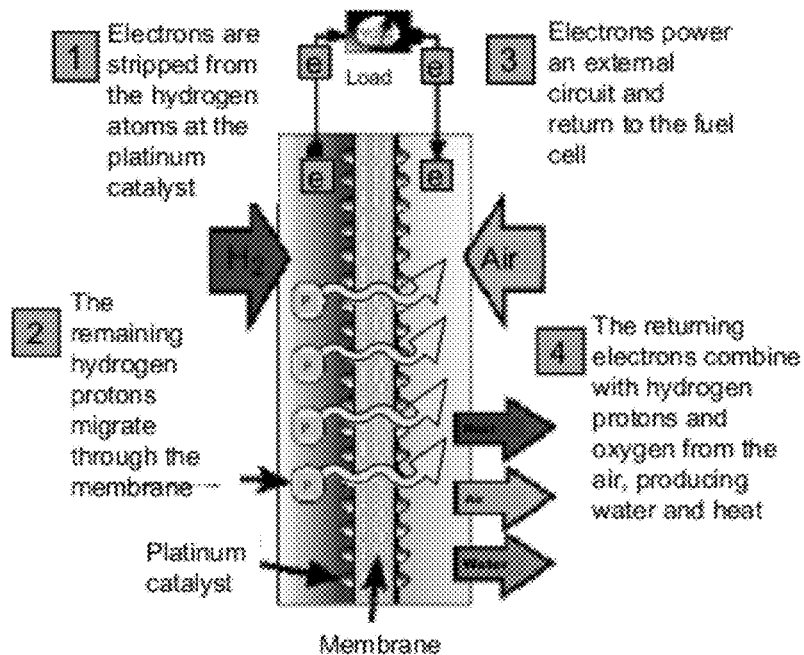
FIG. 29 shows the proton exchange membrane fuel cell (PEM FC).
Figure 31:
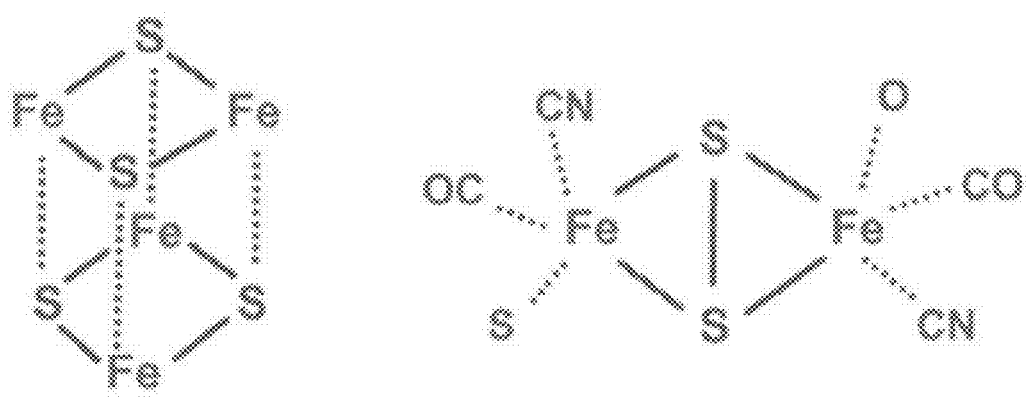
FIG. 31 is a diagram of the four-iron four-sulfur (4Fe-4S) cluster and the two-iron two sulfur (2Fe-2S) active site cluster that is present in Fe-only hydrogenases.

There are a myriad of different types of fuel cells, however the proton exchange membrane (PEM) fuel cell is the most common (FIG. 29) and hydrogen is the ultimate fuel for a fuel cell. In principle, fuel cells operate by chemically combining hydrogen with oxygen to form water, electricity, and heat. In fact, a fuel cell operates similarly to a battery that doesn't require recharging. Specifically, hydrogen gas flows into the anode side of a PEM fuel cell where a platinum catalyst removes the protons of hydrogen from the electrons. The electrons form a current, i.e. electricity, while the protons pass through the membrane that divides the anode from the cathode. Meanwhile, oxygen or air enters the cathode where it is combined with the protons and the electrons in order to form water (FIG. 30). Hydrogen fuel cells perform the reverse electrolysis reaction.

Example 7

Development of a Computational Predictive Model

Six chimeric hydrogenases and a wild type hydrogenase from C. acetobutylicum were used to develop a prediction model for other hydrogenase mutants that were not tested for hydrogen production. The hydrogenase mutants yielded hydrogen productions from zero to 4 times that produced by the wild type control.

In the first step, amino acid sequences were used to construct alpha-helix structures. These structures were then energy minimized using OPLS molecular mechanics technology. Next, the positive and negative electrostatic potential surface areas (EPSA) for each structure were calculated using a probe radius of 1.4 Å. The computations were performed with the HyperChem 7.5 computational chemistry program using a 32 bit PC computer.

Figure 32:
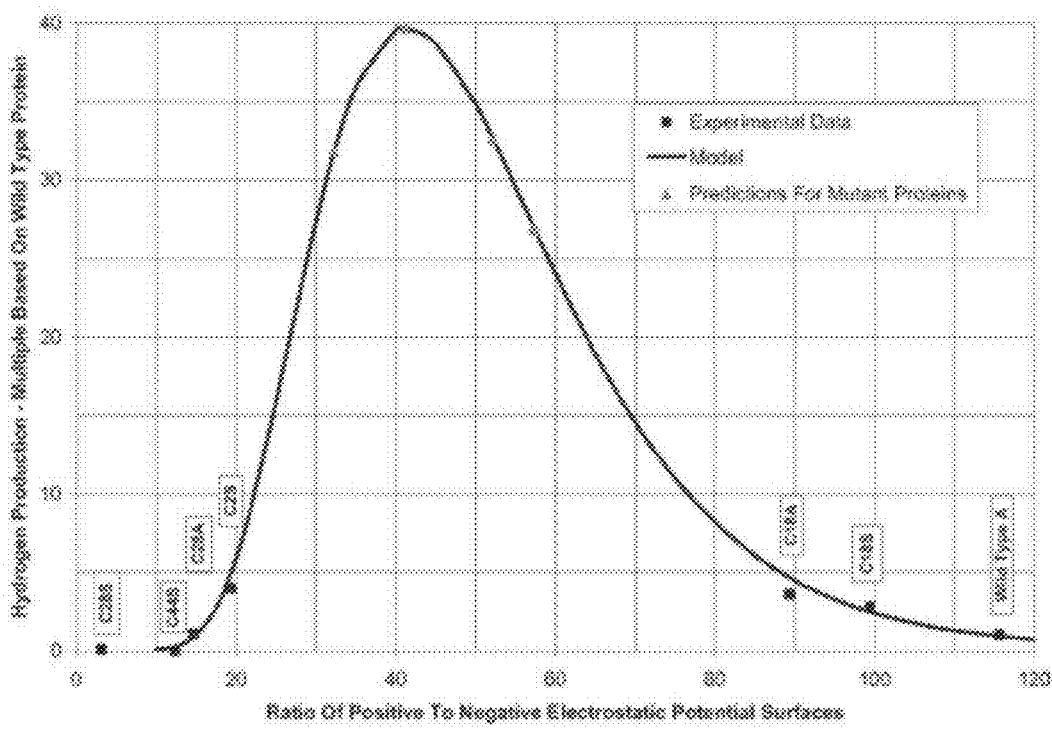
FIG. 32 shows the ratio of positive to negative electrostatic potential surface area (EPSA) plotted against hydrogen production for bacterial mutant hydrogenases. A molecular probe radius of 1.4 Å was used to calculate the EPSA ratios.

In the next step, positive to negative EPSA ratios were calculated (overlapping positive and negative regions were not included in the calculations) for each of the mutant and wild-type hydrogenases. The positive to negative EPSA ratios were plotted versus experimentally measured hydrogen production for the six hydrogenase mutants and the wild type control. The plot was regressed with several mathematical functions using the Microcal Origin 4.1 program. The function that fit the plot with the least error was the Log Normal Gaussian. Hence, this function was chosen as the prediction model. The Log Normal Gaussian function has been successfully used in several other studies relating molecular performance with molecular structure. The plot is shown in FIG. 32.

The selected prediction model suggests that the ratio of positive to negative EPSA is a measure of how a given protein mutant will fold into its tertiary state and how the final tertiary state affects hydrogen production. These results show that an EPSA ratio in the range of about 15 to about 115 is indicative of the capability to produce hydrogen at a greater rate than that observed with the wild type control (EPSA ratio of 116). The maximum hydrogen production was correlated with a positive to negative EPSA ratio of 42 (see FIG. 32).

In the final step of testing the prediction model, fifteen hydrogenase mutants, for which hydrogen productions were not experimentally obtained, were analyzed using the above described procedure. Five mutants exhibited positive to negative EPSA ratios that were within the above-mentioned range. The mutants were named C26S (protein sequence—SEQ ID NO: 207 and DNA sequence—SEQ ID NO: 144), C4S (protein sequence—SEQ ID NO: 187 and DNA sequence—SEQ ID NO: 122), C22S (protein sequence—SEQ ID NO: 203 and DNA sequence—SEQ ID NO: 140), C24S (protein sequence—SEQ ID NO: 205 and DNA sequence—SEQ ID NO: 142), and C25S (protein sequence—SEQ ID NO: 206 and DNA sequence—SEQ ID NO: 143), and each of these are predicted to produce hydrogen at 39.7 times, 32.6 times, 31.8 times, 27.0 times, and 26.8 times, respectively, of that produced by the wild type protein. In contrast, the remaining ten mutants, C6S, (protein sequence—SEQ ID NO: 192 and DNA sequence—SEQ ID NO: 127), C11S (protein sequence—SEQ ID NO: 194 and DNA sequence—SEQ ID NO: 129), C13S (protein sequence—SEQ ID NO: 196 and DNA sequence—SEQ ID NO: 131), C14S (protein sequence—SEQ ID NO: 197 and DNA sequence—SEQ ID NO: 132), C15S (protein sequence—SEQ ID NO: 198 and DNA sequence—SEQ ID NO: 133), C19S (protein sequence—SEQ ID NO: 201 and DNA sequence—SEQ ID NO: 137), C23S (protein sequence—SEQ ID NO: 204 and DNA sequence—SEQ ID NO: 141) and C29S (protein sequence—SEQ ID NO: 209 and DNA sequence—SEQ ID NO: 147) are predicted to yield no significant hydrogen productions since their EPSA ratios were outside the EPSA range of about 15 to about 115. These predictions have proven correct in subsequent tests.

Example 8

Hydrogen Production by Chimeric Hydrogenases

Figure 33:
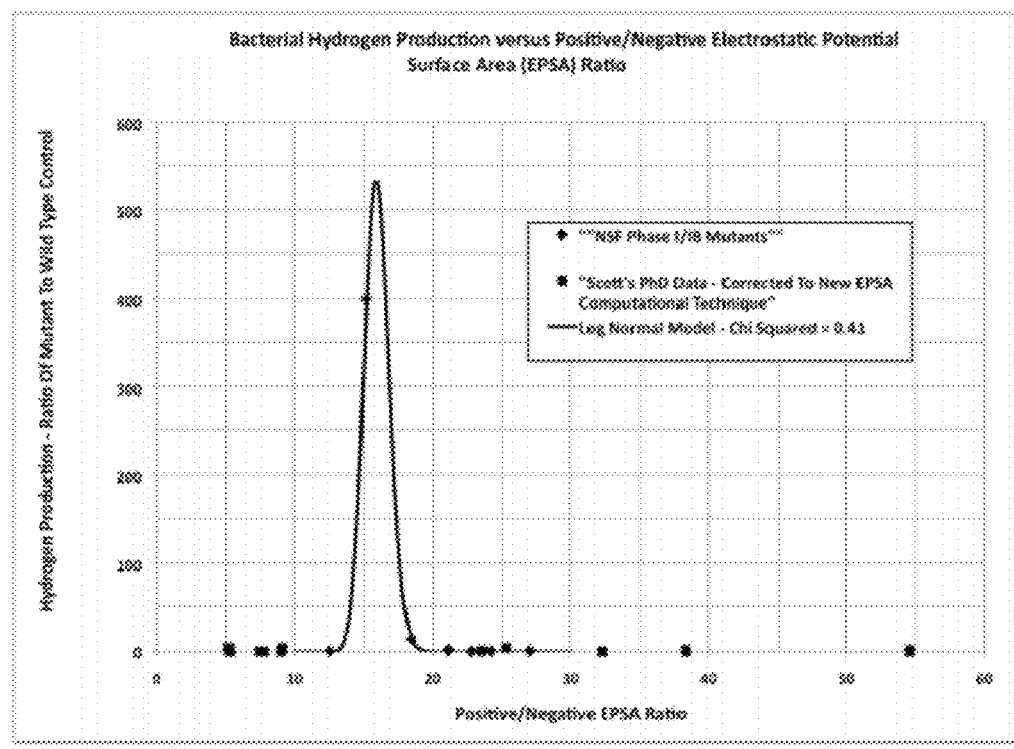
FIG. 33 is a graph of positive to negative EPSA ratios plotted against hydrogen production for bacterial mutant hydrogenases. A molecular probe radius of 1.0 Å was used to calculate the EPSA ratios.

Eleven chimeric bacterial hydrogenases were cloned and expressed in BL21 *E. coli* cells essentially as detailed above. Hydrogen production was determined using the Methyl Viologen assay essentially as described above. A wild-type hydrogenase from *Clostridium acetobutylicum* was used as a positive control. The levels of hydrogen produced by the chimeric hydrogenases ranged from about 0 to about 399 times that produced by the wild-type hydrogenase. (FIG. 33)

Figure 34:
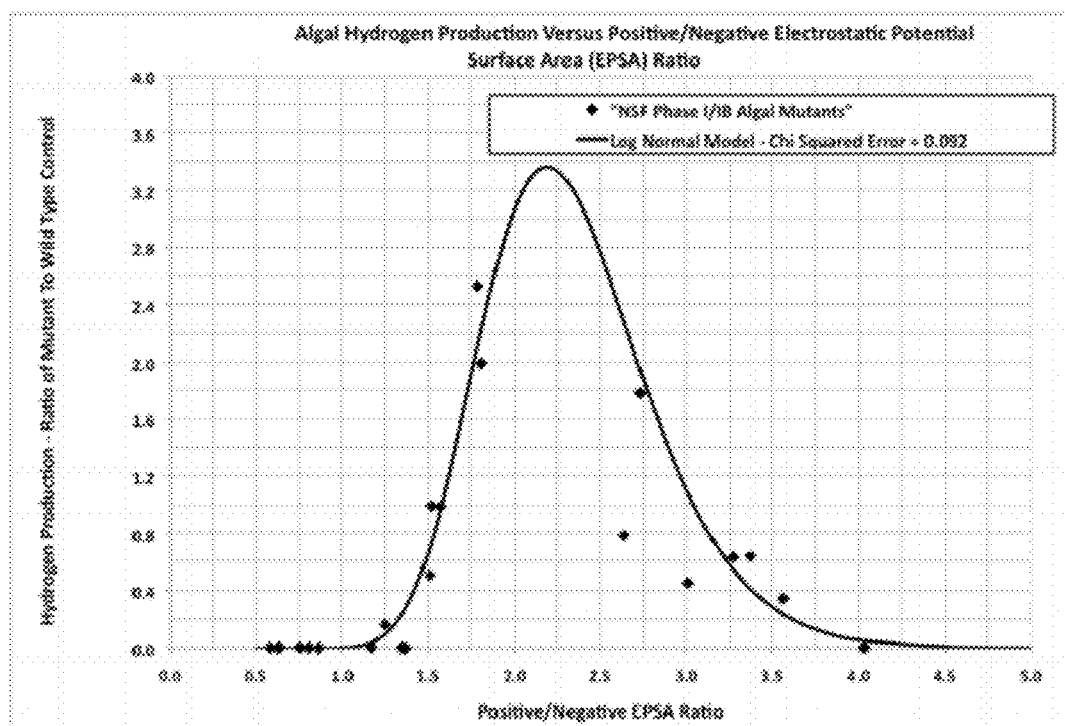
FIG. 34 is a graph of positive to negative EPSA ratios plotted against hydrogen production for algal mutant hydrogenases. A molecular probe radius of 1.0 Å was used to calculate the EPSA ratios.

Twenty-one chimeric algal hydrogenases were cloned and expressed in BL21 *E. coli* cells essentially as detailed above. Hydrogen production was determined using the Methyl Viologen assay essentially as described above. The amount of hydrogen produced by the chimeric algal hydrogenases ranges from about 0 to about 2.5 times that produced by the wild-type hydrogenase. (FIG. 34)

Example 9

Computational Modeling and Calculation of EPSA Ratios

EPSA ratios of all the bacterial and algal chimeric hydrogenases tested above as well as wild-type hydrogenases were calculated essentially as described above in Example 7 except a probe radius of 1.0 Å was used and the overlapping positive and negative EPSA regions were included in calculating the EPSA ratio. Positive to negative EPSA ratios were plotted against hydrogen production for the bacterial and algal mutant hydrogenases. The plots were regressed with several mathematical functions using the Microcal Origin 4.1 program. The Log Normal function was found to yield the least error for both bacteria (FIG. 33) and algal mutants (FIG. 34). Thus, the Log Normal function was chosen to define the range of mutants that yielded the optimum hydrogen production and for use in finding other optimum mutants.

Bacterial mutants with a positive to negative EPSA ratio from about 2 to about 50 yield hydrogen productions greater than that obtained with the wild type control. That is, hydrogen productions of 2.8, 4.0, 3.6 and 1.1 times that for the wild-type control were obtained at EPSA ratios of 5.2, 9.1, 25.4 and 38.3, respectively. The best mutants had EPSA ratios of 15.2 and 18.5, which yielded hydrogen productions of 399 and 13.5 times that of the wild-type control (FIG. 33). The model predicts that an EPSA ratio of about 16 will produce hydrogen of about 530 times that of the wild type. The wild type control has an EPSA ratio of 54.5.

The Log Normal model for the algal mutants (FIG. 34) shows that a positive to negative EPSA ratio from about 1 to about 4 yielded hydrogen productions equal to or greater than that produced by the algal wild-type control. The EPSA ratio of the wild-type algal hydrogenase was about 1.6. The maximum algal hydrogen production of 3.4 times that of the wild type occurred with an EPSA ratio of about 2.2. Other results suggest that algal mutants with positive to negative EPSA ratios in range of about 12 to about 22 will yield hydrogen productions similar to those via bacteria mutants, i.e., about 400 to about 530 times that of the wild type. Hence, there appear to be two EPSA ratio ranges in algal hydrogenases where hydrogen production is optimized.

Example 10

Calculated Positive/Negative EPSA ratios and Corresponding Hydrogen Production

The positive to negative EPSA ratios for several additional bacterial and algal hydrogenase sequences were calculated as described herein above. Those which had a positive to negative EPSA ratio in the preferred range were also found to demonstrate high levels of hydrogen production relative to wild type controls. The bacterial sequences (both DNA and protein), corresponding EPSA ratios and experimentally determined rates of hydrogen production for the bacterial hydrogenases are listed below. In addition, three algal sequences are provided below. These sequences were also experimentally analyzed for EPSA ratios and hydrogen production rate, as described herein, but were analyzed without their leader sequences, although the sequence for the leader is provided as well as the actual sequences tested.

```
Bacterial Hydrogenase Mutant C16A:
Positive/Negative EPSA Ratio: 15.2
Hydrogen Production: 399 times Wild Type
Amino Acid Sequence (SEQ ID NO: 224):
MAKTIILNGNEVHTDKDITILELARENNVDIPTLCFLKDCGNFGKCGVCMVEVEG

KGFRAACVAKVEDGMVINTESDEVKERIKKRVSMLLDKHEFKCGQCSRRENCEFLKLVI
```

-continued

```
KTKAKASKPFLPEDKDALVDNRSKAIVIDRSKCVLCGRCVAACKQHTSTCSIQFIKKDG

QRAVGTVDDVCLDDSTCLLCGQCVIACPVAALKEKSHIEKVQEALNDPKKHVIVAMAP

SIRTSMGELFKLGYGVDVTGKLYASMRALGFDKVFDINFGADMTIMEEATEFIERVKNN

GPFPMFTSCCPAWVRLAQNYHPELLDNLSSAKSPQQIFGTASKTYYPSISGIAPEDVYTV

TIMPCNDKKYEADIPFMETNSLRDIDASLTTRELAKMIKDAKIKFADLEDGEVDPAMGT

YSGAGAIFGATGGVMEAAIRSAKDFAENKELENVDYTEVRGFKGIKEAEVEIAGNKLNV

AVINGASNFFEFMKSGKMNEKQYHFIEVMACPGGCINGGGQPHVNALDRENVDYRKLR

ASVLYNQDKNVLSKRKSHDNPAIIKMYDSYFGKPGEGLAHKLLHVKYTKDKNVSKHE

DNA Sequence (SEQ ID NO: 225):
atggccaaaacaataatcttaaatggcaatgaagtgcatacagataaagatattactatccttgagctagcaagagaaaataatgta gatatcccaacactctgcttttaaaggattgtggcaattttggaaaatgcggagtctgtatggtagaggtagaaggcaagggctttagagctg cttgtgttgccaaagttgaagatggaatggtaataaacacagaatccgatgaagtaaaagaacgaatcaaaaaaagagtttcaatgcttcttg ataagcatgaatttaaatgtggacaatgttctagaagagaaaattgtgaattccttaaacttgtaataaagacaaaagcaaaagcttcaaaacc attttttaccagaagataaggatgctctagttgataatagaagtaaggctattgtaattgacagatcaaaatgtgtactatgcggtagatgcgtag ctgcatgtaaacagcacacaagcacttgctcaattcaatttattaaaaaagatggacaaagggctgttggaactgttgatgatgtttgtcttgatg actcaacatgcttattatgcggtcagtgtgtaatcgcttgtcctgttgctgctttaaaagaaaaatcccatatagaaaaagttcaagaagctctta atgaccctaaaaaacatgtaatagttgctatggcaccatcaatcagaacttctatgggagagttatttaaattaggctatggggttgatgtaactg gaaaattatatgcttcaatgagagcattaggatttgataaggtatttgatattaactttggggctgatatgacaataatggaagaagcaacagag tttattgaaagagttaaaaataatggcccattccctatgtttacatcttgctgtcctgcatgggtaagattagctcaaaattatcatcctgaatta ttagataatctttcatcagcaaaatcaccacaacaaatatttggtactgcatcaaaaacttactatccttcaatttcaggaatagctccagaagat gtttatacagttactatcatgccttgtaatgataaaaaatatgaagcagatattcctttcatggaaactaacagcttaagagatattgatgcatcc ttaactacaagagagcttgcaaaaatgattaaagatgcaaaaattaaatttgcagatcttgaagatggtgaagttgatcctgctatgggtacttac agtggtgctggagctatctttggtgcaaccggtggcgttatggaagctgcaataagatcagctaaagactttgctgaaaataaagaacttgaaaat gttgattacactgaagtaagaggctttaaaggcataaaagaagcggaagttgaaattgctggaaataaactaaacgttgctgttataaatggtgct tctaacttcttcgagtttatgaaatctggaaaaatgaacgaaaaacaatatcactttatagaagtaatggcttgccctggtggatgtataaatggt ggaggtcaacctcacgtaaatgctcttgatagagaaaatgttgattacagaaaactaagagcatcagtattatacaaccaagataaaaatgttc tttcaaagagaaagtcacatgataatccagctattattaaaatgtatgatagctactttggaaaaccaggtgaaggacttgctcacaaattacta cacgtaaaatacacaaaagataaaaatgtttcaaaacatgaa
```

Bacterial Hydrogenase Mutant C15S:
Positive/Negative EPSA Ratio: 18.5
Hydrogen Production: 13.5 times Wild Type
Amino Acid Sequence (SEQ ID NO: 225):

```
MAKTIILNGNEVHTDKDITILELARENNVDIPTLCFLKDCGNFGKCGVCMVEVEG

KGFRAACVAKVEDGMVINTESDEVKERIKKRVSMLLDKHEFKCGQCSRRENCEFLKLVI

KTKAKASKPFLPEDKDALVDNRSKAIVIDRSKCVLCGRCEAACKTKTGTGAISICKSESG

RIVQATGGKCFDDINCLLCGQCVAACPVGALTEKTHVDRVKEALEDPNKHVIVAMAPS

VRTAMGELFKMGYGKDVTGKLYTALRMLGFDKVFDINFGADMTIMEEATELLGRVKN

NGPFPMFTSCCPAWVRQVENYYPEFLENLSSAKSPQQIFGAASKTYYPQISGISAKDVFT

VTIMPCTAKKFEADREEMYNEGIKNIDAVLTTRELAKMIKDAKINFANLEDEQADPAMG

EYTGAGVIFGATGGVMEAALRTAKDFVEDKDLTDIEYTQIRGLQGIKEATVEIGGENYN

VAVINGAANLAEFMNSGKILEKNYHFIEVMACPGGCVNGGGQPHVSAKEREKVDVRTV

RASVLYNQDKNLEKRKSHKNTALLNMYYDYMGAPGQGKAHELLHLKYNK
```

DNA Sequence (SEQ ID NO: 226):
atggccaaaacaataatcttaaatggcaatgaagtgcatacagataaagatattactatccttgagctagcaagagaaaataatgta -continued

```
gatatcccaacactctgcttttaaaggattgtggcaattttggaaaatgcggagtctgtatggtagaggtagaaggcaagggctttagagctg cttgtgttgccaaagttgaagatggaatggtaataaacacagaatccgatgaagtaaaagaacgaatcaaaaaaagagtttcaatgcttcttg ataagcatgaatttaaatgtggacaatgttctagaagagaaaattgtgaattccttaaacttgtaataaagacaaaagcaaaagcttcaaacc attttttaccagaagataaggatgctctagttgataatagaagtaaggctattgtaattgacagatcaaatgtgtgctatgcggaagatgtgaag cagcatgtaaaacaaagacaggtacaggagctatttcaatttgtaagagtgaatcaggaagaatagtgcaagcaacaggcggaaagtgctt tgatgatacaaattgttttattatgtggacaatgcgttgcagcatgtccagtaggagctttaactgaaaaaacacacgttgatagagttaaagaag cattagaagatcctaataagcatgtcattgttgcaatggctccatcagtaagaactgctatgggcgaattattcaaaatgggatatggaaaaga tgtaacaggaaaactatatactgcacttagaatgttaggctttgataaagtatttgatataaactttggtgcagatatgactataatggaagaagc tactgaacttttaggcagagttaaaaataatggaccattcccaatgtttacttcatgttgtccggcatgggttagacaagtggaaaattattaccc agaatttttagaaaacttatcatcagctaaatcaccacaacaaatatttggtgcagcaagcaaaacatactatcctcaaatatcaggtataagtg ctaaagatgtatttactgttacaataatgccttgtacagcaaagaaatttgaggctgatagagaagaaatgtataatgagggaattaaaaatata gatgcagtacttactacaagagaattagcaaaaatgattaaagatgcaaagattaattttgctaatttagaagacgaacaagctgatccagcaa tgggagaatacactggggctggagttatattcggagctacaggtggagttatggaagcagcacttagaactgctaaggatttcgttgaagata aagatttaactgatatagaatatacacaaataagaggattacaaggaataaaagaggctacagtagaaattggtggagaaaattataacgtag ctgtaattaatggtgcagcaaacttagctgaattcatgaatagcggtaaaatccttgaaaagaactatcattttattgaagtaatggcttgcccag gcggatgtgtaaatggtggaggacaaccacacgtaagtgcaaaggaaagagaaaaagtagatgttagaactgtaagagcatctgttttatat aaccaagataaaaatttagagaagagaaaatcacataaaaatacagcattattaaatatgtactatgattatatgggagctccaggacaagga aaagctcatgaattattacacttaaaatacaataaa Chlamydomonas reinhardtii (CrA1) leader sequence:
Amino Acid Sequence (SEQ ID NO: 227):
MSALVLKPCAAVSIRGSSCRARQVAPRAPLAASTVRVALATLEAPARRLGNVACAA DNA Sequence (SEQ ID NO: 228):
atgtcggcgctcgtgctgaagccctgcgcggccgtgtctattcgcggcagctcctgcagggcgcggcaggtcgccccccgcg ctccgctcgcagccagcaccgtgcgtgtagcccttgcaacacttgaggcgcccgcacgccgcctaggcaacgtcgcttgcgcggct Algal Hydrogenase Mutant C7:
Positive/Negative EPSA Ratio: 1.81
Hydrogen Production: 1.99 times Wild Type (tested w/o leader sequence)
Amino Acid Sequence (as tested; SEQ ID NO: 229):
MAAPAAEAPLSHVQQALAELAKPKDDPTRKHVCVQVAPAVRVAIAETLGLAPG

ATTPKQLAEGLRRLGFDEVFDTLFGADLTIMEEGSELLHRLTEHLEAHPHSDEPLPMFTS

CCPGWIAMLEKSYPDLIPYVSSCKSPQMMLAAMVKSYLAEKKGIAPKDMVMVSIMPCT

RKQSEADRDWFCVDADPTLRQLDHVITTVELGNIFKERGINLAELPEGEWDNPMGVGS

GAGVLFGTTGGVMEAALRTAYELFTGTPLPRLSLSEVRGMDGIKETNITMVPAPGSKFE

ELLKHRAAARAEAAAHGTPGPLAWDGGAGFTSEDGRGGITLRVAVANGLGNAKKLITK

MQAGEAKYDFVEIMACPAGCVGGGGQPRSTDKAITQKRQAALYDLDERNTLRRSHEN

EAVNQLYKEFLGEPLSHRAHELLHTHYVPGGAEADA

DNA Sequence (as tested; SEQ ID NO: 230):
atggccgcacccgctgcggaggcgcctttgagtcatgtccagcaggcgctcgccgagcttgccaagcccaaggacgacccca cgcgcaagcacgtctgcgtgcaggtggctccggccgttcgtgtcgctattgccgagaccctgggcctggcgccgggcgccaccacccc aagcagctggccgagggcctccgccgcctcggctttgacgaggtgtttgacacgctgtttggcgccgacctgaccatcatggaggagggc agcgagctgctgcaccgcctcaccgagcacctggaggcccacccgcactccgacgagccgctgcccatgttcaccagctgctgccccg gctggatcgctatgctggagaaatcttacccggacctgatccctacgtgagcagctgcaagagcccccagatgatgctggcggcaatggt caagtcctacctagcggaaaagaagggcatcgcgccaaaggacatggtcatggtgtccatcatgccctgcacgcgcaagcagtcggagg
```

-continued ctgaccgcgactggttctgtgtggacgccgaccccaccctgcgccagctggaccacgtcatcaccaccgtggagctgggcaacatcttca aggagcgcggcatcaacctggccgagctgcccgagggcgagtgggacaatccaatgggcgtgggctcgggcgccggcgtgctgttcg gcaccaccggcggtgtcatggaggcggcgctgcgcacggcctatgagctgttcacgggcacgccgctgccgcgcctgagcctgagcga ggtgcgcggcatggacggcatcaaggagaccaacatcacaatggtgcccgcgcccgggtccaagtttgaggagctgctgaagcaccgc gccgccgcgcgcgccgaggccgccgcgcacggcaccccccgggccgctggcctgggacggcggcgcgggcttcaccagcgaggac ggcaggggcggcatcacactgcgcgtggccgtggccaacgggctgggcaacgccaagaagctgatcaccaagatgcaggccggcga ggccaagtacgactttgtggagatcatggcctgccccgcgggctgtgtgggcggcggcggccagcccgctccaccgacaaggccatc acgcagaagcggcaggcggctctgtacgacctggacgagcgcaacacgctgcgccgcagccacgaaaacgaggcggtcaaccagct gtacaaggagttcctgggcgagcccctgtccaccgcgcccacgagctgctgcacacccactacgtgccaggcggcgccgaggccgat gcttag Algal Hydrogenase Mutant C80:
Positive/Negative EPSA Ratio: 1.79
Hydrogen Production: 2.53 times Wild Type (tested w/o leader sequence)
Amino Acid Sequence (as tested; SEQ ID NO: 231):
MAAPAAEAPLSHVQQALAELAKPKDDPTRKHVCVQVAPAVRVAIAETLGLAPG

ATTPKQLAEGLRRLGFDEVFDTLFGADLTIMEEGSELLHRLTEHLEAHPHSDEPLPMFTS

CCPGWIAMLEKSYPDLIPYVSSCKSPQMMLAAMVKSYLAEKKGIAPKDMVMVSIMPCT

RKQSEADRDWFCVDADPTLRQLDHVITTVELGNIFKERGINLAELPEGEWDNPMGVGS

GAGVLFGTTGGVMEAALRTAYELFTGTPLPRLSLSEVRGMDGIKETNITMVPAPGSKFE

ELLKHRAAARAEAAAHGTPGPLAWDGGAGFTSEDGKGGLKLRVAVANGLGNAKKLIG

KMVSGEAKYDFVEIMACPAGCVGGGGQPRSTDKQITQKRQAALYNLDEKSTLRRSHEN

PSIRELYDTYLGEPLGHKAHELLHTHYVAGGVEEKDEKK

DNA Sequence (as tested; SEQ ID NO: 232):
atggccgcacccgctgcggaggcgcctttgagtcatgtccagcaggcgctcgccgagcttgccaagcccaaggacgacccca cgcgcaagcacgtctgcgtgcaggtggctccggccgttcgtgtcgctattgccgagaccctgggcctggcgccgggcgccaccaccccc aagcagctggccgagggcctccgccgcctcggcttgacgaggtgtttgacacgctgtttggcgccgacctgaccatcatggaggagggc agcgagctgctgcaccgcctcaccgagcacctggaggcccacccgcactccgacgagccgctgcccatgttcaccagctgctgccccg gctggatcgctatgctggagaaatcttacccggacctgatccctacgtgagcagctgcaagagcccccagatgatgctggcggcaatggt caagtcctacctagcggaaaagaagggcatcgcgccaaaggacatggtcatggtgtccatcatgccctgcacgcgcaagcagtcggagg ctgaccgcgactggttctgtgtggacgccgaccccaccctgcgccagctggaccacgtcatcaccaccgtggagctgggcaacatcttca aggagcgcggcatcaacctggccgagctgcccgagggcgagtgggacaatccaatgggcgtgggctcgggcgccggcgtgctgttcg gcaccaccggcggtgtcatggaggcggcgctgcgcacggcctatgagagttcacgggcacgccgctgccgcgcctgagcctgagcga ggtgcgcggcatggacggcatcaaggagaccaacatcacaatggtgcccgcgcccgggtccaagtttgaggagctgctgaagcaccgc gccgccgcgcgcgccgaggccgccgcgcacggcacccccgggccgctggcctgggacggcggcgcgggcttcaccagcgaggac ggcaagggcggcctgaagctgcgggtggcggtggcgaacggcctgggcaacgccaagaagctgatcggcaagatggtatctggcgag gccaagtacgacttcgtagaaatcatggcctgccctgccggctgcgtgggcggcggcggcagcccgctccaccgacaagcagatca cccgaagcggcaggcggcgctgtacaacctggacgagaagtccacgctgcgccgcagccacgagaacccgtccatccgcgagctgt acgacacgtacctcggagagccgctgggccacaaggcgcacgagagctgcacacccactacgtggccggcggcgtggaggagaag gacgagaagaagtga Algal Hydrogenase Mutant C81:
Positive/Negative EPSA Ratio: 2.73
Hydrogen Production: 1.78 times Wild Type (tested w/o leader sequence)
Amino Acid Sequence (as tested; SEQ ID NO: 233):
MAAPAAEAPLSHVQQALAELAKPKDDPTRKHVCVQVAPAVRVAIAETLGLAPG

ATTPKQLAEGLRRLGFDEVFDTLFGADLTIMEEGSELLHRLTEHLEAHPHSDEPLPMFTS

-continued

CCPGWIAMLEKSYPDLIPYVSSCKSPQMMLAAMVKSYLAEKKGIAPKDMVMVSIMPCT

RKQSEADRDWFCVDADPTLRQLDHVITTVELGNIFKERGINLAELPEGEWDNPMGVGS

GAGVLFGTTGGVMEAALRTAYELFTGTPLPRLSLSEVRGLDGIKEASVTLVPAPGSKFA

ELVAERLAHKVEEAAAAEAAAAVEGAVKPPIAYDGGQGFSTDDGRGGITLRVAVANGL

GNAKKLITKMQAGEAKYDFVEIMACPAGCVGGGGQPRSTDKAITQKRQAALYNLDEKS

TLRRSHENPSIRELYDTYLGEPLGHKAHELLHTHYVAGGVEEKDEKK

Figure 35:
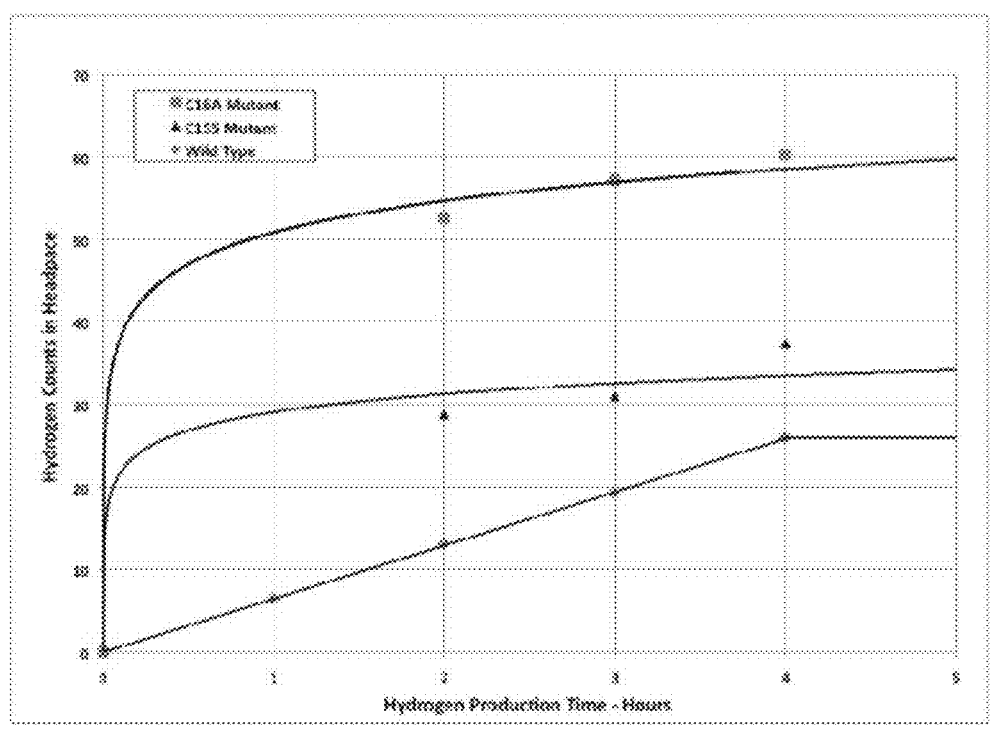
FIG. 35 is a graph of hydrogen production of bacterial hydrogenase mutants assessed by batch reactor headspace hydrogen count following after several hours of production.

DNA Sequence (as tested; SEQ ID NO: 234):
atggccgcacccgctgcggaggcgcctttgagtcatgtccagcaggcgctcgccgagcttgccaagcccaaggacgacccca cgcgcaagcacgtctgcgtgcaggtggctccggccgttcgtgtcgctattgccgagaccctgggcctggcgccgggcgccaccaccccc aagcagctggccgagggcctccgccgcctcggctttgacgaggtgtttgacacgctgtttggcgccgacctgaccatcatggaggagggc agcgagctgctgcaccgcctcaccgagcacctggaggccacccgcactccgacgagccgctgcccatgttcaccagctgctgcccccg gctggatcgctatgctggagaaatcttacccggacctgatccectacgtgagcagctgcaagagccccagatgatgctggcggcaatggt caagtcctacctagcggaaaagaagggcatcgcgccaaaggacatggtcatggtgtccatcgcctgcacgcgcaagcagtcggagg ctgaccgcgactggttctgtgtggacgccgaccccaccctgcgccagctggaccacgtcatcaccaccgtggagctgggcaacatcttca aggagcgcggcatcaacctggccgagctgcccgagggcgagtgggacaatccaatgggcgtgggctcgggcgccggcgtgctgttcg gcaccaccggcggtgtcatggaggcggcgctgcgcacggcctatgagctgttcacgggcacgccgctgccgcgcctgagcctgagcga ggtgcgcggcttggacggcatcaaggaggcgtccgtgacgctggtccccgctccgggctccaagttcgccgagctggtggcggagcgc ctggcgcacaaggtcgaggaggcggccgcggctgaggcggcggcggcggtggagggcgccgtgaagccgcccatcgcgtacgacg gcggccagggtttctccacggatgacggcaggggcggcatcacactgcgcgtggccgtggccaacgggctgggcaacgccaagaagc tgatcaccaagatgcaggccggcgaggccaagtacgactttgtggagatcatggcctgccccgcgggctgtgtgggcggcggcggcca gccccgctccaccgacaaggccatcacgcagaagcggcaggeggcgctgtacaacctggacgagaagtccacgctgcgccgcagcca cgagaacccgtccatccgcgagctgtacgacacgtacctcggagagccgctgggccacaaggcgcacgagctgctgcacacccactac gtggccggcggcgtggaggagaaggacgagaagaagtga Hydrogen content in the vapor space versus time is shown in FIG. 35 for the best performing bacterial mutant (C16A) identified so far, along with the results for the wild type control. Hydrogen produced by the wild type was noted to be linear with time, with the slope varying proportionally to the initial concentration of sodium dithionate (SD). This indicates a first order reaction, with SD being the rate controlling reactant. After four hours of reaction time, under the standard conditions, the wild-type control ceased to hydrogen production. Comparable results were observed with mutants that produced hydrogen at a rate near that of the wild-type control.

In contrast, hydrogen production by the C16A mutant increased exponentially with time over the four hours of evaluation indicating a higher order reaction mechanism. C16A continued to produce hydrogen up to 71 hours, albeit at a much slower rate due to ever decreasing amounts of SD in the batch reactor. Other mutants which displayed much higher rates of hydrogen production than the wild type control also yielded hydrogen production correlations versus time which were similar to that observed for C16A.

Under standard condition, the maximum hydrogen production at four hours for the wild-type control was 25 counts. The time required for the C16A mutant to reach 25 counts under the same conditions was about 0.01 hours. Hence, the efficiency of C16A, the best performing mutant, is about 400 times that of the wild type.

Figure 36:
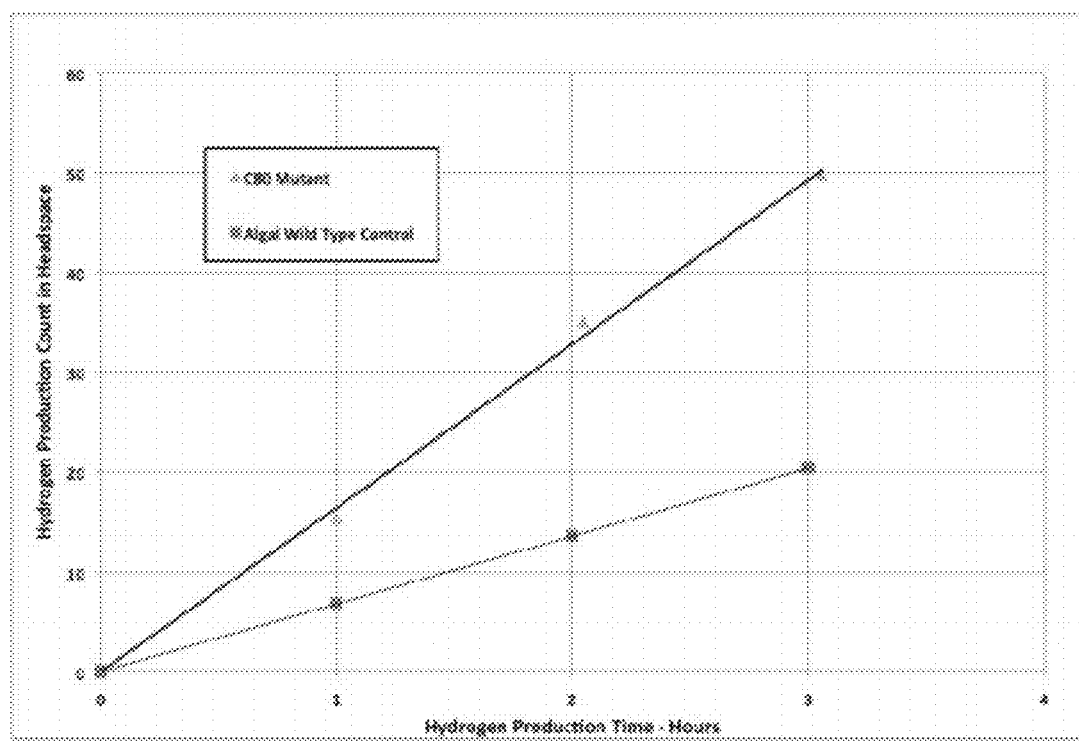
FIG. 36 a graph of hydrogen production by algal hydrogenase mutants assessed by batch reactor headspace hydrogen count following several hours of production.

The computational model described herein which uses the ratio of positive to negative electrostatic potential surface areas (EPSA) as the correlating parameter, fit all the results with a Chi squared error of 0.41 (FIG. 36). The estimated maximum bacterial mutant efficiency, mutant/wild-type hydrogen production ratio, is about 540 under standard conditions. Initial results have indicated that nearly double this ratio can be obtained with higher initial concentrations of SD and methyl viologen MV.

Over 100 algal mutants were experimentally evaluated for hydrogen production. Among the mutants tested, about 35% have yielded hydrogen, with six mutants yielding hydrogen in excess of that produced by the algal wild-type control. All algal hydrogenases were evaluated using the same operating conditions as those used in the bacterial experimental evaluations Most of the algal hydrogenases tested exhibit EPSA ratios in the range of 1-5. The best algal mutant (C80) thus far identified had a hydrogen production rate of 2.5 times that of the algal control and exhibited a linear hydrogen production with time. Further testing of the algal mutants and identification of the best candidates using the computational model, is expected to identify algal mutants showing an exponential rise in hydrogen production, as was observed with the best bacterial mutant hydrogenases. Isolation and testing of algal hydrogenases with EPSA ratios in the expected optimal range has commenced.

One skilled in the art would readily appreciate that the methods described in the present disclosure are well adapted to carry out the objects and obtain the ends and advantages mentioned, as well as those inherent therein. The methods, procedures, treatments, described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method for selecting a chimeric hydrogenase which produces hydrogen at an increased rate relative to the hydrogen production rate of a wild type hydrogenase following transformation of a cell with the chimeric hydrogenase and expression of the chimeric hydrogenase in the transformed cell, the method comprising: calculating a positive to negative electrostatic potential surface area (EPSA) ratio for the chimeric hydrogenase, wherein a positive to negative EPSA ratio of about 1 to about 115 is indicative of an increased hydrogen production rate in the cell by the chimeric hydrogenase relative to the hydrogen production rate of the wild type hydrogenase.

2. The method of claim 1, wherein calculating the positive to negative EPSA ratio comprises computing the positive EPSA, the negative EPSA, and the ratio of the positive EPSA to the negative EPSA.

3. The method of claim 1, wherein the positive to negative EPSA ratio is from about 2 to about 50.

4. The method of claim 1, wherein the positive to negative EPSA ratio is from about 5 to about 20.

5. The method of claim 1, wherein the cell is an algal cell and the chimeric hydrogenase is a chimeric algal hydrogenase.

6. The method of claim 5, wherein the cell is a *Chlamydomonas* cell.

7. The method of claim 1, wherein the cell is a bacterial cell and the chimeric hydrogenase is a chimeric bacterial hydrogenase.

8. A chimeric Fe-only hydrogenase that produces hydrogen at an increased rate relative to the hydrogen production rate of a wild type hydrogenase following transformation of a cell with the chimeric hydrogenase and expression of the chimeric hydrogenase in the transformed cell, wherein the chimeric hydrogenase is selected according to a method comprising: calculating a positive to negative electrostatic potential surface area (EPSA) ratio for the chimeric hydrogenase, wherein a positive to negative EPSA ratio of about 1 to about 115 is indicative of an increased hydrogen production rate in the cell by the chimeric hydrogenase relative to the hydrogen production rate of the wild type hydrogenase.

9. The chimeric Fe-only hydrogenase of claim 8, wherein calculating the positive to negative EPSA ratio comprises computing the positive EPSA, the negative EPSA, and the ratio of the positive EPSA to the negative EPSA.

10. The chimeric Fe-only hydrogenase of claim 8, wherein the positive to negative EPSA ratio is from about 2 to about 50.

11. The chimeric Fe-only hydrogenase of claim 8, wherein the positive to negative EPSA ratio is from about 5 to about 20.

12. The chimeric Fe-only hydrogenase of claim 8, wherein the cell is an algal cell and the chimeric hydrogenase is a chimeric algal hydrogenase.

13. The chimeric Fe-only hydrogenase of claim 12, wherein the cell is a *Chlamydomonas* cell.

14. The chimeric Fe-only hydrogenase of claim 8, wherein the cell is a bacterial cell and the chimeric hydrogenase is a chimeric bacterial hydrogenase.

* * * * *